(12) United States Patent
Long et al.

(10) Patent No.: US 11,589,586 B2
(45) Date of Patent: Feb. 28, 2023

(54) PESTICIDAL AND PARASITICIDAL PYRAZOLE-ISOXAZOLINE COMPOUNDS

(71) Applicant: BOEHRINGER INGELHEIM ANIMAL HEALTH USA INC., Duluth, GA (US)

(72) Inventors: Alan Long, Flowery Branch, GA (US); Hyoung Ik Lee, Alpharetta, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 14 days.

(21) Appl. No.: 16/638,957

(22) PCT Filed: Aug. 14, 2018

(86) PCT No.: PCT/US2018/046601
§ 371 (c)(1),
(2) Date: Feb. 13, 2020

(87) PCT Pub. No.: WO2019/036407
PCT Pub. Date: Feb. 21, 2019

(65) Prior Publication Data
US 2020/0178531 A1    Jun. 11, 2020

Related U.S. Application Data

(60) Provisional application No. 62/545,308, filed on Aug. 14, 2017.

(51) Int. Cl.
| | |
|---|---|
| *A01N 43/80* | (2006.01) |
| *A01N 43/90* | (2006.01) |
| *C07D 413/04* | (2006.01) |
| *C07D 491/107* | (2006.01) |

(52) U.S. Cl.
CPC ............ *A01N 43/80* (2013.01); *A01N 43/90* (2013.01); *C07D 413/04* (2013.01); *C07D 491/107* (2013.01)

(58) Field of Classification Search
CPC ...... A01N 43/80; A01N 43/90; C07D 413/04; C07D 491/107; C07D 493/10; A61P 33/00; A61P 33/14
See application file for complete search history.

(56) References Cited

U.S. PATENT DOCUMENTS

2013/0023526 A1    1/2013   Calderwood et al.

FOREIGN PATENT DOCUMENTS

| EP | 1731512 A1 | 12/2006 |
|---|---|---|
| EP | 1932836 A1 | 6/2008 |
| EP | 1997813 A1 | 12/2008 |
| EP | 2186804 A1 | 5/2010 |
| WO | 2007070606 A2 | 6/2007 |
| WO | 2007079162 A1 | 7/2007 |
| WO | 2007123855 A2 | 11/2007 |

OTHER PUBLICATIONS

Danziger, Automated site-directed drug design: a general algorithm for knowledge acquisition about hydrogen-bonding regions at protein surfaces, Proc. R. Soc. Lond., 1989, 236, pp. 101-113 (Year: 1989).*

P V Badadhe: "Synthesis and characterization of some novel isoxazolines and pyrazolines as potent antimicrobial agents", Indian Journal of Chemistry, Section B, vol. 50B, Apr. 1, 2011 (Apr. 1, 2011), pp. 879-884, XP055509752.

* cited by examiner

*Primary Examiner* — Jared Barsky
*Assistant Examiner* — Andrew P Lee
(74) *Attorney, Agent, or Firm* — John Esteban Ezcurra

(57) ABSTRACT

The present invention relates to pesticidal and parasiticidal isoxazoline of formula (I) and salts thereof:

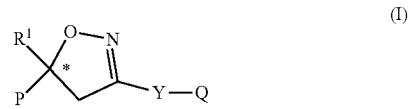

wherein variables $R^1$, P, Y and Q are described herein are as defined in the description. The invention also relates to parasiticidal and pesticidal compositions comprising the isoxazoline compounds of formula (I), processes for their preparation and their uses to prevent or treat parasitic infections or infestations in animals and as pesticides.

15 Claims, No Drawings

PESTICIDAL AND PARASITICIDAL PYRAZOLE-ISOXAZOLINE COMPOUNDS

FIELD OF THE INVENTION

The present invention relates to novel and inventive pesticidal and parasiticidal isoxazoline compounds of formula (I):

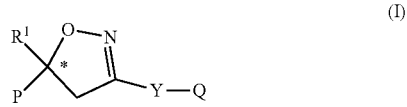

wherein, wherein $R^1$, P, Y and Q are as defined below, and compositions comprising at least one compound of formula (I) in combination with a pharmaceutically acceptable or agriculturally acceptable carrier. The invention also relates to uses of the compounds and methods comprising the compounds for the treatment and prevention of parasitic infections or infestations in or on animals and for controlling pests in crops, plants, plant propagation material and material derived from wood.

CROSS REFERENCE TO RELATED APPLICATIONS

This application is the national stage application of International Patent Application No. PCT/US2018/046601 filed on Aug. 14, 2018, which claims the benefit of priority to U.S. Provisional Application No. 62/545,308 filed Aug. 14, 2017, which is both incorporated herein by reference.

BACKGROUND OF THE INVENTION

Animals such as mammals and birds are often susceptible to parasite infestations/infections. These parasites may be ectoparasites, such as insects, and endoparasites such as nematodes and other worms. Domesticated animals, such as cats and dogs, are often infested with one or more of the following ectoparasites:
- fleas (e.g. *Ctenocephalides* spp., such as *Ctenocephalides felis* and the like);
- ticks (e.g. *Rhipicephalus* spp., *Ixodes* spp., *Dermacentor* spp., *Amblyomma* spp., and the like);
- mites (e.g. *Demodex* spp., *Sarcoptes* spp., *Otodectes* spp., and the like);
- lice (e.g. *Trichodectes* spp., *Cheyletiella* spp., *Linognathus* spp. and the like);
- mosquitoes (*Aedes* spp., *Culex* spp., *Anopheles* spp. and the like); and
- flies (*Haematobia* spp., *Musca* spp., *Stomoxys* spp., *Dermatobia* spp., *Cochliomyia* spp. and the like).

Fleas are a particular problem because not only do they adversely affect the health of the animal, but they also cause a great deal of psychological stress. Moreover, fleas may also transmit pathogenic agents to animals, such as tapeworm (*Dipylidium caninum*).

Similarly, ticks are also harmful to the physical and psychological health of the animal. However, the most serious problem associated with ticks is that they are vectors of pathogenic agents in animals. Major diseases which may be transmitted by ticks include borreliosis (Lyme disease caused by *Borrelia burgdorferi*), babesiosis (or piroplasmosis caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, a parasite which is prevalent among cattle in some regions are ticks of the genus *Rhipicephalus*, especially those of the species *Microplus* (cattle tick), *Decoloratus* and *Annulatus*. Ticks such as *Rhipicephalus microplus* (formerly *Boophilus microplus*) are difficult to control because they lay eggs in the pasture where farm animals graze. This species of ticks is considered a one-host tick and spends immature and adult stages on one animal before the female engorges and falls off the host to lay eggs in the environment. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesiosis ("cattle fever") and anaplasmosis.

Invertebrate pests also destroy growing and harvested crops and attack wooden dwellings and commercial structures, causing large economic loss to the food supply and to property. While a large number of pesticidal agents are known, due to the ability of target pests to develop resistance to said agents, there is an ongoing need for new agents for combating animal pests. In particular, pests such as insects and acaridae are difficult to be effectively controlled. However, it is a continuing objective to provide further pesticidal compounds which, at least in some aspects, offer advantages over the known compounds.

Various patent publications have described isoxazoline compounds having pesticidal properties. Recently, isoxazole and isoxazoline-containing compounds have been demonstrated to be effective against parasites that harm animals. For example, U.S. Pat. No. 7,964,204 (to DuPont, incorporated by reference herein in its entirety) discloses isoxazoline compounds according to Formula (I) below, which are active against ectoparasites and/or endoparasites.

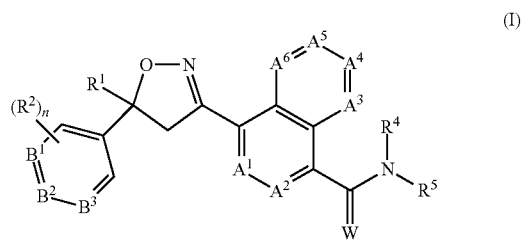

In addition, published patent application nos. US 2010/0254960 A1, WO 2007/070606 A2, WO 2007/123855 A2, WO 2010/003923 A1, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1 and WO 2007/075459 A2 and U.S. Pat. Nos. 7,951,828 and 7,662,972 describe various other parasiticidal isoxazoline compounds. Other published patent applications that describe various other parasiticidal isoxazoline compounds and formulations comprising the same include WO 2007/079162 A1, WO 2008/154528 A1, WO 2009/002809 A2, WO 2011/149749 A1, WO 2014/439475 A1, U.S. Pat. No. 8,466,115, WO 2012/120399, WO 2014/039484, WO 2014/189837, (Zoetis) and WO2012/120135A1 (Novartis). WO 2012/089623 describes topical localized isoxazoline formulations comprising glycofurol. WO 2013/039948 A1 provides for topical veterinary compositions comprising at least one isoxazoline active agent and WO 2013/119442 A1 provides for oral veterinary compositions such as a soft chew, which comprise at least one isoxazoline active agent.

Although some of these publications describe compounds containing a substituted isoxazoline ring having pesticidal and parasiticidal properties, none of the foregoing publications describe compounds of formula (I) of the present invention, that possess parasiticidal and pesticidal activity, particularly for controlling endoparasites or ectoparasites in or on animals.

The foregoing documents and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.
Citation or identification of any document in this application is not an admission that such document is available as prior art to the present invention.

SUMMARY OF THE INVENTION

The present invention provides novel and inventive isoxazoline compounds of formula (I) shown below that are biologically active against parasites that harm animals and against pests that damage crops, plants, plant propagation material and material derived from wood.

Accordingly, the application provides parasiticidal and pesticidal compositions comprising the isoxazoline compounds in combination with a pharmaceutically acceptable carrier or an agriculturally acceptable carrier. The present invention also provides methods for the treatment or prevention of a parasitic infection or infestation in an animal and for controlling pests that harm plants, plant propagation material and material derived from wood, which comprise administering an effective amount of a compound of the invention to the animal or to the plants, plant propagation material, the soil in which the infected plant grows, or the wood-derived material, with a pesticidally effective amount of a compound of formula (I).

A first object of the invention is to provide parasiticidal and pesticidal novel and inventive isoxazoline compounds of formula (I):

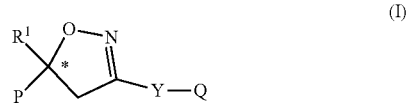

wherein $R^1$, P, Y and Q are as defined below.

Further, this invention provides for antiparasitic compositions for the treatment or prevention of parasitic infections and infestations in animals comprising a parasiticidally effective amount of at least one compound of formula (I), or a pharmaceutically acceptable salt thereof, in combination with a pharmaceutically acceptable carrier. The compositions may be formulated for oral, subcutaneous, parenteral, sublingual, buccal and topical administration, including spot-on and pour-on administration.

Another object of the invention is to provide pesticidal compositions comprising at least one compound of formula (I), or an agriculturally or pharmaceutically acceptable salt thereof, for combating pests that are harmful to plants, plant propagation material or material derived from wood in combination with a pesticidally effective carrier.

Another object of the invention is to provide veterinary and agricultural compositions comprising at least one compound of formula (I), or an agriculturally or pharmaceutically acceptable salt thereof, for combating pests and parasites, in combination with one more other active agent and a veterinarily or agriculturally acceptable carrier or diluent.

Another object of the invention is to provide plant propagation material (e.g. seed), comprising at least one compound of formula (I), or an agriculturally acceptable salt thereof, and plant propagation material that has been treated with at least one compound of formula (I), or an agriculturally acceptable salt thereof, or a composition comprising the compound or salt thereof.

Another object of this invention is to provide methods of treatment and prevention of parasitic infections or infestations in or on an animal, which comprise treating the infected animal with a parasiticidally effective amount of a compound of formula (I), or a pharmaceutically acceptable salt thereof.

Another object of this invention is to provide methods for combating pests on crops, plants, plant propagation material or material derived from wood, which comprises treating the infected plant, or the soil in which the infected plant grows, or the wood-derived material with a pesticidally effective amount of a compound of formula (I), or an agriculturally acceptable salt thereof.

Another object of the invention is to provide methods for combating or controlling pests at a locus (excluding an animal), comprising administering a pesticidally or parasiticidally effective amount of a compound of formula (I), or pharmaceutically or agriculturally acceptable salts thereof, to the locus.

Another object of the invention is to provide use of a compound of formula (I), or a pharmaceutically acceptable salt thereof, for use in the treatment or prevention of a parasitic infection or infestation in or on an animal. Still another object of the invention is use of a compound of formula (I), or a pharmaceutically acceptable salt thereof, in the preparation of a medicament for the treatment or prevention of a parasitic infestation or infection in or on an animal.

Still another object of this invention is to provide processes for the preparation of isoxazoline compounds of formula (I).

The present invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that the applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned; and the applicant(s) explicitly reserve the right to introduce into any claim a disclaimer as to any previously disclosed compound, product, process of making the product or method of using the product. Specifically, the compounds of the invention are not intended to encompass isoxazoline compounds that have been previously disclosed in the art.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law; e.g., they allow for elements not explicitly recited, but exclude elements that are found in the prior art or that affect a basic or novel characteristic of the invention. These and other embodiments are disclosed or are obvious from and encompassed by, the following Detailed Description.

DETAILED DESCRIPTION OF THE INVENTION

The novel and inventive isoxazoline compounds of formula (I) of the invention are active against pests, including parasites that cause harm to animals, and pests that damage plants, plant propagation material and material containing wood or derived from wood. Accordingly, the compounds of the invention are useful for preventing and treating a parasitic infestation/infection in an animal and for controlling and eradicating pests that damage plants, plant propagation material and material derived from wood.

The present invention provides novel and inventive isoxazoline compounds and compositions comprising the compounds. Furthermore, the invention provides methods for preventing and/or treating a parasitic infestation or infection in an animal, and the use of the compounds for treating a parasitic infestation or infection in an animal or the use of the compounds in the manufacture of a medicament for treating a parasitic infestation or infection in an animal.

In one embodiment, the invention provides novel and inventive isoxazoline compounds that are effective against ectoparasites that harm animals. Thus, the compounds described herein may be used to treat and prevent parasitic infestations in or on animals.

In another embodiment, the present invention provides uses of the compounds for controlling and eradicating pests that cause damage to plants, plant propagation material and material derived from wood. In still another embodiment, the present invention provides uses of the isoxazoline compounds to control environmental pests at a locus.

A first object of the invention is to provide parasiticidal and pesticidal novel and inventive isoxazoline compounds of formula (I):

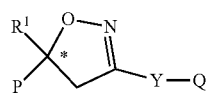

(I)

wherein:
the asterisk (*) signifies a quaternary center;
P is an optionally substituted pyrazole ring;
$R^1$ is alkyl, haloalkyl, alkenyl, alkynyl, cycloalkyl, alkylcycloalkyl or cycloalkylalkyl, each optionally substituted with one or more substituents independently selected from $R^6$;

Y is an optionally substituted phenylene, naphthylene, indanylene, a 5- or 6-membered heteroarylene, an 8-12-membered heterobicyclylene or an 8-12-membered heterotricyclylene, each optionally independently substituted by one or more $R^7$;

Q is $X-NR^5R^6$, $-NR^5R^6$, $X-R^6$, OH, $NH_2$, alkoxy, haloalkoxy, alkylamino, haloalkylamino, dialkylamino, dihaloalkylamino, thiol, alkylthio, haloalkylthio, alkylsulfinyl, haloalkylsulfinyl, alkylsulfonyl, haloalkylsulfonyl, $-SF_5$, $-C(=S)-NH_2$, or an optionally substituted 5- or 6-membered carbocyclyl, heterocyclyl, heteroaryl ring or the groups T1 or T2:

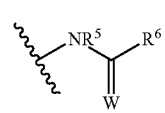

T1

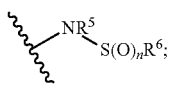

T2 wherein W is O or S;
X is $(CH_2)_n$, $CH(CH_3)$, CH(CN), C(=O) or C(=S);
$R^5$ is H, alkyl, alkenyl, alkynyl, cycloalkyl, alkylcycloalkyl, cycloalkylalkyl, alkylcarbonyl or alkoxycarbonyl;
$R^6$ is H, $OR^{10}$, $NR^{11}R^{12}$ or $Q^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^7$; or
$R^5$ and $R^6$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, $-CN$, $-NO_2$ and alkoxy;
each $R^7$ is independently halogen; alkyl, cycloalkyl, alkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, $-SF_5$, $-C(=S)NH_2$, $-NH_2$, $-CN$ or $-NO_2$; or $Q^2$;
each $R^8$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, $-SF_5$, $-C(=S)NH_2$, $-CN$ or $-NO_2$;
each $R^9$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, $-SF_5$, $-C(=S)NH_2$, $-CN$, $-NO_2$, phenyl or pyridinyl;
$R^{10}$ is H; or alkyl, alkenyl, alkynyl, cycloalkyl, alkylcycloalkyl or cycloalkylalkyl, each optionally substituted with one of more halogen;
$R^{11}$ is H, alkyl, alkenyl, alkynyl, cycloalkyl, alkylcycloalkyl, cycloalkylalkyl, alkylcarbonyl or alkoxycarbonyl;
$R^{12}$ is H; $Q^3$; or alkyl, alkenyl, alkynyl, cycloalkyl, alkylcycloalkyl or cycloalkylalkyl, each optionally substituted with one or more substituents independently selected from $R^7$; or $R^{11}$ and $R^{12}$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

$Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2.

In certain embodiments the optionally substituted pyrazole ring P is $P^1$, $P^2$, $P^3$ or $P^4$ shown below:

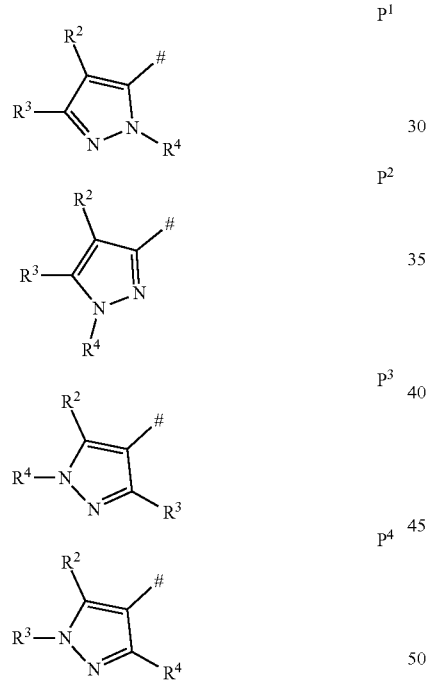

wherein #signifies the point of attachment, $R^2$ and $R^3$ are independently H, halogen, alkyl, haloalkyl, alkenyl, haloalkenyl, alkynyl, haloalkynyl, cycloalkyl, halocycloalkyl, alkoxy, haloalkoxy, alkoxyalkyl, alkoxyalkoxyalkyl, alkylthio, haloalkylthio, alkylsulfinyl, haloalkylsulfinyl, alkylsulfonyl, haloalkylsulfonyl, amino, alkylamino, dialkylamino, haloalkylamino, dihaloalkylamino, alkylcarbonyl, haloalkylcarbonyl, alkoxycarbonyl, aminocarbonyl, alkylaminocarbonyl, dialkylaminocarbonyl, aryl, heteroaryl, arylalkyl, heteroarylalkyl, SF$_5$, —CN, —NO$_2$ or —C(S)NH$_2$, wherein each alkyl, cycloalkyl, alkenyl, alkynyl, aryl or heteroaryl is optionally independently substituted by one or more $R^7$;

$R^4$ is H, alkyl, haloalkyl, alkenyl, haloalkenyl, alkynyl, haloalkynyl, arylalkyl, heteroarylalkyl, alkoxyalkyl, alkoxy-alkoxyalkyl, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, aryl, heteroaryl, arylalkyl or heteroarylalkyl, wherein each optionally substituted by one or more $R^7$.

In another embodiment, P is $P^1$, $P^2$, $P^3$ or $P^4$ wherein #signifies the point of attachment, $R^2$ and $R^3$ are independently H, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, amino, $C_1$-$C_6$-alkylamino, di-$C_1$-$C_6$-alkylamino, $C_1$-$C_6$-haloalkylamino, di-$C_1$-$C_6$-haloalkylamino, $C_1$-$C_6$-alkylcarbonyl, $C_1$-$C_6$-haloalkylcarbonyl, $C_1$-$C_6$-alkoxycarbonyl, aminocarbonyl, $C_1$-$C_6$-alkylaminocarbonyl, di-$C_1$-$C_6$-alkylaminocarbonyl, aryl, heteroaryl, aryl-$C_1$-$C_6$-alkyl, heteroaryl-$C_1$-$C_6$-alkyl, SF$_5$, —CN, —NO$_2$ or —C(S)NH$_2$, wherein each $C_1$-$C_6$-alkyl, $C_3$-$C_8$-cycloalkyl, $C_2$-$C_6$-alkenyl, $C_2$-$C_6$-alkynyl, aryl or heteroaryl is optionally independently substituted by one or more $R^7$;

$R^4$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, aryl-$C_1$-$C_6$-alkyl, heteroaryl-$C_1$-$C_6$-alkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, aryl, heteroaryl, aryl-$C_1$-$C_6$-alkyl or heteroaryl-$C_1$-$C_6$-alkyl, wherein each optionally substituted by one or more $R^7$.

In one embodiment, the invention provides compounds of formula (I) wherein Y is selected from Y-1, Y-2, Y-3 where $Z^1$, $Z^2$, $Z^3$, $Z^4$, $Z^5$ and $Z^6$ are independently N or C—$R^{15}$ and wherein at most 3 Z groups are nitrogen, Y-4, Y-5 where Z is N or C—$R^{15}$, Y-6 or Y-7; wherein $R^{13}$, $R^{14}$ and $R^{15}$ are independently H, halogen, $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$haloalkylsulfonyl, —CN, —NO$_2$ or —SF$_5$:

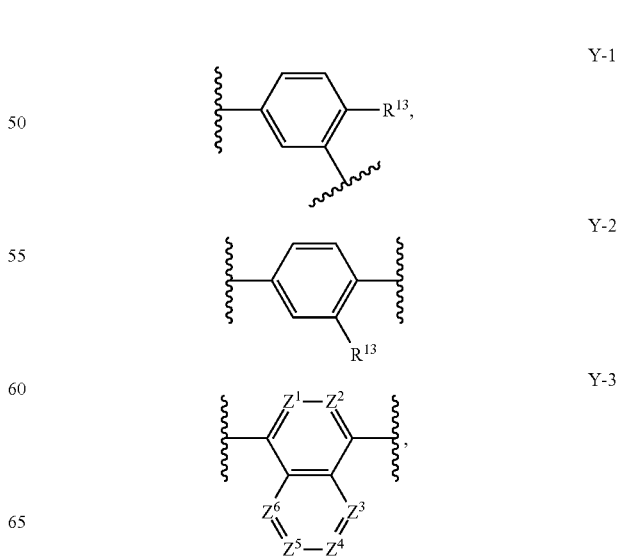

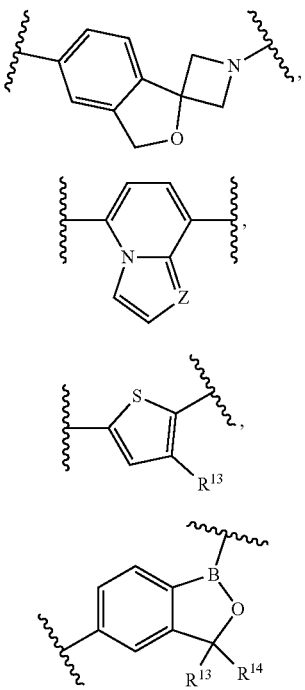

Y-4

Y-5

Y-6

Y-7

In one embodiment of the invention comprising an isoxazoline compound of formula (I), the group Q is X—NR$^5$R$^6$. In another embodiment, Q is X—NR$^5$R$^6$ wherein R$^5$ is H or C$_1$-C$_3$alkyl and R$^6$ is C$_1$-C$_3$alkyl optionally substituted by R$^7$. In yet another embodiment, Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl. In another embodiment, Q is X—NR$^5$R$^6$ wherein R$^5$ is H and R$^6$ is C$_1$-C$_3$alkyl optionally substituted by halogen, alkylthio, haloalkylthio, alkylaminocarbonyl, dialkylaminocarbonyl, haloalkylaminocarbonyl or dihaloalkylaminocarbonyl.

In another embodiment, Q is X—NR$^5$R$^6$ wherein R$^5$ is H or C$_1$-C$_3$alkyl and R$^6$ is C$_3$-C$_8$cycloalkyl, optionally substituted by one or more R$^7$. In yet another embodiment, Q is X—NR$^5$R$^6$ wherein R$^5$ is H or C$_1$-C$_3$alkyl and R$^6$ is C$_3$-C$_6$cycloalkyl, optionally substituted by one or more R$^7$. In still another embodiment, Q is X—NR$^5$R$^6$ wherein R$^5$ is H or C$_1$-C$_3$alkyl and R$^6$ is cyclopropyl, cyclobutyl, cyclopentyl or cyclohexyl.

In another embodiment, Q is X—NR$^5$R$^6$ wherein R$^5$ is H or C$_1$-C$_3$alkyl and R$^6$ is alkylcarbonyl, haloalkylcarbonyl. In another embodiment, Q is —C(O)NHCH$_2$CF$_3$. In another embodiment, Q is —C(O)NHCH$_2$CH$_2$CF$_3$. In yet another embodiment, Q is —C(O)NHCF$_3$. In still another embodiment, Q is —C(O)NHCH$_2$C(O)NHCH$_2$CF$_3$. In another embodiment, Q is —C(O)NHCH$_2$CH$_2$S(O)$_n$CH$_3$ where n is 0, 1 or 2.

In another embodiment, Q is —NR$^5$R$^6$ wherein R$^5$ is H or C$_1$-C$_3$alkyl and R$^6$ is alkylcarbonyl, haloalkylcarbonyl. In another embodiment, Q is —NHC(O)CH$_2$CF$_3$. In another embodiment, Q is —NHC(O)CH$_2$CH$_2$CF$_3$. In yet another embodiment, Q is —NHC(O)CF$_3$. In still another embodiment, Q is —NHC(O)CH$_2$C(O)NHCH$_2$CF$_3$. In another embodiment, Q is —NHC(O)CH$_2$CH$_2$S(O)$_n$CH$_3$ where n is 0, 1 or 2.

In another embodiment, Q is X—R$^6$. In still another embodiment, Q is X—R$^6$ wherein R$^6$ is alkyl substituted by R$^7$. In another embodiment, Q is X—R$^6$ where R$^6$ is C$_1$-C$_3$alkyl substituted by R$^7$. In another embodiment, Q is X—R$^6$ wherein R$^6$ is C$_1$-C$_2$alkyl substituted by S(O)$_n$C$_1$-C$_3$alkyl, wherein n is 0, 1 or 2. In another embodiment, Q is —CH$_2$S(O)$_n$CH$_3$ wherein n is 0, 1 or 2.

In one embodiment, R$^1$ is C$_1$-C$_3$haloalkyl. In yet another embodiment, R$^1$ is CFCl$_2$. In another embodiment R$^1$ is CF$_2$Cl. In another embodiment, R$^1$ is CFBr$_2$. In another embodiment, R$^1$ is CF$_2$Br. In a particularly preferred embodiment, R$^1$ is CF$_3$.

In one embodiment of the compounds of formula (I), Y is Y-1. In another embodiment, Y is Y-1 wherein R$^{13}$ is H. In another embodiment, Y is Y-1 wherein R$^{13}$ is alkyl. In another embodiment, Y is Y-1 wherein R$^{13}$ is halogen, In yet another embodiment, Y is Y-1 wherein R$^{13}$ is C$_1$-C$_3$alkyl. In still another embodiment, Y is Y-1 wherein R$^{13}$ is methyl. In another embodiment, Y is Y-1 where R$^{13}$ is chloro. In still another embodiment, Y is Y-1 where R$^{13}$ is fluoro. In yet another embodiment, Y is Y-1 where R$^{13}$ is bromo. In yet another embodiment, Y is Y-1 where R$^{13}$ is cyano.

In one embodiment of the compounds of formula (I), Y is Y-2. In another embodiment, Y is Y-2 wherein R$^{13}$ is H. In another embodiment, Y is Y-2 wherein R$^{13}$ is alkyl. In another embodiment, Y is Y-2 wherein R$^{13}$ is halogen, In yet another embodiment, Y is Y-2 wherein R$^{13}$ is C$_1$-C$_3$alkyl. In still another embodiment, Y is Y-2 wherein R$^{13}$ is methyl. In another embodiment, Y is Y-2 where R$^{13}$ is chloro. In still another embodiment, Y is Y-2 where R$^{13}$ is fluoro. In yet another embodiment, Y is Y-2 where R$^{13}$ is bromo. In yet another embodiment, Y is Y-2 where R$^{13}$ is cyano.

In another embodiment, Y is Y-3. In one embodiment of the compounds of formula (I), Y is Y-3 wherein Z$^1$ to Z$^6$ are independently C—R$^{15}$. In another embodiment, Y is Y-3 wherein Z$^1$ is N and Z$^2$ to Z$^6$ are each independently C—R$^{15}$. In another embodiment, Y is Y-3 wherein Z$^2$ is N and Z$^1$ and Z$^3$ to Z$^6$ are each independently C—R$^{15}$. In another embodiment, Y is Y-3 wherein Z$^3$ is N and Z$^1$, Z$^2$, Z$^4$, Z$^5$ and Z$^6$ are each independently C—R$^{15}$. In another embodiment, Y is Y-3 wherein Z$^4$ is N and Z$^1$, Z$^2$, Z$^3$, Z$^5$ and Z$^6$ are each independently C—R$^{15}$. In another embodiment, Y is Y-3 wherein Z$^5$ is N and Z$^1$, Z$^2$, Z$^3$, Z$^4$ and Z$^6$ are each independently C—R$^{15}$. In another embodiment, Y is Y-3 wherein Z$^6$ is N and Z$^6$ to Z$^5$ are each independently C—R$^5$.

In another embodiment, Y is Y-3 wherein Z$^1$ and Z$^2$ are N and Z$^3$ to Z$^6$ are independently C—R$^{15}$. In another embodiment, Y is Y-3 wherein Z$^4$ and Z$^5$ are N and Z$^1$, Z$^2$, Z$^3$ and Z$^6$ are independently C—R$^{15}$. In yet another embodiment, Y is Y-3 wherein Z$^5$ and Z$^6$ are N and Z$^1$ to Z$^4$ are independently C—R$^{15}$. In still another embodiment, Z$^3$ and Z$^4$ are N and Z$^1$, Z$^2$, Z$^5$ and Z$^6$ are independently C—R$^{15}$.

In one embodiment of the compounds of formula (I), Y is Y-3 wherein Z$^1$ to Z$^6$ are all C—H. In another embodiment, Y is Y-3 wherein Z$^1$ and Z$^2$ are N and Z$^3$ to Z$^6$ are C—H. In another embodiment, Y is Y-3 wherein Z$^4$ and Z$^5$ are N and Z$^1$, Z$^2$, Z$^3$ and Z$^6$ are C—H. In yet another embodiment, Y is Y-3 wherein Z$^5$ and Z$^6$ are N and Z$^1$ to Z$^4$ are C—H. In still another embodiment, Z$^3$ and Z$^4$ are N and Z$^1$, Z$^2$, Z$^5$ and Z$^6$ are C—H.

In another embodiment of the compounds of formula (I), Y is Y-4. In yet another embodiment, Y is Y-4 and Q is the group —CH$_2$S(O)$_2$CH$_3$.

In another embodiment, Y is Y-5. In another embodiment, Y is Y-5 where Z is C—$R^{55}$. In another embodiment, Y is Y-5 where Z is C—H. In yet another embodiment, Y is Y-5 where Z is N.

In one embodiment of the compounds of formula (I), Y is Y-6. In another embodiment, Y is Y-6 wherein $R^{13}$ is H. In another embodiment, Y is Y-6 wherein $R^{13}$ is alkyl. In another embodiment, Y is Y-6 wherein $R^{13}$ is halogen, In yet another embodiment, Y is Y-6 wherein $R^{13}$ is $C_1$-$C_3$alkyl. In still another embodiment, Y is Y-6 wherein $R^{13}$ is methyl. In another embodiment, Y is Y-6 where $R^{13}$ is chloro. In still another embodiment, Y is Y-6 where $R^{13}$ is fluoro. In yet another embodiment, Y is Y-6 where $R^{13}$ is bromo. In yet another embodiment, Y is Y-6 where $R^{13}$ is cyano.

In one embodiment, Y is Y-7 where $R^{13}$ and $R^{14}$ are both H. In another embodiment, Y is Y-7 wherein $R^{13}$ and $R^{14}$ are both $C_1$-$C_3$alkyl. In another embodiment, Y is Y-7 wherein $R^{13}$ and $R^{14}$ are independently $C_1$-$C_3$alkyl or $C_1$-$C_3$haloalkyl. In another embodiment, Y is Y-7 wherein $R^{13}$ and $R^{14}$ are independently H, methyl or ethyl. In yet another embodiment, Y is Y-7 wherein $R^{13}$ and $R^{14}$ are both methyl.

In one embodiment, the invention provides compounds of formula (I) wherein Y is Y-1 and $R^1$ is $CF_3$. In another embodiment, the invention provides compounds where Y is Y-1 where $R^{13}$ is H and $R^1$ is $CF_3$. In another embodiment, the invention provides compounds where Y is Y-1 where $R^{13}$ is $C_1$-$C_3$alkyl and $R^1$ is $CF_3$. In yet another embodiment, the invention provides compounds where Y is Y-1 where $R^{13}$ is halogen and $R^1$ is $CF_3$. In still another embodiment, the invention provides compounds where Y is Y-1 where $R^{13}$ is methyl or ethyl and $R^1$ is $CF_3$. In still another embodiment, the invention provides compounds where Y is Y-1 and $R^{13}$ is chloro or fluoro and $R^1$ is $CF_3$. In still another embodiment, the invention provides compounds where Y is Y-1 and $R^{13}$ is cyano.

In another embodiment, the invention provides compounds of formula (I) wherein Y is Y-2 and $R^1$ is $CF_3$. In another embodiment, the invention provides compounds where Y is Y-2 where $R^{13}$ is H and $R^1$ is $CF_3$. In another embodiment, the invention provides compounds where Y is Y-2 where $R^{13}$ is $C_1$-$C_3$alkyl and $R^1$ is $CF_3$. In yet another embodiment, the invention provides compounds where Y is Y-2 where $R^{13}$ is halogen and $R^1$ is $CF_3$. In still another embodiment, the invention provides compounds where Y is Y-2 where $R^{13}$ is methyl or ethyl and $R^1$ is $CF_3$. In still another embodiment, the invention provides compounds where Y is Y-2 and $R^{13}$ is chloro or fluoro and $R^1$ is $CF_3$. In still another embodiment, the invention provides compounds where Y is Y-2 and $R^{13}$ is cyano.

In one embodiment of the compounds of formula (I), Y is Y-3 wherein $Z^1$ to $Z^6$ are all independently C—$R^{15}$, and $R^1$ is $CF_3$. In one embodiment of the compounds of formula (I), Y is Y-3 wherein $Z^1$ to $Z^6$ are independently C—$R^{15}$ and $R^1$ is $CF_3$. In another embodiment, Y is Y-3 wherein $Z^1$ is N and $Z^2$ to $Z^6$ are each independently C—$R^{15}$, and $R^1$ is $CF_3$. In another embodiment, Y is Y-3 wherein $Z^2$ is N and $Z^1$ and $Z^3$ to $Z^6$ are each independently C—$R^{15}$, and $R^1$ is $CF_3$. In another embodiment, Y is Y-3 wherein $Z^3$ is N and $Z^1$, $Z^2$, $Z^4$, $Z^5$ and $Z^6$ are each independently C—$R^{15}$, and $R^1$ is $CF_3$. In another embodiment, Y is Y-3 wherein $Z^4$ is N and $Z^1$, $Z^2$, $Z^3$, $Z^5$ and $Z^6$ are each independently C—$R^{15}$, and $R^1$ is $CF_3$. In another embodiment, Y is Y-3 wherein $Z^5$ is N and $Z^1$, $Z^2$, $Z^3$, $Z^4$ and $Z^6$ are each independently C—$R^{15}$, and $R^1$ is $CF_3$. In another embodiment, Y is Y-3 wherein $Z^6$ is N and $Z^1$ to $Z^5$ are each independently C—$R^{15}$, and $R^1$ is $CF_3$.

In another embodiment, Y is Y-3 wherein $Z^1$ and $Z^2$ are N and $Z^3$ to $Z^6$ are independently C—$R^{15}$, and $R^1$ is $CF_3$. In another embodiment, Y is Y-3 wherein $Z^4$ and $Z^5$ are N and $Z^1$, $Z^2$, $Z^3$ and $Z^6$ are independently C—$R^{15}$, and $R^1$ is $CF_3$. In yet another embodiment, Y is Y-3 wherein $Z^5$ and $Z^6$ are N and $Z^1$ to $Z^4$ are independently C—$R^{15}$, and $R^1$ is $CF_3$. In still another embodiment, $Z^3$ and $Z^4$ are N and $Z^1$, $Z^2$, $Z^5$ and $Z^6$ are independently C—$R^{15}$, and $R^1$ is $CF_3$. In yet another embodiment, $Z^3$ and $Z^6$ are N and $Z^1$, $Z^2$, $Z^4$ and $Z^5$ are independently C—$R^{15}$, and $R^1$ is $CF_3$.

In one embodiment of the compounds of formula (I), Y is Y-3 wherein $Z^1$ to $Z^6$ are all C—H, and $R^1$ is $CF_3$. In another embodiment, Y is Y-3 wherein $Z^1$ and $Z^2$ are N and $Z^3$ to $Z^6$ are C—H, and $R^1$ is $CF_3$. In another embodiment, Y is Y-3 wherein $Z^4$ and $Z^5$ are N and $Z^1$, $Z^2$, $Z^3$ and $Z^6$ are C—H, and $R^1$ is $CF_3$. In yet another embodiment, Y is Y-3 wherein $Z^5$ and $Z^6$ are N and $Z^1$ to $Z^4$ are C—H, and $R^1$ is $CF_3$. In still another embodiment, $Z^3$ and $Z^4$ are N and $Z^1$, $Z^2$, $Z^5$ and $Z^6$ are C—H, and $R^1$ is $CF_3$. In yet another embodiment, $Z^3$ and $Z^6$ are N and $Z^1$, $Z^2$, $Z^4$ and $Z^5$ are C—H, and $R^1$ is $CF_3$.

In another embodiment of the invention, Y is Y-4 and $R^1$ is $CF_3$. In another embodiment, the invention provides compounds where Y is Y-4; Q is $R^6$, and $R^1$ is $CF_3$. In another embodiment, the invention provides compounds of formula (I) wherein Y is Y-4, Q is $R^6$ and $R^6$ is alkyl substituted by $R^7$. In another embodiment, the invention provides compounds of formula (I) wherein Y is Y-4, Q is $R^6$ and $R^6$ is $C_1$-$C_2$alkyl substituted by —S(O)$_n$$C_1$-$C_3$alkyl where n is 0, 1 or 2. In yet another embodiment, the invention provides compounds where Y is Y-4; Q is —$CH_2$S(O)$_2$$CH_3$; and $R^1$ is $CF_3$.

In another embodiment, the invention provides compounds of formula (I) wherein Y is Y-5 where Z is C—$R^{15}$ and $R^1$ is $CF_3$. In another embodiment, Y is Y-5 where Z is C—H, and $R^1$ is $CF_3$. In yet another embodiment, Y is Y-5 where Z is N, and $R^1$ is $CF_3$.

In one embodiment, the invention provides compounds of formula (I) wherein Y is Y-6 wherein $R^{13}$ is alkyl, and $R^1$ is $CF_3$. In another embodiment, Y is Y-6 wherein $R^{13}$ is H, and $R^1$ is $CF_3$. In another embodiment, Y is Y-6 wherein $R^{13}$ is halogen, and $R^1$ is $CF_3$. In yet another embodiment, Y is Y-6 wherein $R^{13}$ is $C_1$-$C_3$alkyl, and $R^1$ is $CF_3$. In still another embodiment, Y is Y-6 wherein $R^{13}$ is methyl, and $R^1$ is $CF_3$. In another embodiment, Y is Y-6 where $R^{13}$ is chloro or fluoro, and $R^1$ is $CF_3$. In still another embodiment, Y is Y-6 wherein $R^{13}$ is cyano, and $R^1$ is $CF_3$.

In one embodiment, the invention provides compounds of formula (I) wherein Y is Y-7 where $R^{13}$ and $R^{14}$ are both H, and $R^1$ is $CF_3$. In another embodiment, Y is Y-7 wherein $R^{13}$ and $R^{14}$ are both $C_1$-$C_3$alkyl, and $R^1$ is $CF_3$. In another embodiment, Y is Y-7 wherein $R^{13}$ and $R^{14}$ are independently $C_1$-$C_3$alkyl or $C_1$-$C_3$haloalkyl, and $R^1$ is $CF_3$. In another embodiment, Y is Y-7 wherein $R^{13}$ and $R^{14}$ are independently H, methyl or ethyl, and $R^1$ is $CF_3$. In yet another embodiment, Y is Y-7 wherein $R^{13}$ and $R^{14}$ are both methyl, and $R^1$ is $CF_3$.

In one embodiment, the invention provides compounds of formula (I) wherein Y is Y-1, P is $P^1$ and $R^1$ is $CF_3$. In another embodiment, the invention provides compounds where Y is Y-1, where $R^{13}$ is H; P is $P^1$; and $R^1$ is $CF_3$. In another embodiment, the invention provides compounds where Y is Y-1 where $R^{13}$ is $C_1$-$C_3$alkyl, P is $P^1$, and $R^1$ is $CF_3$. In yet another embodiment, the invention provides compounds where Y is Y-1 where $R^{13}$ is halogen, P is $P^1$, and $R^1$ is $CF_3$. In still another embodiment, the invention provides compounds where Y is Y-1 where $R^{13}$ is methyl or ethyl, P is $P^1$, and $R^1$ is $CF_3$. In still another embodiment, the invention provides compounds where Y is Y-1 and $R^{13}$ is chloro or fluoro, P is $P^1$, and $R^1$ is $CF_3$. In still another embodiment, the invention provides compounds where Y is Y-1 where $R^{13}$ is cyano, P is $P^1$, and $R^1$ is $CF_3$.

In one embodiment, the invention provides compounds of formula (I) wherein Y is Y-1, P is $P^2$ and $R^1$ is $CF_3$. In another embodiment, the invention provides compounds where Y is Y-1, where $R^{13}$ is H; P is $P^2$; and $R^1$ is $CF_3$. In another embodiment, the invention provides compounds where Y is Y-1 where $R^{13}$ is $C_1$-$C_3$alkyl, P is $P^2$, and $R^1$ is $CF_3$. In yet another embodiment, the invention provides compounds where Y is Y-1 where $R^{13}$ is halogen, P is $P^2$, and $R^1$ is $CF_3$. In still another embodiment, the invention provides compounds where Y is Y-1 where $R^{13}$ is methyl or ethyl, P is $P^2$, and $R^1$ is $CF_3$. In still another embodiment, the invention provides compounds where Y is Y-1 and $R^{13}$ is chloro or fluoro, P is $P^2$, and $R^1$ is $CF_3$. In still another embodiment, the invention provides compounds where Y is Y-1 and $R^{13}$ is cyano, P is $P^2$, and $R^1$ is $CF_3$.

In one embodiment, the invention provides compounds of formula (I) wherein Y is Y-1, P is $P^3$ and $R^1$ is $CF_3$. In another embodiment, the invention provides compounds where Y is Y-1, where $R^{13}$ is H; P is $P^3$; and $R^1$ is $CF_3$. In another embodiment, the invention provides compounds where Y is Y-1 where $R^{13}$ is $C_1$-$C_3$alkyl, P is $P^1$, and $R^1$ is $CF_3$. In yet another embodiment, the invention provides compounds where Y is Y-1 where $R^{13}$ is halogen, P is $P^1$, and $R^1$ is $CF_3$. In still another embodiment, the invention provides compounds where Y is Y-1 where $R^{13}$ is methyl or ethyl, P is $P^1$, and $R^1$ is $CF_3$. In still another embodiment, the invention provides compounds where Y is Y-1 and $R^{13}$ is chloro or fluoro, P is $P^1$, and $R^1$ is $CF_3$. In still another embodiment, the invention provides compounds where Y is Y-1 and $R^{13}$ is cyano, P is $P^3$, and $R^1$ is $CF_3$.

In one embodiment, the invention provides compounds of formula (I) wherein Y is Y-1, P is $P^4$ and $R^1$ is $CF_3$. In another embodiment, the invention provides compounds where Y is Y-1, where $R^{13}$ is H; P is $P^4$; and $R^1$ is $CF_3$. In another embodiment, the invention provides compounds where Y is Y-1 where $R^{13}$ is $C_1$-$C_3$alkyl, P is $P^4$, and $R^1$ is $CF_3$. In yet another embodiment, the invention provides compounds where Y is Y-1 where $R^{13}$ is halogen, P is $P^4$, and $R^1$ is $CF_3$. In still another embodiment, the invention provides compounds where Y is Y-1 where $R^{13}$ is methyl or ethyl, P is $P^4$, and $R^1$ is $CF_3$. In still another embodiment, the invention provides compounds where Y is Y-1 and $R^{13}$ is chloro or fluoro, P is $P^4$, and $R^1$ is $CF_3$. In still another embodiment, the invention provides compounds where Y is Y-1 and $R^{13}$ is cyano, P is $P^4$, and $R^1$ is $CF_3$.

In another embodiment, the invention provides compounds of formula (I) wherein Y is Y-2, P is $P^1$, and $R^1$ is $CF_3$. In another embodiment, the invention provides compounds where Y is Y-2 where $R^{13}$ is H, P is $P^1$, and $R^1$ is $CF_3$. In another embodiment, the invention provides compounds where Y is Y-2 where $R^{13}$ is $C_1$-$C_3$alkyl, P is $P^1$, and $R^1$ is $CF_3$. In yet another embodiment, the invention provides compounds where Y is Y-2 where $R^{13}$ is halogen, P is $P^1$, and $R^1$ is $CF_3$. In still another embodiment, the invention provides compounds where Y is Y-2 where $R^{13}$ is methyl or ethyl, P is $P^1$, and $R^1$ is $CF_3$. In still another embodiment, the invention provides compounds where Y is Y-2 and $R^{13}$ is chloro or fluoro, P is $P^1$, and $R^1$ is $CF_3$. In yet another embodiment, the invention provides compounds where Y is Y-2 where $R^{13}$ is cyano, P is $P^1$, and $R^1$ is $CF_3$.

In another embodiment, the invention provides compounds of formula (I) wherein Y is Y-2, P is $P^2$, and $R^1$ is $CF_3$. In another embodiment, the invention provides compounds where Y is Y-2 where $R^{13}$ is H, P is $P^2$, and $R^1$ is $CF_3$. In another embodiment, the invention provides compounds where Y is Y-2 where $R^{13}$ is $C_1$-$C_3$alkyl, P is $P^2$, and $R^1$ is $CF_3$. In yet another embodiment, the invention provides compounds where Y is Y-2 where $R^{13}$ is halogen, P is $P^2$, and $R^1$ is $CF_3$. In still another embodiment, the invention provides compounds where Y is Y-2 where $R^{13}$ is methyl or ethyl, P is $P^2$, and $R^1$ is $CF_3$. In still another embodiment, the invention provides compounds where Y is Y-2 and $R^{13}$ is chloro or fluoro, P is $P^2$, and $R^1$ is $CF_3$. In yet another embodiment, the invention provides compounds where Y is Y-2 where $R^{13}$ is cyano, P is $P^2$, and $R^1$ is $CF_3$.

In another embodiment, the invention provides compounds of formula (I) wherein Y is Y-2, P is $P^1$, and $R^1$ is $CF_3$. In another embodiment, the invention provides compounds where Y is Y-2 where $R^{13}$ is H, P is $P^1$, and $R^1$ is $CF_3$. In another embodiment, the invention provides compounds where Y is Y-2 where $R^{13}$ is $C_1$-$C_3$alkyl, P is $P^1$, and $R^1$ is $CF_3$. In yet another embodiment, the invention provides compounds where Y is Y-2 where $R^{13}$ is halogen, P is $P^1$, and $R^1$ is $CF_3$. In still another embodiment, the invention provides compounds where Y is Y-2 where $R^{13}$ is methyl or ethyl, P is $P^1$, and $R^1$ is $CF_3$. In still another embodiment, the invention provides compounds where Y is Y-2 and $R^{13}$ is chloro or fluoro, P is $P^1$, and $R^1$ is $CF_3$. In yet another embodiment, the invention provides compounds where Y is Y-2 where $R^{13}$ is cyano, P is $P^3$, and $R^1$ is $CF_3$.

In another embodiment, the invention provides compounds of formula (I) wherein Y is Y-2, P is $P^4$, and $R^1$ is $CF_3$. In another embodiment, the invention provides compounds where Y is Y-2 where $R^{13}$ is H, P is $P^4$, and $R^1$ is $CF_3$. In another embodiment, the invention provides compounds where Y is Y-2 where $R^{13}$ is $C_1$-$C_3$alkyl, P is $P^4$, and $R^1$ is $CF_3$. In yet another embodiment, the invention provides compounds where Y is Y-2 where $R^{13}$ is halogen, P is $P^4$, and $R^1$ is $CF_3$. In still another embodiment, the invention provides compounds where Y is Y-2 where $R^{13}$ is methyl or ethyl, P is $P^4$, and $R^1$ is $CF_3$. In still another embodiment, the invention provides compounds where Y is Y-2 and $R^{13}$ is chloro or fluoro, P is $P^4$, and $R^1$ is $CF_3$. In another embodiment, the invention provides compounds where Y is Y-2 where $R^{13}$ is cyano, P is $P^4$, and $R^1$ is $CF_3$.

In one embodiment of the compounds of formula (I), Y is Y-3 wherein $Z^1$ to $Z^6$ are all C—H, P is $P^1$, and $R^1$ is $CF_3$. In another embodiment, Y is Y-3 wherein $Z^1$ is N and $Z^2$ to $Z^6$ are each C—H, P is $P^1$, and $R^1$ is $CF_3$. In another embodiment, Y is Y-3 wherein $Z^2$ is N and $Z^1$ and $Z^3$ to $Z^6$ are each C—H, P is $P^1$, and $R^1$ is $CF_3$. In another embodiment, Y is Y-3 wherein $Z^3$ is N and $Z^1$, $Z^2$, $Z^4$, $Z^5$ and $Z^6$ are each C—H, P is $P^1$, and $R^1$ is $CF_3$. In another embodiment, Y is Y-3 wherein $Z^4$ is N and $Z^1$, $Z^2$, $Z^3$, $Z^5$ and $Z^6$ are each C—H, P is P, and $R^1$ is $CF_3$. In another embodiment, Y is Y-3 wherein $Z^5$ is N and $Z^1$, $Z^2$, $Z^3$, $Z^4$ and $Z^6$ are each C—H, P is $P^1$, and $R^1$ is $CF_3$. In another embodiment, Y is Y-3 wherein $Z^6$ is N and $Z^1$ to $Z^5$ are each C—H, P is $P^1$, and $R^1$ is $CF_3$.

In another embodiment, Y is Y-3 wherein $Z^1$ and $Z^2$ are N and $Z^3$ to $Z^6$ are C—H, P is $P^1$, and $R^1$ is $CF_3$. In another embodiment, Y is Y-3 wherein $Z^4$ and $Z^5$ are N and $Z^1$, $Z^2$, $Z^3$ and $Z^6$ are C—H, P is $P^1$, and $R^1$ is $CF_3$. In yet another embodiment, Y is Y-3 wherein $Z^5$ and $Z^6$ are N and $Z^1$ to $Z^4$ are C—H, P is $P^1$, and $R^1$ is $CF_3$. In still another embodiment, $Z^3$ and $Z^4$ are N and $Z^1$, $Z^2$, $Z^5$ and $Z^6$ are C—H, P is $P^1$, and $R^1$ is $CF_3$. In still another embodiment, $Z^3$ and $Z^6$ are N and $Z^1$, $Z^2$, $Z^4$ and $Z^5$ are C—H, P is $P^1$, and $R^1$ is $CF_3$.

In one embodiment of the compounds of formula (I), Y is Y-3 wherein $Z^1$ to $Z^6$ are all C—H, P is $P^2$, and $R^1$ is $CF_3$.

In another embodiment, Y is Y-3 wherein $Z^1$ is N and $Z^2$ to $Z^6$ are each C—H, P is $P^2$, and $R^1$ is $CF_3$. In another embodiment, Y is Y-3 wherein $Z^2$ is N and $Z^1$ and $Z^3$ to $Z^6$ are each C—H, P is $P^2$, and $R^1$ is $CF_3$. In another embodiment, Y is Y-3 wherein $Z^3$ is N and $Z^1$, $Z^2$, $Z^4$, $Z^5$ and $Z^6$ are each C—H, P is $P^2$, and $R^1$ is $CF_3$. In another embodiment, Y is Y-3 wherein $Z^4$ is N and $Z^1$, $Z^2$, $Z^3$, $Z^5$ and $Z^6$ are each C—H, P is $P^2$, and $R^1$ is $CF_3$. In another embodiment, Y is Y-3 wherein $Z^5$ is N and $Z^1$, $Z^2$, $Z^3$, $Z^4$ and $Z^6$ are each C—H, P is $P^2$, and $R^1$ is $CF_3$. In another embodiment, Y is Y-3 wherein $Z^6$ is N and $Z^1$ to $Z^5$ are each C—H, P is P, and $R^1$ is $CF_3$.

In another embodiment, Y is Y-3 wherein $Z^1$ and $Z^2$ are N and $Z^3$ to $Z^6$ are C—H, P is $P^2$, and $R^1$ is $CF_3$. In another embodiment, Y is Y-3 wherein $Z^4$ and $Z^5$ are N and $Z^1$, $Z^2$, $Z^3$ and $Z^6$ are C—H, P is $P^2$, and $R^1$ is $CF_3$. In yet another embodiment, Y is Y-3 wherein $Z^5$ and $Z^6$ are N and $Z^1$ to $Z^4$ are C—H, P is $P^2$, and $R^1$ is $CF_3$. In still another embodiment, $Z^3$ and $Z^4$ are N and $Z^1$, $Z^2$, $Z^5$ and $Z^6$ are C—H, P is $P^2$, and $R^1$ is $CF_3$. In still another embodiment, $Z^3$ and $Z^6$ are N and $Z^1$, $Z^2$, $Z^4$ and $Z^1$ are C—H, P is $P^2$, and $R^1$ is $CF_3$.

In one embodiment of the compounds of formula (I), Y is Y-3 wherein $Z^1$ to $Z^6$ are all C—H, P is $P^3$, and $R^1$ is $CF_3$. In another embodiment, Y is Y-3 wherein $Z^1$ is N and $Z^2$ to $Z^6$ are each C—H, P is $P^1$, and $R^1$ is $CF_3$. In another embodiment, Y is Y-3 wherein $Z^2$ is N and $Z^1$ and $Z^3$ to $Z^6$ are each C—H, P is $P^3$, and $R^1$ is $CF_3$. In another embodiment, Y is Y-3 wherein $Z^3$ is N and $Z^1$, $Z^2$, $Z^4$, $Z^5$ and $Z^6$ are each C—H, P is $P^1$, and $R^1$ is $CF_3$. In another embodiment, Y is Y-3 wherein $Z^4$ is N and $Z^1$, $Z^2$, $Z^3$, $Z^5$ and $Z^6$ are each C—H, P is $P^3$, and $R^1$ is $CF_3$. In another embodiment, Y is Y-3 wherein $Z^5$ is N and $Z^1$, $Z^2$, $Z^3$, $Z^4$ and $Z^6$ are each C—H, P is $P^3$, and $R^1$ is $CF_3$. In another embodiment, Y is Y-3 wherein $Z^6$ is N and $Z^1$ to $Z^5$ are each C—H, P is $P^1$, and $R^1$ is $CF_3$.

In another embodiment, Y is Y-3 wherein $Z^1$ and $Z^2$ are N and $Z^3$ to $Z^6$ are C—H, P is $P^3$, and $R^1$ is $CF_3$. In another embodiment, Y is Y-3 wherein $Z^4$ and $Z^5$ are N and $Z^1$, $Z^2$, $Z^3$ and $Z^6$ are C—H, P is $P^3$, and $R^1$ is $CF_3$. In yet another embodiment, Y is Y-3 wherein $Z^5$ and $Z^6$ are N and $Z^1$ to $Z^4$ are C—H, P is $P^1$, and $R^1$ is $CF_3$. In still another embodiment, $Z^3$ and $Z^4$ are N and $Z^1$, $Z^2$, $Z^5$ and $Z^6$ are C—H, P is $P^1$, and $R^1$ is $CF_3$. In still another embodiment, $Z^3$ and $Z^6$ are N and $Z^1$, $Z^2$, $Z^4$ and $Z^1$ are C—H, P is $P^1$, and $R^1$ is $CF_3$.

In one embodiment of the compounds of formula (I), Y is Y-3 wherein $Z^1$ to $Z^6$ are all C—H, P is $P^4$, and $R^1$ is $CF_3$. In another embodiment, Y is Y-3 wherein $Z^1$ is N and $Z^2$ to $Z^6$ are each C—H, P is $P^4$, and $R^1$ is $CF_3$. In another embodiment, Y is Y-3 wherein $Z^2$ is N and $Z^1$ and $Z^3$ to $Z^6$ are each C—H, P is $P^4$, and $R^1$ is $CF_3$. In another embodiment, Y is Y-3 wherein $Z^3$ is N and $Z^1$, $Z^2$, $Z^4$, $Z^5$ and $Z^6$ are each C—H, P is $P^4$, and $R^1$ is $CF_3$. In another embodiment, Y is Y-3 wherein $Z^4$ is N and $Z^1$, $Z^2$, $Z^3$, $Z^5$ and $Z^6$ are each C—H, P is $P^4$, and $R^1$ is $CF_3$. In another embodiment, Y is Y-3 wherein $Z^5$ is N and $Z^1$, $Z^2$, $Z^3$, $Z^4$ and $Z^6$ are each C—H, P is $P^4$, and $R^1$ is $CF_3$. In another embodiment, Y is Y-3 wherein $Z^6$ is N and $Z^1$ to $Z^5$ are each C—H, P is $P^4$, and $R^1$ is $CF_3$.

In another embodiment, Y is Y-3 wherein $Z^1$ and $Z^2$ are N and $Z^3$ to $Z^6$ are C—H, P is $P^4$, and $R^1$ is $CF_3$. In another embodiment, Y is Y-3 wherein $Z^4$ and $Z^5$ are N and $Z^1$, $Z^2$, $Z^3$ and $Z^6$ are C—H, P is $P^4$, and $R^1$ is $CF_3$. In yet another embodiment, Y is Y-3 wherein $Z^5$ and $Z^6$ are N and $Z^1$ to $Z^4$ are C—H, P is $P^4$, and $R^1$ is $CF_3$. In still another embodiment, $Z^3$ and $Z^4$ are N and $Z^1$, $Z^2$, $Z^5$ and $Z^6$ are C—H, P is $P^4$, and $R^1$ is $CF_3$. In still another embodiment, $Z^3$ and $Z^6$ are N and $Z^1$, $Z^2$, $Z^4$ and $Z^5$ are C—H, P is $P^4$, and $R^1$ is $CF_3$.

In another embodiment of the invention, Y is Y-4, P is $P^1$, and $R^1$ is $CF_3$. In another embodiment, the invention provides compounds where Y is Y-4, P is $P^1$, Q is $R^6$, and $R^1$ is $CF_3$.

In yet another embodiment, the invention provides compounds where Y is Y-4, P is $P^1$, Q is —$CH_2S(O)_2CH_3$; and $R^1$ is $CF_3$.

In another embodiment of the invention, Y is Y-4, P is $P^2$, and $R^1$ is $CF_3$. In another embodiment, the invention provides compounds where Y is Y-4, P is $P^2$, Q is $R^6$, and $R^1$ is $CF_3$.

In yet another embodiment, the invention provides compounds where Y is Y-4, P is $P^2$, Q is —$CH_2S(O)_2CH_3$; and $R^1$ is $CF_3$.

In another embodiment of the invention, Y is Y-4, P is $P^3$, and $R^1$ is $CF_3$. In another embodiment, the invention provides compounds where Y is Y-4, P is $P^1$, Q is $R^6$, and $R^1$ is $CF_3$.

In yet another embodiment, the invention provides compounds where Y is Y-4, P is $P^3$, Q is —$CH_2S(O)_2CH_3$; and $R^1$ is $CF_3$.

In another embodiment of the invention, Y is Y-4, P is $P^4$, and $R^1$ is $CF_3$. In another embodiment, the invention provides compounds where Y is Y-4, P is $P^4$, Q is $R^6$, and $R^1$ is $CF_3$.

In yet another embodiment, the invention provides compounds where Y is Y-4, P is $P^4$, Q is $CH_2S(O)_2CH_3$; and $R^1$ is $CF_3$.

In another embodiment, the invention provides compounds of formula (I) wherein Y is Y-5 where Z is C—$R^{15}$, P is $P^1$, and $R^1$ is $CF_3$. In another embodiment, Y is Y-5 where Z is C—H, P is $P^1$, and $R^1$ is $CF_3$. In yet another embodiment, Y is Y-5 where Z is N, P is $P^1$, and $R^1$ is $CF_3$.

In another embodiment, the invention provides compounds of formula (I) wherein Y is Y-5 where Z is C—$R^{15}$, P is $P^2$, and $R^1$ is $CF_3$. In another embodiment, Y is Y-5 where Z is C—H, P is $P^2$, and $R^1$ is $CF_3$. In yet another embodiment, Y is Y-5 where Z is N, P is $P^2$, and $R^1$ is $CF_3$.

In another embodiment, the invention provides compounds of formula (I) wherein Y is Y-5 where Z is C—$R^{15}$, P is $P^1$, and $R^1$ is $CF_3$. In another embodiment, Y is Y-5 where Z is C—H, P is $P^1$, and $R^1$ is $CF_3$. In yet another embodiment, Y is Y-5 where Z is N, P is $P^1$, and $R^1$ is $CF_3$.

In another embodiment, the invention provides compounds of formula (I) wherein Y is Y-5 where Z is C—$R^{15}$, P is $P^4$, and $R^1$ is $CF_3$. In another embodiment, Y is Y-5 where Z is C—H, P is $P^4$, and $R^1$ is $CF_3$. In yet another embodiment, Y is Y-5 where Z is N, P is $P^4$, and $R^1$ is $CF_3$.

In one embodiment, the invention provides compounds of formula (I) wherein Y is Y-6 wherein $R^{13}$ is alkyl, P is $P^1$, and $R^1$ is $CF_3$. In another embodiment, Y is Y-6 wherein $R^{13}$ is H, P is $P^1$, and $R^1$ is $CF_3$. In another embodiment, Y is Y-6 wherein $R^{13}$ is halogen, P is $P^1$, and $R^1$ is $CF_3$. In yet another embodiment, Y is Y-6 wherein $R^{13}$ is $C_1$-$C_3$alkyl, P is $P^1$, and $R^1$ is $CF_3$. In still another embodiment, Y is Y-6 wherein $R^{13}$ is methyl, P is $P^1$, and $R^1$ is $CF_3$. In another embodiment, Y is Y-6 where $R^{13}$ is chloro or fluoro, P is $P^1$, and $R^1$ is $CF_3$. In another embodiment, Y is Y-6 where $R^{13}$ is cyano, P is $P^1$, and $R^1$ is $CF_3$.

In one embodiment, the invention provides compounds of formula (I) wherein Y is Y-6 wherein $R^{13}$ is alkyl, P is $P^2$, and $R^1$ is $CF_3$. In another embodiment, Y is Y-6 wherein $R^{13}$ is H, P is $P^2$, and $R^1$ is $CF_3$. In another embodiment, Y is Y-6 wherein $R^{13}$ is halogen, P is $P^2$, and $R^1$ is $CF_3$. In yet another embodiment, Y is Y-6 wherein $R^{13}$ is $C_1$-$C_3$alkyl, P is $P^2$, and $R^1$ is $CF_3$. In still another embodiment, Y is Y-6 wherein $R^{13}$ is methyl, P is $P^2$, and $R^1$ is $CF_3$. In another embodiment, Y is Y-6 where $R^{13}$ is chloro or fluoro, P is $P^2$, and $R^1$ is $CF_3$. In another embodiment, Y is Y-6 where $R^{13}$ is cyano, P is $P^2$, and $R^1$ is $CF_3$.

In one embodiment, the invention provides compounds of formula (I) wherein Y is Y-6 wherein $R^{13}$ is alkyl, P is $P^1$, and $R^1$ is $CF_3$. In another embodiment, Y is Y-6 wherein $R^{13}$ is H, P is $P^1$, and $R^1$ is $CF_3$. In another embodiment, Y is Y-6 wherein $R^{13}$ is halogen, P is $P^3$, and $R^1$ is $CF_3$. In yet another embodiment, Y is Y-6 wherein $R^{13}$ is $C_1$-$C_3$alkyl, P is $P^1$, and $R^1$ is $CF_3$. In still another embodiment, Y is Y-6 wherein $R^{13}$ is methyl, P is $P^1$, and $R^1$ is $CF_3$. In another embodiment, Y is Y-6 where $R^{13}$ is chloro or fluoro, P is $P^1$, and $R^1$ is $CF_3$. In another embodiment, Y is Y-6 where $R^{13}$ is cyano, P is $P^1$, and $R^1$ is $CF_3$.

In one embodiment, the invention provides compounds of formula (I) wherein Y is Y-6 wherein $R^{13}$ is alkyl, P is $P^4$, and $R^1$ is $CF_3$. In another embodiment, Y is Y-6 wherein $R^{13}$ is H, P is $P^4$, and $R^1$ is $CF_3$. In another embodiment, Y is Y-6 wherein $R^{13}$ is halogen, P is $P^4$, and $R^1$ is $CF_3$. In yet another embodiment, Y is Y-6 wherein $R^{13}$ is $C_1$-$C_3$alkyl, P is $P^4$, and $R^1$ is $CF_3$. In still another embodiment, Y is Y-6 wherein $R^{13}$ is methyl, P is $P^4$, and $R^1$ is $CF_3$. In another embodiment, Y is Y-6 where $R^{13}$ is chloro or fluoro, P is $P^4$, and $R^1$ is $CF_3$. In another embodiment, Y is Y-6 where $R^{13}$ is cyano, P is $P^4$, and $R^1$ is $CF_3$.

In one embodiment, the invention provides compounds of formula (I) wherein Y is Y-7 where $R^{13}$ and $R^{14}$ are both H, P is $P^1$, and $R^1$ is $CF_3$. In another embodiment, Y is Y-7 wherein $R^{13}$ and $R^{14}$ are independently H or $C_1$-$C_3$alkyl, P is $P^1$, and $R^1$ is $CF_3$. In another embodiment, Y is Y-7 wherein $R^{13}$ and $R^{14}$ are independently $C_1$-$C_3$alkyl or $C_1$-$C_3$haloalkyl, P is $P^1$, and $R^1$ is $CF_3$. In another embodiment, Y is Y-7 wherein $R^{13}$ and $R^{14}$ are independently H, methyl or ethyl, P is $P^1$, and $R^1$ is $CF_3$. In yet another embodiment, Y is Y-7 wherein $R^{13}$ and $R^{14}$ are both methyl, P is $P^1$, and $R^1$ is $CF_3$.

In one embodiment, the invention provides compounds of formula (I) wherein Y is Y-7 where $R^{13}$ and $R^{14}$ are both H, P is $P^2$, and $R^1$ is $CF_3$. In another embodiment, Y is Y-7 wherein $R^1$ and $R^{14}$ are independently H or $C_1$-$C_3$alkyl, P is $P^2$, and $R^1$ is $CF_3$. In another embodiment, Y is Y-7 wherein $R^{13}$ and $R^{14}$ are independently $C_1$-$C_3$alkyl or $C_1$-$C_3$haloalkyl, P is $P^2$, and $R^1$ is $CF_3$. In another embodiment, Y is Y-7 wherein $R^{13}$ and $R^{14}$ are independently H, methyl or ethyl, P is $P^2$, and $R^1$ is $CF_3$. In yet another embodiment, Y is Y-7 wherein $R^{13}$ and $R^{14}$ are both methyl, P is $P^2$, and $R^1$ is $CF_3$.

In one embodiment, the invention provides compounds of formula (I) wherein Y is Y-7 where $R^{13}$ and $R^{14}$ are both H, P is $P^1$, and $R^1$ is $CF_3$. In another embodiment, Y is Y-7 wherein $R^{13}$ and $R^{14}$ are independently H or $C_1$-$C_3$alkyl, P is $P^1$, and $R^1$ is $CF_3$. In another embodiment, Y is Y-7 wherein $R^{13}$ and $R^{14}$ are independently $C_1$-$C_3$alkyl or $C_1$-$C_3$haloalkyl, P is $P^3$, and $R^1$ is $CF_3$. In another embodiment, Y is Y-7 wherein $R^{13}$ and $R^{14}$ are independently H, methyl or ethyl, P is $P^1$, and $R^1$ is $CF_3$. In yet another embodiment, Y is Y-7 wherein $R^{13}$ and $R^{14}$ are both methyl, P is $P^1$, and $R^1$ is $CF_3$.

In one embodiment, the invention provides compounds of formula (I) wherein Y is Y-7 where $R^{13}$ and $R^{14}$ are both H, P is $P^4$, and $R^1$ is $CF_3$. In another embodiment, Y is Y-7 wherein $R^{13}$ and $R^{14}$ are independently H or $C_1$-$C_3$alkyl, P is $P^4$, and $R^1$ is $CF_3$. In another embodiment, Y is Y-7 wherein $R^{13}$ and $R^{14}$ are independently $C_1$-$C_3$alkyl or $C_1$-$C_3$haloalkyl, P is $P^4$, and $R^1$ is $CF_3$. In another embodiment, Y is Y-7 wherein $R^{13}$ and $R^{14}$ are independently H, methyl or ethyl, P is $P^4$, and $R^1$ is $CF_3$. In yet another embodiment, Y is Y-7 wherein $R^{13}$ and $R^{14}$ are both methyl, P is $P^4$, and $R^1$ is $CF_3$.

In another embodiment, the invention provides compounds of formula (I) wherein Y is Y-1, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In another embodiment, the invention provides compounds where Y is Y-1 where $R^{13}$ is H, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In another embodiment, the invention provides compounds where Y is Y-1 where $R^{13}$ is $C_1$-$C_3$alkyl, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In yet another embodiment, the invention provides compounds where Y is Y-1 where $R^{13}$ is halogen, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In still another embodiment, the invention provides compounds where Y is Y-1 where $R^{13}$ is methyl or ethyl, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In still another embodiment, the invention provides compounds where Y is Y-1 and $R^{13}$ is chloro or fluoro, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In still another embodiment, the invention provides compounds where Y is Y-1 and $R^{13}$ is cyano, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$.

In another embodiment, the invention provides compounds of formula (I) wherein Y is Y-2, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In another embodiment, the invention provides compounds where Y is Y-2 where $R^{13}$ is H, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In another embodiment, the invention provides compounds where Y is Y-2 where $R^{13}$ is $C_1$-$C_3$alkyl, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In yet another embodiment, the invention provides compounds where Y is Y-2 where $R^{13}$ is halogen, $R^1$ is $CF_3$ and Q is X—$NR^5R^6$ wherein $R^5$ is H or $C_1$-$C_3$alkyl and $R^6$ is $C_1$-$C_3$alkyl optionally substituted by $R^7$. In still another embodiment, the invention provides compounds where Y is Y-2 where $R^{13}$ is methyl or ethyl, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In still another embodiment, the invention provides compounds where Y is Y-2 and $R^{13}$ is chloro or fluoro, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In still another embodiment, the invention provides compounds where Y is Y-2 and $R^{13}$ is cyano, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$.

In one embodiment of the compounds of formula (I), Y is Y-3 wherein $Z^1$ to $Z^6$ are independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$.

In another embodiment, Y is Y-3 wherein $Z^1$ is N and $Z^2$ to $Z^6$ are each independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^2$ is N and $Z^1$ and $Z^3$ to $Z^6$ are each independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^3$ is N and $Z^1$, $Z^2$, $Z^4$, $Z^5$ and $Z^6$ are each independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^4$ is N and $Z^1$, $Z^2$, $Z^3$, $Z^5$ and $Z^6$ are each independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^5$ is N and $Z^1$, $Z^2$, $Z^3$, $Z^4$ and $Z^6$ are each independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^6$ is N and $Z^1$ to $Z^5$ are each independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$.

In another embodiment, Y is Y-3 wherein $Z^1$ and $Z^2$ are N and $Z^3$ to $Z^6$ are independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^4$ and $Z^5$ are N and $Z^1$, $Z^2$, $Z^3$ and $Z^6$ are independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In yet another embodiment, Y is Y-3 wherein $Z^5$ and $Z^6$ are N and $Z^1$ to $Z^4$ are independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In still another embodiment, $Z^3$ and $Z^4$ are N and $Z^1$, $Z^2$, $Z^5$ and $Z^6$ are independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In still another embodiment, $Z^3$ and $Z^6$ are N and $Z^1$, $Z^2$, $Z^4$ and $Z^5$ are independently C—$R^{15}$, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$.

In one embodiment of the compounds of formula (I), Y is Y-3 wherein $Z^1$ to $Z^6$ are all C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$.

In another embodiment, Y is Y-3 wherein $Z^1$ is N and $Z^2$ to $Z^6$ are each independently C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^2$ is N and $Z^1$ and $Z^3$ to $Z^6$ are each independently C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^3$ is N and $Z^1$, $Z^2$, $Z^4$, $Z^5$ and $Z^6$ are each independently C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^4$ is N and $Z^1$, $Z^2$, $Z^3$, $Z^5$ and $Z^6$ are each independently C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^5$ is N and $Z^1$, $Z^2$, $Z^3$, $Z^4$ and $Z^6$ are each independently C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^6$ is N and $Z^1$ to $Z^5$ are each independently C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$.

In another embodiment, Y is Y-3 wherein $Z^1$ and $Z^2$ are N and $Z^3$ to $Z^6$ are C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In another embodiment, Y is Y-3 wherein $Z^4$ and $Z^5$ are N and $Z^1$, $Z^2$, $Z^3$ and $Z^6$ are C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In yet another embodiment, Y is Y-3 wherein $Z^5$ and $Z^6$ are N and $Z^1$ to $Z^4$ are C—H, $R^1$ is $CF_3$, and Q is X—$NR^5R^6$ wherein $R^5$ is H or $C_1$-$C_3$alkyl and $R^6$ is $C_1$-$C_3$alkyl optionally substituted by $R^7$. In still another embodiment, $Z^3$ and $Z^4$ are N and $Z^1$, $Z^2$, $Z^5$ and $Z^6$ are C—H, $R^1$ is $CF_3$, and Q is X—$NR^5R^6$ wherein $R^1$ is H or $C_1$-$C_3$alkyl and $R^6$ is $C_1$-$C_3$alkyl optionally substituted by $R^7$. In still another embodiment, $Z^3$ and $Z^6$ are N and $Z^1$, $Z^2$, $Z^4$ and $Z^5$ are C—H, $R^1$ is $CF_3$, and Q is X—$NR^5R^6$ wherein $R^1$ is H or $C_1$-$C_3$alkyl and $R^6$ is $C_1$-$C_3$alkyl optionally substituted by $R^7$.

In another embodiment, the invention provides compounds of formula (I) wherein Y is Y-5 where Z is C—$R^{15}$, and $R^1$ is $CF_3$, and Q is X—$NR^5R^6$ wherein $R^5$ is H or $C_1$-$C_3$alkyl and $R^6$ is $C_1$-$C_6$alkyl, optionally substituted by one or more $R^7$. In yet another embodiment, Y is Y-5 where Z is C—H, $R^1$ is $CF_3$, and Q is X—$NR^5R^6$ wherein $R^5$ is H or $C_1$-$C_3$alkyl and $R^6$ is $C_1$-$C_6$alkyl, optionally substituted by one or more $R^7$. In yet another embodiment, Y is Y-5 where Z is N, $R^1$ is $CF_3$, and Q is X—$NR^5R^6$ wherein $R^5$ is H or $C_1$-$C_3$alkyl and $R^6$ is $C_1$-$C_6$alkyl, optionally substituted by one or more $R^7$.

In another embodiment, the invention provides compounds of formula (I) wherein Y is Y-5 where Z is C—$R^{15}$, and $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In yet another embodiment, Y is Y-5 where Z is C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In yet another embodiment, Y is Y-5 where Z is N, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$.

In one embodiment, the invention provides compounds of formula (I) wherein Y is Y-6 wherein $R^{13}$ is H, $R^1$ is $CF_3$, and Q is X—$NR^5R^6$ wherein $R^5$ is H or $C_1$-$C_3$alkyl and $R^6$ is $C_1$-$C_6$alkyl, optionally substituted by one or more $R^7$. In one embodiment, the invention provides compounds of formula (I) wherein Y is Y-6 wherein $R^{13}$ is alkyl, $R^1$ is $CF_3$, and Q is X—$NR^5R^6$ wherein $R^1$ is H or $C_1$-$C_3$alkyl and $R^6$ is $C_1$-$C_6$alkyl, optionally substituted by one or more $R^7$. In another embodiment, Y is Y-6 wherein $R^{13}$ is halogen, $R^1$ is $CF_3$, and Q is X—$NR^5R^6$ wherein $R^1$ is H or $C_1$-$C_3$alkyl and $R^6$ is $C_1$-$C_6$alkyl, optionally substituted by one or more $R^7$. In yet another embodiment, Y is Y-6 wherein $R^{13}$ is $C_1$-$C_3$alkyl, $R^1$ is $CF_3$, and Q is X—$NR^5R^6$ wherein $R^5$ is H or $C_1$-$C_3$alkyl and $R^6$ is $C_1$-$C_6$alkyl, optionally substituted by one or more $R^7$. In still another embodiment, Y is Y-6 wherein $R^{13}$ is methyl or ethyl, $R^1$ is $CF_3$, and Q is X—$NR^5R^6$ wherein $R^5$ is H or $C_1$-$C_3$alkyl and $R^6$ is $C_1$-$C_6$alkyl, optionally substituted by one or more $R^7$. In another embodiment, Y is Y-6 where $R^{13}$ is chloro or fluoro, $R^1$ is $CF_3$, and Q is X—$NR^5R^6$ wherein $R^1$ is H or $C_1$-$C_3$alkyl and $R^6$ is $C_1$-$C_6$alkyl, optionally substituted by one or more $R^7$.

In one embodiment, the invention provides compounds of formula (I) wherein Y is Y-6 wherein $R^{13}$ is H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In one embodiment, the invention provides compounds of formula (I) wherein Y is Y-6 wherein $R^{13}$ is alkyl, $R^1$ is $CF_3$, and Q is X—$NR^5R^6$ wherein $R^1$ is H or $C_1$-$C_3$alkyl and $R^6$ is $C_3$-$C_8$cycloalkyl, optionally substituted by one or more $R^7$. In another embodiment, Y is Y-6 wherein $R^{13}$ is halogen, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In yet another embodiment, Y is Y-6 wherein $R^{13}$ is $C_1$-$C_3$alkyl, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In still another embodiment, Y is Y-6 wherein $R^{13}$ is methyl or ethyl, $R^1$ is $CF_3$, and Q is X—$NR^5R^6$ wherein $R^1$ is H or $C_1$-$C_3$alkyl and $R^6$ is $C_3$-$C_8$cycloalkyl, optionally substituted by one or more $R^7$. In another embodiment, Y is Y-6 where $R^{13}$ is chloro or fluoro, $R^1$ is $CF_3$, and Q is X—$NR^5R^6$ wherein $R^1$ is H or $C_1$-$C_3$alkyl and $R^6$ is $C_3$-$C_8$cycloalkyl, optionally substituted by one or more $R^7$.

In another embodiment, the invention provides compounds of formula (I) wherein Y is Y-7 where $R^{13}$ and $R^{14}$ are both H, $R^1$ is $CF_3$, and Q is OH or $C_1$-$C_3$alkoxy.

In another embodiment, the invention provides compounds of formula (I) wherein Y is Y-1, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, the invention provides compounds where Y is Y-1 where $R^{13}$ is H, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, the invention provides compounds where Y is Y-1 where $R^{13}$ is $C_1$-$C_3$alkyl, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In yet another embodiment, the invention provides compounds where Y is Y-1 where $R^{13}$ is halogen, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In still another embodiment, the invention provides compounds where Y is Y-1 where $R^{13}$ is methyl or ethyl, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In still another embodiment, the invention provides compounds where Y is Y-1 and $R^{13}$ is chloro or fluoro, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl.

In another embodiment, the invention provides compounds of formula (I) wherein Y is Y-2, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, the invention provides compounds where Y is Y-2 where $R^{13}$ is H, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, the invention provides compounds where Y is Y-2 where $R^{13}$ is $C_1$-$C_3$alkyl, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In yet another embodiment, the invention provides compounds where Y is Y-2 where $R^{13}$ is halogen, $R^1$ is $CF_3$ and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In still another embodiment, the invention provides compounds where Y is Y-2 where $R^{13}$ is methyl or ethyl, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In still another embodiment, the invention provides compounds where Y is Y-2 and $R^{13}$ is chloro or fluoro, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl.

In one embodiment of the compounds of formula (I), Y is Y-3 wherein $Z^1$ to $Z^6$ are independently C—$R^{15}$, $R^1$ is $CF_3$, and Q is X—$NR^5R^6$ wherein R is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, Y is Y-3 wherein $Z^1$ and $Z^2$ are N and $Z^3$ to $Z^6$ are independently C—$R^{15}$, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, Y is Y-3 wherein $Z^4$ and $Z^5$ are N and $Z^1$, $Z^2$, $Z^3$ and $Z^6$ are independently C—$R^{15}$, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In yet another embodiment, Y is Y-3 wherein $Z^5$ and $Z^6$ are N and $Z^1$ to $Z^4$ are independently C—$R^{15}$, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In still another embodiment, $Z^3$ and $Z^4$ are N and $Z^1$, $Z^2$, $Z^5$ and $Z^6$ are independently C—$R^{15}$, $R^1$ is $CF_3$, and Q is X—$NR^5R^6$ wherein $R^5$ is H and $R^6$ is $C_1$-$C_3$alkyl optionally substituted by halogen, alkylthio, haloalkylthio, alkylaminocarbonyl, dialkylaminocarbonyl, haloalkylaminocarbonyl or dihaloalkylaminocarbonyl.

In one embodiment of the compounds of formula (I), Y is Y-3 wherein $Z^1$ to $Z^6$ are all C—H, $R^1$ is $CF_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, Y is Y-3 wherein Z$^1$ and Z$^2$ are N and Z$^3$ to Z$^6$ are C—H, R$^1$ is CF$_3$, and Q is X—NR$^5$R$^6$ wherein R is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, Y is Y-3 wherein Z$^4$ and Z$^5$ are N and Z$^1$, Z$^2$, Z$^3$ and Z$^6$ are C—H, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In yet another embodiment, Y is Y-3 wherein Z$^5$ and Z$^6$ are N and Z$^1$ to Z$^4$ are C—H, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In still another embodiment, Z$^3$ and Z$^4$ are N and Z$^1$, Z$^2$, Z$^5$ and Z$^6$ are C—H, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl.

In one embodiment, the invention provides compounds of formula (I) wherein Y is Y-5 where Z is C—R$^{15}$, and R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, the invention provides compounds of formula (I) wherein Y is Y-5 where Z is CH, and R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In yet another embodiment, Y is Y-5 where Z is N, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl.

In another embodiment, the invention provides compounds of formula (I) wherein Y is Y-6 wherein R$^{13}$ is H, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, the invention provides compounds of formula (I) wherein Y is Y-6 wherein R$^{13}$ is alkyl, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, Y is Y-6 wherein R$^{13}$ is halogen, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In yet another embodiment, Y is Y-6 wherein R$^{13}$ is C$_1$-C$_3$alkyl, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In still another embodiment, Y is Y-6 wherein R$^{13}$ is methyl, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl. In another embodiment, Y is Y-6 where R$^{13}$ is chloro or fluoro, R$^1$ is CF$_3$, and Q is X—NR$^5$R$^6$ wherein R$^5$ is H and R$^6$ is C$_1$-C$_3$alkyl optionally substituted by halogen, alkylthio, haloalkylthio, alkylaminocarbonyl, dialkylaminocarbonyl, haloalkylaminocarbonyl or dihaloalkylaminocarbonyl.

In another embodiment, the invention provides compounds of formula (I) wherein Y is Y-1, R$^1$ is CF$_3$ and Q is —C(O)NHCH$_2$C(O)NHCH$_2$CF$_3$.

In another embodiment, the invention provides compounds where Y is Y-1 where R$^{13}$ is H, methyl, ethyl, chloro or fluoro; P is P$^1$ where R$^2$ and R$^3$ are independently H, halogen, C$_1$-C$_3$alkyl or C$_1$-C$_3$haloalkyl; and R$^4$ is H, C$_1$-C$_3$alkyl or C$_1$-C$_3$haloalkyl; R$^1$ is CF$_3$ and Q is —C(O)NHCH$_2$C(O)NHCH$_2$CF$_3$.

In another embodiment, the invention provides compounds where Y is Y-1 where R$^{13}$ is H, methyl, ethyl, chloro or fluoro, P is P$^2$ where R$^2$ and R$^3$ are independently H, halogen, C$_1$-C$_3$alkyl or C$_1$-C$_3$haloalkyl; and R$^4$ is H, C$_1$-C$_3$alkyl or C$_1$-C$_3$haloalkyl; R$^1$ is CF$_3$ and Q is —C(O)NHCH$_2$C(O)NHCH$_2$CF$_3$.

In another embodiment, the invention provides compounds where Y is Y-1 where R$^{13}$ is H, methyl, ethyl, chloro or fluoro, P is P$^3$ where R$^2$ and R$^3$ are independently H, halogen, C$_1$-C$_3$alkyl or C$_1$-C$_3$haloalkyl and R$^4$ is H, C$_1$-C$_3$alkyl or C$_1$-C$_3$haloalkyl; R$^1$ is CF$_3$ and Q is —C(O)NHCH$_2$C(O)NHCH$_2$CF$_3$.

In another embodiment, the invention provides compounds where Y is Y-1 where R$^{13}$ is H, methyl, ethyl, chloro or fluoro, P is P$^4$ where R$^2$ and R$^3$ are independently H, halogen, C$_1$-C$_3$alkyl or C$_1$-C$_3$haloalkyl and R$^4$ is H, C$_1$-C$_3$alkyl or C$_1$-C$_3$haloalkyl; R$^1$ is CF$_3$ and Q is —C(O)NHCH$_2$C(O)NHCH$_2$CF$_3$.

In another embodiment, the invention provides compounds where Y is Y-1 where R$^{13}$ is H, methyl, ethyl, chloro or fluoro, P is P$^1$ where R$^2$ and R$^3$ are independently H, halogen, C$_1$-C$_3$alkyl or C$_1$-C$_3$haloalkyl and R$^4$ is H, C$_1$-C$_3$alkyl or C$_1$-C$_3$haloalkyl; R$^1$ is CF$_3$ and Q is —C(O)NHCH$_2$CH$_2$S(O)$_n$CH$_3$ where n is 0, 1 or 2.

In another embodiment, the invention provides compounds where Y is Y-1 where R$^{13}$ is H, methyl, ethyl, chloro or fluoro, P is P$^2$ where R$^2$ and R$^3$ are independently H, halogen, C$_1$-C$_3$alkyl or C$_1$-C$_3$haloalkyl and R$^4$ is H, C$_1$-C$_3$alkyl or C$_1$-C$_3$haloalkyl; R$^1$ is CF$_3$ and Q is —C(O)NHCH$_2$CH$_2$S(O)$_n$CH$_3$ where n is 0, 1 or 2.

In another embodiment, the invention provides compounds where Y is Y-1 where R$^{13}$ is H, methyl, ethyl, chloro or fluoro, P is P$^3$ where R$^2$ and R$^3$ are independently H, halogen, C$_1$-C$_3$alkyl or C$_1$-C$_3$haloalkyl and R$^4$ is H, C$_1$-C$_3$alkyl or C$_1$-C$_3$haloalkyl; R$^1$ is CF$_3$ and Q is —C(O)NHCH$_2$CH$_2$S(O)$_n$CH$_3$ where n is 0, 1 or 2.

In another embodiment, the invention provides compounds where Y is Y-1 where $R^{13}$ is H, methyl, ethyl, chloro or fluoro, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$CH$_2$S(O)$_n$CH$_3$ where n is 0, 1 or 2.

In another embodiment, the invention provides compounds of formula (I) wherein Y is Y-2, $R^1$ is $CF_3$ and Q is —C(O)NHCH$_2$C(O)NHCH$_2$CF$_3$.

In another embodiment, the invention provides compounds where Y is Y-2 where $R^{13}$ is H, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is $C_1$-$C_3$alkyl, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is halogen, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$.

In another embodiment, the invention provides compounds where Y is Y-2 where $R^{13}$ is H, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is $C_1$-$C_3$alkyl, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is halogen, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$.

In another embodiment, the invention provides compounds where Y is Y-2 where $R^{13}$ is H, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is $C_1$-$C_3$alkyl, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is halogen, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$.

In another embodiment, the invention provides compounds where Y is Y-2 where $R^{13}$ is H, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is $C_1$-$C_3$alkyl, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$. In another embodiment, the invention provides compounds where Y is Y-2 where $R^{13}$ is halogen, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$C(O)NHCH$_2$CF$_3$.

In still another embodiment, the invention provides compounds where Y is Y-2 where $R^{13}$ is methyl or ethyl, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In still another embodiment, the invention provides compounds where Y is Y-2 where $R^{13}$ is methyl or ethyl, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In still another embodiment, the invention provides compounds where Y is Y-2 where $R^{13}$ is methyl or ethyl, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In still another embodiment, the invention provides compounds where Y is Y-2 where $R^{13}$ is methyl or ethyl, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In still another embodiment, the invention provides compounds where Y is Y-2 and $R^{13}$ is chloro or fluoro, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In still another embodiment, the invention provides compounds where Y is Y-2 and $R^{13}$ is chloro or fluoro, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In still another embodiment, the invention provides compounds where Y is Y-2 and $R^{13}$ is chloro or fluoro, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In still another embodiment, the invention provides compounds where Y is Y-2 and $R^{13}$ is chloro or fluoro, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment, the invention provides compounds where Y is Y-2 where $R^{13}$ is H, methyl, ethyl, chloro or fluoro, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$CH$_2$S(O)$_n$CH$_3$ where n is 0, 1 or 2.

In another embodiment, the invention provides compounds where Y is Y-2 where $R^{13}$ is H, methyl, ethyl, chloro or fluoro, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$CH$_2$S(O)$_n$CH$_3$ where n is 0, 1 or 2.

In another embodiment, the invention provides compounds where Y is Y-2 where $R^{13}$ is H, methyl, ethyl, chloro or fluoro, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$CH$_2$S(O)$_n$CH$_3$ where n is 0, 1 or 2.

In another embodiment, the invention provides compounds where Y is Y-2 where $R^{13}$ is H, methyl, ethyl, chloro or fluoro, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$ and Q is —C(O)NHCH$_2$CH$_2$S(O)$_n$CH$_3$ where n is 0, 1 or 2.

In one embodiment of the compounds of formula (I), Y is Y-3 wherein $Z^1$ to $Z^6$ are all independently C—$R^{15}$, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In one embodiment of the compounds of formula (I), Y is Y-3 wherein $Z^1$ to $Z^6$ are all independently C—$R^{15}$, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In one embodiment of the compounds of formula (I), Y is Y-3 wherein $Z^1$ to $Z^6$ are all independently C—$R^{15}$, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In one embodiment of the compounds of formula (I), Y is Y-3 wherein $Z^1$ to $Z^6$ are all independently C—$R^{15}$, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In one embodiment of the compounds of formula (I), Y is Y-3 wherein $Z^1$ to $Z^6$ are all C—H, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In one embodiment of the compounds of formula (I), Y is Y-3 wherein $Z^1$ to $Z^6$ are all C—H, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In one embodiment of the compounds of formula (I), Y is Y-3 wherein $Z^1$ to $Z^6$ are all C—H, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In one embodiment of the compounds of formula (I), Y is Y-3 wherein $Z^1$ to $Z^6$ are all C—H, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment of the compounds of formula (I), Y is Y-3 wherein $Z^1$ to $Z^6$ are all C—H, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is O, 1 or 2.

In another embodiment of the compounds of formula (I), Y is Y-3 wherein $Z^1$ to $Z^6$ are all C—H, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is O, 1 or 2.

In another embodiment of the compounds of formula (I), Y is Y-3 wherein $Z^1$ to $Z^6$ are all C—H, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment of the compounds of formula (I), Y is Y-3 wherein $Z^1$ to $Z^6$ are all C—H, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment, Y is Y-3 wherein $Z^1$ is N and $Z^2$ to $Z^6$ are each independently C—$R^{15}$, $R^1$ is $CF_3$, and Q is —C(O)NHCH$_2$C(O)NHCH$_2$CF$_3$. In another embodiment, Y is Y-3 wherein $Z^2$ is N and $Z^1$ and $Z^3$ to $Z^6$ are each independently C—$R^{15}$, $R^1$ is $CF_3$, and Q is —C(O)NHCH$_2$C(O)NHCH$_2$CF$_3$. In another embodiment, Y is Y-3 wherein $Z^3$ is N and $Z^1$, $Z^2$, $Z^4$, $Z^5$ and $Z^6$ are each independently C—$R^{15}$, $R^1$ is $CF_3$, and Q is —C(O)NHCH$_2$C(O)NHCH$_2$CF$_3$.

In another embodiment, Y is Y-3 wherein $Z^4$ is N and $Z^1$, $Z^2$, $Z^3$, $Z^5$ and $Z^6$ are each independently C—$R^{15}$, $R^1$ is $CF_3$, and Q is —C(O)NHCH$_2$C(O)NHCH$_2$CF$_3$. In another embodiment, Y is Y-3 wherein $Z^5$ is N and $Z^1$, $Z^2$, $Z^3$, $Z^4$ and $Z^6$ are each independently C—$R^{15}$, $R^1$ is $CF_3$, and Q is —C(O)NHCH$_2$C(O)NHCH$_2$CF$_3$. In another embodiment, Y is Y-3 wherein $Z^6$ is N and $Z^1$ to $Z^5$ are each independently C—$R^{15}$, $R^1$ is $CF_3$, and Q is —C(O)NHCH$_2$C(O)NHCH$_2$CF$_3$.

In another embodiment, Y is Y-3 wherein $Z^1$ and $Z^2$ are N and $Z^3$ to $Z^6$ are independently C—$R^{15}$, $R^1$ is $CF_3$, and Q is —C(O)NHCH$_2$C(O)NHCH$_2$CF$_3$. In another embodiment, Y is Y-3 wherein $Z^1$ and $Z^2$ are N and $Z^3$ to $Z^6$ are C—H, $R^1$ is $CF_3$, and Q is —C(O)NHCH$_2$C(O)NHCH$_2$CF$_3$.

In another embodiment, Y is Y-3 wherein $Z^3$ and $Z^4$ are N and $Z^1$, $Z^2$, $Z^5$ and $Z^6$ are independently C—$R^{15}$, $R^1$ is $CF_3$, and Q is —C(O)NHCH$_2$C(O)NHCH$_2$CF$_3$. In another embodiment, Y is Y-3 wherein $Z^3$ and $Z^4$ are N and $Z^1$, $Z^2$, $Z^5$ and $Z^6$ are C—H, $R^1$ is $CF_3$, and Q is —C(O)NHCH$_2$C(O)NHCH$_2$CF$_3$.

In another embodiment, Y is Y-3 wherein $Z^4$ and $Z^5$ are N and $Z^1$, $Z^2$, $Z^3$ and $Z^6$ are independently C—$R^{15}$, $R^1$ is $CF_3$, and Q is —C(O)NHCH$_2$C(O)NHCH$_2$CF$_3$. In another embodiment, Y is Y-3 wherein $Z^4$ and $Z^5$ are N and $Z^1$, $Z^2$, $Z^3$ and $Z^6$ are C—H, $R^1$ is $CF_3$, and Q is —C(O)NHCH$_2$C(O)NHCH$_2$CF$_3$.

In another embodiment, Y is Y-3 wherein $Z^5$ and $Z^6$ are N and $Z^1$, $Z^2$, $Z^3$ and $Z^4$ are independently C—$R^{15}$, $R^1$ is $CF_3$, and Q is —C(O)NHCH$_2$C(O)NHCH$_2$CF$_3$. In another embodiment, Y is Y-3 wherein $Z^5$ and $Z^6$ are N and $Z^1$, $Z^2$, $Z^3$ and $Z^4$ are C—H, $R^1$ is $CF_3$, and Q is —C(O)NHCH$_2$C(O)NHCH$_2$CF$_3$.

In another embodiment, the invention provides compounds of formula (I) wherein Y is Y-5 where Z is C—$R^{15}$, $R^1$ is $CF_3$, and Q is —C(O)NHCH$_2$C(O)NHCH$_2$CF$_3$. In another embodiment, the invention provides compounds of formula (I) wherein Y is Y-5 where Z is C—H, $R^1$ is $CF_3$, and Q is —C(O)NHCH$_2$C(O)NHCH$_2$CF$_3$. In another embodiment, the invention provides compounds of formula (I) wherein Y is Y-5 where Z is N, $R^1$ is $CF_3$, and Q is —C(O)NHCH$_2$C(O)NHCH$_2$CF$_3$.

In another embodiment, the invention provides compounds of formula (I) wherein Y is Y-5 where Z is C—H, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment, the invention provides compounds of formula (I) wherein Y is Y-5 where Z is C—H, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment, the invention provides compounds of formula (I) wherein Y is Y-5 where Z is C—H, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment, the invention provides compounds of formula (I) wherein Y is Y-5 where Z is C—H, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment, the invention provides compounds of formula (I) wherein Y is Y-5 where Z is C—H or N, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment, the invention provides compounds of formula (I) wherein Y is Y-5 where Z is C—H or N, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment, the invention provides compounds of formula (I) wherein Y is Y-5 where Z is C—H or N, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment, the invention provides compounds of formula (I) wherein Y is Y-5 where Z is C—H or N, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment, the invention provides compounds of formula (I) wherein Y is Y-6 wherein $R^{13}$ is H, $R^1$ is $CF_3$, and Q is —C(O)NHCH$_2$C(O)NHCH$_2$CF$_3$. In another embodiment, the invention provides compounds of formula (I) wherein Y is Y-6 wherein $R^{13}$ is $C_1$-$C_3$alkyl, $R^1$ is $CF_3$, and Q is —C(O)NHCH$_2$C(O)NHCH$_2$CF$_3$. In another embodiment, the invention provides compounds of formula (I) wherein Y is Y-6 wherein $R^{13}$ is methyl, $R^1$ is $CF_3$, and Q is —C(O)NHCH$_2$C(O)NHCH$_2$CF$_3$. In another embodiment, the invention provides compounds of formula (I) wherein Y is Y-6 wherein $R^{13}$ is halogen, $R^1$ is $CF_3$, and Q is —C(O)NHCH$_2$C(O)NHCH$_2$CF$_3$.

In another embodiment of the compounds of formula (I), Y is Y-6 wherein $R^{13}$ is H or methyl, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment of the compounds of formula (I), Y is Y-6 wherein $R^{13}$ is H or methyl, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment of the compounds of formula (I), Y is Y-6 wherein $R^{13}$ is H or methyl, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment of the compounds of formula (I), Y is Y-6 wherein $R^{13}$ is H or methyl, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$C(O)NHCH$_2$CF$_3$.

In another embodiment of the compounds of formula (I), Y is Y-6 wherein $R^{13}$ is H or methyl, P is $P^1$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment of the compounds of formula (I), Y is Y-6 wherein $R^{13}$ is H or methyl, P is $P^2$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment of the compounds of formula (I), Y is Y-6 wherein $R^{13}$ is H or methyl, P is $P^3$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment of the compounds of formula (I), Y is Y-6 wherein $R^{13}$ is H or methyl, P is $P^4$ where $R^2$ and $R^3$ are independently H, halogen, $C_1$-$C_3$alkyl or $C_1$-$C_3$haloalkyl and $R^4$ is H, $C_1$-$C_3$alkyl or $C_1$-$C_3$haloalkyl; $R^1$ is $CF_3$, and Q is —C(O)NHCH$_2$CH$_2$S(O)$_n$CH$_3$ where n is 0, 1 or 2.

In another embodiment, the invention provides compounds of formula (I) wherein Y is Y-1, $R^1$ is $CF_3$ and Q is X—NR$^5$R$^6$ wherein $R^5$ is H or $C_1$-$C_3$alkyl and $R^6$ is $C_3$-$C_8$cycloalkyl, optionally substituted by one or more $R^7$. In another embodiment, the invention provides compounds where Y is Y-1 where $R^{13}$ is H, $R^1$ is $CF_3$ and Q is X—NR$^5$R$^6$ wherein $R^5$ is H or $C_1$-$C_3$alkyl and $R^6$ is $C_3$-$C_8$cycloalkyl, optionally substituted by one or more $R^7$. In another embodiment, the invention provides compounds where Y is Y-1 where $R^{13}$ is $C_1$-$C_3$alkyl, $R^1$ is $CF_3$ and Q is X—NR$^5$R$^6$ wherein $R^5$ is H or $C_1$-$C_3$alkyl and $R^6$ is $C_3$-$C_8$cycloalkyl, optionally substituted by one or more $R^7$. In yet another embodiment, the invention provides compounds where Y is Y-1 where $R^{13}$ is halogen, $R^1$ is $CF_3$ and Q is X—NR$^5$R$^6$ wherein $R^5$ is H or $C_1$-$C_3$alkyl and $R^6$ is $C_3$-$C_8$cycloalkyl, optionally substituted by one or more $R^7$. In still another embodiment, the invention provides compounds where Y is Y-1 where $R^{13}$ is methyl or ethyl, $R^1$ is $CF_3$, and Q is X—NR$^5$R$^6$ wherein $R^5$ is H or $C_1$-$C_3$alkyl and $R^6$ is $C_3$-$C_8$cycloalkyl, optionally substituted by one or more $R^7$. In still another embodiment, the invention provides compounds where Y is Y-1 and $R^{13}$ is chloro or fluoro, $R^1$ is $CF_3$, and Q is X—NR$^5$R$^6$ wherein $R^5$ is H or $C_1$-$C_3$alkyl and $R^6$ is $C_3$-$C_8$cycloalkyl, optionally substituted by one or more $R^7$.

In another embodiment, the invention provides compounds of formula (I) wherein Y is Y-2, $R^1$ is $CF_3$ and Q is X—NR$^5$R$^6$ wherein $R^1$ is H or $C_1$-$C_3$alkyl and $R^6$ is $C_3$-$C_8$cycloalkyl, optionally substituted by one or more $R^7$. In another embodiment, the invention provides compounds where Y is Y-2 where $R^{13}$ is H, $R^1$ is $CF_3$ and Q is X—NR$^5$R$^6$ wherein $R^1$ is H or $C_1$-$C_3$alkyl and $R^6$ is $C_3$-$C_8$cycloalkyl, optionally substituted by one or more $R^7$. In another embodiment, the invention provides compounds where Y is Y-2 where $R^{13}$ is $C_1$-$C_3$alkyl, $R^1$ is $CF_3$ and Q is X—NR$^5$R$^6$ wherein $R^5$ is H or $C_1$-$C_3$alkyl and $R^6$ is $C_3$-$C_8$cycloalkyl, optionally substituted by one or more $R^7$. In yet another embodiment, the invention provides compounds where Y is Y-2 where $R^{13}$ is halogen, $R^1$ is $CF_3$ and Q is X—$NR^5R^6$ wherein $R^1$ is H or $C_1$-$C_3$alkyl and $R^6$ is $C_3$-$C_8$cycloalkyl, optionally substituted by one or more $R^7$. In still another embodiment, the invention provides compounds where Y is Y-2 where $R^3$ is methyl or ethyl, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In still another embodiment, the invention provides compounds where Y is Y-2 and $R^{13}$ is chloro or fluoro, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$.

In one embodiment of the compounds of formula (I), Y is Y-3 wherein $Z^1$ to $Z^6$ are independently C—$R^{15}$, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In another embodiment of the compounds of formula (I), Y is Y-3 wherein $Z^1$ to $Z^6$ are C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$.

In another embodiment, Y is Y-3 wherein $Z^1$ is N and $Z^2$ to $Z^6$ are each C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In another embodiment, Y is Y-3 wherein $Z^2$ is N and $Z^1$ and $Z^3$ to $Z^6$ are each C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In another embodiment, Y is Y-3 wherein $Z^3$ is N and $Z^1$, $Z^2$, $Z^4$, $Z^5$ and $Z^6$ are each C—H, $R^1$ is $CF_3$, and Q is X—$NR^5R^6$ wherein $R^1$ is H or $C_1$-$C_3$alkyl and $R^6$ is $C_3$-$C_8$cycloalkyl, optionally substituted by one or more $R^7$. In another embodiment, Y is Y-3 wherein $Z^4$ is N and $Z^1$, $Z^2$, $Z^3$, $Z^5$ and $Z^6$ are each C—H, $R^1$ is $CF_3$, and Q is X—$NR^5R^6$ wherein $R^1$ is H or $C_1$-$C_3$alkyl and $R^6$ is $C_3$-$C_8$cycloalkyl, optionally substituted by one or more $R^7$. In another embodiment, Y is Y-3 wherein $Z^5$ is N and $Z^1$, $Z^2$, $Z^3$, $Z^4$ and $Z^6$ are each C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In another embodiment, Y is Y-3 wherein $Z^6$ is N and $Z^1$ to $Z^5$ are each C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$.

In another embodiment, Y is Y-3 wherein $Z^1$ and $Z^2$ are N and $Z^3$ to $Z^6$ are C—H, $R^1$ is $CF_3$, and Q is X—$NR^5R^6$ wherein $R^1$ is H or $C_1$-$C_3$alkyl and $R^6$ is $C_3$-$C_8$cycloalkyl, optionally substituted by one or more $R^7$. In another embodiment, Y is Y-3 wherein $Z^4$ and $Z^5$ are N and $Z^1$, $Z^2$, $Z^3$ and $Z^6$ are C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In yet another embodiment, Y is Y-3 wherein $Z^5$ and $Z^6$ are N and $Z^1$ to $Z^4$ are C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In still another embodiment, $Z^3$ and $Z^4$ are N and $Z^1$, $Z^2$, $Z^5$ and $Z^6$ are C—H, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$.

In another embodiment, the invention provides compounds of formula (I) wherein Y is Y-5 where Z is C—$R^{15}$, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In another embodiment, the invention provides compounds of formula (I) wherein Y is Y-5 where Z is CH, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$. In yet another embodiment, Y is Y-5 where Z is N, $R^1$ is $CF_3$, and Q is X—$NR^5R^6$ wherein $R^5$ is H or $C_1$-$C_3$alkyl and $R^6$ is $C_3$-$C_8$cycloalkyl, optionally substituted by one or more $R^7$.

In another embodiment, the invention provides compounds of formula (I) wherein Y is Y-1, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, the invention provides compounds where Y is Y-1 where $R^{13}$ is H, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, the invention provides compounds where Y is Y-1 where $R^{13}$ is $C_1$-$C_3$alkyl, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In yet another embodiment, the invention provides compounds where Y is Y-1 where $R^{13}$ is halogen, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In still another embodiment, the invention provides compounds where Y is Y-1 where $R^{13}$ is methyl or ethyl, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In still another embodiment, the invention provides compounds where Y is Y-1 and $R^{13}$ is chloro or fluoro, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl.

In another embodiment, the invention provides compounds of formula (I) wherein Y is Y-2, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, the invention provides compounds where Y is Y-2 where $R^{13}$ is H, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, the invention provides compounds where Y is Y-2 where $R^{13}$ is $C_1$-$C_3$alkyl, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In yet another embodiment, the invention provides compounds where Y is Y-2 where $R^{13}$ is halogen, $R^1$ is $CF_3$ and Q is X—$NR^5R^6$ wherein $R^5$ is H or $C_1$-$C_3$alkyl and $R^6$ is cyclopropyl, cyclobutyl, cyclopentyl or cyclohexyl. In still another embodiment, the invention provides compounds where Y is Y-2 where $R^{13}$ is methyl or ethyl, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In still another embodiment, the invention provides compounds where Y is Y-2 and $R^{13}$ is chloro or fluoro, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl.

In one embodiment of the compounds of formula (I), Y is Y-3 wherein $Z^1$ to $Z^6$ are all C—$R^{15}$, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In another embodiment of the compounds of formula (I), Y is Y-3 wherein $Z^1$ to $Z^6$ are all C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl.

In another embodiment, Y is Y-3 wherein $Z^1$ is N and $Z^2$ to $Z^6$ are each C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, Y is Y-3 wherein $Z^2$ is N and $Z^1$ and $Z^3$ to $Z^6$ are each C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, Y is Y-3 wherein $Z^3$ is N and $Z^1$, $Z^2$, $Z^4$, $Z^5$ and $Z^6$ are each C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, Y is Y-3 wherein $Z^4$ is N and $Z^1$, $Z^2$, $Z^3$, $Z^5$ and $Z^6$ are each C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, Y is Y-3 wherein $Z^5$ is N and $Z^1$, $Z^2$, $Z^3$, $Z^4$ and $Z^6$ are each C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, Y is Y-3 wherein $Z^6$ is N and $Z^1$ to $Z^5$ are each C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl.

In another embodiment, Y is Y-3 wherein $Z^1$ and $Z^2$ are N and $Z^3$ to $Z^6$ are C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In yet another embodiment, Y is Y-3 wherein $Z^4$ and $Z^5$ are N and $Z^1$, $Z^2$, $Z^3$ and $Z^6$ are C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In yet another embodiment, Y is Y-3 wherein $Z^5$ and $Z^6$ are N and $Z^1$ to $Z^4$ are C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In still another embodiment, $Z^3$ and $Z^4$ are N and $Z^1$, $Z^2$, $Z^5$ and $Z^6$ are C—H, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl.

In another embodiment, the invention provides compounds of formula (I) wherein Y is Y-5 where Z is C—$R^{15}$, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In another embodiment, the invention provides compounds of formula (I) wherein Y is Y-5 where Z is CH, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl. In yet another embodiment, Y is Y-5 where Z is N, $R^1$ is $CF_3$, and Q is X—$NR^5R^6$ wherein $R^5$ is H or $C_1$-$C_3$alkyl and $R^6$ is cyclopropyl, cyclobutyl, cyclopentyl or cyclohexyl.

In one embodiment, the invention provides compounds of formula (I) wherein:
P is $P^1$;
Y is Y-2;
$R^{13}$ is H, $C_1$-$C_3$alkyl or halogen;
$R^1$ is $CF_3$;
$R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$;
$R^4$ is H, $C_1$-$C_6$alkyl, aryl-$C_1$-$C_6$alkyl or $C_1$-$C_6$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
P is $P^2$;
Y is Y-2;
$R^{13}$ is H, $C_1$-$C_3$alkyl or halogen;
$R^1$ is $CF_3$;
$R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$;
$R^4$ is H, $C_1$-$C_6$alkyl, aryl-$C_1$-$C_6$alkyl or $C_1$-$C_6$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
P is $P^3$;
Y is Y-2;
$R^{13}$ is H, $C_1$-$C_3$alkyl or halogen;
$R^1$ is $CF_3$;
$R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$;
$R^4$ is H, $C_1$-$C_6$alkyl, aryl-$C_1$-$C_6$alkyl or $C_1$-$C_6$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
P is $P^4$;
Y is Y-2;
$R^{13}$ is H, $C_1$-$C_3$alkyl or halogen;
$R^1$ is $CF_3$;
$R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$;
$R^4$ is H, $C_1$-$C_6$alkyl, aryl-$C_1$-$C_6$alkyl or $C_1$-$C_6$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
P is $P^1$;
Y is Y-2;
$R^{13}$ is $CH_3$;
$R^1$ is $CF_3$;
$R^2$ and $R^3$ are independently H, halogen, $C_1$-$C_3$alkyl optionally substituted by one or more $R^7$ or $C_1$-$C_3$haloalkyl;
$R^4$ is H, $C_1$-$C_3$alkyl, $C_1$-$C_3$haloalkyl, benzyl or $C_1$-$C_3$alkylcarbonyl; and
Q is X—$NR^5R^6$ where $R^5$ is hydrogen and $R^6$ is $C_1$-$C_3$alkyl optionally substituted by $R^7$.

In another embodiment, the invention provides compounds of formula (I) wherein:
P is $P^2$;
Y is Y-2;
$R^{13}$ is $CH_3$;
$R^1$ is $CF_3$;
$R^2$ and $R^3$ are independently H, halogen, $C_1$-$C_3$alkyl optionally substituted by one or more $R^7$ or $C_1$-$C_3$haloalkyl;
$R^4$ is H, $C_1$-$C_3$alkyl, $C_1$-$C_3$haloalkyl, benzyl or $C_1$-$C_3$alkylcarbonyl; and
Q is X—$NR^5R^6$ where $R^5$ is hydrogen and $R^6$ is $C_1$-$C_3$alkyl optionally substituted by $R^7$.

In another embodiment, the invention provides compounds of formula (I) wherein:
P is P³;
Y is Y-2;
$R^{13}$ is $CH_3$;
$R^1$ is $CF_3$;
$R^2$ and $R^3$ are independently H, halogen, $C_1$-$C_3$alkyl optionally substituted by one or more $R^7$ or $C_1$-$C_3$haloalkyl;
$R^4$ is H, $C_1$-$C_3$alkyl, $C_1$-$C_3$haloalkyl, benzyl or $C_1$-$C_3$alkylcarbonyl; and
Q is X—$NR^5R^6$ where $R^5$ is hydrogen and $R^6$ is $C_1$-$C_3$alkyl optionally substituted by $R^7$.

In another embodiment, the invention provides compounds of formula (I) wherein:
P is P⁴;
Y is Y-2;
$R^{13}$ is $CH_3$;
$R^1$ is $CF_3$;
$R^2$ and $R^3$ are independently H, halogen, $C_1$-$C_3$alkyl optionally substituted by one or more $R^7$ or $C_1$-$C_3$haloalkyl;
$R^4$ is H, $C_1$-$C_3$alkyl, $C_1$-$C_3$haloalkyl, benzyl or $C_1$-$C_3$alkylcarbonyl; and
Q is X—$NR^5R^6$ where $R^5$ is hydrogen and $R^6$ is $C_1$-$C_3$alkyl optionally substituted by $R^7$.

In another embodiment, the invention provides compounds of formula (I) wherein:
Y is Y-3;
$Z^1$, $Z^2$, $Z^3$, $Z^4$, $Z^5$ and $Z^6$ are each C—H, C—$C_1$-$C_3$alkyl or C-halogen;
$R^1$ is $CF_3$;
$R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$;
$R^4$ is H, $C_1$-$C_6$alkyl, aryl-$C_1$-$C_6$.alkyl or $C_1$-$C_6$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
Y is Y-3;
$Z^1$, $Z^2$, $Z^3$, $Z^4$, $Z^5$ and $Z^6$ are each C—H;
$R^1$ is $CF_3$;
$R^2$ and $R^3$ are independently H, halogen, $C_1$-$C_3$alkyl optionally substituted by one or more $R^7$ or $C_3$-$C_8$cycloalkyl;
$R^4$ is H, $C_1$-$C_3$alkyl, $C_1$-$C_3$haloalkyl, benzyl or $C_1$-$C_3$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
Y is Y-5;
Z is CH or N;
$R^1$ is $CF_3$;
$R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$;
$R^4$ is H, $C_1$-$C_6$alkyl, aryl-$C_1$-$C_6$.alkyl or $C_1$-$C_6$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
Y is Y-6;
$R^{13}$ is H or $C_1$-$C_3$alkyl;
$R^1$ is $CF_3$;
$R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$;
$R^4$ is H, $C_1$-$C_6$alkyl, aryl-$C_1$-$C_6$.alkyl or $C_1$-$C_6$alkylcarbonyl; and
Q is X—$NR^5R^6$ where $R^5$ is hydrogen and $R^6$ is alkyl optionally substituted by $R^7$.

In another embodiment, the invention provides compounds of formula (I) wherein:
Y is Y-2;
$R^{13}$ is $CH_3$;
$R^1$ is $CF_3$;
$R^2$ and $R^3$ are independently H, cloro, fluoro, methyl, ethyl, n-propyl, isopropyl or $CF_3$;
$R^4$ is H, methyl, ethyl, or acetyl; and
Q is —C(O)NHCH$_2$C(O)NHCH$_2$CF$_3$ or —C(O)NHCH$_2$CH$_2$S(O)$_n$CH$_3$ where n is 0, 1 or 2.

In another embodiment, the invention provides compounds of formula (I) wherein:
Y is Y-3;
$Z^1$, $Z^2$, $Z^3$, $Z^4$, $Z^5$ and $Z^6$ are each C—H;
$R^1$ is $CF_3$;
$R^2$ and $R^3$ are independently H, cloro, fluoro, methyl, ethyl, n-propyl, isopropyl or $CF_3$;
$R^4$ is H, methyl, ethyl, or acetyl; and
Q is —C(O)NHCH$_2$C(O)NHCH$_2$CF$_3$ or —C(O)NHCH$_2$CH$_2$S(O)CH$_3$ where n is 0, 1 or 2.

In another embodiment, the invention provides compounds of formula (I) wherein:
Y is Y-5;
Z is CH or N;
$R^1$ is $CF_3$;
$R^2$ and $R^3$ are independently H, cloro, fluoro, methyl, ethyl, n-propyl, isopropyl or $CF_3$;
$R^4$ is H, methyl, ethyl, or acetyl; and
Q is —C(O)NHCH$_2$C(O)NHCH$_2$CF$_3$ or —C(O)NHCH$_2$CH$_2$S(O)CH$_3$ where n is 0, 1 or 2.

In another embodiment, the invention provides compounds of formula (I) wherein:
Y is Y-6;
$R^{13}$ is H or $C_1$-$C_3$alkyl;
$R^1$ is $CF_3$;
$R^2$ and $R^3$ are independently H, cloro, fluoro, methyl, ethyl, n-propyl, isopropyl or $CF_3$;
$R^4$ is H, methyl, ethyl, or acetyl; and
Q is —C(O)NHCH$_2$C(O)NHCH$_2$CF$_3$ or —C(O)NHCH$_2$CH$_2$S(O)CH$_3$ where n is 0, 1 or 2.

In several embodiments, the invention provides compounds of formula (I) wherein Y is Y-1, Y-2, Y-3, Y-4, Y-5, Y-6 or Y-7; $R^1$ is $CF_3$; $R^2$ and $R^3$ are independently H, halogen, $C_1$-$C_3$alkyl, $C_3$-$C_8$cycloalkyl, $C_1$-$C_3$haloalkyl, $C_2$-$C_6$alkenyl, $C_2$-$C_6$alkynyl, $C_1$-$C_3$alkoxy, $C_1$-$C_3$haloalkoxy, aryl, heteroaryl, heterocyclyl or —CN, wherein each $C_1$-$C_3$alkyl, $C_3$-$C_8$cycloalkyl, $C_2$-$C_6$alkenyl, $C_2$-$C_6$alkynyl, aryl, heteroaryl or heterocyclyl is optionally substituted by one or more $R^7$; $R^4$ is H, $C_1$-$C_3$alkyl, benzyl or $C_1$-$C_3$alkylcarbonyl; and Q is X—$NR^5R^6$ where X is (C=O) or (C=S), $R^5$ is H or $C_1$-$C_3$alkyl and $R^6$ is as defined in Table 1 below:

TABLE 1

| # | $R^6$ |
|---|---|
| 1 | Ethyl |
| 2 | 2,2,2-trifluoro-ethyl |
| 3 | prop-2-yl |
| 4 | Methyl |
| 5 | 2-fluoro-cycloprop-1-yl |
| 6 | prop-1-yl |
| 7 | 2-fluoro-ethyl |
| 8 | 2-cyano-ethyl |
| 9 | 1-fluoroethyl |
| 10 | 2-methylprop-1-yl |
| 11 | Cyclopropylmethyl |
| 12 | 2-methoxy-ethyl |
| 13 | 3-methyloxetan-3-yl |
| 14 | 1-methylcyclopropyl |
| 15 | dihydrofuran-4-yl |
| 16 | Cyclopropyl |
| 17 | Cyclobutyl |
| 18 | Methylsulfonylmethyl |
| 19 | propen-1-yl |
| 20 | Methylsulfanylmethyl |
| 21 | 1-methoxyeth-1-yl |
| 22 | 5-pyrimidyl |
| 23 | but-2-yl |
| 24 | 1-fluoroprop-2-yl |
| 25 | 2-methylpropen-1-yl |
| 26 | 1-cyanocyclopropyl |
| 27 | N-formylaminomethyl |
| 28 | 2-methylsulfinyl-ethyl |
| 29 | 2-(methylsulfonyl)-ethyl |
| 30 | 1-oxo-tetrahydrofuran-3-yl |
| 31 | 1-oxo-thietan-3-yl |
| 32 | 1,1-dioxo-tetrahydrofuran-3-yl |
| 33 | 1,1-dioxo-thietan-3-yl |
| 34 | 3-chloroprop-1-yl |
| 35 | 3,3,3-trifluoro-propyl |
| 36 | thietan-3-yl |
| 37 | tetrahydrofuran-2-yl |
| 38 | 1,1,1-trifluoroprop-2-yl |
| 39 | but-1-yl |
| 40 | 2,2-difluoroethyl |
| 41 | OH |
| 42 | Methoxy |
| 43 | Ethoxy |

Stereoisomers and Polymorphic Forms

It will be appreciated by those of skill in the art that the compounds of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I) are also the subject of the invention.

The compounds of formula (I) can exist as stereoisomers since there is a chiral center in the molecule. The individual stereoisomers are encompassed by the structural formulas depicted herein. The various stereoisomers include enantiomers, diastereomers and atropisomers. One of skill in the art will understand that one stereoisomer may be more active and/or may exhibit beneficial properties relative to the other enantiomer. In addition, the skilled person in the art knows how to separate, enrich, and/or selectively prepare a stereoisomer of the isoxazoline compounds described herein. The isoxazoline compounds of formula (I) described herein contain a chiral quaternary carbon atom in the five-membered isoxazoline ring (shown by the asterisk (*)); therefore, the compounds will contain at least two possible stereoisomers. As an example for the compounds of formula (I) where P is $P^1$, the two possible stereoisomers resulting from the quaternary carbon are shown as formula (R)-I and (S)-I:

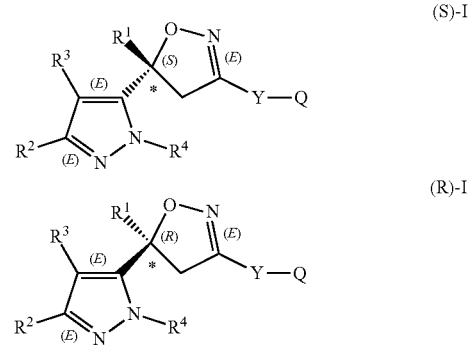

The compound of formula (S)-I above has the (S) configuration at the chiral carbon atom and the compound of formula (R)-I has the (R) configuration.

Molecular depictions drawn herein follow standard conventions for depicting stereochemistry. To indicate stereo configuration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the wide end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereo configuration is intended to be specified.

Hence, in another embodiment, the invention provides a pesticidal and antiparasitic compound of formula (I) which is enriched in one enantiomer, or a pharmaceutically acceptable salt thereof.

In one embodiment, the invention provides a pesticidal and antiparasitic compound of formula (I), or a pharmaceutically acceptable salt thereof, or a composition comprising the compound which is enriched an enantiomer that displays significant in vitro and in vivo activity with a favorable toxicity profile (the eutomer). In one embodiment of the invention, the more biologically active enantiomer of the compound of Formula (I) is believed to be compound of Formula (S)-I shown above, which has the (S)-configuration at the chiral carbon atom.

In another embodiment, the invention provides compounds of formula (I), or pharmaceutically acceptable salts thereof, and compositions comprising the compounds, which are enriched in one enantiomer over the other enantiomer in a weight:weight ratio of at least 1.5:1. In another embodiment, the compound of Formula (I), or a pharmaceutically acceptable salt thereof, are enriched in one enantiomer in a weight:weight ratio of at least 2:1, at least 5:1 or at least 10:1.

In another embodiment, the compounds of Formula (I), or pharmaceutically acceptable salts thereof, of the invention are essentially pure enantiomers.

In one embodiment, the invention provides a compound of formula (I), or a pharmaceutically acceptable salt thereof, that is substantially enriched in an enantiomer. The term "substantially enriched" is meant wherein the weight:weight ratio is at least about 1.5:1 or higher in favor of the desired enantiomer. In another embodiment, the invention provides a compound of formula (I), that is substantially enriched in the (S)-enantiomer. In another embodiment, the invention provides a compound of formula (I) that is substantially enriched in the (R)-enantiomer.

In another embodiment of the invention, a compound of formula (I) is provided that is enriched in the (S)-enantiomer in a weight:weight ratio of at least about 2:1, (S) to (R), or greater. In yet another embodiment, the invention provides a compound of formula (I) that is enriched in the (S)-enantiomer in a weight:weight ratio of at least about 5:1, (S) to (R), or greater. In still another embodiment, the invention provides a compound of formula (I), that is enriched in the (S)-enantiomer in a weight:weight ratio of at least about 10:1, (S) to (R), or greater. In still another embodiment, the invention provides a compound of formula (I), that is essentially the pure (S)-enantiomer.

In one embodiment, the invention provides compounds of formula (I) described above, wherein Y is Y-1 and P is any of $P^1$ to $P^4$, that that is enriched in the (S)-enantiomer in a weight:weight ratio of at least about 2:1, (S) to (R), or greater. In yet another embodiment, the invention provides a compound of formula (I) described above where Y is Y-1 and P is any of $P^1$ to $P^4$, that is enriched in the (S)-enantiomer in a weight:weight ratio of at least about 5:1, (S) to (R), or greater. In still another embodiment, the invention provides a compound of formula (I) described above where Y is Y-1 and P is any of $P^1$ to $P^4$, that is enriched in the (S)-enantiomer in a weight:weight ratio of at least about 10:1, (S) to (R), or greater. In still another embodiment, the invention provides a compound of formula (I) described above where Y is Y-1 and P is any of $P^1$ to $P^4$, that is essentially the pure (S)-enantiomer.

In another embodiment, the invention provides compounds of formula (I) described above wherein Y is Y-2 and P is any of $P^1$ to $P^4$, that that is enriched in the (S)-enantiomer in a weight:weight ratio of at least about 2:1, (S) to (R), or greater. In yet another embodiment, the invention provides a compound of formula (I) described above where Y is Y-2 and P is any of $P^1$ to $P^4$, that is enriched in the (S)-enantiomer in a weight:weight ratio of at least about 5:1, (S) to (R), or greater. In still another embodiment, the invention provides a compound of formula (I) described above where Y is Y-2 and P is any of $P^1$ to $P^4$, that is enriched in the (S)-enantiomer in a weight:weight ratio of at least about 10:1, (S) to (R), or greater. In still another embodiment, the invention provides a compound of formula (I) described above where Y is Y-2 and P is any of $P^1$ to $P^4$, that is essentially the pure (S)-enantiomer.

In one embodiment, the invention provides compounds of formula (I) described above wherein Y is Y-3 and P is any of $P^1$ to $P^4$, that that is enriched in the (S)-enantiomer in a weight:weight ratio of at least about 2:1, (S) to (R), or greater. In yet another embodiment, the invention provides a compound of formula (I) described above where Y is Y-3 and P is any of $P^1$ to $P^4$, that is enriched in the (S)-enantiomer in a weight:weight ratio of at least about 5:1, (S) to (R), or greater. In still another embodiment, the invention provides a compound of formula (I) described above where Y is Y-3 and P is any of $P^1$ to $P^4$, that is enriched in the (S)-enantiomer in a weight:weight ratio of at least about 10:1, (S) to (R), or greater. In still another embodiment, the invention provides a compound of formula (I) described above where Y is Y-3 and P is any of $P^1$ to $P^4$, that is essentially the pure (S)-enantiomer.

In one embodiment, the invention provides compounds of formula (I) described above wherein Y is Y-4 and P is any of $P^1$ to $P^4$, that that is enriched in the (S)-enantiomer in a weight:weight ratio of at least about 2:1, (S) to (R), or greater. In yet another embodiment, the invention provides a compound of formula (I) described above where Y is Y-4 and P is any of $P^1$ to $P^4$, that is enriched in the (S)-enantiomer in a weight:weight ratio of at least about 5:1, (S) to (R), or greater. In still another embodiment, the invention provides a compound of formula (I) described above where Y is Y-4 and P is any of $P^1$ to $P^4$, that is enriched in the (S)-enantiomer in a weight:weight ratio of at least about 10:1, (S) to (R), or greater. In still another embodiment, the invention provides a compound of formula (I) described above where Y is Y-4 and P is any of $P^1$ to $P^4$, that is essentially the pure (S)-enantiomer.

In one embodiment, the invention provides compounds of formula (I) described above wherein Y is Y-5 and P is any of $P^1$ to $P^4$, that that is enriched in the (S)-enantiomer in a weight:weight ratio of at least about 2:1, (S) to (R), or greater. In yet another embodiment, the invention provides a compound of formula (I) described above where Y is Y-5 and P is any of $P^1$ to $P^4$, that is enriched in the (S)-enantiomer in a weight:weight ratio of at least about 5:1, (S) to (R), or greater. In still another embodiment, the invention provides a compound of formula (I) described above where Y is Y-5 and P is any of $P^1$ to $P^4$, that is enriched in the (S)-enantiomer in a weight:weight ratio of at least about 10:1, (S) to (R), or greater. In still another embodiment, the invention provides a compound of formula (I) described above where Y is Y-5 and P is any of $P^1$ to $P^4$, that is essentially the pure (S)-enantiomer.

In one embodiment, the invention provides compounds of formula (I) described above, wherein Y is Y-6 and P is any of $P^1$ to $P^4$, that that is enriched in the (S)-enantiomer in a weight:weight ratio of at least about 2:1, (S) to (R), or greater. In yet another embodiment, the invention provides a compound of formula (I) described above where Y is Y-6 and P is any of $P^1$ to $P^4$, that is enriched in the (S)-enantiomer in a weight:weight ratio of at least about 5:1, (S) to (R), or greater. In still another embodiment, the invention provides a compound of formula (I) described above where Y is Y-6 and P is any of $P^1$ to $P^4$, that is enriched in the (S)-enantiomer in a weight:weight ratio of at least about 10:1, (S) to (R), or greater. In still another embodiment, the invention provides a compound of formula (I) described above where Y is Y-6 and P is any of $P^1$ to $P^4$, that is essentially the pure (S)-enantiomer.

In one embodiment, the invention provides compounds of formula (I) described above, wherein Y is Y-7 and P is any of $P^1$ to $P^4$, that that is enriched in the (S)-enantiomer in a weight:weight ratio of at least about 2:1, (S) to (R), or greater. In yet another embodiment, the invention provides a compound of formula (I) described above where Y is Y-7 and P is any of $P^1$ to $P^4$, that is enriched in the (S)-enantiomer in a weight:weight ratio of at least about 5:1, (S) to (R), or greater. In still another embodiment, the invention provides a compound of formula (I) described above where Y is Y-7 and P is any of $P^1$ to $P^4$, that is enriched in the (S)-enantiomer in a weight:weight ratio of at least about 10:1, (S) to (R), or greater. In still another embodiment, the invention provides a compound of formula (I) described above where Y is Y-7 and P is any of $P^1$ to $P^4$, that is essentially the pure (S)-enantiomer.

When enantiomerically enriched, one enantiomer is present in greater amounts than the other, and the extent of enrichment may be defined by an expression of enantiomeric excess ("ee"), which is defined as (2x−1)·100%, where x is the mole fraction of the dominant enantiomer in the mixture (e.g., an ee of 20% corresponds to a 60:40 ratio of enantiomers). In some embodiments, the compositions of the invention comprise compounds that have at least a 50% enantiomeric excess. In other embodiments, the compositions of the invention comprise compounds that have at least a 75% enantiomeric excess, at least a 90% enantiomeric excess, or at least a 94% enantiomeric excess of the more active isomer. Of particular note are enantiomerically pure embodiments of the more active isomer (the eutomer).

Compounds of this invention can exist as one or more conformational isomers due to restricted rotation about the amide bond bonded to the aryl or heteroaryl ring (e.g. the amide X—$NR^5R^6$ where X is C(=O) bonded to the naphthyl group in formula (I)). This invention comprises mixtures of conformational isomers. In addition, this invention includes compounds that are enriched in one conformer relative to others.

It will be appreciated that in addition to the chiral carbon atom in the isoxazoline ring of the compounds of formula (I), certain compounds may include other chiral centers in one or more substituents. Thus, these compounds will have a greater number of possible stereoisomers (e.g. diastereomers). All possible stereoisomers are encompassed in the extended release injectable compositions of the invention.

In various embodiments, the invention provides the compounds of formula (I) in Table 2 below. The compounds depicted may be a racemic mixture, enriched in the (S)-enantiomer or enriched in the (R)-enantiomer.

TABLE 2

| Compound # | Structure |
|---|---|
| 2-1 | 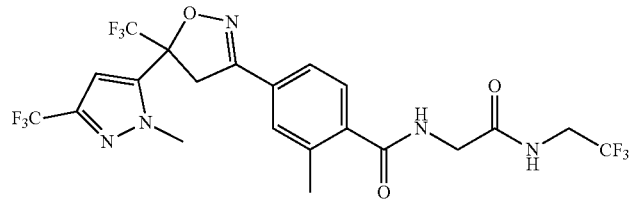 [SMILES: Cc1cc(C2=NOC(c3cc(C(F)(F)F)nn3C)(C(F)(F)F)C2)ccc1C(=O)NCC(=O)NCC(F)(F)F] |
| 2-2 | 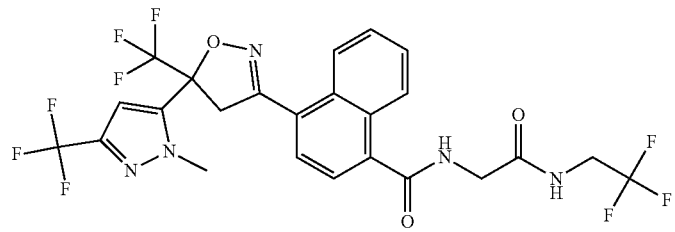 [SMILES: Cn1nc(C(F)(F)F)cc1C1(C(F)(F)F)CC(c2ccc(C(=O)NCC(=O)NCC(F)(F)F)c3ccccc23)=NO1] |
| 2-3 | 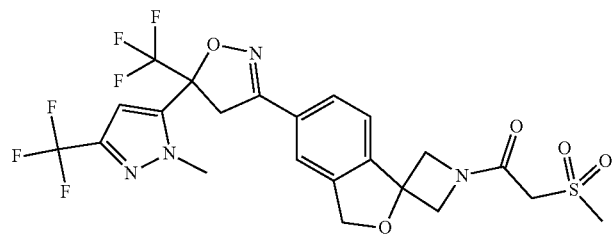 [SMILES: Cn1nc(C(F)(F)F)cc1C1(C(F)(F)F)CC(c2ccc3c(c2)COC32CN(C(=O)CS(C)(=O)=O)C2)=NO1] |

TABLE 2-continued
| Compound # | Structure |
|---|---|
| 2-4 | 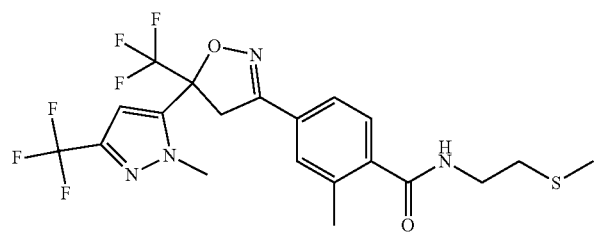 [SMILES: CSCCNC(=O)c1ccc(C2=NOC(c3cc(C(F)(F)F)nn3C)(C(F)(F)F)C2)cc1C] |
| 2-5 | 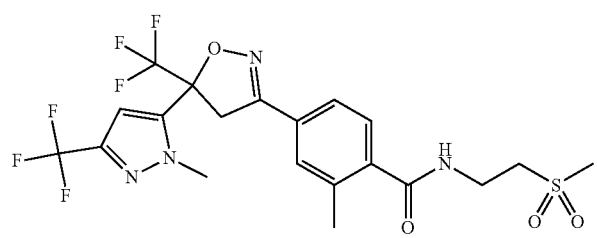 [SMILES: Cc1cc(C2=NOC(c3cc(C(F)(F)F)nn3C)(C(F)(F)F)C2)ccc1C(=O)NCCS(C)(=O)=O] |
| 2-6 | 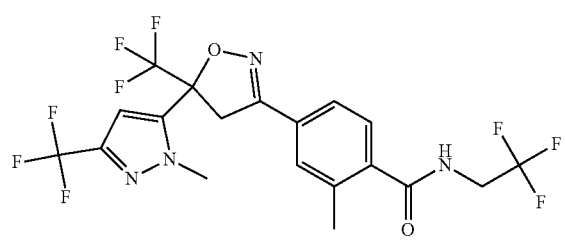 [SMILES: Cc1cc(C2=NOC(c3cc(C(F)(F)F)nn3C)(C(F)(F)F)C2)ccc1C(=O)NCC(F)(F)F] |
| 2-7 | 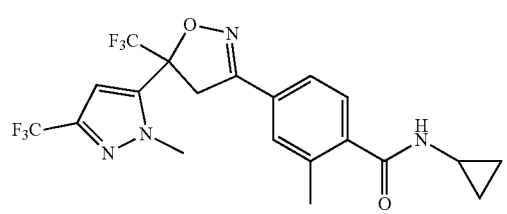 [SMILES: Cc1cc(C2=NOC(c3cc(C(F)(F)F)nn3C)(C(F)(F)F)C2)ccc1C(=O)NC1CC1] |
| 2-8 | 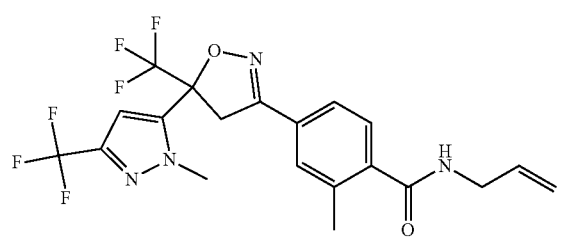 [SMILES: C=CCNC(=O)c1ccc(C2=NOC(c3cc(C(F)(F)F)nn3C)(C(F)(F)F)C2)cc1C] |
| 2-9 | 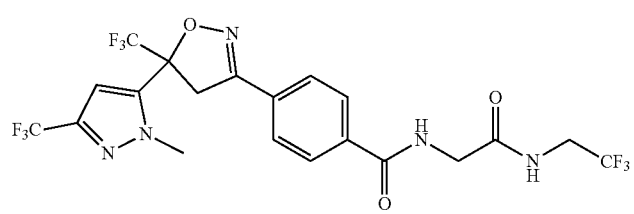 [SMILES: Cn1nc(C(F)(F)F)cc1C1(C(F)(F)F)CC(c2ccc(C(=O)NCC(=O)NCC(F)(F)F)cc2)=NO1] |
| 2-10 | 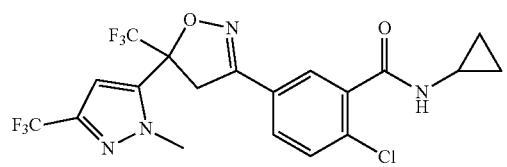 [SMILES: Cn1nc(C(F)(F)F)cc1C1(C(F)(F)F)CC(c2ccc(Cl)c(C(=O)NC3CC3)c2)=NO1] |

TABLE 2-continued

| Compound # | Structure |
|---|---|
| 2-11 | 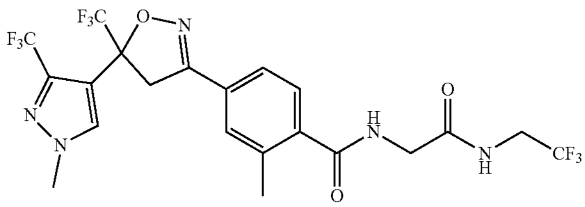 [SMILES: Cc1cc(C2=NOC(c3cn(C)nc3C(F)(F)F)(C(F)(F)F)C2)ccc1C(=O)NCC(=O)NCC(F)(F)F] |
| 2-12 | 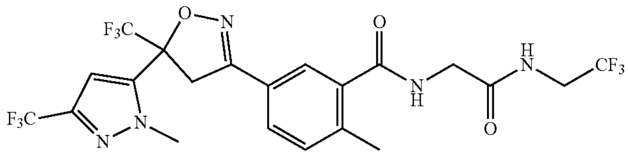 [SMILES: Cc1ccc(C2=NOC(c3cc(C(F)(F)F)nn3C)(C(F)(F)F)C2)cc1C(=O)NCC(=O)NCC(F)(F)F] |
| 2-13 | 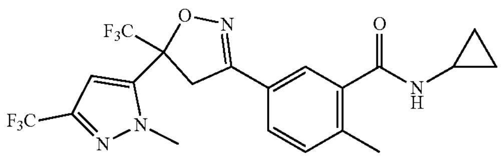 [SMILES: Cc1ccc(C2=NOC(c3cc(C(F)(F)F)nn3C)(C(F)(F)F)C2)cc1C(=O)NC1CC1] |
| 2-14 | 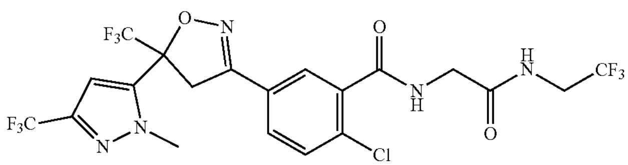 [SMILES: Cn1nc(C(F)(F)F)cc1C1(C(F)(F)F)CC(c2ccc(Cl)c(C(=O)NCC(=O)NCC(F)(F)F)c2)=NO1] |
| 2-15 | 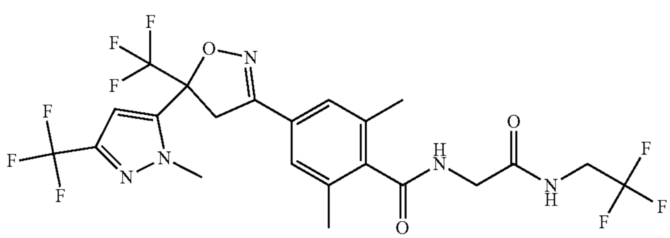 [SMILES: Cc1cc(C2=NOC(c3cc(C(F)(F)F)nn3C)(C(F)(F)F)C2)cc(C)c1C(=O)NCC(=O)NCC(F)(F)F] |
| 2-16 | 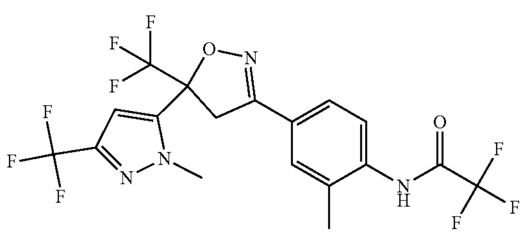 [SMILES: Cc1cc(C2=NOC(c3cc(C(F)(F)F)nn3C)(C(F)(F)F)C2)ccc1NC(=O)C(F)(F)F] |
| 2-17 | 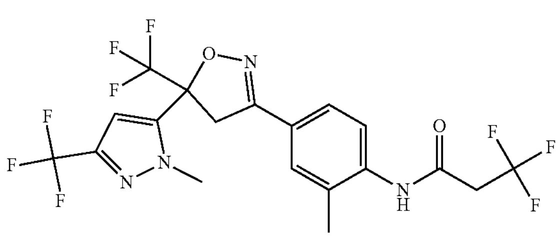 [SMILES: Cc1cc(C2=NOC(c3cc(C(F)(F)F)nn3C)(C(F)(F)F)C2)ccc1NC(=O)CC(F)(F)F] |

TABLE 2-continued
| Compound # | Structure |
|---|---|
| 2-18 | 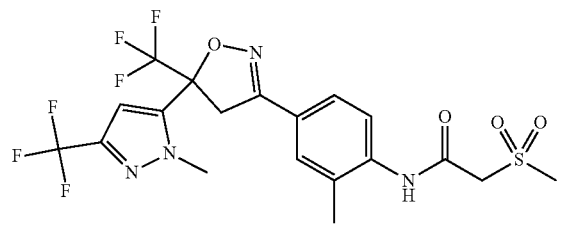 [SMILES: Cc1cc(C2=NOC(c3cc(C(F)(F)F)nn3C)(C(F)(F)F)C2)ccc1NC(=O)CS(C)(=O)=O] |
| 2-19 | 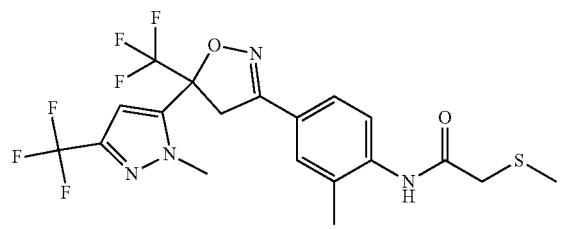 [SMILES: CSCC(=O)Nc1ccc(C2=NOC(c3cc(C(F)(F)F)nn3C)(C(F)(F)F)C2)cc1C] |
| 2-20 | 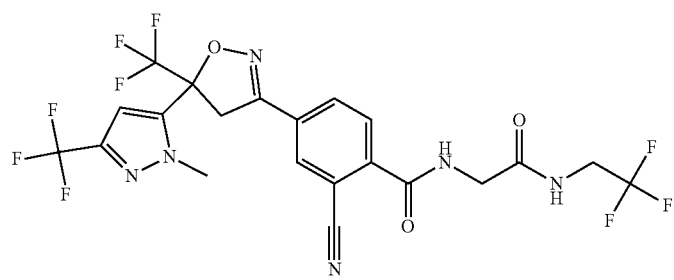 [SMILES: Cn1nc(C(F)(F)F)cc1C1(C(F)(F)F)CC(c2ccc(C(=O)NCC(=O)NCC(F)(F)F)c(C#N)c2)=NO1] |
| 2-21 | 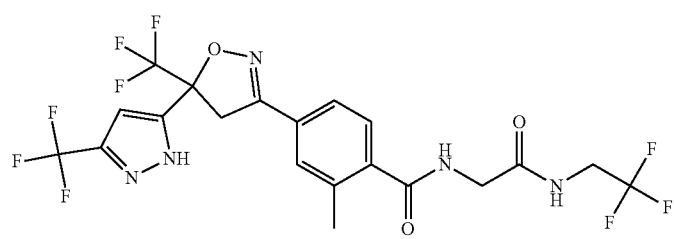 [SMILES: Cc1cc(C2=NOC(c3cc(C(F)(F)F)n[nH]3)(C(F)(F)F)C2)ccc1C(=O)NCC(=O)NCC(F)(F)F] |
| 2-22 | 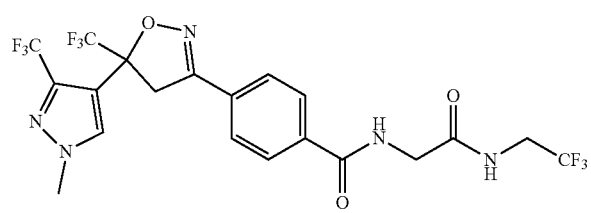 [SMILES: Cn1cc(C2(C(F)(F)F)CC(c3ccc(C(=O)NCC(=O)NCC(F)(F)F)cc3)=NO2)c(C(F)(F)F)n1] |
| 2-23 | 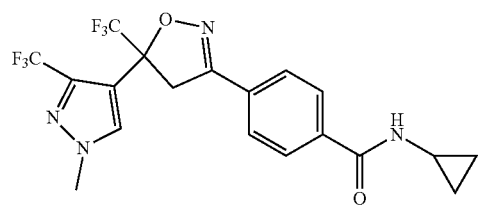 [SMILES: Cn1cc(C2(C(F)(F)F)CC(c3ccc(C(=O)NC4CC4)cc3)=NO2)c(C(F)(F)F)n1] |
| 2-24 | 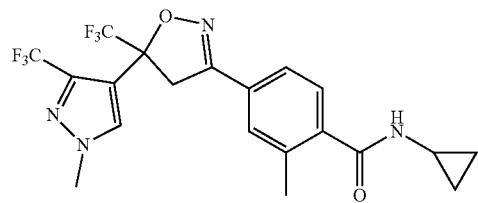 [SMILES: Cc1cc(C2=NOC(c3cn(C)nc3C(F)(F)F)(C(F)(F)F)C2)ccc1C(=O)NC1CC1] |

TABLE 2-continued
| Compound # | Structure |
|---|---|
| 2-25 | 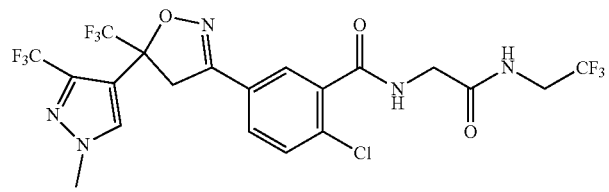 [SMILES: Cn1cc(C2(C(F)(F)F)CC(c3ccc(Cl)c(C(=O)NCC(=O)NCC(F)(F)F)c3)=NO2)c(C(F)(F)F)n1] |
| 2-26 | 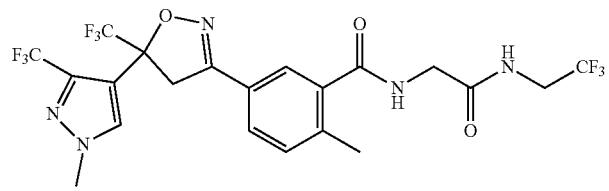 [SMILES: Cc1ccc(C2=NOC(c3cn(C)nc3C(F)(F)F)(C(F)(F)F)C2)cc1C(=O)NCC(=O)NCC(F)(F)F] |
| 2-27 | 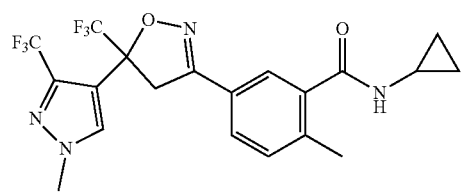 [SMILES: Cc1ccc(C2=NOC(c3cn(C)nc3C(F)(F)F)(C(F)(F)F)C2)cc1C(=O)NC1CC1] |
| 2-28 | 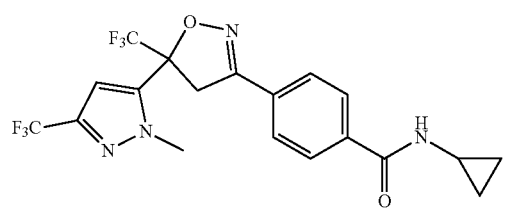 [SMILES: Cn1nc(C(F)(F)F)cc1C1(C(F)(F)F)CC(c2ccc(C(=O)NC3CC3)cc2)=NO1] |
| 2-29 | 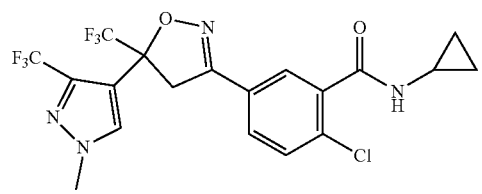 [SMILES: Cn1cc(C2(C(F)(F)F)CC(c3ccc(Cl)c(C(=O)NC4CC4)c3)=NO2)c(C(F)(F)F)n1] |
| 2-30 | 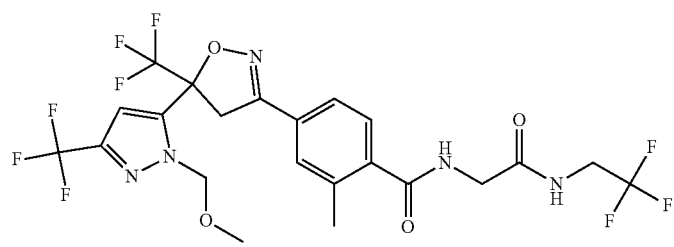 [SMILES: COCn1nc(C(F)(F)F)cc1C1(C(F)(F)F)CC(c2ccc(C(=O)NCC(=O)NCC(F)(F)F)c(C)c2)=NO1] |
| 2-31 | 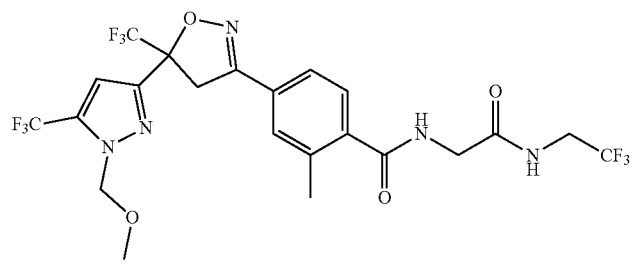 [SMILES: COCn1nc(C2(C(F)(F)F)CC(c3ccc(C(=O)NCC(=O)NCC(F)(F)F)c(C)c3)=NO2)cc1C(F)(F)F] |

Salts

In addition to the neutral compounds of formula (I), salt forms of the compounds are also active against animal pests. The terms "veterinarily acceptable salt" and "agriculturally acceptable salt" are used throughout the specification to described any salts of the compounds that are acceptable for administration for veterinary and agricultural applications, and which provides the active compound upon administration.

In cases where compounds are sufficiently basic or acidic to form stable non-toxic acid or base salts, the compounds may be in the form of a veterinarily or agriculturally acceptable salt. Veterinarily or agriculturally acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable.

Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartrate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal. Veterinarily and agriculturally acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Definitions

For the purposes of this application, unless otherwise stated in the specification, the following terms have the terminology cited below:

(1) Alkyl refers to both straight and branched carbon chains hydrocarbon groups. In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-6, 1-4, 1-3 or 1-2 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups may be referred to as "cycloalkyl" and include those with 3 to 10 carbon atoms having single or multiple fused rings. In other embodiments, the cycloalkyl groups may have 3 to 8 carbon atoms or 3 to 6 carbon atoms in the ring. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Fourth Edition, 2007, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10, 2-8 or 2-6. In yet another embodiment of alkenyl, the number of carbon atoms is 2-4. Other ranges of carbon-carbon double bonds and carbon numbers are also contemplated depending on the location of the alkenyl moiety on the molecule.

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2- butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10, 2-8 or 2-6. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{14}$ aromatic carbocyclic ring structure having a single ring or multiple fused rings. In some embodiments, the aryl ring may be fused to a non-aromatic ring, as long as the point of attachment to the core structure is through the aromatic ring. Aryl groups include, but are not limited to, phenyl, biphenyl, and naphthyl. In some embodiments aryl includes tetrahydronapthyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkylsulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl)amino, or $SF_5$. In one embodiment of aryl, the moiety is phenyl, naphthyl, tetrahydronapthyl, phenylcyclopropyl and indanyl; in another embodiment of aryl, the moiety is phenyl.

(5) Alkoxy refers to —O-alkyl, wherein alkyl is as defined in (1);

(6) Alkoxycarbonyl refers to —C(=O)—O-alkyl, wherein alkoxy is as defined in (5);

(7) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(8) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(9) Heterocycle, heterocyclic or heterocyclo refers to fully saturated or unsaturated cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(10) Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic groups include, but are not limited to, indolyl, benzothiazolyl, benzoxazolyl, benzodioxolyl, benzothienyl, quinuclidinyl, tetra-hydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means a isoxazoline compound of the invention.

The term "locus" is intended to mean a habitat, breeding ground, area, material or environment in which a parasite is growing or may grow. The term "locus" does not include the body of an animal.

Synthesis of Compounds

The isoxazoline compounds of formula (I) may be prepared by processes described herein or by adaptation of these processes or process known in the art to prepare compounds with different substitution patterns. For example, the compounds of formula (I) and intermediates used in the processes to make the compounds may be prepared by processes adapted from those described in U.S. Pat. Nos. 7,964,204, 8,410,153, 8,217,180, 8,546,613, 7,662,972, 8,466,115, 8,383,659, 8,853,186, 8,618,126, US 2014/0371464, US 2015/0291612 and WO 2014/090918, all of which are incorporated herein by reference in their entirety.

Accordingly, Schemes 1 to 3 below describe certain embodiments of the synthesis of certain compounds of formula (I) of the invention. Scheme 1 describes a representative preparation of a compound of formula (I) wherein P is $P^1$ and Y is Y-2 starting from commercially available starting material 2-1A and the known intermediate 2-1H. This compound is prepared using a process similar to the processes described in U.S. Pat. No. 7,662,972 with the exception that the pyrazole-containing intermediate 2-1D is used to form the isoxazoline ring rather than a phenyl substituted with a trifluorovinyl group (see for example, U.S. Pat. No. 7,662,972). It will be appreciated by skilled persons in the art that alternative compounds may be made by modifying the substitution patterns of starting material 2-1A and compound 2-1H.

Scheme 1

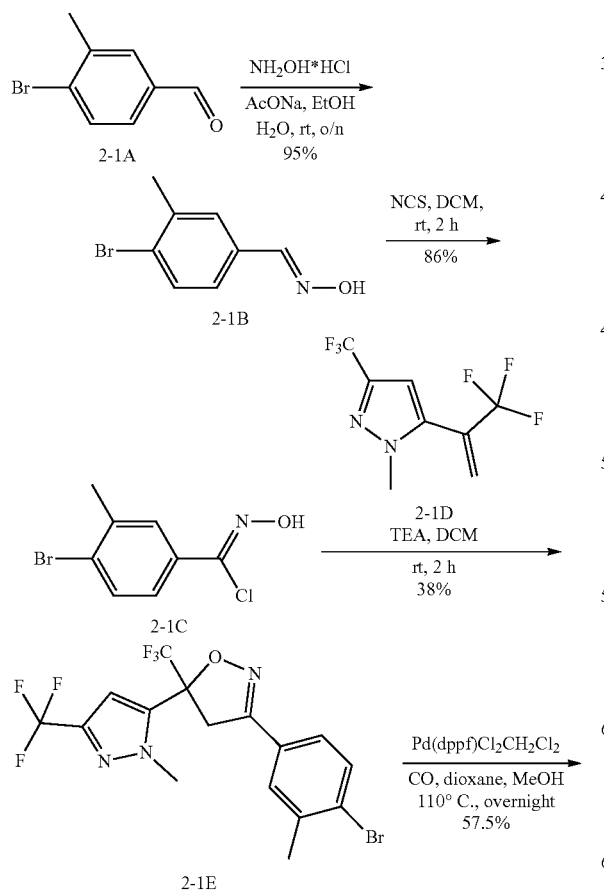

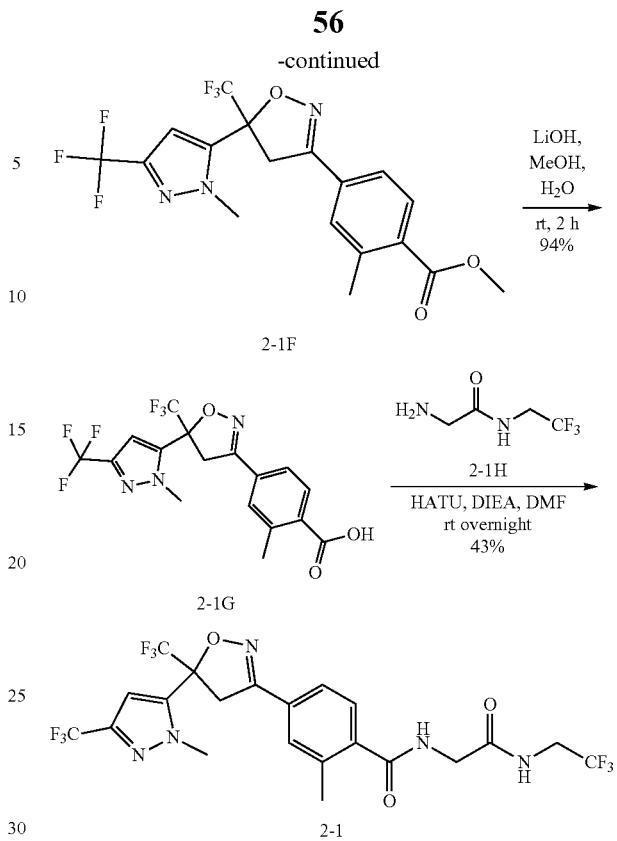

Scheme 2 below describes the synthesis of a compound of formula (I) where Y is Y-3 where each of $Z^1$ to $Z^6$ are C—H, and P is $P^1$ using the intermediate 2-2A as described in U.S. Pat. No. 7,964,204 with the exception that it is reacted with intermediate 2-2A instead of a substituted phenyl group bearing a trifluoromethylvinyl group.

Scheme 2

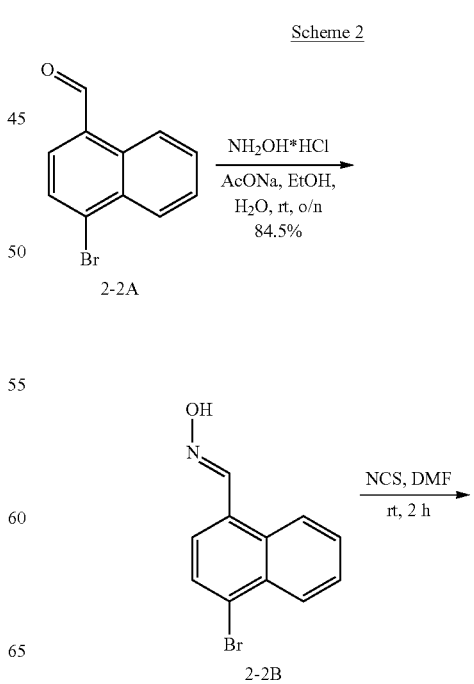

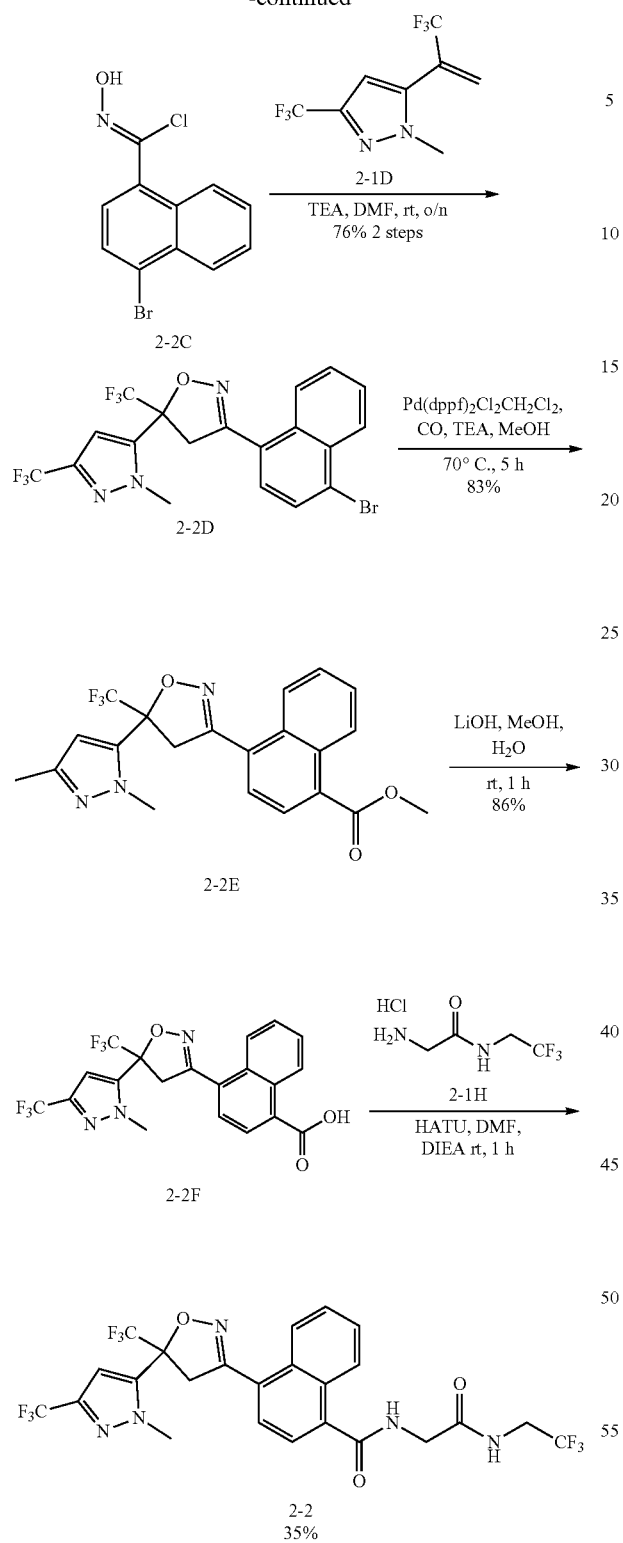
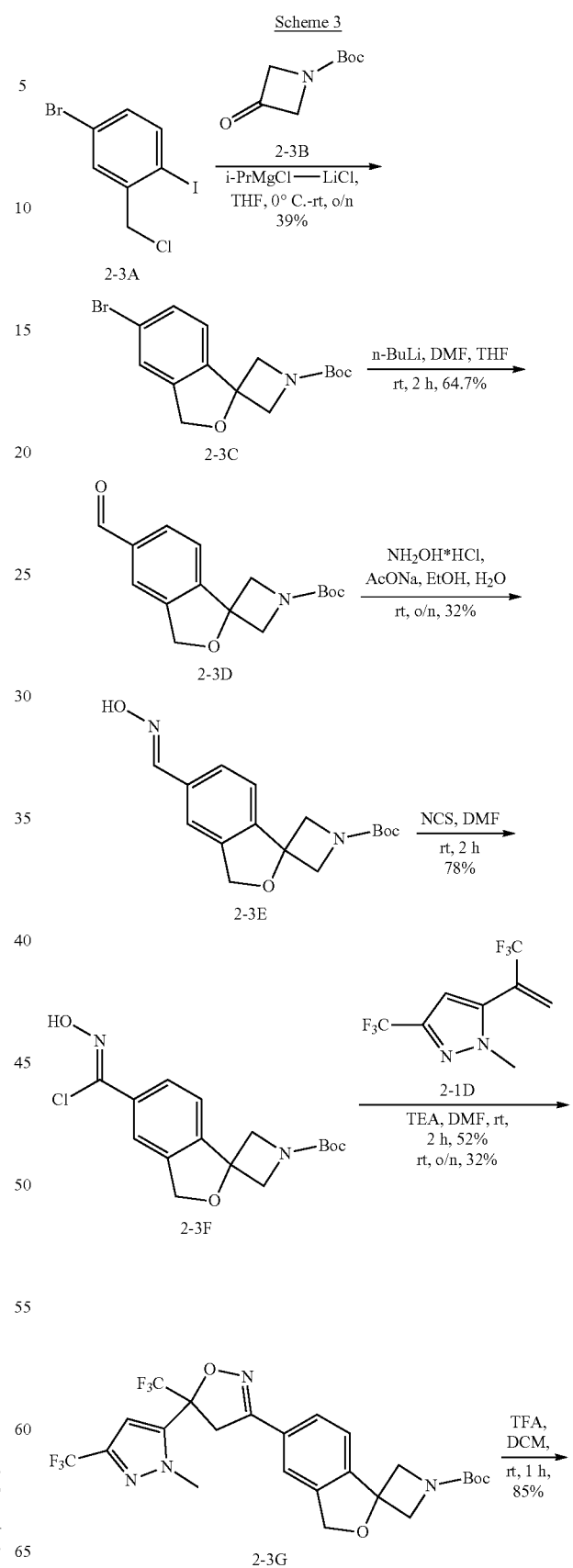
Scheme 3 below shows a process for preparing a compound of formula (I) where Y is Y-4 using intermediate 2-3F as described in U.S. Pat. No. 8,466,115 with the exception that it is reacted with intermediate 2-1D instead of a substituted phenyl group bearing a trifluoromethylvinyl substituent.

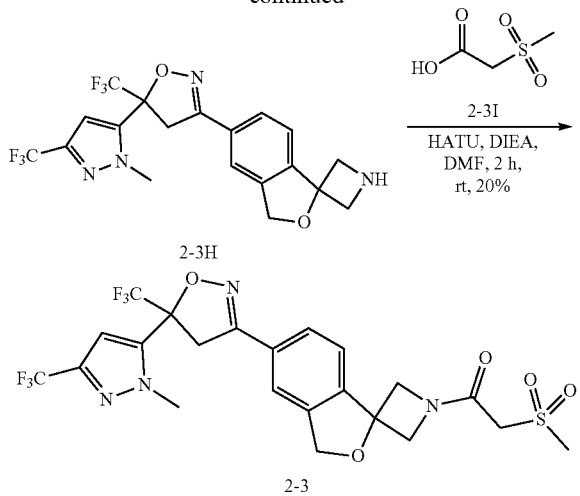

It will be appreciated by skilled persons in the art that alternative compounds of the invention may be prepared according to the processes described in Schemes 1-3 by using alternative starting materials and intermediates.

Veterinary Compositions

Another aspect of the invention is the formation of parasiticidal compositions which comprise the isoxazoline compounds of the invention. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, polyethylene glycols (PEGs) and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or *arachis* oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the co-surfactants include short-chain alcohols, such as ethanol and propanol.

Some compounds are common to the three components discussed above, i.e., aqueous phase, surfactant and co-surfactant. However, it is well within the skill level of the practitioner to use different compounds for each component of the same formulation. In one embodiment for the amount of surfactant/co-surfactant, the co-surfactant to surfactant ratio will be from about ⅐ to about ½. In another embodiment for the amount of co-surfactant, there will be from about 25 to about 75% v/v of surfactant and from about 10 to about 55% v/v of co-surfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the isoxazoline compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the isoxazoline compound into the carrier by mixing;
(b) adding the fumed silica to the carrier containing the dissolved isoxazoline compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing isoxazoline compound, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier including PEG 200, PEG 300, PEG 400, PEG 600, monoethanolamine, triethanolamine, glycerol, propylene glycol, polyoxyethylene (20) sorbitan monooleate (POLYSORBATE 80 or TWEEN 80), and poloxamers (e.g., PLURONIC L 81); an absorbent including magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension or an injectable solution. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, spot-on solutions and suspensions, dips and sprays. Topical application of an inventive compound or of a composition including at least one inventive compound among active agent(s) therein, in the form of a spot-on or pour-on composition, can allow for the inventive compound to be absorbed through the skin to achieve systemic levels, distributed through the sebaceous glands or on the surface of the skin achieving levels throughout the hair coat. When the compound is distributed through the sebaceous glands, they can act as a reservoir, whereby there can be a long-lasting effect (up to several months) effect. Spot-on formulations are typically applied in a localized region which refers to a relatively small area on the animal rather than to a large portion of the surface of the animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. In some embodiments, the pour-on formulations may be oily, and generally comprise a diluent or vehicle and also a solvent (e.g. an organic solvent) for the active ingredient if the latter is not soluble in the diluent. In other embodiments, the pour-on formulations may be non-oily, including alcohol-based formulations.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. In one embodiment, the emollient and/or spreading and/or film-forming agent is those agents selected from the group consisting of:
(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil,
(b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulphosuccinate; fatty acids (e.g. those derived from coconut oil),
(c) cationic surfactants such as water-soluble quaternary ammonium salts of formula N$^+$R'R''R'''R'''', Y$^-$ in which the radicals R are optionally hydroxylated hydrocarbon radicals and Y is an anion of a strong acid such as the halide, sulfate and sulfonate anions; cetyltrimethylammonium bromide is among the cationic surfactants which can be used,
(d) amine salts of formula N$^+$HR'R''R''' in which the radicals R are optionally hydroxylated hydrocarbon radicals; octadecylamine hydrochloride is among the cationic surfactants which can be used,
(e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide,
(f) amphoteric surfactants such as the substituted lauryl compounds of betaine; or
(g) a mixture of at least two of these agents.

The solvent will be used in proportion with the concentration of the isoxazoline compound and its solubility in this solvent. It will be sought to have the lowest possible volume.

The vehicle makes up the difference to 100%.

In one embodiment of the amount of emollient, the emollient is used in a proportion of from 0.1 to 50% and 0.25 to 5%, by volume.

In another embodiment of the invention, the composition can be in ready-to-use solution for localized topical application, including a spot-on formulation, as is described in U.S. Pat. No. 6,395,765, incorporated herein by reference. In addition to the isoxazoline compound, the solution may contain a crystallization inhibitor, an organic solvent and an organic co-solvent.

In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by a the test in which 0.3 ml of a solution comprising 10% (w/v) of isoxazoline compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystals.

In one embodiment, the organic solvent has a dielectric constant of about 2 to about 35, about 10 to about 35 or about 20 to about 30. In other embodiments, the solvent will have a dielectric constant of between about 2 and about 20, or between about 2 and about 10. The content of this organic solvent in the overall composition will complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, the co-solvent may be present in the composition in an organic co-solvent/organic solvent weight/weight (W/W) ratio of about 1/15 to about 1/2. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:
(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsulfoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;
(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil);
(c) cationic surfactants, such as water-soluble quaternary ammonium salts of formula $N^+R'R''R'''R''''Y^+$, in which the R radicals are identical or different optionally hydroxylated hydrocarbon radicals and $Y^+$ is an anion of a strong acid, such as halide, sulfate and sulfonate anions; cetyltrimethylammonium bromide is one of the cationic surfactants which can be used;
(d) amine salts of formula $N^+HR'R''R'''$, in which the R radicals are identical or different optionally hydroxylated hydrocarbon radicals; octadecylamine hydrochloride is one of the cationic surfactants which can be used;
(e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;
(f) amphoteric surfactants, such as substituted lauryl compounds of betaine; or
(g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulfate or a mixture of not more than two of them.

The non-active formulation components discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients are added.

The volume of the topical formulations applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal. In other embodiments, the volume applied may be about 5 ml to about 10 ml, about 5 ml to about 15 ml, about 10 ml to about 20 ml, or about 20 ml to about 30 ml, depending on the size of the animal treated and the concentration of the active agent in the formulation, among other factors.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference). In one embodiment, the spot-on formulation comprises a solvent and a co-solvent wherein the solvent may be acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents. In another embodiment, the spot-on formulations include a co-solvent that is absolute ethanol, isopropanol or methanol, or a mixture thereof. In another embodiment, the compositions include benzyl alcohol as a co-solvent.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent. More typically the dosage is about 1 mg to about 25 mg, 1 mg to about 50 mg, 10 mg to about 100 mg, or 20 mg to about 200 mg. In other embodiments, the dosage is about 50 mg to about 300 mg, 50 mg to about 400 mg, 50 mg to about 500 mg, 50 mg to about 600 mg, 50 mg to about 800 mg, or 100 mg to about 1000 mg.

In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

In a particular advantageous embodiment of the invention, the dosage administered of the inventive compounds is about 0.01 mg/kg to about 100 mg/kg of weight of animal. In another embodiment, the dose is about 0.1 mg/kg to about 100 mg/kg of weight of animal. In other embodiments, the dose of the inventive compounds is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the active compounds is about 0.01 mg/kg to 5 mg/kg, 0.1 mg/kg to about 5 mg/kg, about 0.1 mg/kg to about 3 mg/kg, or about 0.1 mg/kg to 1.5 mg/kg. In still other embodiments of the invention, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

Agricultural Compositions

The compounds of formula (I), or agriculturally acceptable salts thereof, can be formulated in various ways, depending on the prevailing biological and/or physical-chemical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell, Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula (I).

The concentration of compounds of formula (I) in wettable powders is, for example, about 10 to about 90% by weight, the remainder to 100% by weight being composed of customary formulation components. In the case of emulsifiable concentrates, the concentration of compounds of formula (I) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and about 5% to about 20% by weight of compounds of formula (I). For sprayable solutions comprise a range selected from the group consisting of about 0.05% to about 80% by weight of compounds of formula (I) and about 2% to about 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The following are examples of agricultural compositions:

1. Products for dilution with water. For seed treatment purposes, such products may be applied to the seed diluted or undiluted.

A) Water-Soluble Concentrates 10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions 25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders 75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders 5 parts by weight of the active compound are ground finely and mixed intimately with 95 parts by weight of finely divided kaolin. This gives a dustable product having 5% (w/w) of active compound.

J) Granules 0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Methods of Treatment

In another aspect of the invention, a method for preventing or treating a parasite infestation/infection in an animal is provided, comprising administering to the animal at least one compound of formula (I), optionally together with a pharmaceutically acceptable carrier. The compounds of the invention have long-lasting efficacy against ectoparasites (e.g. fleas and ticks) and in certain embodiments, when combined with an appropriate endoparasiticide, may also active against endoparasites that harm animals.

In one embodiment of the invention, methods for the treatment or prevention of a parasitic infestation or infection in a domestic animal are provided, which comprise administering to the animal an effective amount of at least one isoxazoline active agent of the invention to the animal. Ectoparasites against which the methods and compositions of the invention are effective include, but are not limited to, fleas, ticks, mites, mosquitoes, flies and lice. In certain embodiments wherein the compositions include one or more additional active agents that are active against internal parasites, the compositions and methods of the invention may also be effective against endoparasites including, but not limited to, cestodes, nematodes, hookworms and roundworms of the digestive tract of animals and humans.

In one embodiment for treatment against ectoparasites, the ectoparasite is one or more insect or arachnid including those of the genera *Ctenocephalides*, *Rhipicephalus*, *Dermacentor*, *Ixodes*, *Boophilus*, *Amblyomma*, *Haemaphysalis*, *Hyalomma*, *Sarcoptes*, *Psoroptes*, *Otodectes*, *Chorioptes*, *Hypoderma*, *Damalinia*, *Linognathus*, *Haematopinus*, *Solenopotes*, *Trichodectes*, and *Felicola*.

In another embodiment for the treatment against ectoparasites, the ectoparasite is from the genera *Ctenocephalides*, *Rhipicephalus*, *Dermacentor*, *Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp. and the like), ticks (*Rhipicephalus* sp., *Ixodes* sp., *Dermacentor* sp., *Amblyomma* sp. and the like), and mites (*Demodex* sp., *Sarcoptes* sp., *Otodectes* sp. and the like), lice (*Trichodectes* sp., *Cheyletiella* sp., *Linognathus* sp., and the like), mosquitoes (*Aedes* sp., *Culex* sp., *Anopheles* sp., and the like) and flies (*Haematobia* sp. including *Haematobia irritans, Musca* sp., *Stomoxys* sp. including *Stomoxys calcitrans, Dermatobia* sp., *Cochliomyia* sp., and the like).

Additional examples of ectoparasites include but are not limited to the tick genus *Boophilus*, especially those of the species *Microplus* (cattle tick), *Decoloratus* and *Annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In some embodiments of the invention, the composition can also be used to treat against endoparasites such as those helminths selected from the group consisting of *Anoplocephala, Ancylostoma, Necator, Ascaris, Capillaria, Cooperia, Dipylidium, Dirofilaria, Echinococcus, Enterobius, Fasciola, Haemonchus, Oesophagostomum, Ostertagia, Toxocara, Strongyloides, Toxascaris, Trichinella, Trichuris*, and *Trichostrongylus*, among others.

In one embodiment, the invention provides methods for the treatment and prevention of parasitic infections and infestations of animals (either wild or domesticated), including livestock and companion animals such as cats, dogs, horses, birds including chickens, sheep, goats, pigs, turkeys and cattle, with the aim of ridding these hosts of parasites commonly encountered by such animals.

In a preferred embodiment, the invention provides methods for the treatment or prevention of parasitic infections and infestations in companion animals including, but not limited to, cats and dogs. The methods of the invention are particularly effective for preventing or treating parasitic infestations of cats and dogs with fleas and ticks.

In another preferred embodiment, the methods of the invention are used for the treatment or prevention of parasitic infections and infestations in cattle or sheep. When treating livestock animals such as cattle or sheep, the methods and compositions are particularly effective against *Rhipicephalus* (*Boophilus*) *Microplus, Haematobia irritans* (horn fly), *Stomoxys calcitrans* (stable fly), and sheep myiasis such as *Lucilia sericata, Lucilia cuprina* (known as blowfly strike in Australia, New Zealand and South Africa).

The terms "treating" or "treat" or "treatment" are intended to mean the application or administration of an isoxazoline compound of the invention to an animal that has a parasitic infestation for the eradication of the parasite or the reduction of the number of the parasites infesting the animal undergoing treatment. It is noted that the compositions of the invention comprising an isoxazoline compound together with a pharmaceutically acceptable carrier may be used to prevent such a parasitic infestation.

The compounds and compositions of the invention are administered in parasiticidally effective amounts which are which are suitable to control the parasite in question to the desired extent, as described below. In each aspect of the invention, the compounds and compositions of the invention can be applied against a single pest or combinations thereof. The compounds and compositions of the invention may be administered continuously, for treatment or prevention of parasitic infections or infestations. In this manner, an effective amount of the active isoxazoline compounds of the invention are delivered to the animal in need thereof to control the target parasites. By "effective amount" is intended a sufficient amount of a composition of the invention to eradicate or reduce the number of parasites infesting the animal. In one embodiment, an effective amount of the active agent achieves at least 70% efficacy against the target parasite compared to a negative control according to known methods used in the art (animal not treated or treated with a placebo). In other embodiments, an effective amount of the active agent achieves at least 80%, or at least 90% efficacy against the target pests. Preferably, an effective amount of the active agent will achieve at least 95% efficacy against the target pests. In some embodiments, an effective amount of the compounds and compositions of the invention achieve at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In some embodiments for companion animals, the dosage of the isoxazoline active agent administered is between about 0.1 to about 50 mg per kg of body weight. In other embodiments, the dosage of the compounds of formula (I) administered is between about 0.1 to about 30 mg/kg of body weight. More typically the dose of the isoxazoline active agent administered is about 0.5 to about 20 mg/kg or about 0.5 to about 15 mg/kg body weight. Preferably, the dose of the isoxazoline active agent administered is about 0.5 to about 10 mg/kg, about 0.5 to about 8 mg/kg or about 0.5 to about 5 mg/kg of body weight.

In certain embodiments for the treatment and prevention of parasite infestations and infections in smaller animals (e.g. cats and other smaller mammals), the dose of the isoxazoline active agent administered will be about 0.5 to about 2 mg/kg of body weight, preferably about 1 mg/kg of bodyweight. In other embodiments for the very long lasting treatment and protection of smaller animals against parasitic infestations or infections a dose of about 2 to about 15 mg/kg of bodyweight or preferably about 5 to about 15 mg/kg of bodyweight will be administered.

In some embodiments for the treatment and protection of dogs from parasitic infestations and infections, a dose of about 2 to about 15 mg/kg of bodyweight of the isoxazoline active agent will be administered. In other embodiments, a dose of about 2 to about 8 mg/kg or about 2 to about 5 mg/kg of bodyweight will be administered.

In other embodiments for the treatment of livestock animals such as cattle or sheep, doses of the isoxazoline active agent administered may be about 1 to about 30 mg/kg of body weight. More typically the doses administered will be about 1 to about 20 mg/kg or about 1 to about 15 mg/kg. Preferably, a dose of the isoxazoline active agent administered to livestock animals will be about 1 to about 10 mg/kg of body weight.

Higher amounts may be provided for very prolonged release in or on the body of the animal. In another treatment embodiment, the amount of active agents for birds and other animals which are small in size is greater than about 0.01 mg/kg, and in another embodiment for the treatment of small-sized birds and other animals, the amount of is between about 0.01 and about 20 mg/kg of weight of animal. More typically the dose of the isoxazoline for small-sized animals and birds is about 0.5 to about 15 mg/kg, about 0.5 to about 10 mg/kg of body weight, or about 0.5 mg/kg to about 5 mg/kg of body weight.

In one embodiment of the method of use in dogs or cats, a composition comprising an isoxazoline compound of the invention has an efficacy against fleas and/or ticks of at least about 90.0% or higher for about 1 month, or longer. In another embodiment, the compositions of the invention provide an efficacy against fleas and/or ticks of at least 95.0% or higher for about 30 days, or longer.

In another embodiment, the compounds and compositions of the invention provide an efficacy against fleas and/or ticks in cats and dogs of at least about 80% for two months, or longer. In another embodiment, the compounds and compositions provide efficacy against fleas and/or ticks in cats and dogs of about 90% for about two months, or longer. In still another embodiment, the compounds and compositions provide an efficacy of about 95% for about 2 months or longer. In other embodiments, the compounds and composition provide longer-lasting efficacy against fleas and/or ticks including for about 3 months, or longer.

In one embodiment of the invention, the isoxazoline compounds may be administered in the form of topical compositions to the animal. Topical compositions include dips, shampoos, sprays, spot-ons, pour-ons, and the like. Application of topical compositions is to animals to control parasites is well known in the art.

In some embodiments, the isoxazoline compounds may be administered in solutions using any means known in the art, including using an applicator gun or a metering flask, pipette, syringes, roll on, droppers, capsules, foil packages, vials, twist tip containers, metered-dose aerosols or sprays and other single dose and multi-dose containers.

In another aspect of the invention, a kit for the treatment or prevention of a parasitic infestation in an animal is provided, which comprises at least one isoxazoline active agent of the invention together with a pharmaceutically acceptable carrier and a dispensing device for application of the composition. The dispensing device may be a pipette, syringes, roll on, droppers, capsules, foil packages, vials, twist tip containers, metered-dose aerosols or sprays and other single dose and multi-dose containers, which includes an effective dose of each active agent in the pharmaceutically acceptable carrier or diluent.

In other embodiments, the isoxazoline compounds may be administered in the form of capsules, tablets, chewable tablets or soft chew compositions known in the art.

In another embodiment of the invention, the compounds and compositions of the invention are suitable for controlling pests at a locus. Therefore, an additional embodiment of the invention is a method for controlling pests at a locus, comprising applying a pesticidally effective amount of compound of formula (I) or a composition comprising the compound to the locus. Pests that may be controlled with the compounds of the invention include insects such as *Blatella germanica, Heliothis virescens, Leptinotarsa decemlineata, Tetramorium caespitum* and combinations thereof.

In still another embodiment, the compounds and compositions of the invention are effective for protecting crops, plants and material made from wood against pests. Thus, the invention provides a method for protecting crops, plants, plant propagation material and material made from wood from pests that harm these materials comprising applying the compounds of the invention or compositions comprising the compounds to the crops, plants, plant propagation material and material made from wood.

In other embodiments, the compounds and compositions of the invention may be used against the phytoparasitic nematodes including, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, the compounds and compositions of the invention can also be used against pests which include, but are not limited to, the following pests:

(1) from the order of Isopoda, for example *Oniscus asellus, Armadillidium vulgare* and *Porcellio scaber;*
(2) from the order of Diplopoda, for example *Blaniulus guttulatus;*
(3) from the order of Chilopoda, for example *Geophilus carpophagus* and *Scutigera* spp.;
(4) from the order of Symphyla, for example *Scutigerella immaculata;*
(5) from the order of Thysanura, for example *Lepisma saccharina;*
(6) from the order of Collembola, for example *Onychiurus armatus;*
(7) from the order of *Blattaria*, for example *Blatta orientalis, Periplaneta americana, Leucophaea maderae* and *Blattella germanica;*
(8) from the order of Hymenoptera, for example *Diprion* spp., *Hoplocampa* spp., *Lasius* spp., *Monomorium pharaonis* and *Vespa* spp.;
(9) from the order of Siphonaptera, for example *Xenopsylla cheopis* and *Ceratophyllus* spp.;
(10) from the order of Anoplura (Phthiraptera), for example, *Damalinia* spp., *Haematopinus* spp., *Linognathus* spp., *Pediculus* spp., *Trichodectes* spp.;
(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*
(12) from the class of Bivalva, for example, *Dreissena* spp.;
(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetoniajucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulusfilaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinellapseudopsiralis, Trichostrongulus* spp., *Trichuris trichiura, Wuchereria bancrofti;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphisjuglandicola, Chrysomphalusficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoeciapodana, Capua reticulana, Carpocapsapomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolisflammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothripsflavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

Active Agent Combinations

The isoxazoline compounds of the invention or their salts can be employed as such or in the form of their preparations (formulations) as combinations with other active substances.

For agricultural uses, the isoxazoline compounds of the invention may be used in combination with, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed with the isoxazoline compounds of the invention include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzothiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones.

Other fungicides that may optionally be admixed with the isoxazoline compounds of the invention may also be from the classes of compounds described in U.S. Pat. Nos. 7,001,903 and 7,420,062, each incorporated herein by reference.

Herbicides that are known from the literature and classified by HRAC (Herbicide Resistance Action Committee) and may be combined with the compounds of the invention are, for example: aryloxyphenoxy-propionate; cyclohexanedione; phenylpyrazoline; sulfonylurea; imidazolinone, such as imazapic and imazethapyr; triazolopyrimidine; pyrimidinyl(thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluroxypyr and picloram; quinoline carboxylic acid;

phthalamate semicarbazone; qrylaminopropionic acid; qrylaminopropionic acid; organoarsenical.

Other herbicides that may optionally be admixed are compounds described in U.S. Pat. Nos. 7,432,226, 7,012,041, and 7,365,082, all incorporated herein by reference.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/acaricides/nematicides include those compounds mentioned in U.S. Pat. Nos. 7,420,062 and 7,001,903, U.S. Patent publication 2008/0234331, each incorporated herein by reference, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; Bacillus sphaericus; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; $P^{450}$-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

Veterinary compositions may include one or more isoxazoline compounds of the invention in combination with additional pharmaceutically or veterinarily active agents. In some embodiments, the additional active agent(s) may be one or more acaricide, anthelmintic, endectocide and insecticide active agent. Anti-parasitic agents can include both ectoparasiticisal and endoparasiticidal agents.

Veterinary pharmaceutical agents that may be included in the compositions of the invention are well-known in the art (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, Propionibacterium Acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds, such as phenylpyrazoles, known in the art may be combined with the isoxazoline compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.). A particularly preferred arylpyrazole compound is fipronil.

In another embodiment of the invention, one or more macrocyclic lactones, which act as an acaricide, anthelmintic agent and/or insecticide, can be combined with the isoxazoline compounds of the invention. The macrocyclic lactones include, but are not limited to, avermectins such as abamectin, dimadectin, doramectin, emamectin, eprinomectin, ivermectin, latidectin, lepimectin, selamectin and ML-1, 694,554, and milbemycins such as milbemectin, milbemycin D, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569 (both incorporated herein by reference). Mention is also made of U.S. Pat. Nos. 4,468,390, 5,824,653, EP 0 007 812 A1, U.K. Patent Specification 1 390 336, EP 0 002 916, and New Zealand Patent No. 237 086 (all incorporated by reference), inter alia. Naturally occurring milbemycins are described in U.S. Pat. No. 3,950,360, which is incorporated herein by reference, as well as in the various references cited in "The Merck Index" 12 ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054 (all incorporated by reference).

In another embodiment, the isoxazoline compounds of the invention may be combined with a class of compounds known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoro-ethoxy)-phenylurea and 1-(2,6-difluorobenzoyl)-3-(2-fluoro-4-trifluoromethyl)phenylurea.

In yet another embodiment of the invention, adulticide insecticides and acaricides can also be combined with the isoxazoline compounds of the invention. These include pyrethrins (which include cinerin I, cinerin II, jasmolin I, jasmolin II, pyrethrin I, pyrethrin II and mixtures thereof) and pyrethroids (including permethrin cyhalothrin, cypermethrin, deltamethrin, fenvalerate, flucythrinate), and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the isoxazoline compounds of the invention may be combined with one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the isoxazoline compounds of the invention may be combined with an imidazothiazole compounds including, but not limited to, tetramisole, levamisole and butamisole. In still other embodiments, the isoxazoline compounds of the invention may be combined with tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the isoxazoline compounds of the invention may be combined with the antinematodal compounds phenothiazine and piperazine as the neutral compound, or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the isoxazoline compounds of the invention may be combined with antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously combined with isoxazoline compounds of the invention including, but not limited to, arecoline in various salt forms, bunamidine, niclosamide, nitroscanate, paromomycin and paromomycin II.

In yet other embodiments, the isoxazoline compounds of the invention may be combined with other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio) ethanol (MGK-874).

In another embodiment, the isoxazoline compounds of the invention be combined with pyrethroid active agents including, but not limited to, permethrin, deltamethrin, cypermethrin, cyphenothrin, etofenprox, fenvalerate and cyfluthrin. Another antiparasitic agent that can be combined with the isoxazoline compounds of the invention include a biologically active peptide or protein including, but not limited to, depsipeptides, which act at the neuromuscular junction by stimulating presynaptic receptors belonging to the secretin receptor family resulting in the paralysis and death of parasites. In one embodiment, the depsipeptide is emodepside (see Willson et al., *Parasitology*, January 2003, 126(Pt 1):79-86).

In another embodiment, the isoxazoline compounds of the invention may be combined with an active agent from the neonicotinoid class of pesticides. The neonicotinoids bind and inhibit insect specific nicotinic acetylcholine receptors. In one embodiment, the neonicotinoid insecticidal agent is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060 (incorporated herein by reference).

In another embodiment, the neonicotinoid active agent is nitenpyram. Nitenpyram is the active ingredient in the oral product CAPSTAR™ Tablets sold by Novartis Animal Health. Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day.

In certain embodiments, an insecticidal agent that can be combined with the isoxazoline compounds of the invention is a semicarbazone, such as metaflumizone.

In another embodiment, the isoxazoline compounds of the invention may advantageously be combined with another isoxazoline compounds known in the art. These active agents are described in U.S. Pat. Nos. 7,964,204, 8,410,153, US 2011/0152312, US 2010/0254960 A1, US2011/ 0159107, US2012/0309620, US2012/0030841, US2010/ 0069247, WO 2007/125984, WO 2012/086462, U.S. Pat. No. 8,318,757, US 2011/0144349, U.S. Pat. No. 8,053,452; US 2010/0137612, US 2010/0254959, US 2011/152081, WO 2012/089623, WO 2012/089622, U.S. Pat. Nos. 8,119, 671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, U.S. Pat. Nos. 7,897,630, 7,951,828 and 7,662,972, all of which are incorporated herein by reference in their entirety.

In another embodiment of the invention, nodulisporic acid and its derivatives (a class of known acaricidal, anthelmintic, anti-parasitic and insecticidal agents) may be combined with the isoxazoline compounds of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety.

In another embodiment, anthelmintic compounds of the amino acetonitrile class (AAD) of compounds such as monepantel (ZOLVIX), and the like, may be combined with the isoxazoline compounds of the invention. These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The isoxazoline compounds of the invention may also be combined with aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621, also incorporated herein by reference.

The isoxazoline compounds of the invention may also be combined with paraherquamide compounds and derivatives of these compounds, including derquantel (see Ostlind et al., Research in Veterinary Science, 1990, 48, 260-61; and Ostlind et al., Medical and Veterinary Entomology, 1997, 11, 407-408). The paraherquamide family of compounds is a known class of compounds that include a spirodioxepino indole core with activity against certain parasites (see Tet. Lett. 1981, 22, 135; J. Antibiotics 1990, 43, 1380, and J. Antibiotics 1991, 44, 492). In addition, the structurally related marcfortine family of compounds, such as marcfortines A-C, are also known and may be combined with the formulations of the invention (see J. Chem. Soc.—Chem. Comm. 1980, 601 and Tet. Lett. 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In general, the additional active agent is included in the composition in an amount of between about 0.1 µg and about 1000 mg. More typically, the additional active agent may be included in an amount of about 10 µg to about 500 mg, about 1 mg to about 300 mg, about 10 mg to about 200 mg or about 10 mg to about 100 mg.

In other embodiments of the invention, the additional active agent may be included in the composition to deliver a dose of about 5 µg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

EXAMPLES

List of Abbreviations

ACN acetonitrile
A-Phos-Pd Palladium G3-(4-(N,N-Dimethylamino)phenyl) di-tert-butylphosphine
Pd(dppf)Cl$_2$.CH$_2$Cl$_2$ DCM, [1,1'-Bis(diphenylphosphino) ferrocene]dichloropalladium(II) (1:1)
DCM dichloromethane
DIEA diisopropylethylamine
DMF N,N-dimethylformamide
DMSO dimethylsulfoxide
EtOH ethanol
EtOAc or EA ethyl acetate
HATU 1-[bis(dimethylamino)methylene]-1H-1,2,3-triazolo [4,5 b]pyridinium 3-oxide hexafluorophosphate
m-CPBA meta-chloroperoxybenzoic acid
NaOAc sodium acetate
NCS N-chlorosuccinimide
PE petroleum ether
TEA triethylamine
THF tetrahydrofuran Preparation Examples The compounds of the invention shown in Table 2 above were prepared according to the Preparation Examples 1-28 shown below.

Preparation Example 1

Compound 2-1 was prepared as shown in Scheme 4 below.

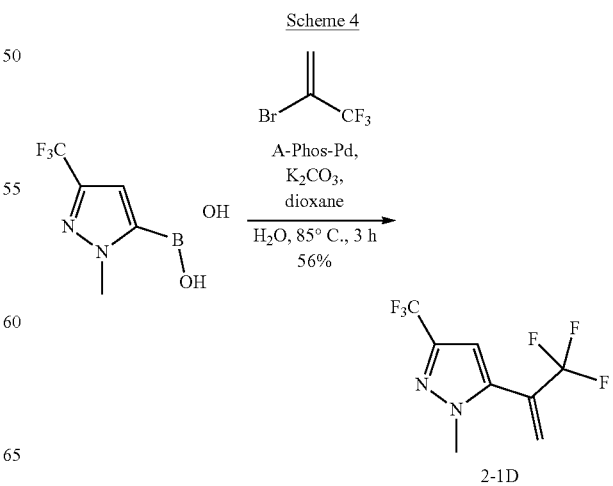

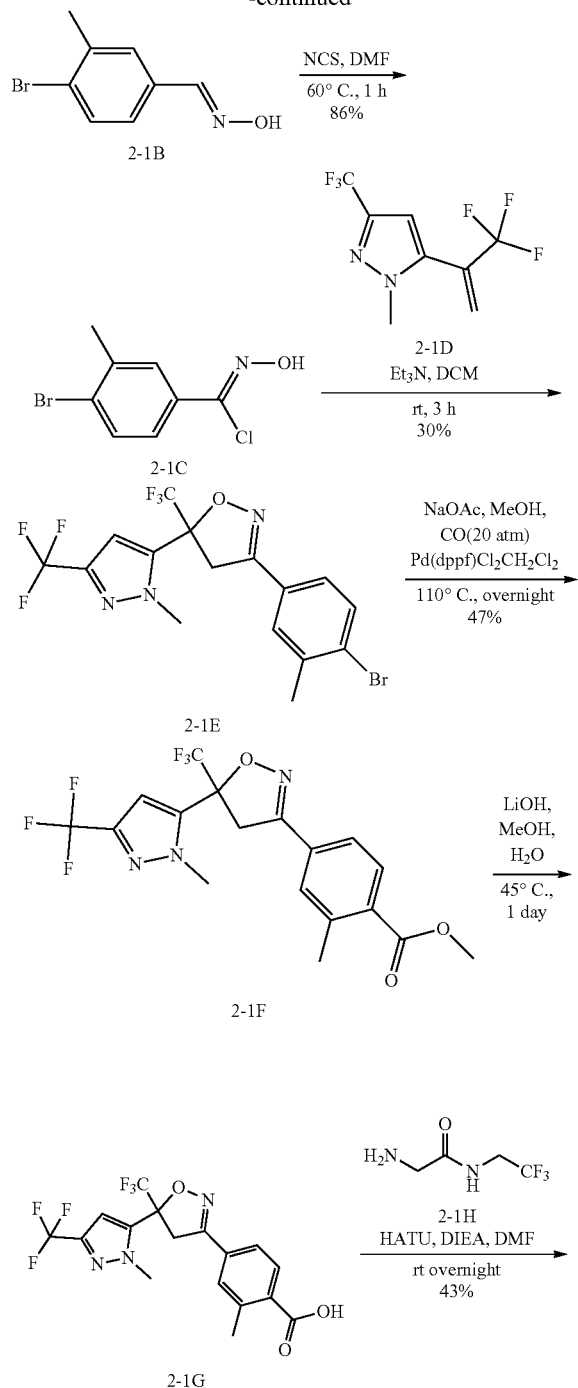

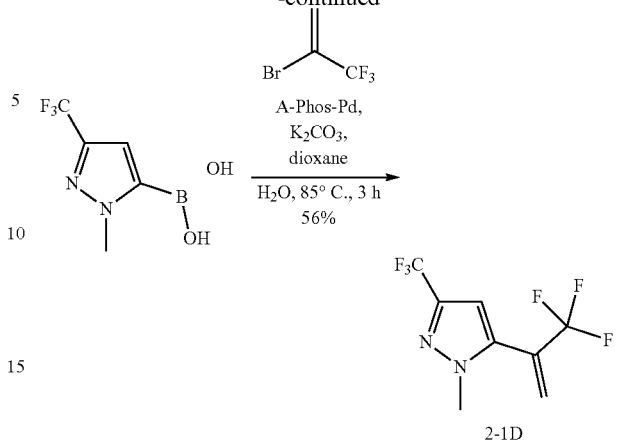

1-Methyl-3-(trifluoromethyl)-5-(3,3,3-trifluoroprop-1-en-2-yl)-1H-pyrazole

Into a 500-mL round-bottom flask purged and maintained with an inert atmosphere of nitrogen, was placed 2-bromo-3,3,3-trifluoroprop-1-ene (10 mL), A-Phos-Pd (0.9 g), potassium carbonate (3 g, 21.71 mmol, 2.10 equiv), dioxane (200 mL), water (20 mL). This was followed by the addition of [1-methyl-3-(trifluoromethyl)-1H-pyrazol-5-yl]boronic acid (2 g, 10.31 mmol, 1.00 equiv) dropwise with stirring at 85° C. The resulting solution was stirred for 3 h at 85° C. The reaction mixture was quenched with 150 mL of water, then extracted with 3×200 mL of ethyl acetate and the organic layers combined and concentrated under vacuum. The residue was applied onto a silica gel column with ethyl acetate/petroleum ether (1:5). This resulted in 1.4 g (56%) of 1-methyl-3-(trifluoromethyl)-5-(3,3,3-trifluoroprop-1-en-2-yl)-1H-pyrazole as brown oil. MS (ESI, m/z): 245 [M+H]$^+$.

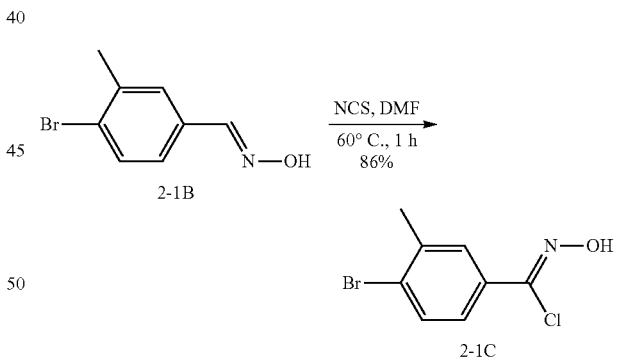

(Z)-4-bromo-N-hydroxy-3-methylbenzene-1-carbonimidoyl chloride

Into a 25-mL round-bottom flask, was placed (E)-N-[(4-bromo-3-methylphenyl)methylidene]hydroxylamine (1 g, 4.67 mmol, 1.00 equiv), NCS (600 mg, 4.49 mmol, 0.96 equiv) and N,N-dimethylformamide (10 mL). The resulting solution was stirred for 1 h at 60° C. The reaction mixture was concentrated under vacuum and the residue was applied onto a silica gel column with ethyl acetate/petroleum ether (1:3). This resulted in 1 g (86%) of (Z)-4-bromo-N-hydroxy-3-methylbenzene-1-carbonimidoyl chloride as brown oil.

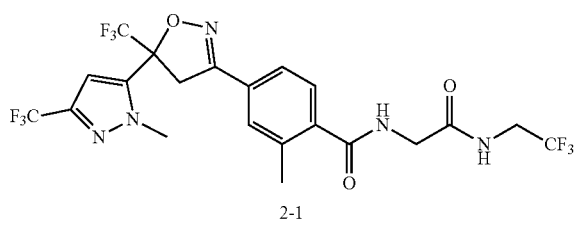

89

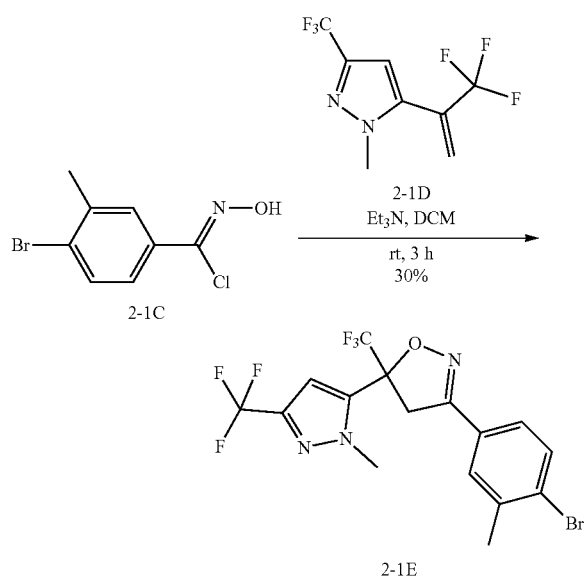

3-(4-Bromo-3-methylphenyl)-5-[1-methyl-3-(trifluoromethyl)-1H-pyrazol-5-yl]-5-(trifluoromethyl)-4,5-dihydro-1,2-oxazole Into a 50-mL round-bottom flask, was placed 1-methyl-3-(trifluoromethyl)-5-(3,3,3-trifluoroprop-1-en-2-yl)-1H-pyrazole (800 mg, 3.28 mmol, 1.20 equiv), (Z)-4-bromo-N-hydroxy-3-methylbenzene-1-carbonimidoyl chloride (1.0 g, 4.02 mmol, 1.00 equiv), triethylamine (1 g, 9.88 mmol, 2.46 equiv) and dichloromethane (20 mL). The resulting solution was stirred for 3 h at room temperature. The solid was filtered out and the filtrate was concentrated under vacuum. The residue was applied onto a silica gel column with ethyl acetate/petroleum ether (1:5). This resulted in 550 mg (30%) of 3-(4-bromo-3-methylphenyl)-5-[1-methyl-3-(trifluoromethyl)-1H-pyrazol-5-yl]-5-(trifluoromethyl)-4,5-dihydro-1,2-oxazole as brown oil. MS (ESI, m/z): 456 [M+H]$^+$.

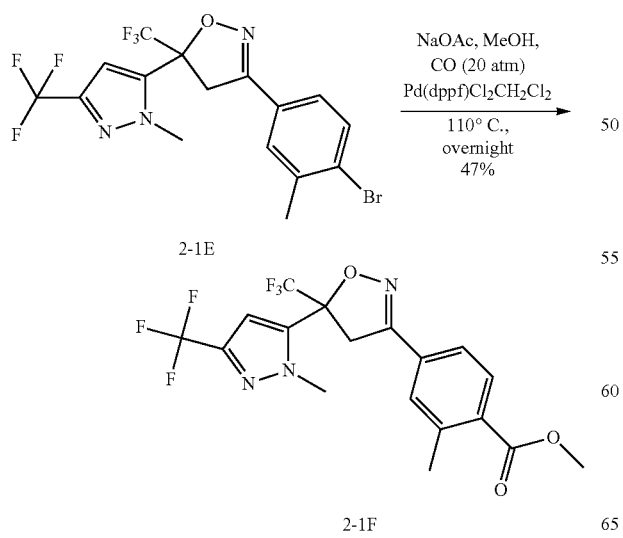

90

Methyl 2-methyl-4-[5-[1-methyl-3-(trifluoromethyl)-4,5-dihydro-1H-pyrazol-5-yl]-5-(trifluoromethyl)-4,5-dihydro-1,2-oxazol-3-yl]benzoate Into a 50-mL pressure tank reactor was placed 3-(4-bromo-3-methylphenyl)-5-[1-methyl-3-(trifluoromethyl)-4,5-dihydro-1H-pyrazol-5-yl]-5-(trifluoromethyl)-4,5-dihydro-1,2-oxazole (450 mg, 0.98 mmol, 1.00 equiv), NaOAc (225 mg, 2.73 mmol, 3.00 equiv), Pd(dppf)Cl$_2$CH$_2$Cl$_2$ (81 mg, 0.10 mmol, 0.10 equiv) and methanol (25 mL). This mixture was purged and maintained with an atmosphere of CO (20 atm). The resulting solution was stirred overnight at 110° C. The solids were filtered out, and the filtrate was concentrated under vacuum. The residue was applied onto a silica gel column with ethyl acetate/petroleum ether (1:5). This resulted in 203 mg (47%) of methyl 2-methyl-4-[5-[1-methyl-3-(trifluoromethyl)-4,5-dihydro-1H-pyrazol-5-yl]-5-(trifluoromethyl)-4,5-dihydro-1,2-oxazol-3-yl]benzoate as a brown solid. MS (ESI, m/z): 436 [M+H]$^+$.

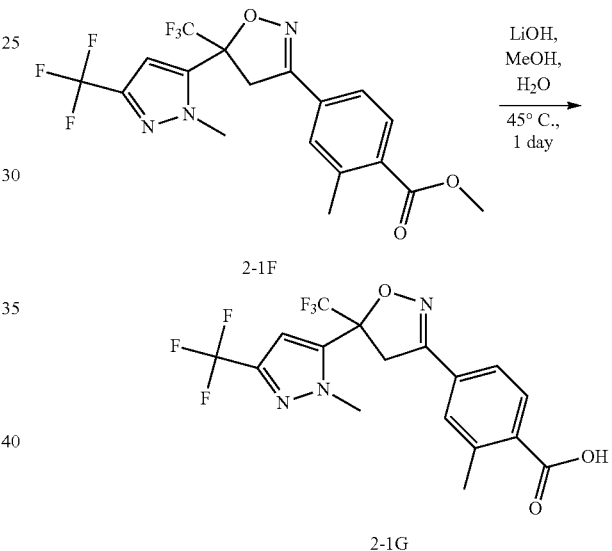

2-Methyl-4-[5-[1-methyl-3-(trifluoromethyl)-1H-pyrazol-5-yl]-5-(trifluoromethyl)-4,5-dihydro-1,2-oxazol-3-yl]benzoic acid Into a 50-mL round-bottom flask, was placed methyl 2-methyl-4-[5-[1-methyl-3-(trifluoromethyl)-1H-pyrazol-5-yl]-5-(trifluoromethyl)-4,5-dihydro-1,2-oxazol-3-yl]benzoate (200 mg, 0.46 mmol, 1.00 equiv), LiOH (100 mg, 4.18 mmol, 10.0 equiv), methanol (10 mL) and water (10 mL). The resulting solution was stirred for 1 day at 45° C. The organic solvent was concentrated under vacuum and the pH of the solution was adjusted to 4 with hydrogen chloride (6 mol/L). The resulting solution was extracted with 3×50 mL of ethyl acetate and the organic layers were combined and dried over anhydrous sodium sulfate and concentrated under vacuum. This resulted in 200 mg (crude) of 2-methyl-4-[5-[1-methyl-3-(trifluoromethyl)-1H-pyrazol-5-yl]-5-(trifluoromethyl)-4,5-dihydro-1,2-oxazol-3-yl]benzoic acid as a yellow solid. MS (ESI, m/z): 422 [M+H]$^+$.

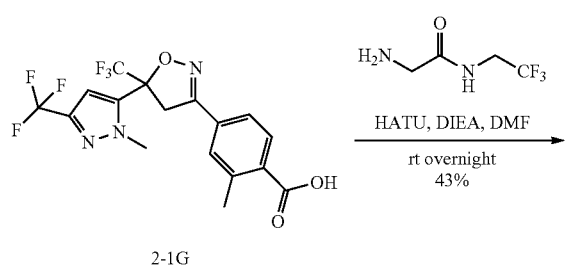

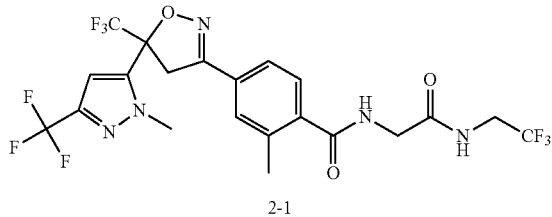

2-1

2-[(2-Methyl-4-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl)acetamide Into a 25-mL round-bottom flask, was placed 2-amino-N-(2,2,2-trifluoroethyl)acetamide (37 mg, 0.24 mmol, 1.00 equiv), 2-methyl-4-[5-[1-methyl-3-(trifluoromethyl)-1H-pyrazol-5-yl]-5-(trifluoromethyl)-4,5-dihydro-1,2-oxazol-3-yl]benzoic acid (100 mg, 0.24 mmol, 1.00 equiv), HATU (185 mg, 0.49 mmol, 2.00 equiv), DIEA (61 mg, 0.49 mmol, 2.00 equiv) and N,N-dimethylformamide (5 mL). The resulting solution was stirred overnight at room temperature. The resulting mixture was concentrated under vacuum and the residue was applied onto a silica gel column with ethyl acetate/petroleum ether (1:3). This resulted in 57.3 mg (43%) of 2-[(2-methyl-4-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl)acetamide as a light yellow solid. MS (ESI, m/z): 560 [M+H]$^+$; $^1$H NMR (300 MHz, DMSO-d$_6$, ppm) δ: 8.62-8.61 (m, 1H), 7.65-7.63 (m, 2H), 7.51 (d, J=8.4 Hz, 1H), 7.15 (s, 1H), 4.50-4.49 (m, 2H), 4.05 (s, 3H), 3.98-3.91 (m, 4H), 2.41 (s, 3H).

Preparation Example 2

Compound 2-6 was prepared by coupling carboxylic acid intermediate 2-1G with 2,2,2-trifluoroethylamine as shown below.

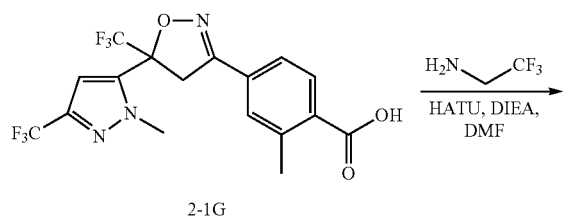

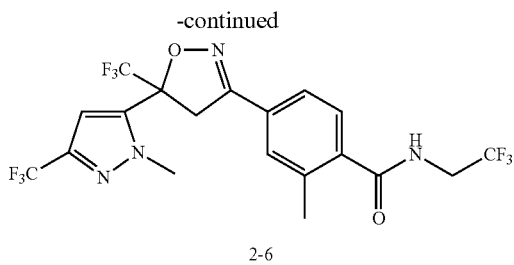

2-6

2-methyl-4-[5-[1-methyl-3-(trifluoromethyl)-1H-pyrazol-5-yl]-5-(trifluoromethyl)-4,5-dihydro-1,2-oxazol-3-yl]-N-(2,2,2-trifluoroethyl)benzamide Into a 50-mL round-bottom flask, were placed 2-methyl-4-[5-[1-methyl-3-(trifluoromethyl)-1H-pyrazol-5-yl]-5-(trifluoromethyl)-4,5-dihydro-1,2-oxazol-3-yl]benzoic acid (150 mg, 0.36 mmol, 1.00 equiv), HATU (203 mg, 0.53 mmol, 1.50 equiv), N,N-dimethylformamide (5 mL), 2,2,2-trifluoroethan-1-amine (53 mg, 0.54 mmol, 1.50 equiv) and DIEA (138 mg, 1.07 mmol, 3.00 equiv). The resulting solution was stirred for 2 h at room temperature. The crude solution was purified by Flash-Prep-HPLC with the following conditions (IntelFlash-1): Column, C18 silica gel; mobile phase, H$_2$O and CH$_3$CN (65% CH$_3$CN increasing to 70% within 6 min); Detector, UV 254 nm, 220 nm. This resulted in 58.9 mg (33%) of 2-methyl-4-[5-[1-methyl-3-(trifluoromethyl)-1H-pyrazol-5-yl]-5-(trifluoromethyl)-4,5-dihydro-1,2-oxazol-3-yl]-N-(2,2,2-trifluoroethyl)benzamide as a off-white solid. (ES, m/z): 503 [M+H]$^+$; $^1$H NMR (300 MHz, DMSO-d$_6$, ppm) δ 9.08 (t, J=5.4 Hz, 1H), 7.68-7.65 (m, 2H), 7.46 (d, J=7.8 Hz, 1H), 7.15 (s, 1H), 4.51-4.49 (m, 2H), 4.11-4.05 (m, 5H), 2.37 (s, 3H).

Preparation Example 3

Compound 2-9 was prepared according to Scheme 5 shown below.

Scheme 5

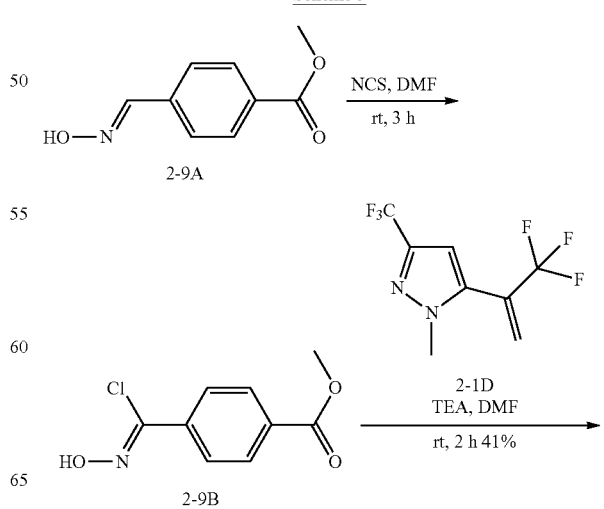

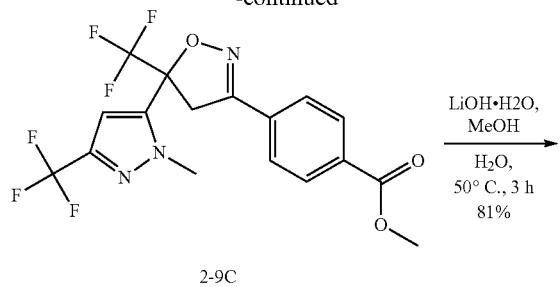

2-9C

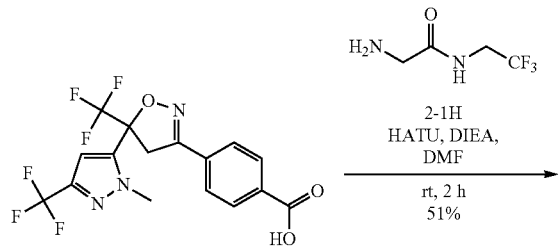

2-9D

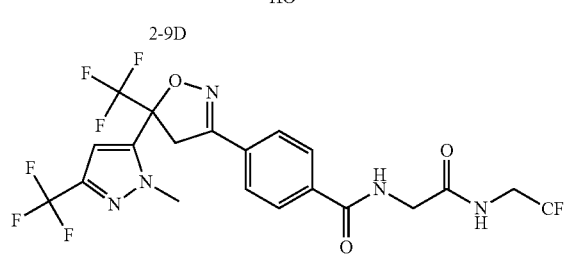

Compound 2-9

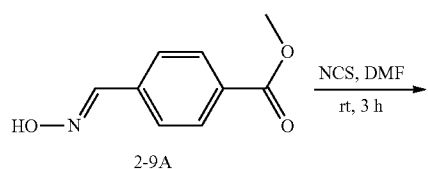

2-9A

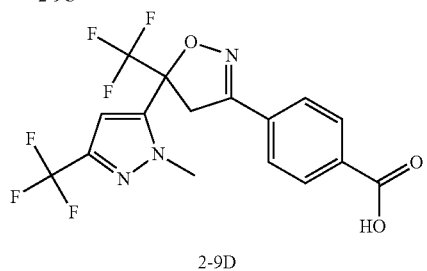

2-9B

Methyl 4-[(1Z)-chloro(hydroxyimino)methyl]benzoate (5-2)

Into a 100-mL round-bottom flask, were placed methyl 4-[(1E)-(hydroxyimino)methyl]benzoate (600 mg, 3.35 mmol, 1.00 equiv), NCS (670 mg, 5.02 mmol, 1.50 equiv) and N,N-dimethylformamide (10 mL). The resulting solution was stirred for 3 h at room temperature. The resulting solution was used to next step directly. MS (ESI, m/z): 214 [M+H]$^+$.

4-[5-[1-Methyl-3-(trifluoromethyl)-1H-pyrazol-5-yl]-5-(trifluoromethyl)-4,5-dihydro-1,2-oxazol-3-yl] benzoate (5-3)

Into a 100-mL round-bottom flask, were placed methyl 4-[(1Z)-chloro(hydroxyimino)methyl]benzoate (above reaction mixture), 1-methyl-3-(trifluoromethyl)-5-(3,3,3-trifluoroprop-1-en-2-yl)-1H-pyrazole (500 mg, 2.05 mmol, 0.61 equiv) and TEA (0.9 mL). The resulting solution was stirred for 2 h at room temperature and the solids were filtered out. The filtrate was concentrated under vacuum. The residue was applied onto a silica gel column with ethyl acetate/petroleum ether (1:10-1:5). This resulted in 362 mg (41%) of methyl 4-[5-[1-methyl-3-(trifluoromethyl)-1H-pyrazol-5-yl]-5-(trifluoromethyl)-4,5-dihydro-1,2-oxazol-3-yl]benzoate as a white solid. MS (ESI, m/z): 422 [M+H]$^+$.

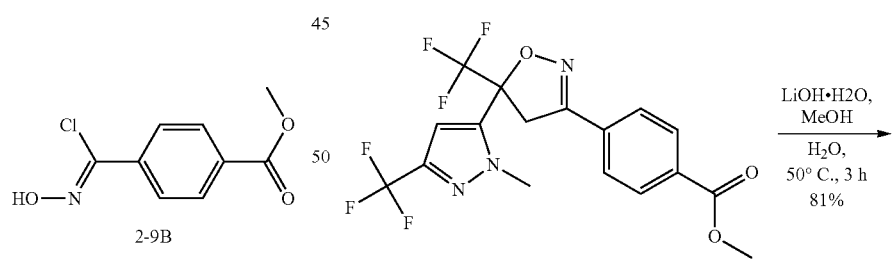

2-9C 2-9D

4-[5-[1-methyl-3-(trifluoromethyl)-1H-pyrazol-5-yl]-5-(trifluoromethyl)-4,5-dihydro-1,2-oxazol-3-yl]benzoic acid (5-4)

Into a 100-mL round-bottom flask, were placed methyl 4-[5-[1-methyl-3-(trifluoromethyl)-1H-pyrazol-5-yl]-5-(trifluoromethyl)-4,5-dihydro-1,2-oxazol-3-yl]benzoate (362 mg, 0.86 mmol, 1.00 equiv), LiOH.H$_2$O (180 mg, 4.30 mmol, 5.00 equiv), methanol (20 mL) and water (20 mL). The resulting solution was stirred for 3 h at 50° C. The organic solvent was removed under vacuum. The pH value of the solution was adjusted to 2 with hydrogen chloride (6 N) and the solid was collected by filtration. This resulted in 301 mg (86%) of 4-[5-[1-methyl-3-(trifluoromethyl)-1H-pyrazol-5-yl]-5-(trifluoromethyl)-4,5-dihydro-1,2-oxazol-3-yl]benzoic acid as a white solid. MS (ESI, m/z): 408 [M+H]$^+$.

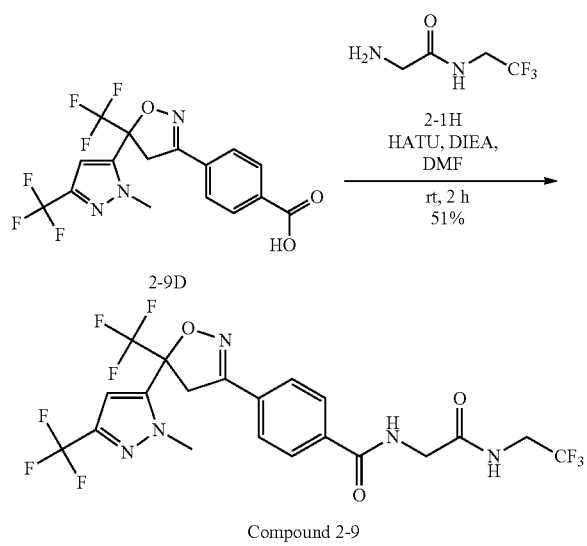

Compound 2-9

2-[(4-[5-[1-Methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl) acetamide (2-9)

Into a 50-mL round-bottom flask, were placed 4-[5-[1-methyl-3-(trifluoromethyl)-1H-pyrazol-5-yl]-5-(trifluoromethyl)-4,5-dihydro-1,2-oxazol-3-yl]benzoic acid (150 mg, 0.37 mmol, 1.00 equiv), 2-amino-N-(2,2,2-trifluoroethyl) acetamide (86 mg, 0.55 mmol, 1.50 equiv), HATU (210 mg, 0.55 mmol, 1.50 equiv), DIEA (80 mg, 0.62 mmol, 1.50 equiv) and N,N-dimethylformamide (15 mL). The resulting solution was stirred for 2 h at room temperature. The crude solution was purified by Prep-HPLC with the following conditions (Waters-2767): Column, SunFire Prep C18, 5 um, 19*150 mm; mobile phase: Water and CH$_3$CN (30% CH$_3$CN up to 80% in 25 min); Detector, UV 254 nm. This resulted in 102 mg (51%) of 2-[(4-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl) acetamide as a white solid. MS (ESI, m/z): 546 [M+H]$^+$; $^1$H NMR (300 MHz, DMSO-d$_6$, ppm) δ: 8.97 (t, J=6.0 Hz, 1H), 8.64 (t, J=6.3 Hz, 1H), 8.02 (d, J=8.4 Hz, 2H), 7.88 (d, J=8.4 Hz, 2H), 7.16 (s, 1H), 4.64-4.45 (m, 2H), 4.06 (s, 3H), 4.01-3.85 (m, 4H).

Preparation Example 4

Compound 2-21 was prepared in a similar manner as Compound 2-1 shown in Scheme 4 above except reacting the unmethylated vinylpyrazole intermediate 2-21B shown below with Compound 2-1C to form the corresponding unmethylated pyrazole-substituted isoxazoline compound 2-21C which is taken forward in the same manner to obtain compound 2-21.

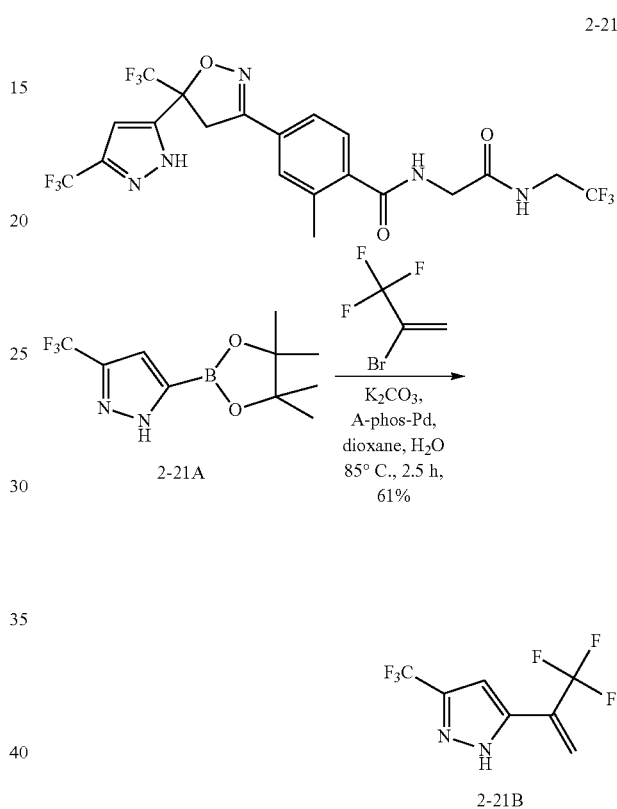

3-(trifluoromethyl)-5-(3,3,3-trifluoroprop-1-en-2-yl)-1H-pyrazole (6-2)

Into a 50-mL 3-necked round-bottom flask (1 atm) purged and maintained with an inert atmosphere of nitrogen, were placed water (2 mL), 1.4-dioxane (10 mL), potassium carbonate (1.32 g, 9.55 mmol, 2.50 equiv), A-Phos-Pd (0.27 g, 0.10 equiv) and 2-bromo-3,3,3-trifluoroprop-1-ene (3.98 g, 22.75 mmol, 6.00 equiv). This was followed by the addition of a solution of 5-(tetramethyl-1,3,2-dioxaborolan-2-yl)-3-(trifluoromethyl)-1H-pyrazole (1 g, 3.82 mmol, 1.00 equiv) in 1.4-dioxane (10 mL) dropwise with stirring at 85° C. The resulting solution was stirred for 2.5 h at 85° C. The resulting solution was diluted with 100 mL of H$_2$O and extracted with 2×100 mL of ethyl acetate. The organic layers combined and dried over anhydrous sodium sulfate and concentrated under vacuum. The residue was applied on a silica gel column and eluted with ethyl acetate/petroleum ether (0:100-1:9). This resulted in 540 mg (61%) of 3-(trifluoromethyl)-5-(3,3,3-trifluoroprop-1-en-2-yl)-1H-pyrazole as a yellow solid.

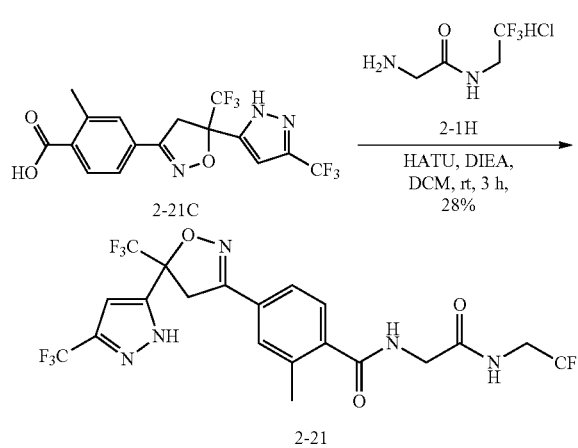

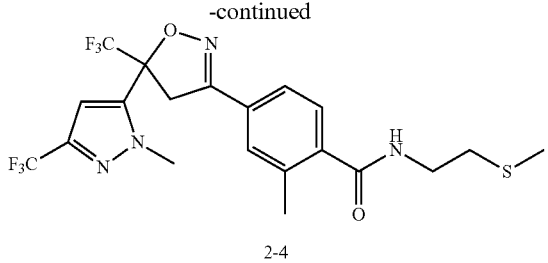

2-methyl-4-[5-[1-methyl-3-(trifluoromethyl)-1H-pyrazol-5-yl]-5-(trifluoromethyl)-4,5-dihydro-1,2-oxazol-3-yl]-N-[2-(methylsulfanyl)ethyl]benzamide Into a 50-mL round-bottom flask, were placed 2-methyl-4-[5-[1-methyl-3-(trifluoromethyl)-1H-pyrazol-5-yl]-5-(trifluoromethyl)-4,5-dihydro-1,2-oxazol-3-yl]benzoic acid (150 mg, 0.36 mmol, 1.00 equiv), HATU (203 mg, 0.53 mmol, 1.50 equiv), N,N-dimethylformamide (5 mL), 2-(methylsulfanyl)ethan-1-amine (49 mg, 0.54 mmol, 1.50 equiv) and DIEA (138 mg, 1.07 mmol, 3.00 equiv). The resulting solution was stirred for 2 h at room temperature. The crude solution was purified by Flash-Prep-HPLC with the following conditions (IntelFlash-1): Column, C18 silica gel; mobile phase, $H_2O$ and $CH_3CN$ (35% $CH_3CN$ increasing to 80% within 15 min); Detector, UV 254 nm; 220 nm. This resulted in 55.9 mg (32%) of 2-methyl-4-[5-[1-methyl-3-(trifluoromethyl)-1H-pyrazol-5-yl]-5-(trifluoromethyl)-4,5-dihydro-1,2-oxazol-3-yl]-N-[2-(methylsulfanyl)ethyl]benzamide as a white solid. (ES, m/z): 495 [M+H]$^+$; $^1$H NMR (300 MHz, DMSO-d$_6$, ppm) δ 8.47 (m, 1H), 7.64-7.62 (m, 2H), 7.44 (d, J=7.2 Hz, 1H), 7.15 (s, 1H), 4.50-4.48 (m, 2H), 4.05 (s, 3H), 3.46-3.40 (m, 2H), 2.65 (t, J=6.9 Hz, 2H), 2.39 (s, 3H), 2.10 (s, 3H). $^1$H NMR (300 MHz, DMSO-d$_6$, ppm) δ 8.47 (t, J=6.0 Hz, 1H), 7.72-7.60 (m, 2H), 7.44 (d, J=7.9 Hz, 1H), 7.15 (s, 1H), 4.57-4.44 (m, 2H), 4.05 (s, 3H), 3.52-3.38 (m, 2H), 2.66 (t, J=7.0 Hz, 2H), 2.39 (s, 3H), 2.11 (s, 3H).

Preparation Example 6

Compound 2-5 was prepared by coupling carboxylic acid 1-7 with 2-methanesulfonylethan-1-amine.

2-([2-methyl-4-[5-(trifluoromethyl)-5-[3-(trifluoromethyl)-1H-pyrazol-5-yl]-4,5-dihydro-1,2-oxazol-3-yl]phenyl]formamido)-N-(2,2,2-trifluoroethyl)acetamide (2-21)

Into a 50-mL 3-necked round-bottom flask (1 atm) purged and maintained with an inert atmosphere of nitrogen, were placed 2-methyl-4-[5-(trifluoromethyl)-5-[3-(trifluoromethyl)-1H-pyrazol-5-yl]-4,5-dihydro-1,2-oxazol-3-yl]benzoic acid (80 mg, 0.20 mmol, 1.00 equiv), dichloromethane (10 mL) and HATU (89 mg, 0.23 mmol, 1.20 equiv), and the resulting solution was stirred for 0.5 h at room temperature. To this was added a solution of 2-amino-N-(2,2,2-trifluoroethyl)acetamide hydrochloride (61.3 mg, 0.32 mmol, 2.00 equiv) in dichloromethane (10 mL), DIEA (101.1 mg, 0.78 mmol, 4.00 equiv). The resulting solution was stirred for 3 h at room temperature. The resulting mixture was washed with 1×20 mL of $H_2O$. The organic layer was collected and dried over anhydrous sodium sulfate and concentrated under vacuum. The crude product was purified by Flash-Prep-HPLC with the following conditions (IntelFlash-1): Column, C18 silica gel; mobile phase, $H_2O$ and $CH_3CN$ (30% $CH_3CN$ increasing to 80% within 10 min); Detector, UV 254 nm. This resulted in 22.8 mg (22%) of 2-([2-methyl-4-[5-(trifluoromethyl)-5-[3-(trifluoromethyl)-1H-pyrazol-5-yl]-4,5-dihydro-1,2-oxazol-3-yl]phenyl]formamido)-N-(2,2,2-trifluoroethyl)acetamide as a white solid. MS (ESI, m/z): 545 [M+H]$^+$; $^1$H NMR (300 MHz, DMSO-d$_6$, ppm) δ 8.68-8.58 (m, 2H), 7.64-7.62 (m, 2H), 7.50 (d, J=8.2 Hz, 1H), 6.99 (s, 1H), 4.46 (d, J=18.1 Hz, 1H), 4.29 (d, J=18.3 Hz, 1H), 4.11-3.88 (m, 4H), 2.41 (s, 3H).

Preparation Example 5

Compound 2-4 was prepared by coupling carboxylic acid 1-7 shown in Scheme 4 with 2-(methylsulfanyl)ethan-1-amine.

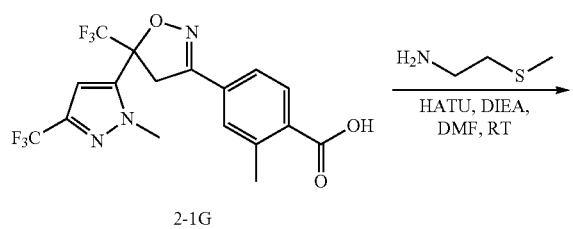

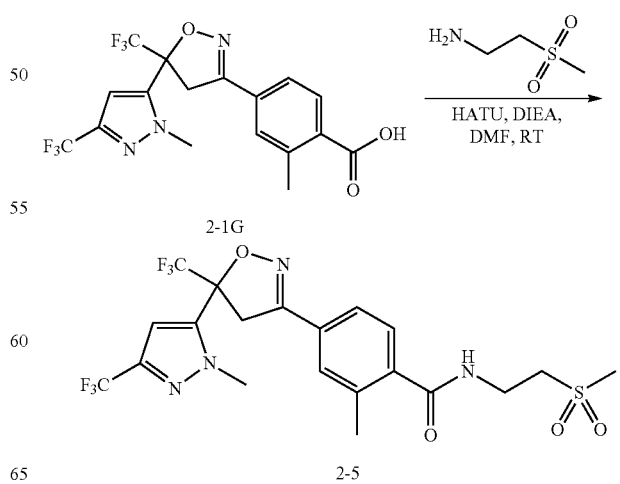

N-(2-methanesulfonylethyl)-2-methyl-4-[5-[1-methyl-3-(trifluoromethyl)-1H-pyrazol-5-yl]-5-(trifluoromethyl)-4,5-dihydro-1,2-oxazol-3-yl]benzamide Into a 50-mL round-bottom flask, were placed 2-methyl-4-[5-[1-methyl-3-(trifluoromethyl)-1H-pyrazol-5-yl]-5-(trifluoromethyl)-4,5-dihydro-1,2-oxazol-3-yl]benzoic acid (150 mg, 0.36 mmol, 1.00 equiv), HATU (203 mg, 0.53 mmol, 1.50 equiv), N,N-dimethylformamide (5 g, 68.41 mmol, 192.13 equiv), 2-methanesulfonylethan-1-amine (66 mg, 0.54 mmol, 1.50 equiv) and DIEA (138 mg, 1.07 mmol, 3.00 equiv), and the resulting solution was stirred for 2 h at room temperature. The crude solution was purified by Flash-Prep-HPLC with the following conditions (IntelFlash-1): Column, C18 silica gel; mobile phase, $H_2O$ and $CH_3CN$ (30% $CH_3CN$ increasing to 80% within 20 min); Detector, UV 254 nm; 220 nm. This resulted in 67.7 mg (36%) of N-(2-methanesulfonylethyl)-2-methyl-4-[5-[1-methyl-3-(trifluoromethyl)-1H-pyrazol-5-yl]-5-(trifluoromethyl)-4,5-dihydro-1,2-oxazol-3-yl]benzamide as a white solid. (ES, m/z): 527 [M+H]$^+$; $^1$H NMR (300 MHz, DMSO-d, ppm) δ 8.67-8.57 (m, 1H), 7.72-7.60 (m, 2H), 7.47 (d, J=7.8 Hz, 1H), 7.15 (s, 1H), 4.56-4.43 (m, 2H), 4.05 (s, 3H), 3.73-3.61 (m, 2H), 3.39 (t, J=6.9 Hz, 2H), 3.06 (s, 3H), 2.39 (s, 3H).

Preparation Example 7

Compound 2-28 was prepared by coupling carboxylic acid 2-9D shown in Scheme 5 with cyclopropylamine.

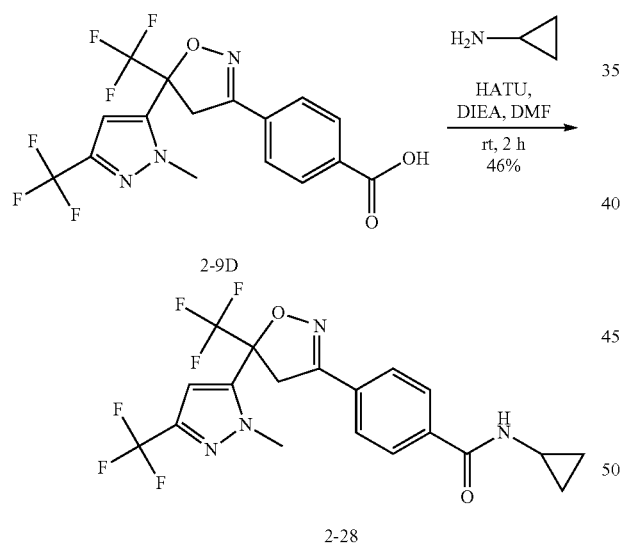

2-28

N-cyclopropyl-4-[5-[1-methyl-3-(trifluoromethyl)-1H-pyrazol-5-yl]-5-(trifluoromethyl)-4,5-dihydro-1,2-oxazol-3-yl]benzamide Into a 50-mL round-bottom flask, were placed 4-[5-[1-methyl-3-(trifluoromethyl)-1H-pyrazol-5-yl]-5-(trifluoromethyl)-4,5-dihydro-1,2-oxazol-3-yl]benzoic acid (150 mg, 0.37 mmol, 1.00 equiv), cyclopropylamine (30 mg, 0.53 mmol, 1.50 equiv), HATU (210 mg, 0.55 mmol, 1.50 equiv), DIEA (80 mg, 0.62 mmol, 1.50 equiv) and N,N-dimethylformamide (15 mL). The resulting solution was stirred for 2 h at room temperature. The crude solution was purified by Prep-HPLC with the following conditions (Waters-2767): Column, SunFire Prep C18, 5 um, 19*150 mm; mobile phase: Water and $CH_3CN$ (30% $CH_3CN$ up to 80% in 25 min); Detector, UV 254 nm. This resulted in 75.7 mg (46%) of as a white solid. MS (ESI, m/z): 447 [M+H]$^+$; $^1$H NMR (300 MHz, DMSO-d$_6$, ppm) δ 8.58 (d, J=4.2 Hz, 1H), 7.95 (d, J=8.4 Hz, 2H), 7.84 (d, J=8.4 Hz, 2H), 7.16 (s, 1H), 4.63-4.43 (m, 2H), 4.06 (s, 3H), 2.95-2.81 (m, 1H), 0.79-0.67 (m, 2H), 0.66-0.55 (m, 2H).

Preparation Example 8

Compound 2-7 was prepared by coupling carboxylic acid 2-1G shown in Scheme 4 with cyclopropylamine.

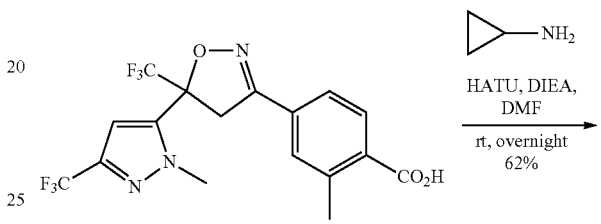

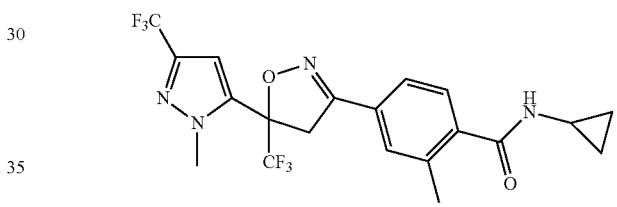

2-7

N-cyclopropyl-2-methyl-4-[5-[1-methyl-3-(trifluoromethyl)-1H-pyrazol-5-yl]-5-(trifluoromethyl)-4,5-dihydro-1,2-oxazol-3-yl]benzamide Into a 25-mL round-bottom flask, were placed cyclopropylamine (13.5 mg, 0.24 mmol, 1.00 equiv), 2-methyl-4-[5-[1-methyl-3-(trifluoromethyl)-1H-pyrazol-5-yl]-5-(trifluoromethyl)-4,5-dihydro-1,2-oxazol-3-yl]benzoic acid (100 mg, 0.24 mmol, 1.00 equiv), HATU (185 mg, 0.49 mmol, 2.00 equiv), DIEA (61 mg, 0.47 mmol, 2.00 equiv) and N,N-dimethylformamide (5 mL), and the resulting solution was stirred overnight at room temperature. The reaction mixture was diluted with 10 mL of EA. The resulting mixture was washed with 2×20 mL water of and 2×20 mL of brine. The organic phase was concentrated under vacuum and the residue was applied onto a silica gel column with ethyl acetate/petroleum ether (1:3). This resulted in 67.7 mg (62%) of N-cyclopropyl-2-methyl-4-[5-[1-methyl-3-(trifluoromethyl)-1H-pyrazol-5-yl]-5-(trifluoromethyl)-4,5-dihydro-1,2-oxazol-3-yl]benzamide as a light yellow solid. MS (ESI, m/z): 461[M+H]$^+$; $^1$H NMR (300 MHz, Chloroform-d, ppm) δ 7.53-7.51 (m, 2H), 7.41 (d, J=8.5 Hz, 1H), 6.67 (s, 1H), 5.87 (s, 1H), 4.16 (s, 3H), 4.13 (d, J=16.9 Hz, 1H), 3.86 (d, J=17.5 Hz, 1H), 2.99-2.86 (m, 1H), 2.50 (s, 3H), 1.00-0.86 (m, 2H), 0.70-0.56 (m, 2H).

Preparation Example 9

Compound 2-25 was prepared according to Scheme 6 shown below.

Scheme 6

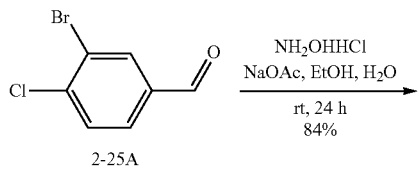

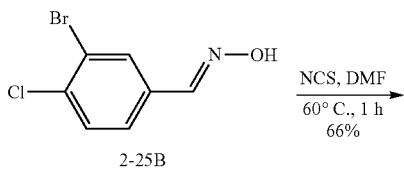

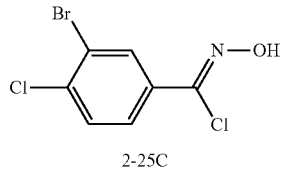

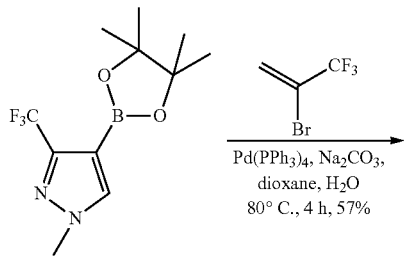

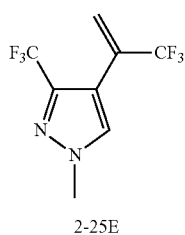

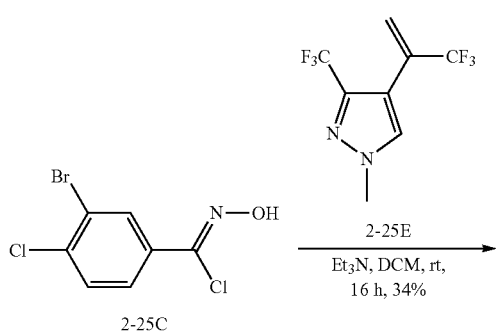

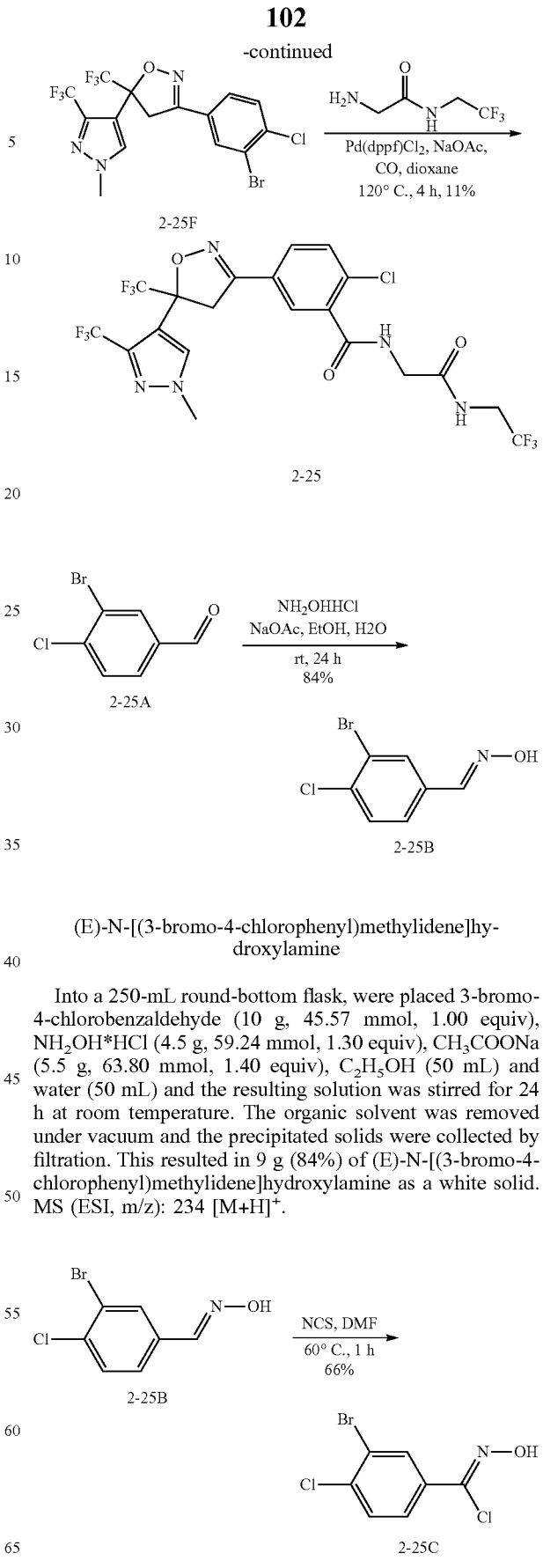

(E)-N-[(3-bromo-4-chlorophenyl)methylidene]hydroxylamine

Into a 250-mL round-bottom flask, were placed 3-bromo-4-chlorobenzaldehyde (10 g, 45.57 mmol, 1.00 equiv), $NH_2OH \cdot HCl$ (4.5 g, 59.24 mmol, 1.30 equiv), $CH_3COONa$ (5.5 g, 63.80 mmol, 1.40 equiv), $C_2H_5OH$ (50 mL) and water (50 mL) and the resulting solution was stirred for 24 h at room temperature. The organic solvent was removed under vacuum and the precipitated solids were collected by filtration. This resulted in 9 g (84%) of (E)-N-[(3-bromo-4-chlorophenyl)methylidene]hydroxylamine as a white solid. MS (ESI, m/z): 234 [M+H]$^+$.

3-bromo-4-chloro-N-hydroxybenzene-1-carbonimidoyl chloride

Into a 250-mL round-bottom flask were placed (E)-N-[(3-bromo-4-chlorophenyl)methylidene]hydroxylamine (10.5 g, 44.78 mmol, 1.00 equiv), NCS (8 g, 59.91 mmol, 1.20 equiv) and N,N-dimethylformamide (80 mL). The resulting solution was stirred for 1 h at 60° C. The reaction mixture was diluted with 150 ml of EA, and washed with 2×50 mL of water and 1×50 mL of brine. The organic phase was collected and dried over anhydrous sodium sulfate and concentrated under vacuum. The crude product was washed with hexane (50 mL). This resulted in 8 g (66%) of 3-bromo-4-chloro-N-hydroxybenzene-1-carbonimidoyl chloride as a white solid. MS (ESI, m/z): 268 [M+H]$^+$.

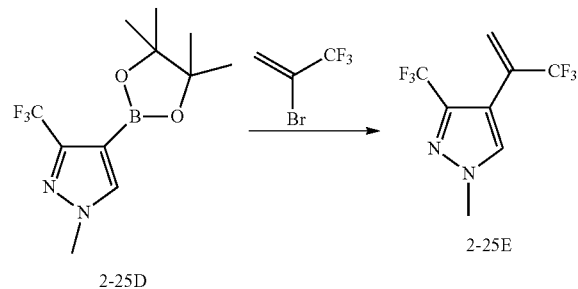

2-25D 2-25E

1-methyl-3-(trifluoromethyl)-4-(3,3,3-trifluoroprop-1-en-2-yl)-1H-pyrazole

Into a 500-mL 3-necked round-bottom flask purged and maintained with an inert atmosphere of nitrogen, were placed 1-methyl-4-(tetramethyl-1,3,2-dioxaborolan-2-yl)-3-(trifluoromethyl)-1H-pyrazole (12 g, 43.47 mmol, 1.00 equiv), 2-bromo-3,3,3-trifluoroprop-1-ene (30.26 g, 172.97 mmol, 3.98 equiv), Pd(PPh$_3$)$_4$ (5.02 g, 4.34 mmol, 0.10 equiv), sodium carbonate (18.43 g, 173.88 mmol, 4.00 equiv), dioxane (220 mL) and water (22 mL). The resulting solution was stirred for 4 h at 80° C. and then the solids were filtered out. The resulting mixture was concentrated under vacuum and the residue was applied onto a silica gel column with ethyl acetate/petroleum ether (¼). This resulted in 6 g (57%) of 1-methyl-3-(trifluoromethyl)-4-(3,3,3-trifluoroprop-1-en-2-yl)-1H-pyrazole as light yellow oil.

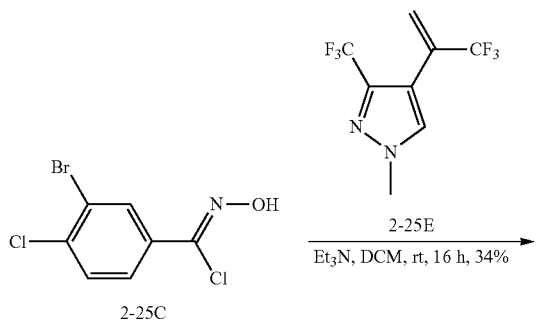

2-25C → 2-25E

Et$_3$N, DCM, rt, 16 h, 34%

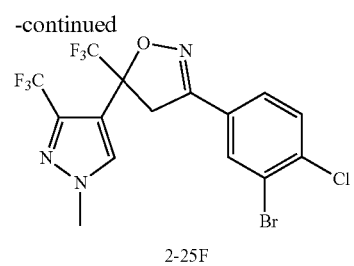

2-25F

3-(3-bromo-4-chlorophenyl)-5-[1-methyl-3-(trifluoromethyl)-1H-pyrazol-4-yl]-5-(trifluoromethyl)-4,5-dihydro-1,2-oxazole Into a 100-mL round-bottom flask, were placed 1-methyl-3-(trifluoromethyl)-4-(3,3,3-trifluoroprop-1-en-2-yl)-1H-pyrazole (1 g, 4.10 mmol, 1.00 equiv), (Z)-3-bromo-4-chloro-N-hydroxybenzene-1-carbonimidoyl chloride (1.31 g, 4.87 mmol, 1.19 equiv), dichloromethane (60 mL) and triethylamine (1.242 g, 12.27 mmol, 3.00 equiv). The resulting solution was stirred for 16 h at room temperature. The resulting mixture was concentrated under vacuum and the residue was applied onto a silica gel column with ethyl acetate/petroleum ether (⅓). This resulted in 670 mg (34%) of 3-(3-bromo-4-chlorophenyl)-5-[1-methyl-3-(trifluoromethyl)-1H-pyrazol-4-yl]-5-(trifluoromethyl)-4,5-dihydro-1,2-oxazole as light yellow oil.

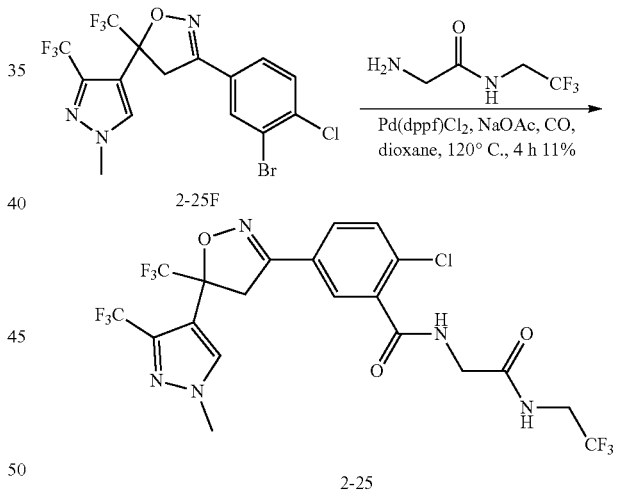

2-25F 2-25

2-[(2-chloro-5-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide Into a 50-mL pressure tank reactor were placed 3-(3-bromo-4-chlorophenyl)-5-[1-methyl-3-(trifluoromethyl)-1H-pyrazol-4-yl]-5-(trifluoromethyl)-4,5-dihydro-1,2-oxazole (200 mg, 0.42 mmol, 1.00 equiv), 2-amino-N-(2,2,2-trifluoroethyl)acetamide hydrochloride (323 mg, 1.68 mmol, 4.00 equiv), Pd(dppf)Cl$_2$ (93 mg, 0.13 mmol, 0.30 equiv), CH$_3$COONa (104 mg, 1.27 mmol, 3.02 equiv) and dioxane (15 mL). To this mixture was introduced CO (5 atm) and the resulting solution was stirred for 4 h at 120° C. The solids were filtered out. The filtrate was concentrated under vacuum. The crude product was purified by Flash-Prep-HPLC with the following conditions (IntelFlash-1): Column, C18 silica gel; mobile phase, H$_2$O and CH$_3$CN (33% CH$_3$CN increasing to 83% within 30 min; Detector, UV 254 nm, 220 nm. This resulted in 27 mg (11.097%) of 2-[(2-chloro-5-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide as a white solid. MS (ESI, m/z): 580 [M+H]$^+$; $^1$H NMR (300 MHz, CDCl$_3$, ppm) δ: 7.92 (s, 1H), 7.81 (d, J=8.4 Hz, 1H), 7.79 (s, 1H), 7.54 (d, J=8.4 Hz, 1H), 7.13 (s, 1H), 6.64 (s, 1H), 4.27 (br, 2H), 4.05-4.01 (m, 6H), 3.73 (d, J=17.2 Hz, 1H).

Preparation Example 10

Compound 2-14 was prepared in a similar manner to compound 2-25 as shown in Scheme 6 with the exception that compound 2-25C is reacted with compound 2-1D (see Scheme 4) to form the corresponding isoxazoline intermediate which is then converted to the methyl ester and then the carboxylic acid as shown in Scheme 7 below.

Scheme 7

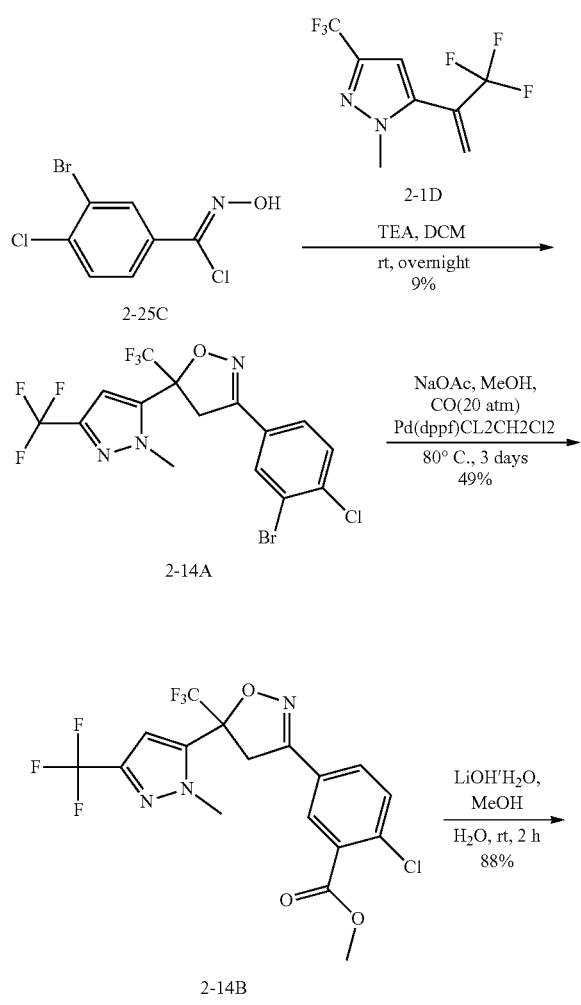

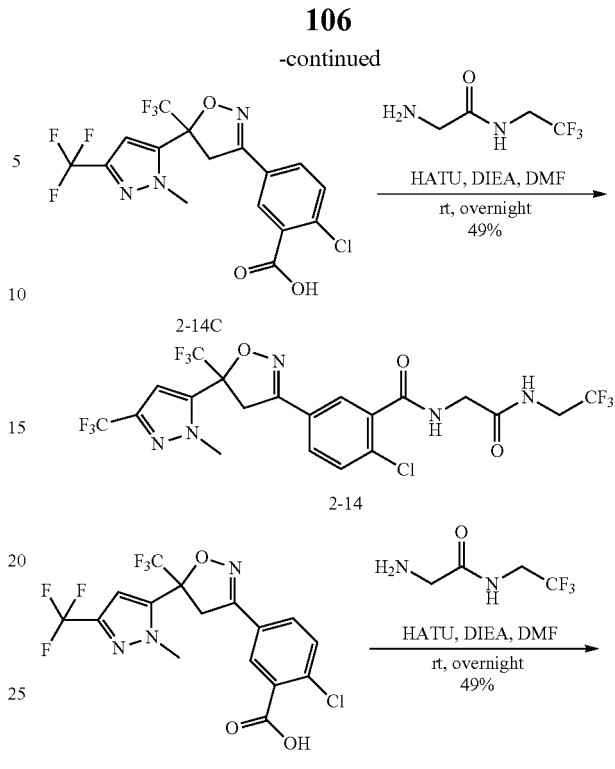

2-[(2-Chloro-5-[5-[1-methyl-3-(trifluoromethyl)-1H-pyrazol-5-yl]-5-(trifluoromethyl)-4,5-dihydro-1,2-oxazol-3-yl]phenyl)formamido]-N-(trifluoromethyl)acetamide Into a 50-mL round-bottom flask, was placed 2-chloro-5-[5-[1-methyl-3-(trifluoromethyl)-1H-pyrazol-5-yl]-5-(trifluoromethyl)-4,5-dihydro-1,2-oxazol-3-yl]benzoic acid (110 mg, 0.25 mmol, 1.00 equiv), 2-amino-N-(2,2,2-trifluoroethyl)acetamide (47 mg, 0.30 mmol, 1.20 equiv), HATU (142 mg, 0.37 mmol, 1.50 equiv), DIEA (48 mg, 0.37 mmol, 1.50 equiv), N,N-dimethylformamide (7 mL). The resulting solution was stirred overnight at room temperature. The crude product was purified by Prep-HPLC with the following conditions (Waters-2767): Column, SunFire Prep C18, 5 um, 19*150 mm; mobile phase: Water and CH$_3$CN (30% CH$_3$CN up to 85% in 30 min); Detector, UV 254 nm. This resulted in 68.6 mg (49%) of 2-[(2-chloro-5-[5-[1-methyl-3-(trifluoromethyl)-1H-pyrazol-5-yl]-5-(trifluoromethyl)-4,5-dihydro-1,2-oxazol-3-yl]phenyl)formamido]-N-(trifluoromethyl)acetamide as a white solid. MS (ESI, m/z): 580 [M+H]$^+$; $^1$H NMR (300 MHz, DMSO-d$_6$, ppm) δ: 8.84 (t, J=5.7 Hz, 1H), 8.64 (t, J=6.0 Hz, 1H), 7.87 (s, 1H), 7.82 (d, J=8.4 Hz, 1H), 7.69 (d, J=8.4 Hz, 1H), 7.16 (s, 1H), 4.59-4.45 (m, 2H), 4.05 (s, 3H), 4.00-3.91 (m, 4H).

Preparation Example 11

Compound 2-12 was prepared in a similar manner as compound 2-1 as shown in Scheme 4 with the exception that hydroxylamine compound 2-12C is used to form the isoxazoline compound bearing a phenyl ring with a 3-bromo-4-methyl substitution pattern as shown in Scheme 8. The isoxazoline compound is taken forward in the same manner as in Scheme 4 to the corresponding carboxylic acid 2-12F which is coupled with the required amine to form the product.

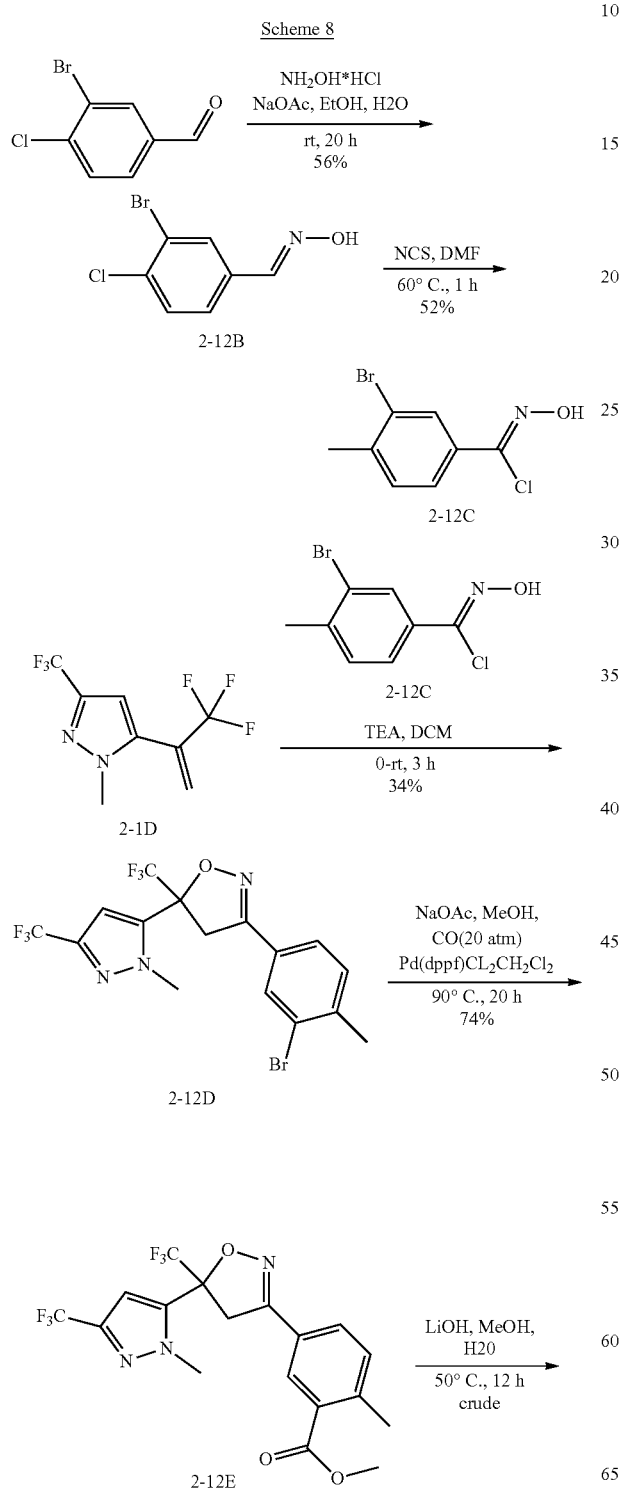

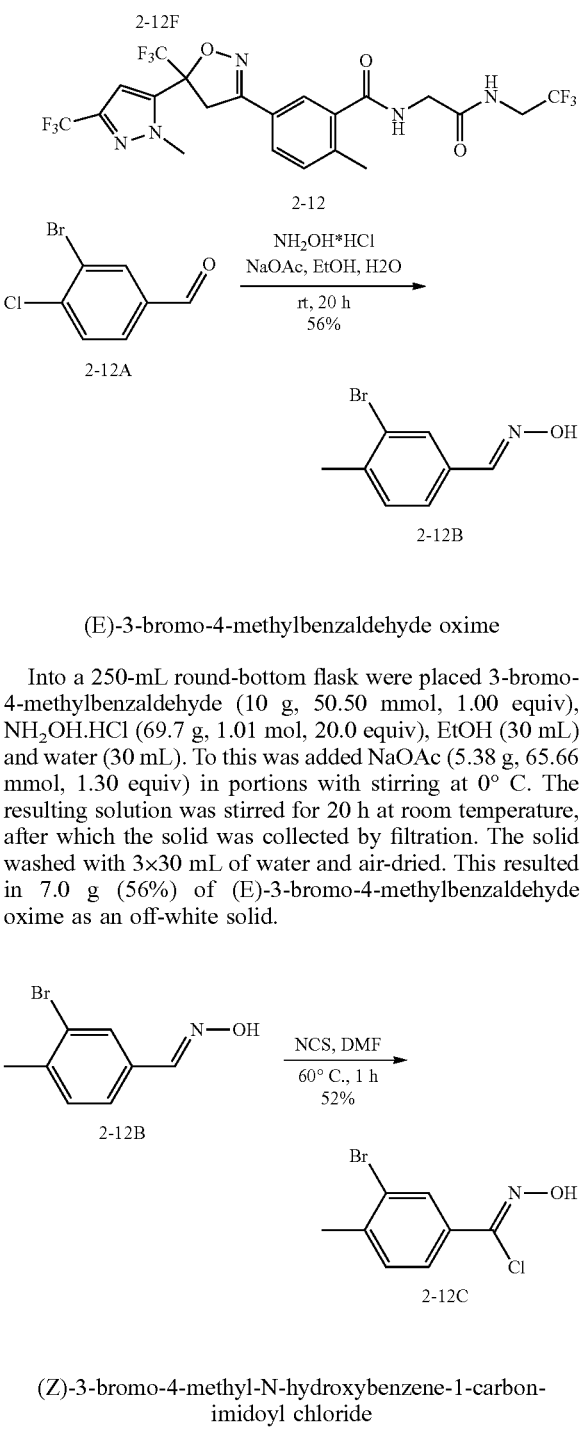

(E)-3-bromo-4-methylbenzaldehyde oxime

Into a 250-mL round-bottom flask were placed 3-bromo-4-methylbenzaldehyde (10 g, 50.50 mmol, 1.00 equiv), NH$_2$OH.HCl (69.7 g, 1.01 mol, 20.0 equiv), EtOH (30 mL) and water (30 mL). To this was added NaOAc (5.38 g, 65.66 mmol, 1.30 equiv) in portions with stirring at 0° C. The resulting solution was stirred for 20 h at room temperature, after which the solid was collected by filtration. The solid washed with 3×30 mL of water and air-dried. This resulted in 7.0 g (56%) of (E)-3-bromo-4-methylbenzaldehyde oxime as an off-white solid.

(Z)-3-bromo-4-methyl-N-hydroxybenzene-1-carbonimidoyl chloride

Into a 250-mL round-bottom flask were placed (E)-3-bromo-4-methylbenzaldehyde oxime (7.0 g, 32.9 mmol, 1.00 equiv), NCS (6.56 g, 49.3 mmol, 1.50 equiv) and N,N-dimethylformamide (30 mL). The resulting solution was stirred for 1 h at 60° C. The reaction mixture was diluted with 10 ml of water, then extracted with 2×5 mL of ethyl acetate. The organic layers were combined and washed with brine and concentrated under vacuum. This resulted in 4.22 g (52%) of (Z)-3-bromo-4-methyl-N-hydroxybenzene-1-carbonimidoyl chloride as a white solid.

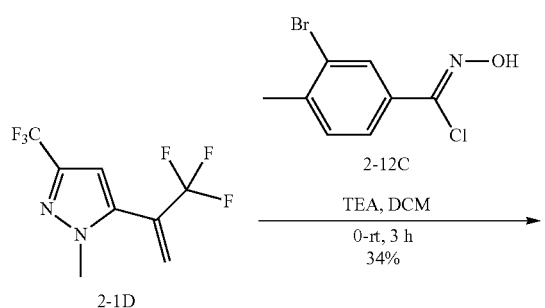

3-(3-Bromo-4-methylphenyl)-5-[1-methyl-3-(trifluoromethyl)-1H-pyrazol-5-yl]-5-(trifluoromethyl)-4,5-dihydro-1,2-oxazole Into a 40-mL vial were placed dichloromethane (24 mL), (Z)-3-bromo-N-hydroxy-4-methylbenzene-1-carbonimidoyl chloride (1.2 g, 4.83 mmol, 1.00 equiv) and 1-methyl-3-(trifluoromethyl)-5-(3,3,3-trifluoroprop-1-en-2-yl)-1H-pyrazole (1.1 g, 4.51 mmol, 0.90 equiv). This was followed by the addition of TEA (0.98 g, 9.66 mmol, 2.00 equiv) at 0° C. The resulting solution was stirred for 3 h at room temperature. The solid was filtered out and the filtrate was concentrated under vacuum. The residue was applied onto a silica gel column with ethyl acetate/petroleum ether (1:5). This resulted in 750 mg (34%) of 3-(3-bromo-4-methylphenyl)-5-[1-methyl-3-(trifluoromethyl)-1H-pyrazol-5-yl]-5-(trifluoromethyl)-4,5-dihydro-1,2-oxazole as yellow oil. MS (ESI, m/z): 456 [M+H]$^+$.

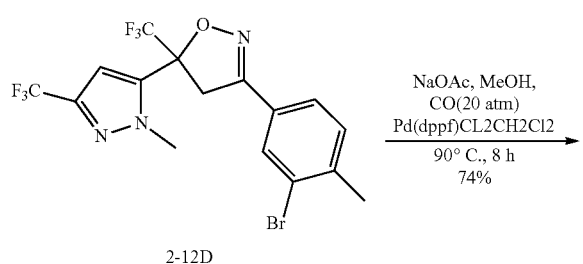

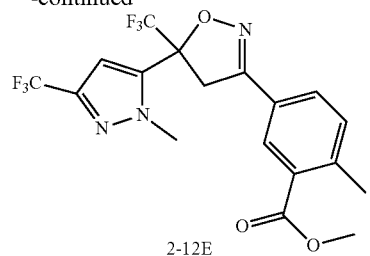

Methyl 2-methyl-5-[5-[1-methyl-3-(trifluoromethyl)-1H-pyrazol-5-yl]-5-(trifluoromethyl)-4,5-dihydro-1,2-oxazol-3-yl]benzoate Into a 50-mL pressure tank reactor (20 atm) purged and maintained with an atmosphere of CO (20 atm), was placed methanol (6 mL), 3-(3-bromo-4-methylphenyl)-5-[1-methyl-3-(trifluoromethyl)-1H-pyrazol-5-yl]-5-(trifluoromethyl)-4,5-dihydro-1,2-oxazole (270 mg, 0.59 mmol, 1.00 equiv), NaOAc (146 mg, 1.77 mmol, 3.00 equiv) and Pd(dppf)Cl$_2$CH$_2$Cl$_2$ (48.5 mg, 0.06 mmol, 0.10 equiv). The resulting solution was stirred for 8 h at 90° C. The solids were filtered out and the filtrate was concentrated under vacuum. The residue was applied onto a silica gel column with ethyl acetate/petroleum ether (1:7). This resulted in 190 mg (74%) of methyl 2-methyl-5-[5-[1-methyl-3-(trifluoromethyl)-1H-pyrazol-5-yl]-5-(trifluoromethyl)-4,5-dihydro-1,2-oxazol-3-yl]benzoate as a yellow solid. MS (ESI, m/z): 436 [M+H]$^+$.

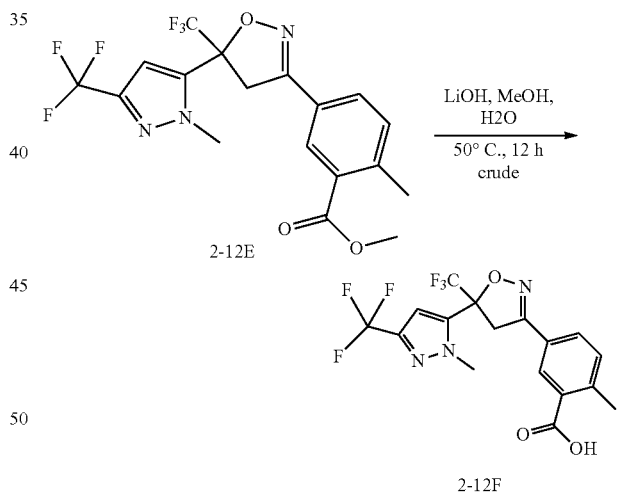

2-Methyl-5-[5-[1-methyl-3-(trifluoromethyl)-1H-pyrazol-5-yl]-5-(trifluoromethyl)-4,5-dihydro-1,2-oxazol-3-yl]benzoic acid Into a 50-mL round-bottom flask were placed methyl 2-methyl-5-[5-[1-methyl-3-(trifluoromethyl)-1H-pyrazol-5-yl]-5-(trifluoromethyl)-4,5-dihydro-1,2-oxazol-3-yl]benzoate (190 mg, 0.44 mmol, 1.00 equiv), water (10 mL), methanol (10 mL) and LiOH (210 mg, 20.00 equiv). The resulting solution was stirred for 12 h at 50° C. The organic solvent was removed under vacuum and the pH value of the resulting solution was adjusted to 4 with hydrogen chloride (6 mol/L). The resulting solution was extracted with 3×50 mL of ethyl acetate and the organic layers combined and dried over anhydrous sodium sulfate and concentrated under vacuum. This resulted in 200 mg (crude) of 2-methyl-5-[5-[1-methyl-3-(trifluoromethyl)-1H-pyrazol-5-yl]-5-(trifluoromethyl)-4,5-dihydro-1,2-oxazol-3-yl]benzoic acid as a yellow solid. MS (ESI, m/z): 422 [M+H]$^+$.

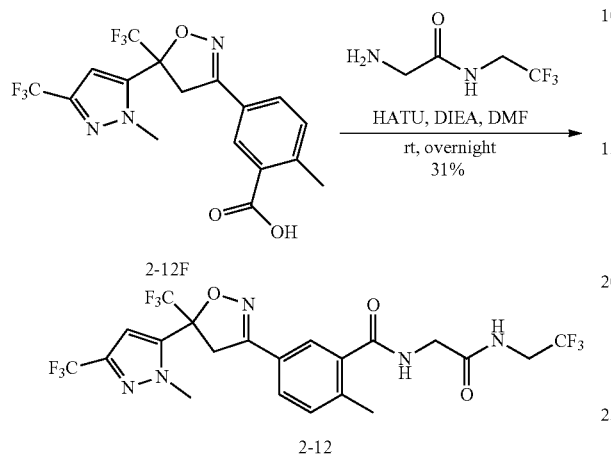

2-[(2-Methyl-5-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl)acetamide Into a 40-mL vial were placed N,N-dimethylformamide (4 mL), 2-methyl-5-[5-[1-methyl-3-(trifluoromethyl)-1H-pyrazol-5-yl]-5-(trifluoromethyl)-4,5-dihydro-1,2-oxazol-3-yl] benzoic acid (175 mg, 0.42 mmol, 1.00 equiv), 2-amino-N-(2,2,2-trifluoroethyl)acetamide (65 mg, 0.42 mmol, 1.00 equiv) and HATU (237 mg, 1.50 equiv). This was followed by the addition of DIEA (80 mg, 1.50 equiv) at room temperature. The resulting solution was stirred overnight at room temperature. The crude product was purified by Prep-HPLC with the following conditions (Waters-2767): Column, SunFire Prep C18, 5 um, 19*150 mm; mobile phase: Water and CH$_3$CN (35% CH$_3$CN up to 65% in 25 min); Detector, UV 254 nm. This resulted in 71.3 mg (31%) of 2-[(2-methyl-5-[5-[1-methyl-3-(trifluoromethyl)-1H-pyrazol-5-yl]-5-(trifluoromethyl)-4,5-dihydro-1,2-oxazol-3-yl] phenyl)formamido]-N-(2,2,2-trifluoroethyl)acetamide as a white solid. MS (ESI, m/z): 560 [M+H]$^+$; $^1$H NMR (300 MHz, DMSO-d, ppm) δ 8.64 (t, J=6.0 Hz, 2H), 7.78 (s, 1H), 7.72 (d, J=7.5 Hz, 1H), 7.41 (d, J=8.4 Hz, 1H), 7.16 (s, 1H), 4.47 (s, 2H), 4.05 (s, 3H), 4.02-3.90 (m, 4H), 2.42 (s, 3H).

Preparation Example 12

Compound 2-22 was prepared in a similar manner as Compound 2-9 as shown in Scheme 5 except vinylpyrazole Compound 2-25E (see Scheme 6) was used to form the isoxazoline ring instead of vinylpyrazole Compound 2-1D. The methyl ester was hydrolyzed to form the corresponding carboxylic acid 2-22A which was coupled to the amine as shown below to form the product.

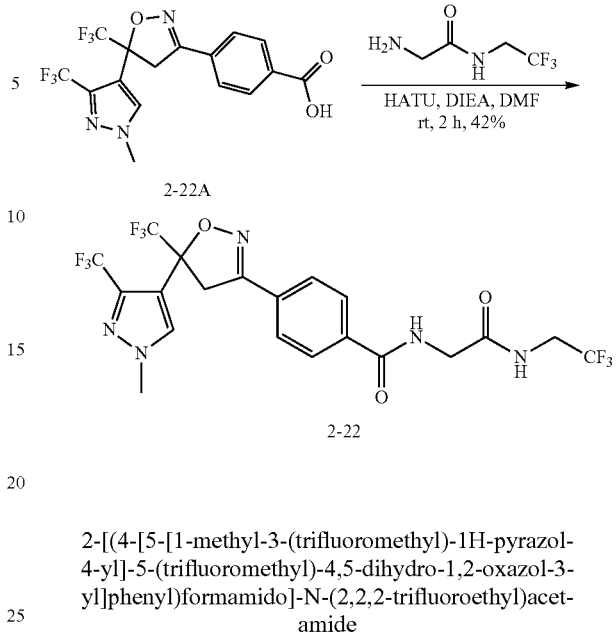

2-[(4-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide Into a 50-mL round-bottom flask were placed N,N-dimethylformamide (5 mL), 4-[5-[1-methyl-3-(trifluoromethyl)-1H-pyrazol-4-yl]-5-(trifluoromethyl)-4,5-dihydro-1,2-oxazol-3-yl]benzoic acid (150 mg, 0.37 mmol, 1.00 equiv), 2-amino-N-(2,2,2-trifluoroethyl)acetamide (120 mg, 0.77 mmol, 2.09 equiv), HATU (400 mg, 1.05 mmol, 2.86 equiv) and DIEA (200 mg, 1.55 mmol, 4.20 equiv). The resulting solution was stirred for 2 h at room temperature. The crude product was purified by Flash-Prep-HPLC with the following conditions (IntelFlash-1): Column, C18 silica gel; mobile phase, H$_2$O:CH$_3$CN=100:0 increasing to H$_2$O:CH$_3$CN=40:60 within 20 min; Detector, UV 254 nm. This resulted in 84.3 mg (42%) of 2-[(4-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide as a white solid. MS (ESI, m/z): 545 [M+H]$^+$; $^1$H NMR (300 MHz, CDCl$_3$, ppm) δ 7.90 (d, J=8.4 Hz, 2H), 7.77-7.84 (m, 3H), 7.27-7.17 (brs, 1H), 6.96 (brs, 1H), 4.26-4.25 (m, 2H), 4.06-3.95 (m, 6H), 3.79-3.70 (m, 1H).

Preparation Example 13

Compound 2-23 was prepared by coupling carboxylic acid 2-22A with cyclopropyl amine as shown below.

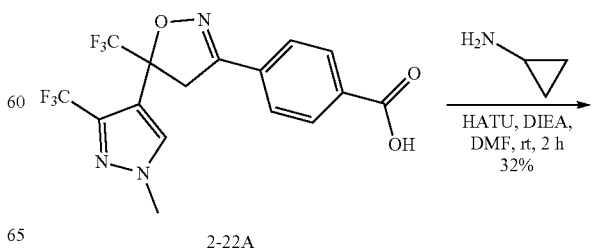

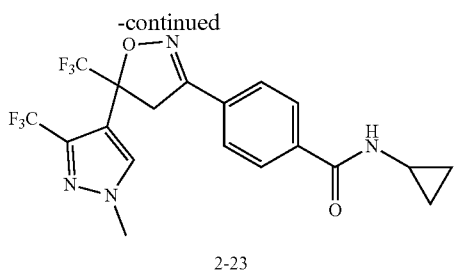

2-23

N-cyclopropyl-4-[5-[1-methyl-3-(trifluoromethyl)-1H-pyrazol-4-yl]-5-(trifluoromethyl)-4,5-dihydro-1,2-oxazol-3-yl]benzamide Into a 50-mL round-bottom flask were placed N,N-dimethylformamide (5 mL), 4-[5-[1-methyl-3-(trifluoromethyl)-1H-pyrazol-4-yl]-5-(trifluoromethyl)-4,5-dihydro-1,2-oxazol-3-yl]benzoic acid (150 mg, 0.37 mmol, 1.00 equiv), HATU (400 mg, 1.05 mmol, 2.86 equiv), DIEA (250 mg, 1.93 mmol, 5.25 equiv) and cyclopropanamine (70 mg, 1.23 mmol, 3.33 equiv). The resulting solution was stirred for 2 h at room temperature. The resulting mixture was concentrated under vacuum and the crude product was purified by Flash-Prep-HPLC with the following conditions (IntelFlash-1): Column, C18 silica gel; mobile phase, H$_2$O:CH$_3$CN=100:0 increasing to H$_2$O:CH$_3$CN=40:60 within 20 min; Detector, UV 254 nm. This resulted in 51.9 mg (32%) of N-cyclopropyl-4-[5-[1-methyl-3-(trifluoromethyl)-1H-pyrazol-4-yl]-5-(trifluoromethyl)-4,5-dihydro-1,2-oxazol-3-yl]benzamide as a white solid. MS (ESI, m/z): 476 [M+H]$^+$; $^1$H NMR (300 MHz, Chloroform-d, ppm) δ 7.82 (d, J=8.3 Hz, 2H), 7.79-7.71 (m, 3H), 6.26 (brs, 1H), 4.03 (d, J=17.7 Hz, 1H), 4.00 (s, 3H), 3.76 (d, J=17.6 Hz, 1H), 3.04-2.87 (m, 1H), 1.01-0.86 (m, 2H), 0.77-0.63 (m, 2H).

Preparation Example 14

Compound 2-13 was prepared by coupling carboxylic acid 2-12F (see Scheme 8) with cyclopropylamine.

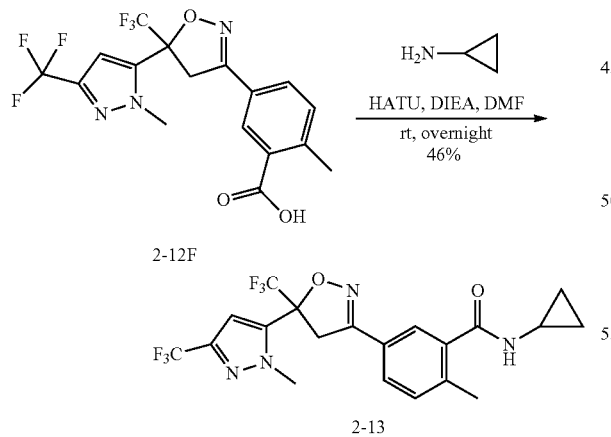

2-12F 2-13

N-cyclopropyl-2-methyl-5-[5-[1-methyl-3-(trifluoromethyl)-1H-pyrazol-5-yl]-5-(trifluoromethyl)-4,5-dihydro-1,2-oxazol-3-yl]benzamide Into a 40-mL vial were placed N,N-dimethylformamide (4 mL), 2-methyl-5-[5-[1-methyl-3-(trifluoromethyl)-1H-pyrazol-5-yl]-5-(trifluoromethyl)-4,5-dihydro-1,2-oxazol-3-yl]benzoic acid (175 mg, 0.42 mmol, 1.00 equiv), cyclopropanamine (24 mg, 0.42 mmol, 1.00 equiv) and HATU (237 mg, 0.63 mmol, 1.50 equiv). To this was added DIEA (80 mg, 0.63 mmol, 1.50 equiv) dropwise at room temperature. The resulting solution was stirred overnight at room temperature. The crude product was purified by Flash-Prep-HPLC with the following conditions (CombiFlash-1): Column, C18 silica gel; mobile phase, CH$_3$CN:H$_2$O=35:65 increasing to CH$_3$CN:H$_2$O=65:35 within 25 min; Detector, UV 220 nm. This resulted in 87.6 mg (46%) of N-cyclopropyl-2-methyl-5-[5-[1-methyl-3-(trifluoromethyl)-1H-pyrazol-5-yl]-5-(trifluoromethyl)-4,5-dihydro-1,2-oxazol-3-yl]benzamide as a white solid. MS (ESI, m/z): 461 [M+H]$^+$; $^1$H NMR (300 MHz, DMSO-d$_6$, ppm): δ 8.40 (d, J=4.2 Hz, 1H), 7.71 (d, J=8.4 Hz, 1H), 7.64 (s, 1H), 7.39 (d, J=8.1 Hz, 1H), 7.16 (s, 1H), 4.47 (s, 2H), 4.05 (s, 3H), 2.87-2.80 (m, 1H), 2.37 (s, 3H), 0.74-0.68 (m, 2H), 0.56-0.51 (m, 2H).

Preparation Example 15

Compound 2-29 was prepared from intermediate 2-25F (see Scheme 6) by coupling with cyclopropyl amine in the presence of a palladium catalyst.

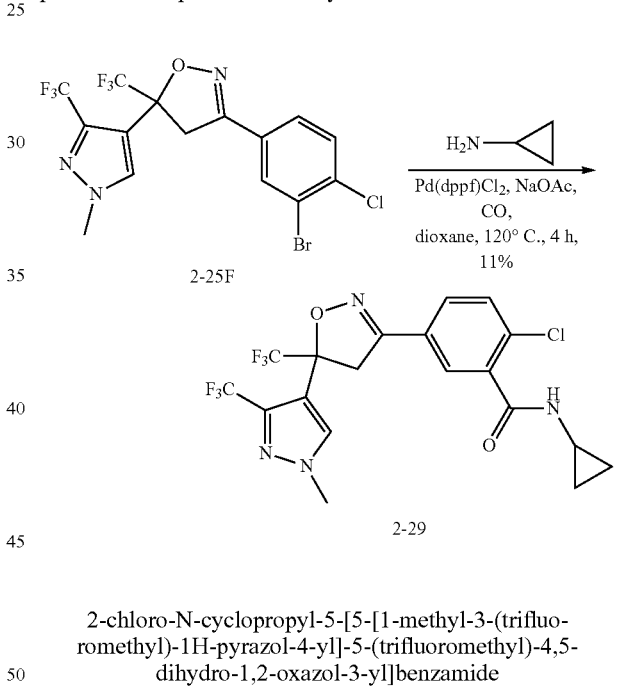

2-25F 2-29

2-chloro-N-cyclopropyl-5-[5-[1-methyl-3-(trifluoromethyl)-1H-pyrazol-4-yl]-5-(trifluoromethyl)-4,5-dihydro-1,2-oxazol-3-yl]benzamide Into a 50-mL pressure tank reactor were placed 3-(3-bromo-4-chlorophenyl)-5-[1-methyl-3-(trifluoromethyl)-1H-pyrazol-4-yl]-5-(trifluoromethyl)-4,5-dihydro-1,2-oxazole (200 mg, 0.42 mmol, 1.00 equiv), cyclopropylamine (96 mg, 1.68 mmol, 4.01 equiv), Pd(dppf)Cl$_2$ (96 mg, 0.13 mmol, 0.31 equiv), CH$_3$COONa (104 mg), dioxane (15 mL). To this mixture was introduced CO (5 atm). The resulting solution was stirred for 4 h at 120° C. The solids were filtered out and the filtrate was concentrated under vacuum. The crude product was purified by Flash-Prep-HPLC with the following conditions (IntelFlash-1): Column, C18 silica gel; mobile phase, H$_2$O and CH$_3$CN (33% CH$_3$CN increasing to 80% within 30 min); Detector, UV 254 nm, 220 nm. This resulted in 30.9 mg (15%) of 2-chloro-N-cyclopropyl-5-[5-[1-methyl-3-(trifluoromethyl)-1H-pyrazol-4-yl]-5-(trifluoromethyl)-4,5-dihydro-1,2-oxazol-3-yl]benzamide as a white solid. MS (ESI, m/z): 481 [M+H]+; 1H NMR (300 MHz, Chloroform-d, ppm) δ 7.88 (d, J=2.1 Hz, 1H), 7.80-7.72 (m, 2H), 7.48 (d, J=8.4 Hz, 1H), 6.34 (s, 1H), 4.09-3.95 (m, 4H), 3.73 (d, J=17.7 Hz, 1H), 3.04-2.90 (m, 1H), 0.96-0.89 (m, 2H), 0.75-0.64 (m, 2H).

Preparation Example 16

Compound 2-10 was prepared by coupling intermediate carboxylic acid 2-14C with cyclopropylamine as shown below.

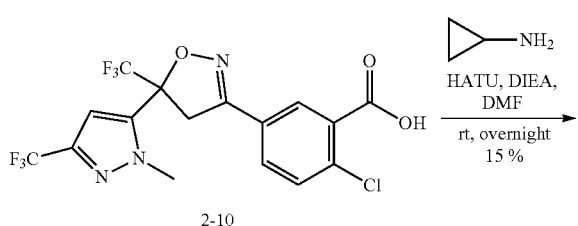

2-Chloro-N-cyclopropyl-5-[5-[1-methyl-3-(trifluoromethyl)-1H-pyrazol-5-yl]-5-(trifluoromethyl)-4,5-dihydro-1,2-oxazol-3-yl]benzamide Into a 50-mL round-bottom flask were placed 2-chloro-5-[5-[1-methyl-3-(trifluoromethyl)-1H-pyrazol-5-yl]-5-(trifluoromethyl)-4,5-dihydro-1,2-oxazol-3-yl]benzoic acid (110 mg, 0.25 mmol, 1.00 equiv), N,N-dimethylformamide (7 mL), cyclopropylamine (17 mg, 0.30 mmol, 1.20 equiv), HATU (142 mg, 0.37 mmol, 1.50 equiv) and DIEA (48 mg, 0.37 mmol, 1.50 equiv). The resulting solution was stirred overnight at room temperature. The crude product was purified by Prep-HPLC with the following conditions (Waters-2767): Column, SunFire Prep C18, 5 um, 19*150 mm; mobile phase: Water and CH3CN (30% CH3CN up to 85% in 30 min); Detector, UV 254 nm. This resulted in 17.5 mg (15%) of 2-chloro-N-cyclopropyl-5-[5-[1-methyl-3-(trifluoromethyl)-1H-pyrazol-5-yl]-5-(trifluoromethyl)-4,5-dihydro-1,2-oxazol-3-yl]benzamide as a white solid. MS (ESI, m/z): 481 [M+H]+; 1H NMR (300 MHz, DMSO, ppm) δ: 8.60 (s, 1H), 7.81 (d, J=7.8 Hz, 1H), 7.75 (s, 1H), 7.66 (d, J=7.8 Hz, 1H), 7.15 (s, 1H), 4.54-4.50 (m, 2H), 4.05 (s, 1H), 2.90-2.75 (m, 1H), 0.73-0.71 (m, 2H), 0.54-0.45 (m, 2H).

Preparation Example 17

Compound 2-26 was prepared as shown in Scheme 9 shown below.

Scheme 9

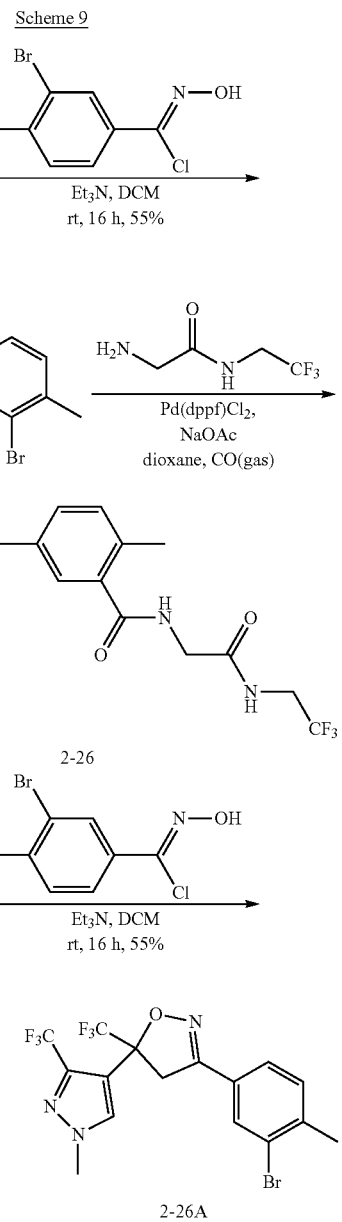

3-(3-bromo-4-methylphenyl)-5-[1-methyl-3-(trifluoromethyl)-1H-pyrazol-4-yl]-5-(trifluoromethyl)-4,5-dihydro-1,2-oxazole Into a 250-mL round-bottom flask were placed 1-methyl-3-(trifluoromethyl)-4-(3,3,3-trifluoroprop-1-en-2-yl)-1H-pyrazole (1 g, 4.10 mmol, 1.00 equiv), (Z)-3-bromo-N-hydroxy-4-methylbenzene-1-carbonimidoyl chloride (1.215 g, 4.89 mmol, 1.19 equiv), dichloromethane (60 mL) and triethylamine (1.242 g, 12.27 mmol, 3.00 equiv). The resulting solution was stirred for 16 h at room temperature. The resulting mixture was concentrated under vacuum and the residue was applied onto a silica gel column with ethyl acetate/petroleum ether (⅓). This resulted in 1.02 g (55%) of 3-(3-bromo-4-methylphenyl)-5-[1-methyl-3-(trifluoromethyl)-1H-pyrazol-4-yl]-5-(trifluoromethyl)-4,5-dihydro-1,2-oxazole as a light yellow solid.

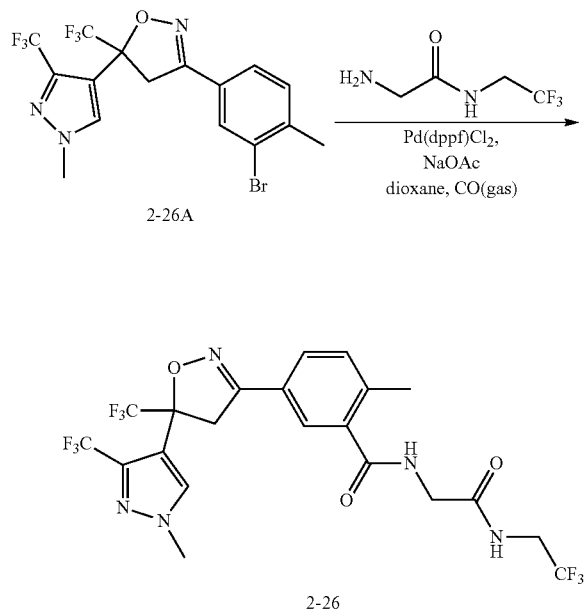

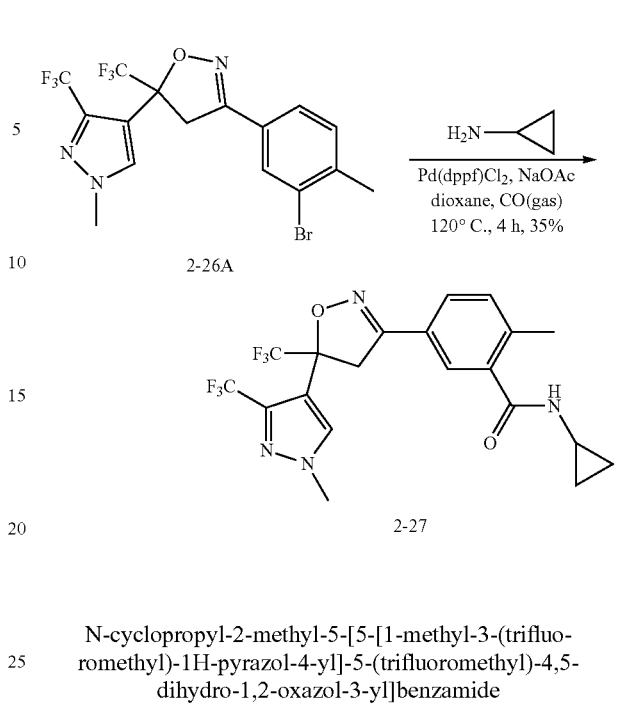

2-[(2-methyl-5-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide Into a 50-mL pressure tank reactor were placed 3-(3-bromo-4-methylphenyl)-5-[1-methyl-3-(trifluoromethyl)-1H-pyrazol-4-yl]-5-(trifluoromethyl)-4,5-dihydro-1,2-oxazole (200 mg, 0.44 mmol, 1.00 equiv), 2-amino-N-(2,2,2-trifluoroethyl)acetamide hydrochloride (338 mg, 1.76 mmol, 4.00 equiv), Pd(dppf)Cl$_2$ (32 mg, 0.04 mmol, 0.10 equiv), AcONa (108 mg, 1.32 mmol, 3.00 equiv) and dioxane (15 mL). To this solution CO (5 atm) was introduced. The resulting solution was stirred for 4 h at 120° C. after which the solids were filtered out. The filtrate was concentrated under vacuum and the crude product was purified by Flash-Prep-HPLC with the following conditions (IntelFlash-1): Column, C18 silica gel; mobile phase, H$_2$O/CH$_3$CN=5:1 increasing to H$_2$O/CH$_3$CN=1:5 within 30 min; Detector, UV 254, 220 nm. This resulted in 75.9 mg (31%) of 2-[(2-methyl-5-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide as a white solid. MS (ESI, m/z): 560 [M+H]*; $^1$H NMR (300 MHz, CDCl$_3$, ppm) δ: 7.76 (br, 2H), 7.65 (d, J=7.6 Hz, 1H), 7.34 (d, J=7.9 Hz, 1H), 6.74 (brs, 1H), 6.68 (brs, 1H), 4.22 (br, 2H), 4.00 (br, 6H), 3.76-3.71 (m, 1H), 2.51 (s, 3H).

Preparation Example 18

Compound 2-27 was prepared by coupling intermediate 2-26A with cyclopropylamine as shown below.

N-cyclopropyl-2-methyl-5-[5-[1-methyl-3-(trifluoromethyl)-1H-pyrazol-4-yl]-5-(trifluoromethyl)-4,5-dihydro-1,2-oxazol-3-yl]benzamide Into a 50-mL pressure tank reactor purged and maintained with an atmosphere of CO, were placed 3-(3-bromo-4-methylphenyl)-5-[1-methyl-3-(trifluoromethyl)-1H-pyrazol-4-yl]-5-(trifluoromethyl)-4,5-dihydro-1,2-oxazole (200 mg, 0.44 mmol, 1.00 equiv), cyclopropylamine (100 mg, 1.75 mmol, 3.99 equiv), Pd(dppf)Cl$_2$ (32 g, 43.73 mmol, 99.75 equiv), AcONa (108 mg, 1.32 mmol, 3.00 equiv) and dioxane (15 mL). To this solution CO was introduced. The resulting solution was stirred for 4 h at 120° C. The solids were filtered out and the filtrate was concentrated under vacuum. The crude product was purified by Flash-Prep-HPLC with the following conditions (IntelFlash-1): Column, C18; mobile phase, H$_2$O and CH$_3$CN (16% CH$_3$CN increasing to 85% within 40 min); Detector, UV 254 nm. This resulted in 70 mg (35%) of N-cyclopropyl-2-methyl-5-[5-[1-methyl-3-(trifluoromethyl)-1H-pyrazol-4-yl]-5-(trifluoromethyl)-4,5-dihydro-1,2-oxazol-3-yl]benzamide as a white solid. MS (ESI, m/z): 461 [M+H]$^+$; $^1$H NMR (300 MHz, Chloroform-d, ppm) δ 7.76 (brs, 1H), 7.68 (brs, 1H), 7.56 (d, J=7.4 Hz, 1H), 7.32-7.29 (m, 1H), 6.09-5.84 (m, 1H), 4.09-3.91 (m, 3H), 3.88-3.64 (m, 1H), 3.06-2.85 (m, 1H), 1.02-0.85 (m, 2H), 0.75-0.60 (m, 2H).

Preparation Example 19

Compound 2-11 was prepared according to Scheme 10 below.

Scheme 10

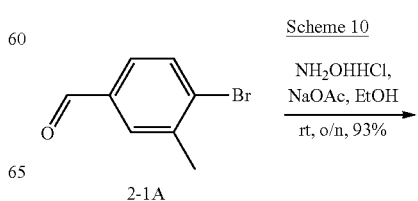

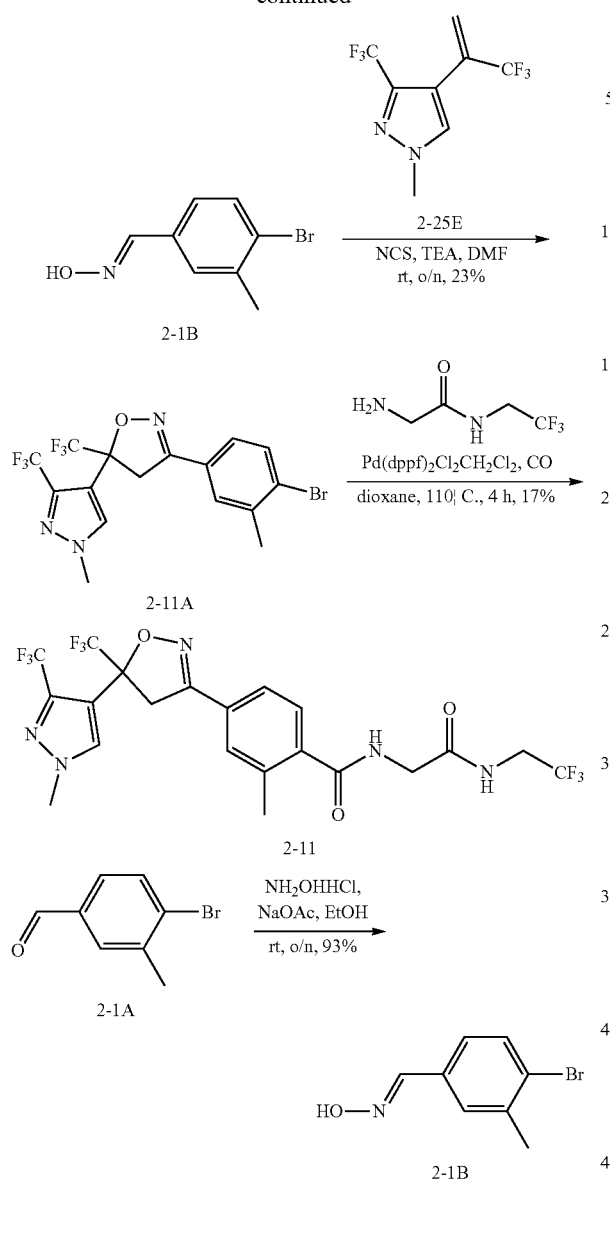

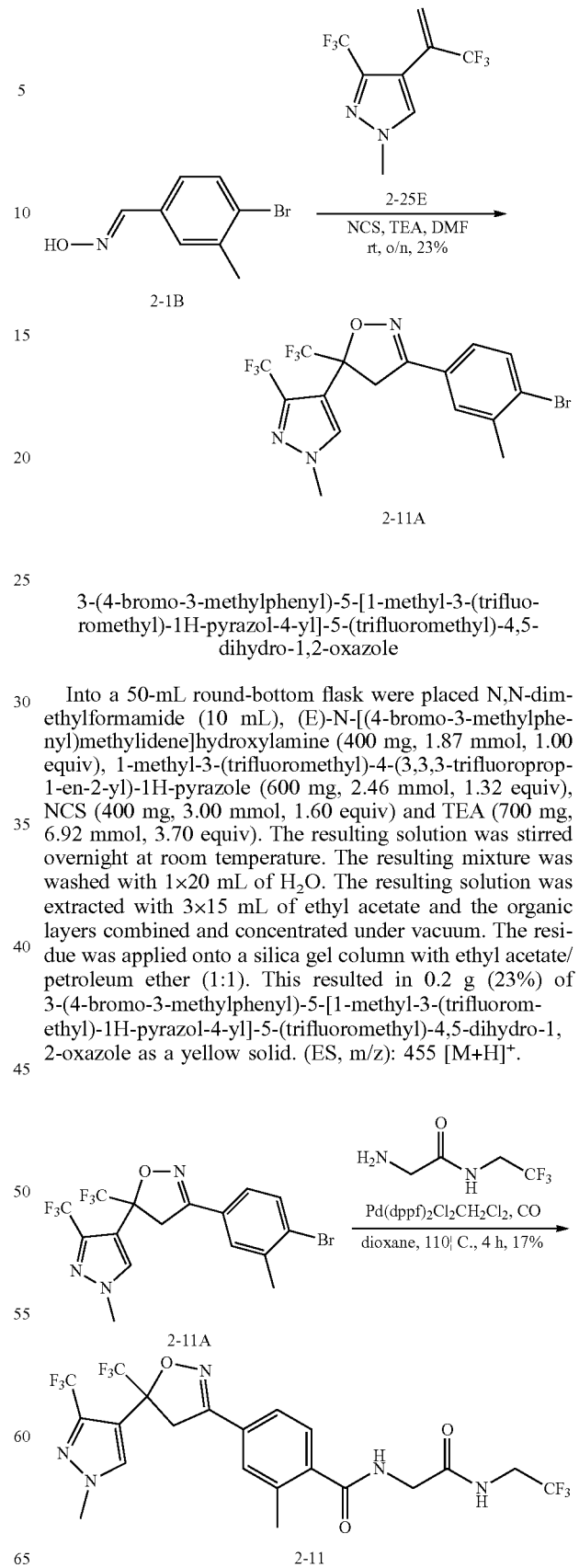

(E)-N-[(4-bromo-3-methylphenyl)methylidene]hydroxylamine

Into a 500-mL round-bottom flask were placed water (30 mL), ethanol (150 mL), 4-bromo-3-methylbenzaldehyde (10 g, 50.24 mmol, 1.00 equiv), $NH_2OH \cdot HCl$ (6 g) and $CH_3COONa$ (9 g). The resulting solution was stirred overnight at room temperature. The resulting mixture was concentrated under vacuum. The solids were collected by filtration. This resulted in 10 g (93%) of (E)-N-[(4-bromo-3-methylphenyl)methylidene]hydroxylamine as a white solid. (ES, m/z): 213 $[M+H]^+$.

3-(4-bromo-3-methylphenyl)-5-[1-methyl-3-(trifluoromethyl)-1H-pyrazol-4-yl]-5-(trifluoromethyl)-4,5-dihydro-1,2-oxazole Into a 50-mL round-bottom flask were placed N,N-dimethylformamide (10 mL), (E)-N-[(4-bromo-3-methylphenyl)methylidene]hydroxylamine (400 mg, 1.87 mmol, 1.00 equiv), 1-methyl-3-(trifluoromethyl)-4-(3,3,3-trifluoroprop-1-en-2-yl)-1H-pyrazole (600 mg, 2.46 mmol, 1.32 equiv), NCS (400 mg, 3.00 mmol, 1.60 equiv) and TEA (700 mg, 6.92 mmol, 3.70 equiv). The resulting solution was stirred overnight at room temperature. The resulting mixture was washed with 1×20 mL of $H_2O$. The resulting solution was extracted with 3×15 mL of ethyl acetate and the organic layers combined and concentrated under vacuum. The residue was applied onto a silica gel column with ethyl acetate/petroleum ether (1:1). This resulted in 0.2 g (23%) of 3-(4-bromo-3-methylphenyl)-5-[1-methyl-3-(trifluoromethyl)-1H-pyrazol-4-yl]-5-(trifluoromethyl)-4,5-dihydro-1,2-oxazole as a yellow solid. (ES, m/z): 455 $[M+H]^+$.

2-[(2-methyl-4-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide Into a 50-mL pressure tank reactor were placed NaOAc (120 mg), 3-(4-bromo-3-methylphenyl)-5-[1-methyl-3-(trifluoromethyl)-1H-pyrazol-4-yl]-5-(trifluoromethyl)-4,5-dihydro-1,2-oxazole (200 mg, 0.44 mmol, 1.00 equiv), 2-amino-N-(2,2,2-trifluoroethyl)acetamide (120 mg, 0.77 mmol, 1.62 equiv), Pd(dppf)Cl$_2$CH$_2$Cl$_2$ (110 mg, 0.15 mmol, 0.32 equiv) and dioxane (15 mL). To this mixture was introduced CO (20 atm). The reaction mixture was stirred for 4 h at 110° C. The resulting mixture was concentrated under vacuum and the crude product was purified by Flash-Prep-HPLC with the following conditions (IntelFlash-1): Column, C18 silica gel; mobile phase, H$_2$O:ACN=100:0 increasing to H$_2$O:ACN=40:60 within 20 min; Detector, UV 254 nm. This resulted in 41.9 mg (17%) of 2-[(2-methyl-4-[5-[1-methyl-3-(trifluoromethyl)-1H-pyrazol-4-yl]-5-(trifluoromethyl)-4,5-dihydro-1,2-oxazol-3-yl]phenyl)formamido]-N-(2,2,2-trifluoroethyl)acetamide as a white solid. MS (ESI, m/z): 560 [M+H]$^+$; $^1$H NMR (300 MHz, CDCl$_3$, ppm) δ: 7.70 (s, 1H), 7.63 (s, 1H), 7.56-7.50 (m, 2H), 6.75-6.72 (m, 1H), 6.68-6.59 (m, 1H), 4.21 (br, 2H), 4.13-3.99 (m, 6H), 3.77-3.51 (m, 1H), 2.55 (s, 3H).

Preparation Example 20

Compound 2-24 was prepared by coupling intermediate 10-5 with cyclopropylamine as shown below.

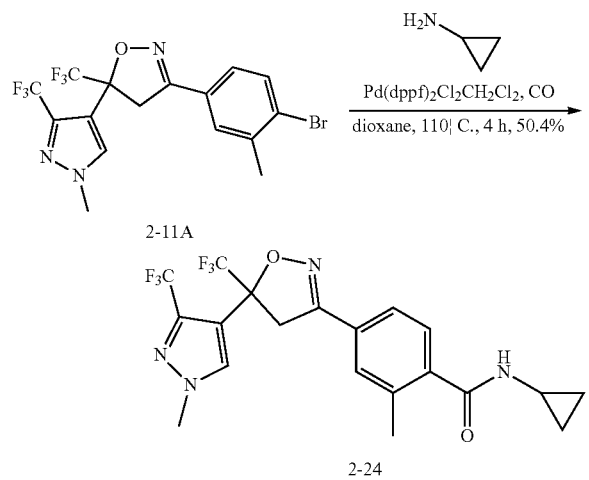

2-24

N-cyclopropyl-2-methyl-4-[5-[1-methyl-3-(trifluoromethyl)-1H-pyrazol-4-yl]-5-(trifluoromethyl)-4,5-dihydro-1,2-oxazol-3-yl]benzamide Into a 50-mL pressure tank reactor were placed dioxane (15 mL), 3-(4-bromo-3-methylphenyl)-5-[1-methyl-3-(trifluoromethyl)-1H-pyrazol-4-yl]-5-(trifluoromethyl)-4,5-dihydro-1,2-oxazole (200 mg, 0.44 mmol, 1.00 equiv), Pd(dppf)Cl$_2$CH$_2$Cl$_2$ (110 mg, 0.15 mmol, 0.34 equiv), NaOAc (110 mg) and cyclopropylamine (150 mg, 2.63 mmol, 5.99 equiv). To the reaction mixture was introduced CO (20 atm). The resulting solution was stirred for 4 h at 120° C. The reaction mixture was concentrated under vacuum and the crude product was purified by Flash-Prep-HPLC with the following conditions (IntelFlash-1): Column, C18 silica gel; mobile phase, H$_2$O:CH$_3$CN=100:0 increasing to H$_2$O: CH$_3$CN=40:60 within 20 min; Detector, UV 254 nm. This resulted in 101.8 mg (50.4%) of N-cyclopropyl-2-methyl-4-[5-[1-methyl-3-(trifluoromethyl)-1H-pyrazol-4-yl]-5-(trifluoromethyl)-4,5-dihydro-1,2-oxazol-3-yl]benzamide as a white solid. MS (ESI, m/z): 460 [M+H]$^+$; $^1$H-NMR (300 MHz, CDCl$_3$, ppm) δ 7.73 (s, 1H), 7.60-7.54 (m, 2H), 7.49-7.46 (m, 1H), 5.58 (s, 1H), 4.00-3.97 (m, 4H), 3.73-3.68 (m, 1H), 2.91-2.88 (m, 1H), 2.47 (s, 3H), 0.92-0.88 (m, 2H), 0.64-0.59 (m, 2H).

Preparation Example 21

Compound 2-16 was prepared according the Scheme 11 below.

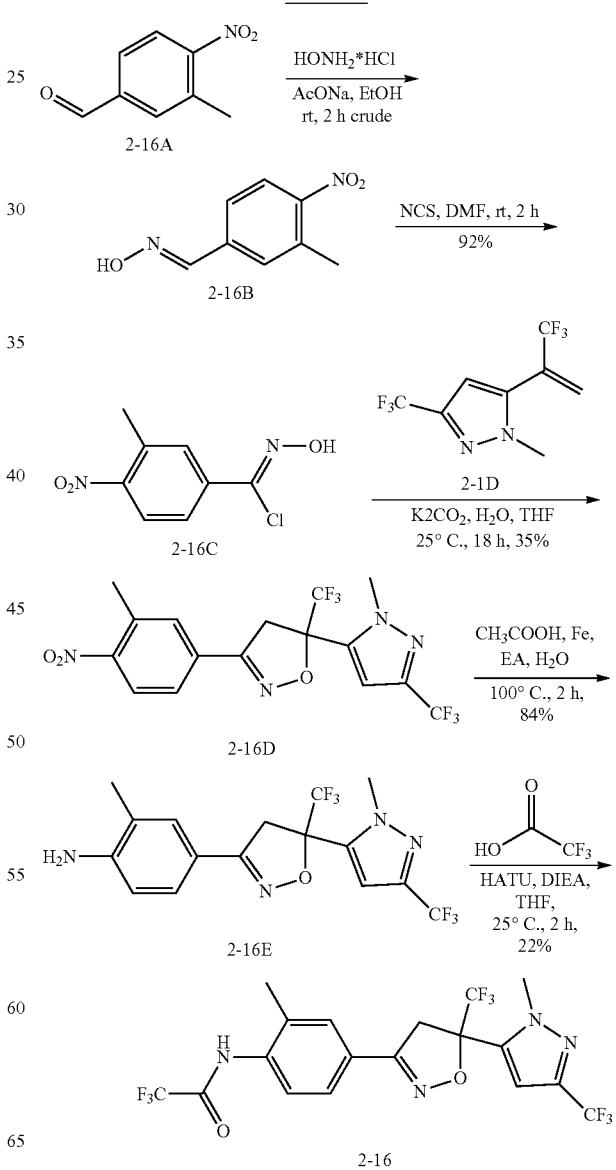

2-16

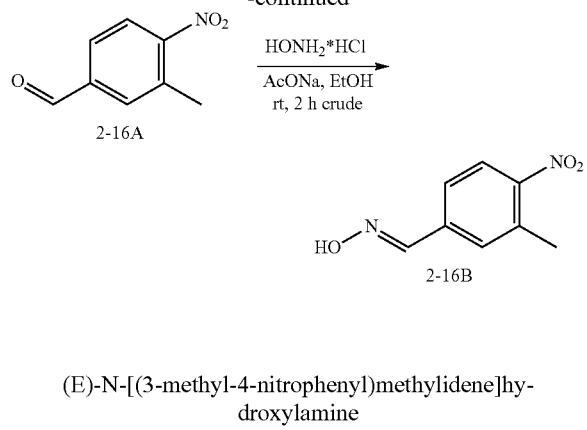

(E)-N-[(3-methyl-4-nitrophenyl)methylidene]hydroxylamine

Into a 500-mL round-bottom flask purged and maintained with an inert atmosphere of nitrogen were placed 3-methyl-4-nitrobenzaldehyde (5 g, 30.28 mmol, 1.00 equiv), ethanol (100 mL), AcONa (5 g, 2.00 equiv) and NH₂OH.HCl (3.2 g, 1.50 equiv). The resulting solution was stirred for 2 h at room temperature. The resulting solution was concentrated under vacuum and then diluted with 100 ml of water. The resulting mixture was extracted with 2×200 mL of ethyl acetate. The organic layers were combined and washed with 3×100 mL of brine, dried over anhydrous sodium sulfate and concentrated under vacuum. This resulted in 5.5 g (crude) of (E)-N-[(3-methyl-4-nitrophenyl)methylidene]hydroxylamine as a yellow solid. MS (ESI, m/z): 181 [M+H]⁺.

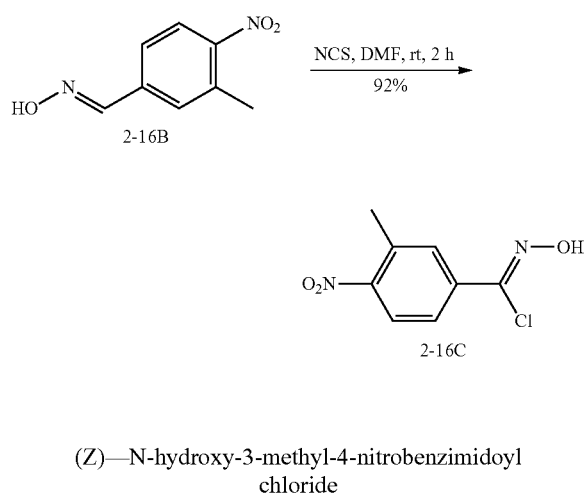

(Z)—N-hydroxy-3-methyl-4-nitrobenzimidoyl chloride

Into a 100-mL round-bottom flask were placed (E)-N-[(3-methyl-4-nitrophenyl)methylidene]hydroxylamine (5.5 g, 30.53 mmol, 1.00 equiv) and N,N-dimethylformamide (30 mL). This was followed by the addition of NCS (5 g, 37.44 mmol, 1.20 equiv). The resulting solution was stirred for 2 h at room temperature. The resulting mixture was diluted with 200 mL of H₂O and then extracted with 200 mL of ethyl acetate. The organic layers were combined and washed with 3×200 mL of saturated brine, dried over anhydrous sodium sulfate and concentrated under vacuum. This resulted in 6 g (92%) of (Z)—N-hydroxy-3-methyl-4-nitrobenzene-1-carbonimidoyl chloride as a yellow solid. MS (ESI, m/z): 215 [M+H]⁺.

5-[1-methyl-3-(trifluoromethyl)-1H-pyrazol-5-yl]-3-(3-methyl-4-nitrophenyl)-5-(trifluoromethyl)-4,5-dihydro-1,2-oxazole Into a 250-mL round-bottom flask purged and maintained with an inert atmosphere of nitrogen were placed (Z)—N-hydroxy-3-methyl-4-nitrobenzene-1-carbonimidoyl chloride (2 g, 9.32 mmol, 1.50 equiv), tetrahydrofuran (60 mL), H₂O (12 mL), potassium carbonate (1.7 g, 12.30 mmol, 2.00 equiv) and 1-methyl-3-(trifluoromethyl)-5-(3,3,3-trifluoroprop-1-en-2-yl)-1H-pyrazole (1.5 g, 6.14 mmol, 1.00 equiv). The resulting solution was stirred for 18 h at 25° C. The reaction mixture was diluted with 50 ml of water and then extracted with 3×100 mL of ethyl acetate. The combined organic layers were dried over anhydrous sodium sulfate and concentrated under vacuum. The residue was applied onto a silica gel column with ethyl acetate/petroleum ether (1:6). This resulted in 900 mg (35%) of 5-[1-methyl-3-(trifluoromethyl)-1H-pyrazol-5-yl]-3-(3-methyl-4-nitrophenyl)-5-trifluoromethyl)-4,5-dihydro-1,2-oxazole as yellow oil. MS (ESI, m/z): 423 [M+H]⁺.

2-methyl-4-[5-[1-methyl-3-(trifluoromethyl)-1H-pyrazol-5-yl]-5-(trifluoromethyl)-4,5-dihydro-1,2-oxazol-3-yl]aniline Into a 100-mL round-bottom flask were placed a solution of 5-[1-methyl-3-(trifluoromethyl)-1H-pyrazol-5-yl]-3-(3-methyl-4-nitrophenyl)-5-(trifluoromethyl)-4,5-dihydro-1,2- oxazole (900 mg, 2.13 mmol, 1.00 equiv) in ethyl acetate (18 mL) and a solution of acetic acid (9 mL) in water (9 mL). This was followed by the addition of Fe (594 mg) in portions at 0° C. The resulting solution was stirred for 2 h at 100° C. The reaction mixture was cooled to room temperature. The pH value of the solution was adjusted to 8 with sodium bicarbonate (1 mol/L). The resulting solution was extracted with 3×100 mL of ethyl acetate and the organic layers combined. The organic layer was washed with 3×50 mL of saturated brine, then dried over anhydrous sodium sulfate and concentrated under vacuum. This resulted in 700 mg (84%) of 2-methyl-4-[5-[1-methyl-3-(trifluoromethyl)-1H-pyrazol-5-yl]-5-(trifluoromethyl)-4,5-dihydro-1,2-oxazol-3-yl]aniline as a yellow solid. MS (ESI, m/z): 393 [M+H]⁺.

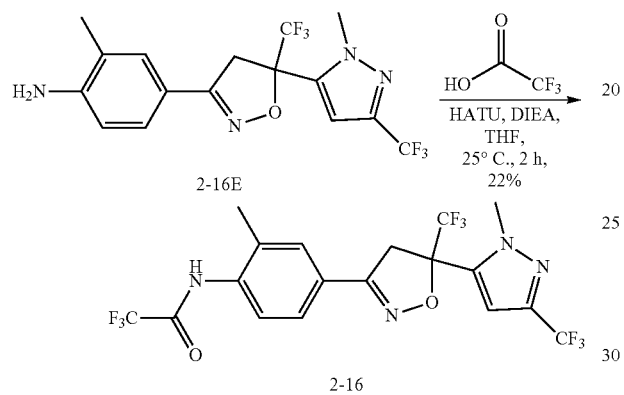

2,2,2-trifluoro-N-(2-methyl-4-[5-[1-methyl-3-(trifluoromethyl)-1H-pyrazol-5-yl]-5-(trifluoromethyl)-4,5-dihydro-1,2-oxazol-3-yl]phenyl)acetamide Into a 50-mL round-bottom flask purged and maintained with an inert atmosphere of nitrogen were placed 2-methyl-4-[5-[1-methyl-3-(trifluoromethyl)-1H-pyrazol-5-yl]-5-(trifluoromethyl)-4,5-dihydro-1,2-oxazol-3-yl]aniline (100 mg, 0.25 mmol, 1.00 equiv), tetrahydrofuran (15 mL), HATU (145 mg, 0.38 mmol, 1.50 equiv), DIEA (66 mg, 0.51 mmol, 2.00 equiv) and trifluoroacetic acid (43 mg, 0.38 mmol, 1.50 equiv). The resulting solution was stirred for 2 h at 25° C. The reaction mixture was concentrated under vacuum and the crude product was purified by Flash-Prep-HPLC with the following conditions (IntelFlash-1): Column, C18 silica gel; mobile phase, H₂O and CH₃CN (0% CH₃CN increasing to 100% within 25 min); Detector, UV 254 nm. This resulted in 27.3 mg (22%) of 2,2,2-trifluoro-N-(2-methyl-4-[5-[1-methyl-3-(trifluoromethyl)-H-pyrazol-5-yl]-5-(trifluoromethyl)-4,5-dihydro-1,2-oxazol-3-yl]phenyl)acetamide as an off-white solid. MS (ESI, m/z): 489 [M+H]⁺; ¹H NMR (300 MHz, CDCl₃, ppm) δ: 8.11 (d, J=8.4 Hz, 1H), 7.80 (s, 1H), 7.66 (s, 1H), 7.57 (d, J=8.4 Hz, 1H), 6.68 (s, 1H), 4.17 (s, 3H), 4.14 (d, J=15.6 Hz, 1H), 3.90 (d, J=17.1 Hz, 1H), 2.39 (s, 3H).

Preparation Example 22

Compound 2-17 was made in a similar way to Compound 2-16 by coupling amine 2-16E to 3,3,3-trifluoropropanoic acid as shown below.

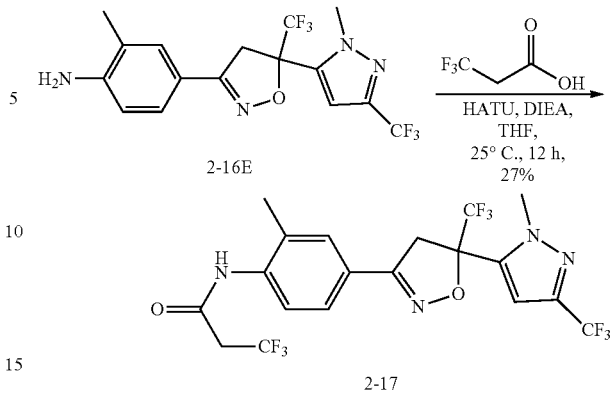

3,3,3-trifluoro-N-(2-methyl-4-[5-[1-methyl-3-(trifluoromethyl)-1H-pyrazol-5-yl]-5-(trifluoromethyl)-4,5-dihydro-1,2-oxazol-3-yl]phenyl)propanamide Into a 50-mL round-bottom flask were placed 2-methyl-4-[5-[1-methyl-3-(trifluoromethyl)-1H-pyrazol-5-yl]-5-(trifluoromethyl)-4,5-dihydro-1,2-oxazol-3-yl]aniline (150 mg, 0.38 mmol, 1.00 equiv), tetrahydrofuran (10 mL), HATU (200 mg, 0.53 mmol, 1.50 equiv), DIEA (150 mg, 1.16 mmol, 3.00 equiv) and 3,3,3-trifluoropropanoic acid (100 mg, 0.78 mmol, 1.50 equiv). The resulting solution was stirred for 12 h at 25° C. The reaction mixture was concentrated under vacuum and the residue was applied onto a silica gel column with ethyl acetate/petroleum ether (1:2). This resulted in 51.3 mg (27%) of 3,3,3-trifluoro-N-(2-methyl-4-[5-[1-methyl-3-(trifluoromethyl)-1H-pyrazol-5-yl]-5-(trifluoromethyl)-4,5-dihydro-1,2-oxazol-3-yl]phenyl)propanamide as an off-white solid. MS (ESI, m/z): 503 [M+H]⁺; ¹H NMR (300 MHz, DMSO-d₆, ppm) δ: 9.80 (s, 1H), 7.66-7.61 (m, 3H), 7.14 (s, 1H), 4.46 (s, 2H), 4.04 (s, 3H), 3.63-3.59 (m, 2H), 2.27 (s, 3H).

Preparation Example 23

Compound 2-19 was prepared by coupling amine intermediate 2-16E with 2-(methylsulfanyl)acetic acid as shown below.

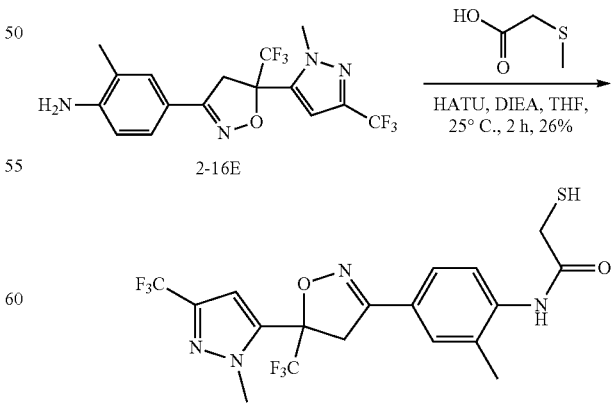

N-(2-methyl-4-[5-[1-methyl-3-(trifluoromethyl)-1H-pyrazol-5-yl]-5-(trifluoromethyl)-4,5-dihydro-1,2-oxazol-3-yl]phenyl)-2-(methylsulfanyl)acetamide Into a 50-mL round-bottom flask were placed 2-methyl-4-[5-[1-methyl-3-(trifluoromethyl)-1H-pyrazol-5-yl]-5-(trifluoromethyl)-4,5-dihydro-1,2-oxazol-3-yl]aniline (100 mg, 0.25 mmol, 1.00 equiv), 2-(methylsulfanyl)acetic acid (40 mg, 0.38 mmol, 1.50 equiv), tetrahydrofuran (15 mL), HATU (145 mg, 0.38 mmol, 1.50 equiv) and DIEA (66 mg, 0.51 mmol, 2.00 equiv). The resulting solution was stirred for 2 h at 25° C. The reaction mixture was concentrated under vacuum and the crude product was purified by Flash-Prep-HPLC with the following conditions (CombiFlash-1): Column, C18 silica gel; mobile phase, H$_2$O and CH$_3$CN (0% CH$_3$CN increasing to 80% within 20 min); Detector, UV 254 nm. This resulted in 31.4 mg (26%) of N-(2-methyl-4-[5-[1-methyl-3-(trifluoromethyl)-1H-pyrazol-5-yl]-5-(trifluoromethyl)-4,5-dihydro-1,2-oxazol-3-yl]phenyl)-2-(methylsulfanyl)acetamide as an off-white solid. MS (ESI, m/z): 481 [M+H]$^+$; $^1$H NMR (300 MHz, CDCl$_3$, ppm) δ 9.05 (s, 1H), 8.30 (d, J=8.4 Hz, 1H), 7.62 (s, 1H), 7.51 (d, J=8.4 Hz, 1H), 6.68 (s, 1H), 4.16 (s, 3H), 4.14 (d, J=16.5 Hz, 4H), 3.89 (d, J=17.4 Hz, 1H), 3.44 (s, 2H), 2.39 (s, 3H), 2.26 (s, 3H).

Preparation Example 24

Compound 2-20 was prepared according to Scheme 12 shown below.

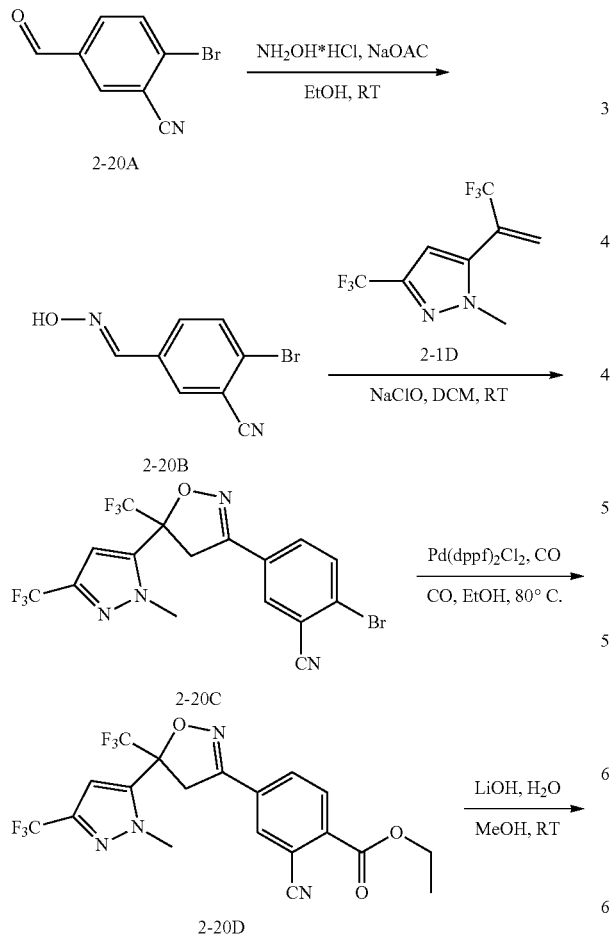

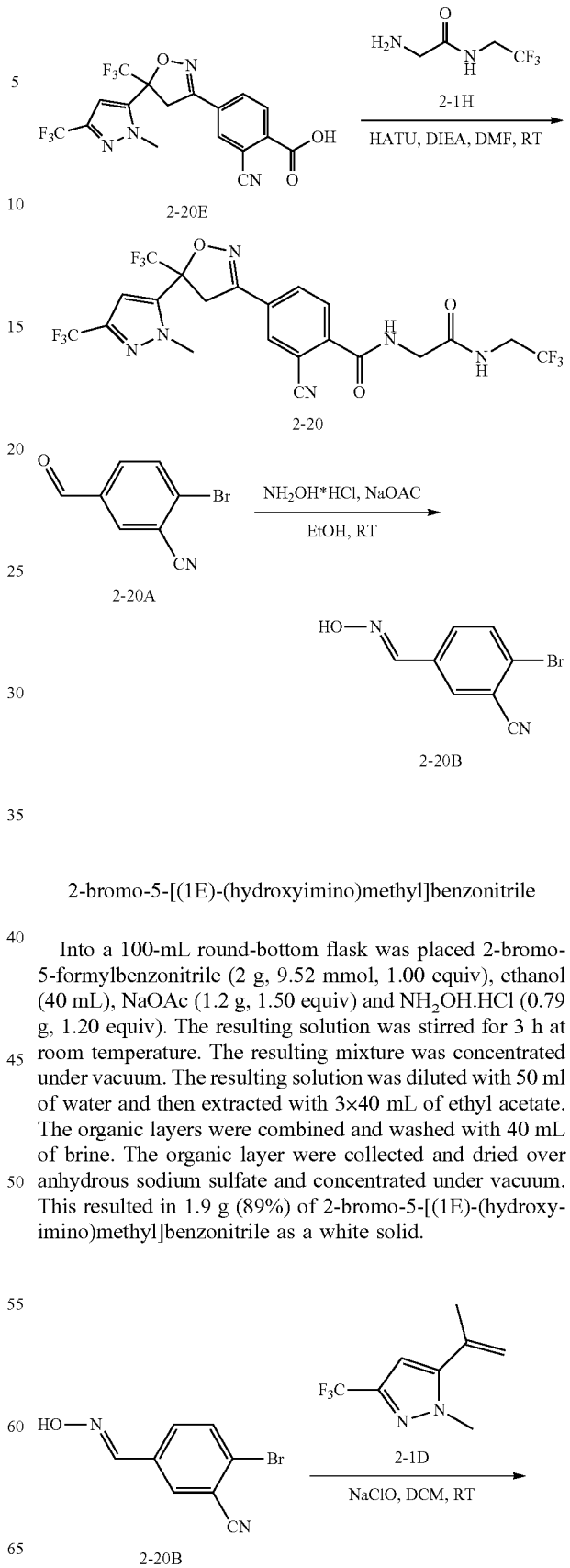

2-bromo-5-[(1E)-(hydroxyimino)methyl]benzonitrile

Into a 100-mL round-bottom flask was placed 2-bromo-5-formylbenzonitrile (2 g, 9.52 mmol, 1.00 equiv), ethanol (40 mL), NaOAc (1.2 g, 1.50 equiv) and NH$_2$OH.HCl (0.79 g, 1.20 equiv). The resulting solution was stirred for 3 h at room temperature. The resulting mixture was concentrated under vacuum. The resulting solution was diluted with 50 ml of water and then extracted with 3×40 mL of ethyl acetate. The organic layers were combined and washed with 40 mL of brine. The organic layer were collected and dried over anhydrous sodium sulfate and concentrated under vacuum. This resulted in 1.9 g (89%) of 2-bromo-5-[(1E)-(hydroxyimino)methyl]benzonitrile as a white solid.

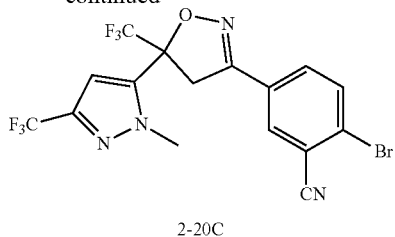

2-20C

2-bromo-5-[5-[1-methyl-3-(trifluoromethyl)-1H-pyrazol-5-yl]-5-(trifluoromethyl)-4,5-dihydro-1,2-oxazol-3-yl]benzonitrile Into a 100-mL round-bottom flask were placed 1-methyl-3-(trifluoromethyl)-5-(3,3,3-trifluoroprop-1-en-2-yl)-1H-pyrazole (900 mg, 3.69 mmol, 1.00 equiv), dichloromethane (12 mL), sodium hypochlorite (18 mL) and 2-bromo-5-[(1E)-(hydroxyimino)methyl]benzonitrile (826 mg, 3.67 mmol, 1.00 equiv). The resulting solution was stirred for 2 h at room temperature. The reaction mixture was diluted with 100 mL of H₂O. The resulting solution was extracted with 3×50 mL of dichloromethane and the organic layers were combined and washed with 50 mL of brine. The organic layer was collected and dried over anhydrous sodium sulfate and then concentrated under vacuum. The residue was applied onto a silica gel column with ethyl acetate/petroleum ether (1:9). This resulted in 220 mg (13%) of 2-bromo-5-[5-[1-methyl-3-(trifluoromethyl)-1H-pyrazol-5-yl]-5-(trifluoromethyl)-4,5-dihydro-1,2-oxazol-3-yl]benzonitrile as yellow oil.

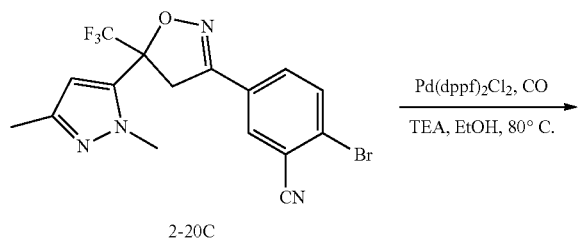

2-20C

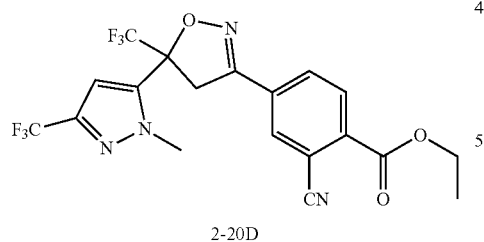

2-20D

Ethyl 2-cyano-4-[5-[1-methyl-3-(trifluoromethyl)-1H-pyrazol-5-yl]-5-(trifluoromethyl)-4,5-dihydro-1,2-oxazol-3-yl]benzoate Into a 50-mL pressure tank reactor purged and maintained with an inert atmosphere of nitrogen, was placed 2-bromo-5-[5-[1-methyl-3-(trifluoromethyl)-1H-pyrazol-5-yl]-5-(trifluoromethyl)-4,5-dihydro-1,2-oxazol-3-yl]benzonitrile (180 mg, 0.39 mmol, 1.00 equiv), ethanol (18 mL), triethylamine (98 mg, 0.97 mmol, 2.50 equiv), Pd(dppf)Cl₂ (56 mg, 0.08 mmol, 0.20 equiv). The resulting solution was stirred for 4 h at 80° C. The solids were filtered out. The filtrate was concentrated under vacuum. The residue was applied onto a silica gel column with ethyl acetate/petroleum ether (1:3). This resulted in 90 mg (51%) of ethyl 2-cyano-4-[5-[1-methyl-3-(trifluoromethyl)-1H-pyrazol-5-yl]-5-(trifluoromethyl)-4,5-dihydro-1,2-oxazol-3-yl]benzoate as yellow oil.

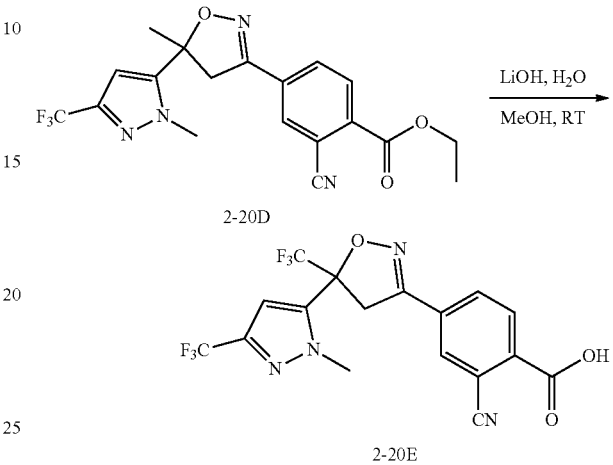

2-20D 2-20E

2-cyano-4-[5-[1-methyl-3-(trifluoromethyl)-1H-pyrazol-5-yl]-5-(trifluoromethyl)-4,5-dihydro-1,2-oxazol-3-yl]benzoic acid Into a 50-mL round-bottom flask were placed ethyl 2-cyano-4-[5-[1-methyl-3-(trifluoromethyl)-1H-pyrazol-5-yl]-5-(trifluoromethyl)-4,5-dihydro-1,2-oxazol-3-yl]benzoate (90 mg, 0.20 mmol, 1.00 equiv), methanol (6 mL), LiOH (43 mg, 1.80 mmol, 9.00 equiv) and water (1 mL). The resulting solution was stirred for 2 h at room temperature. The reaction mixture was concentrated under vacuum; 10 mL of water was added to the residue and the pH was adjusted to 4-5. The resulting solution was extracted with 2×50 mL of DCM. The organic phase was collected and dried over anhydrous sodium sulfate and concentrated under vacuum. This resulted in 90 mg (crude) of 2-cyano-4-[5-[1-methyl-3-(trifluoromethyl)-1H-pyrazol-5-yl]-5-(trifluoromethyl)-4,5-dihydro-1,2-oxazol-3-yl]benzoic acid as an off-white solid.

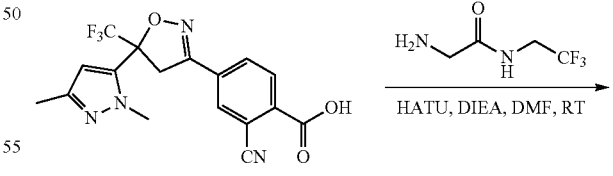

2-20E

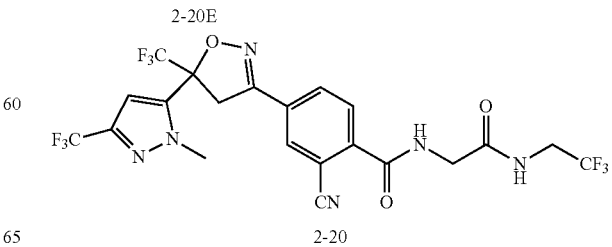

2-20

2-[(2-cyano-4-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl)acetamide Into a 50-mL round-bottom flask were placed 2-cyano-4-[5-[1-methyl-3-(trifluoromethyl)-1H-pyrazol-5-yl]-5-(trifluoromethyl)-4,5-dihydro-1,2-oxazol-3-yl]benzoic acid (100 mg, 0.23 mmol, 1.00 equiv), HATU (132 mg, 0.35 mmol, 1.50 equiv), N,N-dimethylformamide (5 mL), 2-amino-N-(2,2,2-trifluoroethyl)acetamide (67 mg, 0.43 mmol, 1.50 equiv) and DIEA (90 mg, 0.70 mmol, 3.00 equiv). The resulting solution was stirred for 2 h at room temperature. The crude solution was purified by Prep-HPLC with the following conditions (Waters I): Column, XBridge Prep C18 OBD Column 19*150 mm, 5 um; Mobile Phase, Water and CH$_3$CN (35% CH$_3$CN up to 70% in 7 min); Detector, UV 254 nm, 220 nm. This resulted in 14.3 mg (11%) of 2-[(2-cyano-4-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl)acetamide as a white solid. (ES, m/z): 571 [M+H]$^+$; $^1$H NMR (300 MHz, CDCl$_3$, ppm) δ 8.27 (s, 1H), 8.04-7.98 (m, 2H), 6.71 (s, 1H), 6.58 (br, 1H), 4.64 (s, 2H), 4.26-4.18 (m, 1H), 4.18 (s, 3H), 3.99-3.90 (m, 3H).

Preparation Example 25

Compound 2-15 was prepared according to Scheme 13 below.

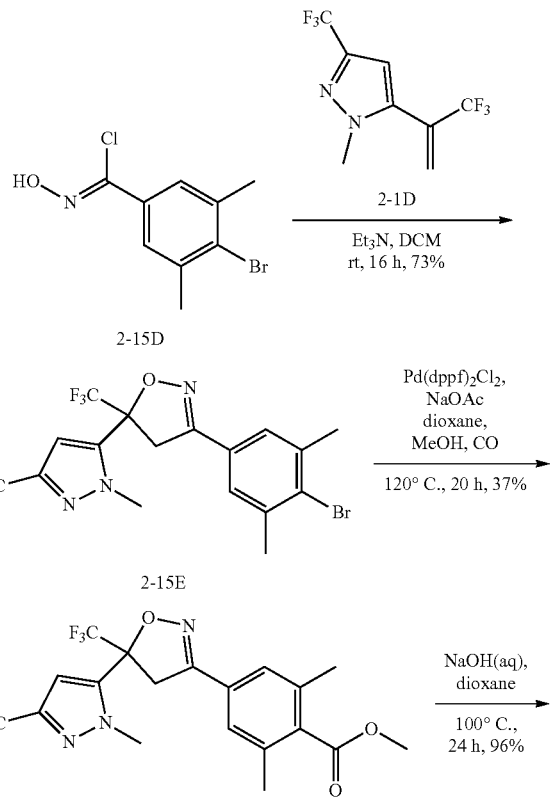

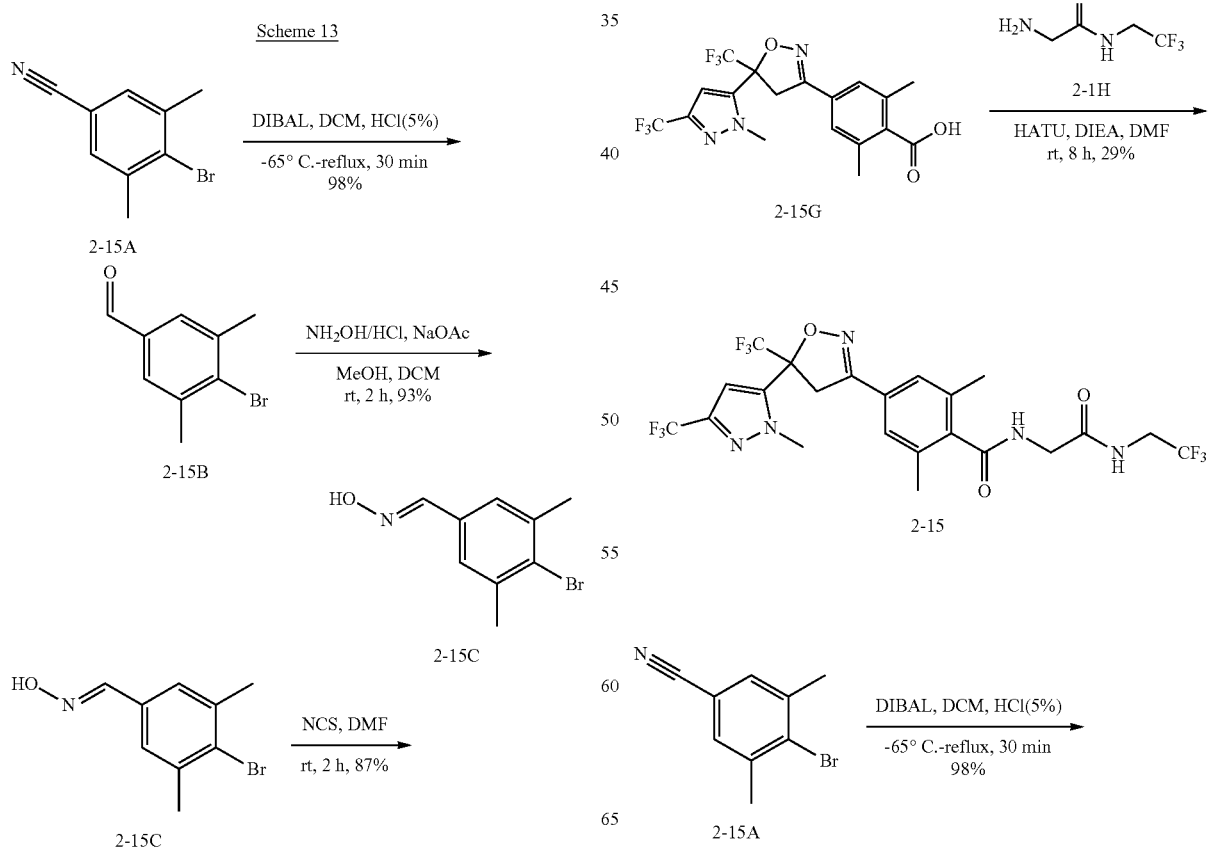

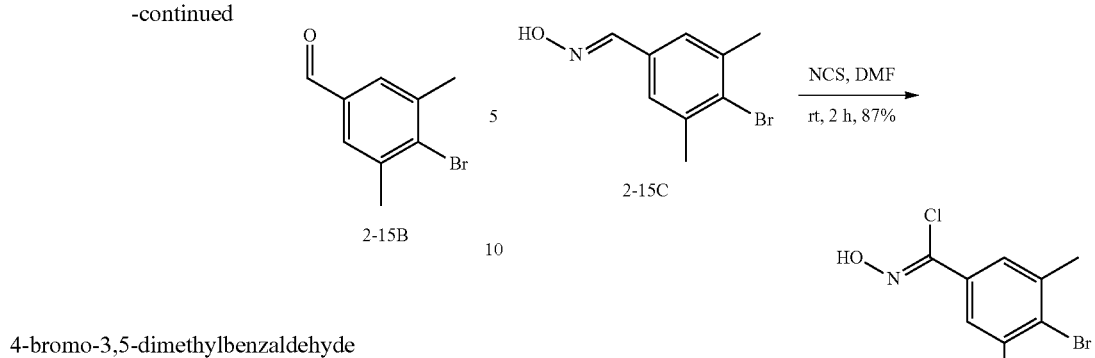

2-15B 4-bromo-3,5-dimethylbenzaldehyde

Into a 500-mL 3-necked round-bottom flask purged and maintained with an inert atmosphere of nitrogen, were placed 4-bromo-3,5-dimethylbenzonitrile (4 g, 19.04 mmol, 1.00 equiv) and dichloromethane (50 mL). This was followed by the addition of diisobutylaluminum hydride (40 mL) dropwise with stirring at −65° C. The resulting solution was stirring for 2 h at room temperature. To the reaction mixture was added hydrogen chloride (5%, 40 mL) dropwise with stirring at room temperature. The resulting solution was heated to reflux for 30 min and then cooled to room temperature. The resulting solution was diluted with 200 mL of DCM. The organic layer was washed with 3×100 mL of brine and then dried over anhydrous sodium sulfate and concentrated under vacuum. This resulted in 4 g (crude) of 4-bromo-3,5-dimethylbenzaldehyde as light yellow oil.

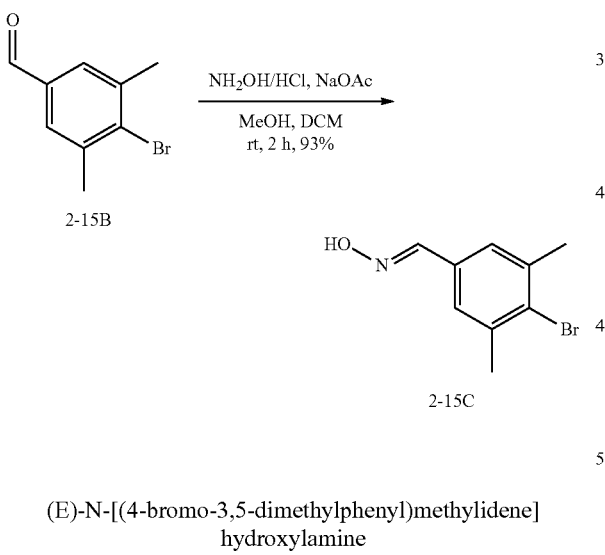

(E)-N-[(4-bromo-3,5-dimethylphenyl)methylidene]hydroxylamine

Into a 100-mL round-bottom flask were placed 4-bromo-3,5-dimethylbenzaldehyde (2 g, 9.39 mmol, 1.00 equiv), methanol (20 mL), dichloromethane (20 mL), NH₂OH.HCl (976 mg, 14.14 mmol, 1.51 equiv) and NaOAc (1.547 g, 18.87 mmol, 2.01 equiv). The resulting solution was stirred for 2 h at room temperature. The resulting mixture was concentrated under vacuum. The residue was dissolved in 100 mL of EA and washed with 3×100 mL of H₂O. The organic layer was dried over anhydrous sodium sulfate and concentrated under vacuum. This resulted in 2 g (93%) of (E)-N-[(4-bromo-3,5-dimethylphenyl)methylidene]hydroxylamine as a light yellow solid.

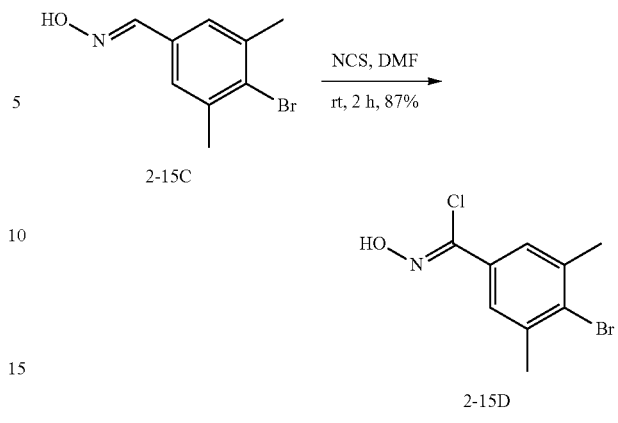

Z-4-bromo-N-hydroxy-3,5-dimethylbenzene-1-carbonimidoyl chloride

Into a 100-mL round-bottom flask were placed (E)-N-[(4-bromo-3,5-dimethylphenyl)methylidene]hydroxylamine (2 g, 8.77 mmol, 1.00 equiv), NCS (1.78 g, 13.33 mmol, 1.52 equiv) and N,N-dimethylformamide (50 mL). The resulting solution was stirred for 2 h at room temperature. The resulting solution was diluted with 200 mL of EA and washed with 3×100 mL of water and 3×100 mL of brine. The organic layer was collected and dried over anhydrous sodium sulfate and concentrated under vacuum. This resulted in 2 g (crude) of (Z)-4-bromo-N-hydroxy-3,5-dimethylbenzene-1-carbonimidoyl chloride as light yellow oil.

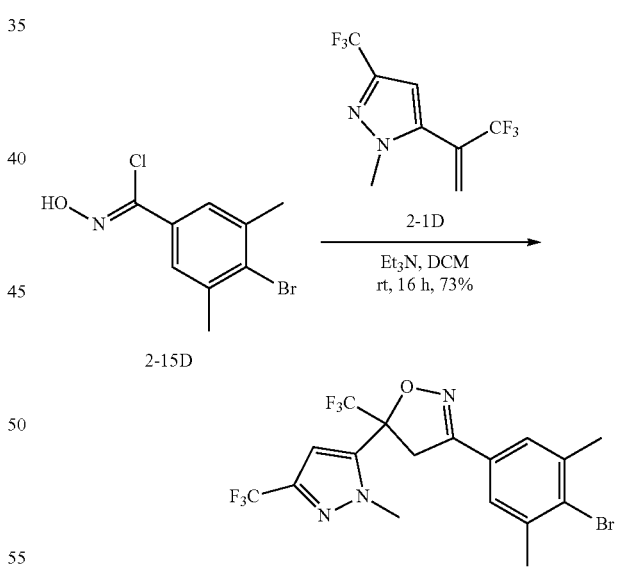

3-(4-bromo-3,5-dimethylphenyl)-5-[1-methyl-3-(trifluoromethyl)-1H-pyrazol-5-yl]-5-(trifluoromethyl)-4,5-dihydro-1,2-oxazole Into a 100-mL round-bottom flask were placed 1-methyl-3-(trifluoromethyl)-5-(3,3,3-trifluoroprop-1-en-2-yl)-1H-pyrazole (400 mg, 1.64 mmol, 1.00 equiv), (Z)-4-bromo-N-hydroxy-3,5-dimethylbenzene-1-carbonimidoyl chloride (426 mg, 1.62 mmol, 0.99 equiv), triethylamine (300 mg, 2.96 mmol, 1.81 equiv) and dichloromethane (30 mL). The resulting solution was stirred for 16 h at room temperature. The resulting mixture was concentrated under vacuum and residue was applied onto a silica gel column with ethyl acetate/petroleum ether (⅕). This resulted in 560 mg (73%) of 3-(4-bromo-3,5-dimethylphenyl)-5-[1-methyl-3-(trifluoromethyl)-1H-pyrazol-5-yl]-5-(trifluoromethyl)-4,5-dihydro-1,2-oxazole as a light yellow solid.

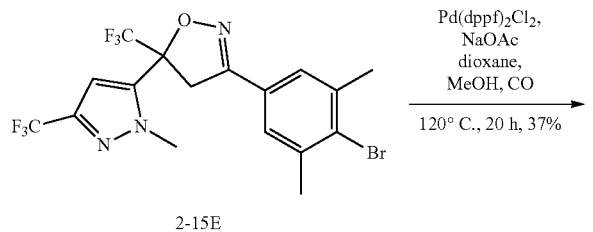

2-15E

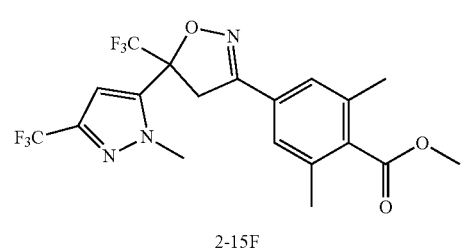

2-15F

Methyl 2,6-dimethyl-4-[5-[1-methyl-3-(trifluoromethyl)-1H-pyrazol-5-yl]-5-(trifluoromethyl)-4,5-dihydro-1,2-oxazol-3-yl]benzoate Into a 30-mL pressure tank reactor, were placed 3-(4-bromo-3,5-dimethylphenyl)-5-[1-methyl-3-(trifluoromethyl)-1H-pyrazol-5-yl]-5-(trifluoromethyl)-4,5-dihydro-1,2-oxazole (200 mg, 0.43 mmol, 1.00 equiv), Pd(dppf)Cl₂ (93.52 mg, 0.13 mmol, 0.30 equiv), NaOAc (105 mg, 1.28 mmol, 3.01 equiv), methanol (4 mL), dioxane (5 mL). To this mixture was added CO. The resulting solution was stirred for 20 h at 120° C. The resulting mixture was concentrated under vacuum and the residue was applied onto a silica gel column with ethyl acetate/petroleum ether (⅓). This resulted in 70 mg (37%) of methyl 2,6-dimethyl-4-[5-[1-methyl-3-(trifluoromethyl)-1H-pyrazol-5-yl]-5-(trifluoromethyl)-4,5-dihydro-1,2-oxazol-3-yl]benzoate as light yellow oil.

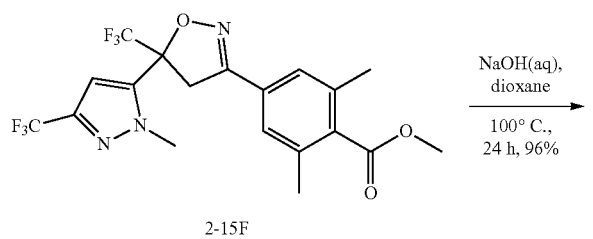

2-15F

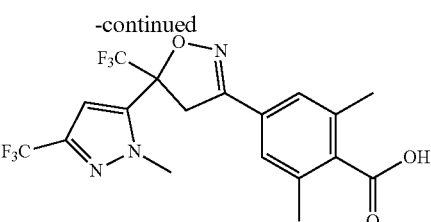

2-15G 2,6-dimethyl-4-[5-[1-methyl-3-(trifluoromethyl)-1H-pyrazol-5-yl]-5-(trifluoromethyl)-4,5-dihydro-1,2-oxazol-3-yl]benzoic acid Into a 25-mL round-bottom flask were placed methyl 2,6-dimethyl-4-[5-[1-methyl-3-(trifluoromethyl)-1H-pyrazol-5-yl]-5-(trifluoromethyl)-4,5-dihydro-1,2-oxazol-3-yl]benzoate (50 mg, 0.11 mmol, 1.00 equiv), dioxane (5 mL), sodium hydroxide (1 N, 2 mL). The resulting solution was stirred for 24 h at 100° C. The pH value of the solution was adjusted to 2 with Con. HCl. The resulting solution was extracted with 3×10 mL of dichloromethane. The combined organic layers were dried over anhydrous sodium sulfate and concentrated under vacuum. This resulted in 65 mg (96%) of 2,6-dimethyl-4-[5-[1-methyl-3-(trifluoromethyl)-1H-pyrazol-5-yl]-5-(trifluoromethyl)-4,5-dihydro-1,2-oxazol-3-yl] benzoic acid as light yellow oil.

2-[(2,6-dimethyl-4-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl)acetamide Into a 50-mL round-bottom flask were placed 2,6-dimethyl-4-[5-[1-methyl-3-(trifluoromethyl)-1H-pyrazol-5-yl]-5-(trifluoromethyl)-4,5-dihydro-1,2-oxazol-3-yl]benzoic acid (65 mg, 0.15 mmol, 1.00 equiv), 2-amino-N-(2,2,2-trifluoroethyl)acetamide hydrochloride (30 mg, 0.19 mmol, 1.20 equiv), HATU (116 mg, 0.3 mmol, 2.00 equiv), DIEA (57.8 mg, 0.45 mmol, 3.00 equiv) and N,N-dimethylformamide (8 mL). The resulting solution was stirred for 8 h at room temperature. The resulting solution was diluted with 30 mL of EA and washed with 3×20 mL of H₂O. The organic layer was concentrated under vacuum and the crude product was purified by Flash-Prep-HPLC with the following conditions (IntelFlash-1): Column, C18 silica gel; mobile phase, H$_2$O and CH$_3$CN (10% CH$_3$CN increasing to 70% within 15 min); Detector, UV 220 nm. This resulted in 25.2 mg (29%) of 2-[(2,6-dimethyl-4-[5-[1-methyl-3-(trifluoromethyl)-1H-pyrazol-5-yl]-5-(trifluoromethyl)-4,5-dihydro-1,2-oxazol-3-yl]phenyl)formamido]-N-(2,2,2-trifluoroethyl)acetamide as a white solid. (ES, m/z):573[M+H]$^+$; $^1$H NMR (300 MHz, CDCl$_3$, ppm) δ 7.36 (s, 2H), 6.91 (s, 1H), 6.56 (brs, 1H), 6.37 (brs, 1H), 4.19-4.08 (m, 6H), 3.99-3.96 (m, 2H), 3.93-3.81 (m, 1H), 2.35 (s, 6H).

Preparation Example 26

Compound 2-2 was prepared according to Scheme 14 below.

Scheme 14

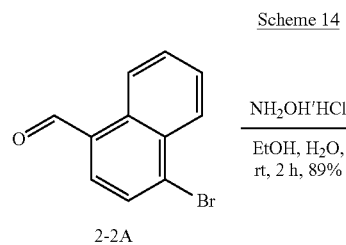

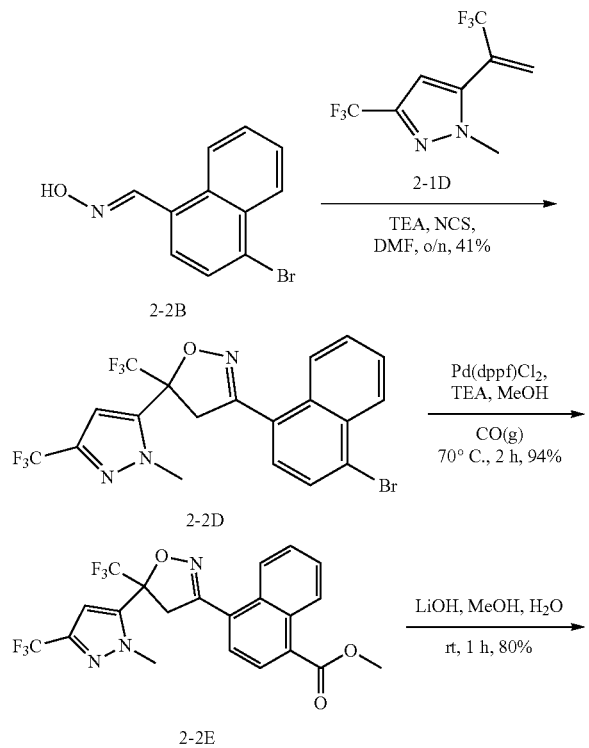

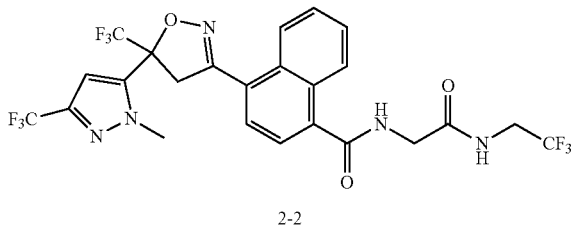

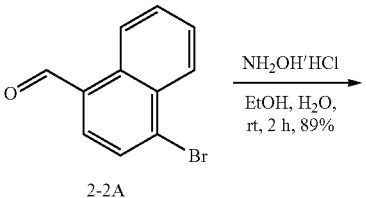

3-(4-bromonaphthalen-1-yl)-5-[1-methyl-3-(trifluoromethyl)-1H-pyrazol-5-yl]-5-(trifluoromethyl)-4,5-dihydro-1,2-oxazole Into a 50-mL round-bottom flask were placed N,N-dimethylformamide (5 mL), (E)-N-[(4-bromonaphthalen-1-yl)methylidene]hydroxylamine (200 mg, 0.80 mmol, 1.00 equiv) and NCS (170 mg, 1.27 mmol, 1.59 equiv); the reaction was stirred for 30 min at room temperature. Then 1-methyl-3-(trifluoromethyl)-5-(3,3,3-trifluoroprop-1-en-2-yl)-1H-pyrazole (200 mg, 0.82 mmol, 1.02 equiv) and TEA (260 mg, 2.57 mmol, 3.21 equiv) were added. The resulting solution was stirred overnight at room temperature. The crude product was purified by Flash-Prep-HPLC with the following conditions (IntelFlash-1): Column, C18 silica gel; mobile phase, H$_2$O and CH$_3$CN (20% CH$_3$CN increasing to 80% within 20 min); Detector, UV 254 nm. This resulted in 160 mg (41%) of 3-(4-bromonaphthalen-1-yl)-5-[1-methyl-3-(trifluoromethyl)-1H-pyrazol-5-yl]-5-(trifluoromethyl)-4,5-dihydro-1,2-oxazole as a yellow solid.

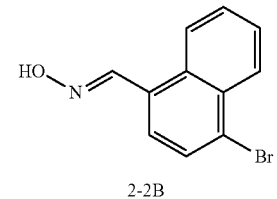

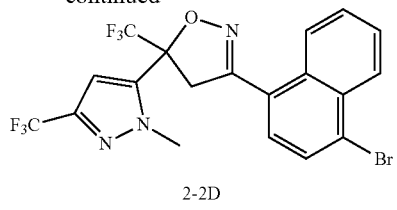

2-2D

3-(4-bromonaphthalen-1-yl)-5-[1-methyl-3-(trifluoromethyl)-1H-pyrazol-5-yl]-5-(trifluoromethyl)-4,5-dihydro-1,2-oxazole Into a 50-mL round-bottom flask were placed N,N-dimethylformamide (5 mL), (E)-N-[(4-bromonaphthalen-1-yl)methylidene]hydroxylamine (200 mg, 0.80 mmol, 1.00 equiv) and NCS (170 mg, 1.27 mmol, 1.59 equiv), the reaction was stirred for 30 min at room temperature. Then 1-methyl-3-(trifluoromethyl)-5-(3,3,3-trifluoroprop-1-en-2-yl)-1H-pyrazole (200 mg, 0.82 mmol, 1.02 equiv) and TEA (260 mg, 2.57 mmol, 3.21 equiv) were added. The resulting solution was stirred overnight at room temperature. The crude product was purified by Flash-Prep-HPLC with the following conditions (IntelFlash-1): Column, C18 silica gel; mobile phase, H₂O and CH₃CN (20% CH₃CN increasing to 80% within 20 min); Detector, UV 254 nm. This resulted in 160 mg (41%) of 3-(4-bromonaphthalen-1-yl)-5-[1-methyl-3-(trifluoromethyl)-1H-pyrazol-5-yl]-5-(trifluoromethyl)-4,5-dihydro-1,2-oxazole as a yellow solid.

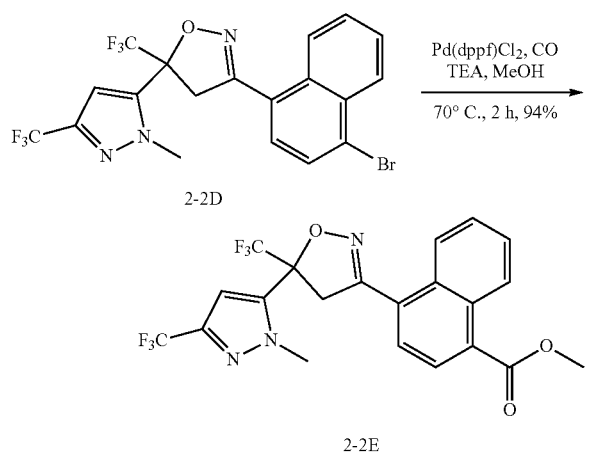

Methyl 4-[5-[1-methyl-3-(trifluoromethyl)-1H-pyrazol-5-yl]-5-(trifluoromethyl)-4,5-dihydro-1,2-oxazol-3-yl]naphthalene-1-carboxylate Into a 50-mL pressure tank reactor (20 atm), were placed methanol (10 mL), 3-(4-bromonaphthalen-1-yl)-5-[1-methyl-3-(trifluoromethyl)-1H-pyrazol-5-yl]-5-(trifluoromethyl)-4,5-dihydro-1,2-oxazole (200 mg, 0.41 mmol, 1.00 equiv), Pd(dppf)Cl₂ (40 mg, 0.05 mmol, 0.13 equiv) and TEA (130 mg, 1.28 mmol, 3.16 equiv). To this solution was introduced CO (g). The resulting solution was stirred for 2 h at 70° C. The resulting mixture was concentrated under vacuum and the residue was applied onto a silica gel column with ethyl acetate/petroleum ether (1:4). This resulted in 180 mg (94%) of methyl 4-[5-[1-methyl-3-(trifluoromethyl)-1H-pyrazol-5-yl]-5-(trifluoromethyl)-4,5-dihydro-1,2-oxazol-3-yl]naphthalene-1-carboxylate as a yellow solid.

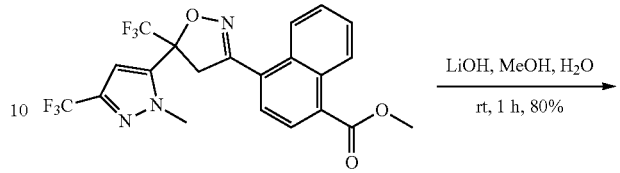

2-2E

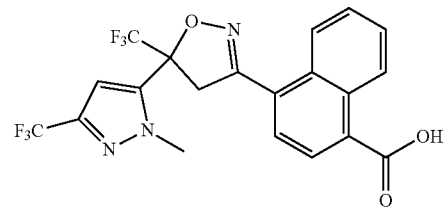

2-2F

4-[5-[1-methyl-3-(trifluoromethyl)-1H-pyrazol-5-yl]-5-(trifluoromethyl)-4,5-dihydro-1,2-oxazol-3-yl]naphthalene-1-carboxylic acid Into a 50-mL round-bottom flask were placed methanol (10 mL), water (2 mL), methyl 4-[5-[1-methyl-3-(trifluoromethyl)-1H-pyrazol-5-yl]-5-(trifluoromethyl)-4,5-dihydro-1,2-oxazol-3-yl]naphthalene-1-carboxylate (180 mg, 0.38 mmol, 1.00 equiv) and LiOH (80 mg, 3.34 mmol, 8.75 equiv). The resulting solution was stirred for 1 h at room temperature and then the pH value of the solution was adjusted to 4 with hydrogen chloride (2 mol/L). The resulting solution was extracted with 3×10 mL of ethyl acetate and the organic layers combined and dried over anhydrous sodium sulfate and concentrated under vacuum. This resulted in 140 mg (80%) of 4-[5-[1-methyl-3-(trifluoromethyl)-1H-pyrazol-5-yl]-5-(trifluoromethyl)-4,5-dihydro-1,2-oxazol-3-yl]naphthalene-1-carboxylic acid as a yellow solid.

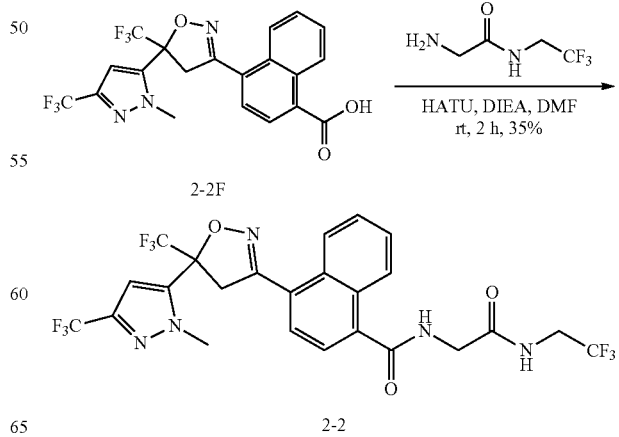

2-[(4-[5-[1-methyl-3-(trifluoromethyl)-1H-pyrazol-5-yl]-5-(trifluoromethyl)-4,5-dihydro-1,2-oxazol-3-yl]naphthalen-1-yl)formamido]-N-(2,2,2-trifluoroethyl)acetamide Into a 50-mL round-bottom flask were placed N,N-dimethylformamide (5 mL), 4-[5-[1-methyl-3-(trifluoromethyl)-1H-pyrazol-5-yl]-5-(trifluoromethyl)-4,5-dihydro-1,2-oxazol-3-yl]naphthalene-1-carboxylic acid (150 mg, 0.33 mmol, 1.00 equiv), 2-amino-N-(2,2,2-trifluoroethyl)acetamide (85 mg, 0.54 mmol, 1.66 equiv), HATU (250 mg, 0.66 mmol, 2.00 equiv) and DIEA (130 mg, 1.01 mmol, 3.07 equiv). The resulting solution was stirred for 2 h at room temperature. The crude solution was purified by Flash-Prep-HPLC with the following conditions (IntelFlash-1): Column, C18 silica gel; mobile phase, H₂O and CH₃CN (0% CH₃CN increasing to 80% within 20 min); Detector, UV 254 nm. This resulted in 68.3 mg (35%) of 2-[(4-[5-[1-methyl-3-(trifluoromethyl)-1H-pyrazol-5-yl]-5-(trifluoromethyl)-4,5-dihydro-1,2-oxazol-3-yl]naphthalen-1-yl)formamido]-N-(2,2,2-trifluoroethyl)acetamide as an off-white solid. (ES, m/z): 596 [M+H]⁺; ¹H NMR (CDCl₃, 300 MHz, ppm) δ 8.82 (d, J=8.4 Hz, 1H), 8.32 (d, J=7.8 Hz, 1H), 7.73-7.63 (m, 3H), 7.55-7.52 (m, 1H), 7.01 (br, 2H), 6.72 (s, 1H), 4.34-4.28 (m, 3H), 4.23 (s, 3H), 4.23-3.95 (m, 3H).

Preparation Example 27

Compound 2-3 was prepared according to Scheme 15 below.

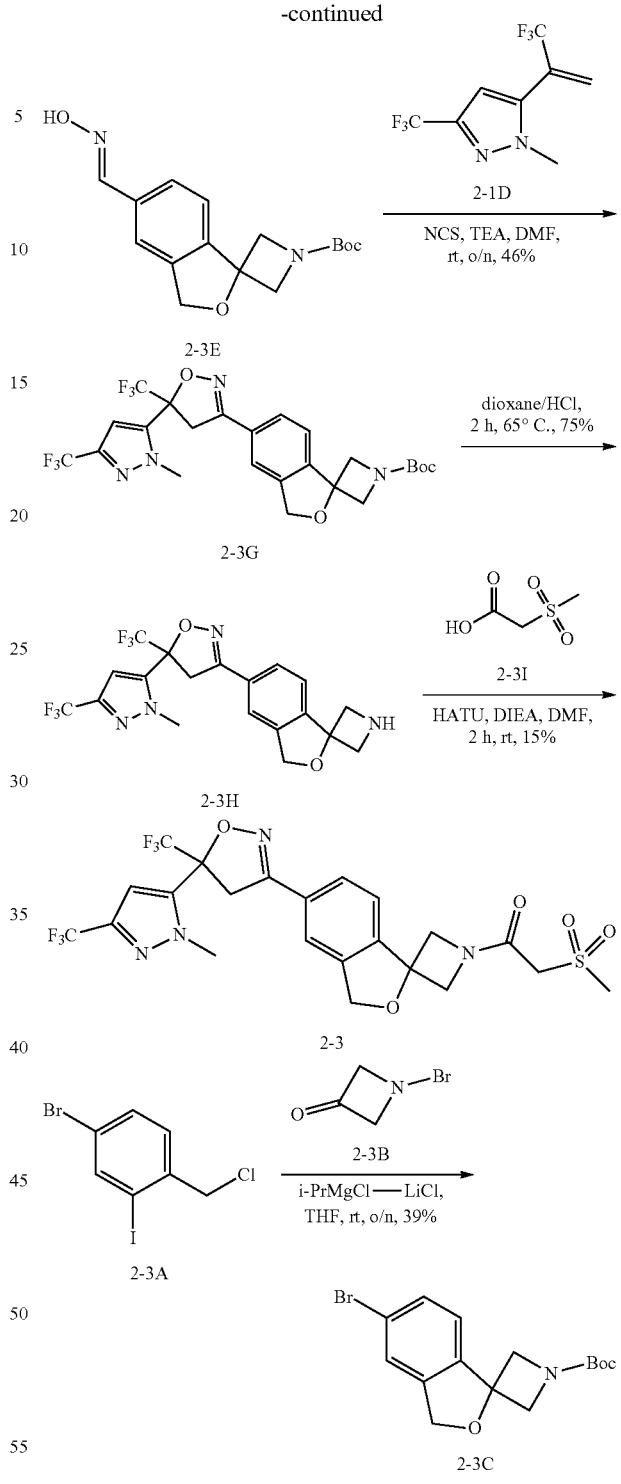

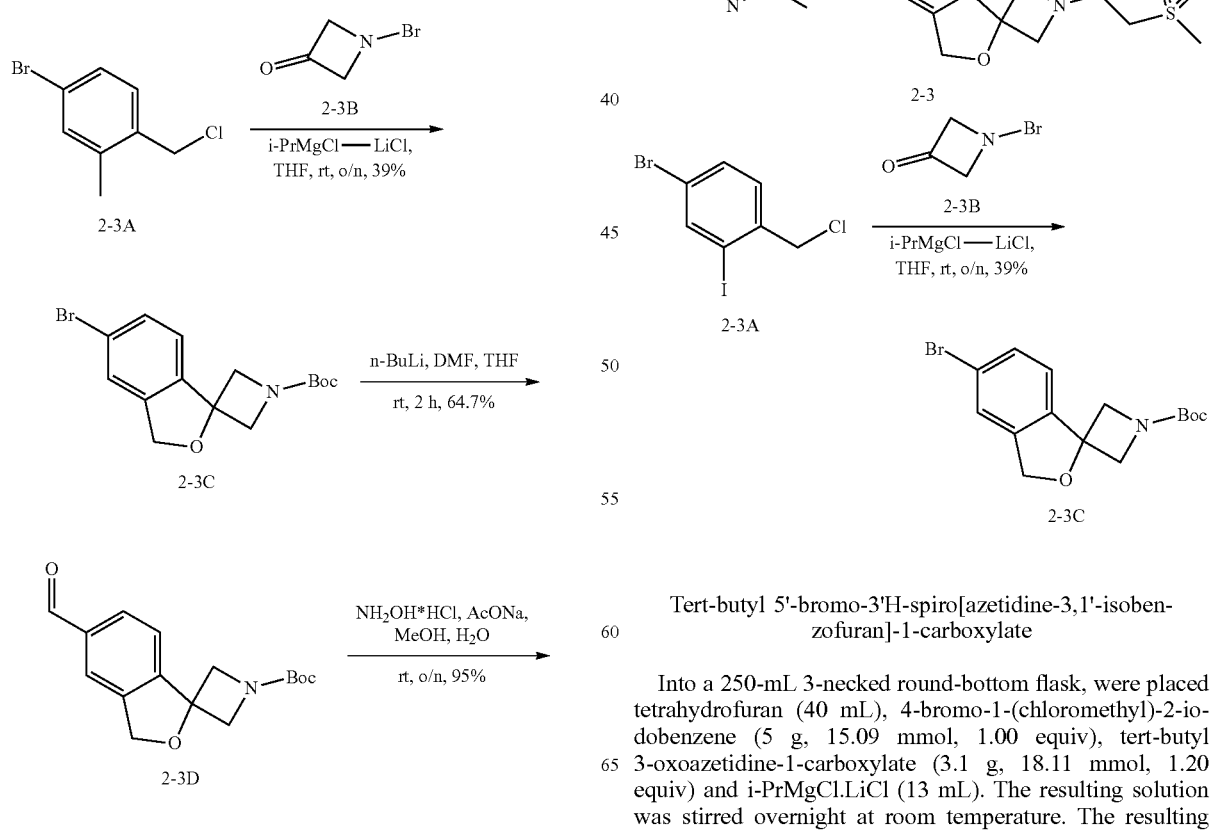

Tert-butyl 5'-bromo-3'H-spiro[azetidine-3,1'-isobenzofuran]-1-carboxylate

Into a 250-mL 3-necked round-bottom flask, were placed tetrahydrofuran (40 mL), 4-bromo-1-(chloromethyl)-2-iodobenzene (5 g, 15.09 mmol, 1.00 equiv), tert-butyl 3-oxoazetidine-1-carboxylate (3.1 g, 18.11 mmol, 1.20 equiv) and i-PrMgCl·LiCl (13 mL). The resulting solution was stirred overnight at room temperature. The resulting mixture was concentrated under vacuum. The residue was applied onto a silica gel column with ethyl acetate/petroleum ether (1:3). This resulted in 2 g (39%) of tert-butyl 5'-bromo-3'H-spiro[azetidine-3,1'-isobenzofuran]-1-carboxylate as colorless oil.

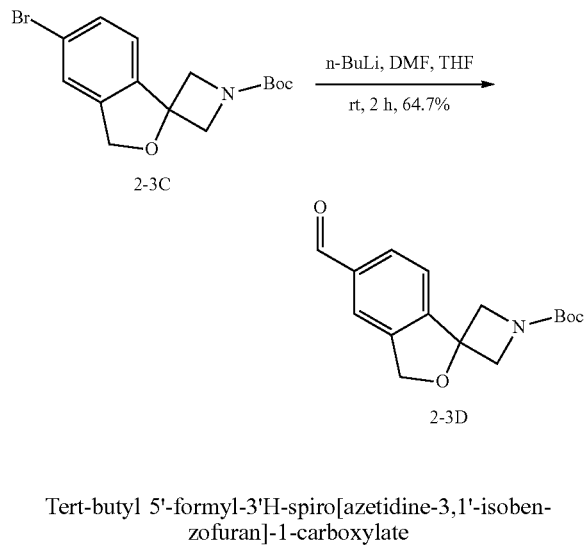

Tert-butyl 5'-formyl-3'H-spiro[azetidine-3,1'-isobenzofuran]-1-carboxylate

Into a 50-mL 3-necked round-bottom flask purged and maintained with an inert atmosphere of argon, was placed tert-butyl 5'-bromo-3'H-spiro[azetidine-3,1'-isobenzofuran]-1-carboxylate (2 g, 5.9 mmol, 1.00 equiv). This was followed by the addition of n-BuLi (3 mL) dropwise with stirring at −78° C. To this was added N,N-dimethylformamide (860 mg, 11.8 mmol, 2.00 equiv) dropwise with stirring at −78° C. The resulting solution was stirred for 2 h at room temperature and then quenched by addition of NH₄Cl (Sat.). The resulting solution was extracted with 3×20 mL of ethyl acetate. The organic layers were combined, dried over anhydrous sodium sulfate and concentrated under vacuum. The residue was applied onto a silica gel column with ethyl acetate/petroleum ether (1:4). This resulted in 1.1 g (64.7%) of tert-butyl 5'-formyl-3'H-spiro [azetidine-3,1'-isobenzofuran]-1-carboxylate as colorless oil.

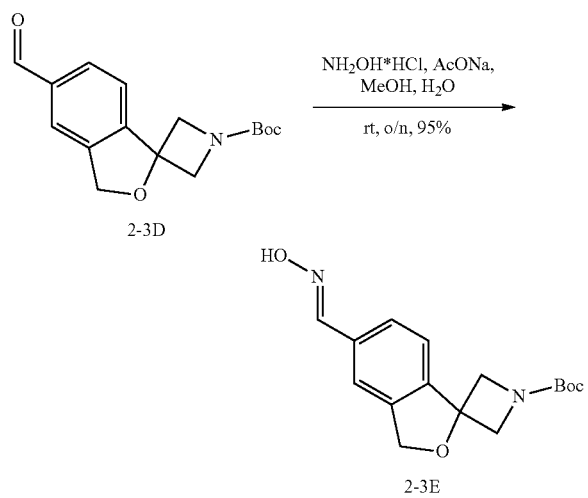

Tert-butyl (E)-5'-((hydroxyimino)methyl)-3'H-spiro [azetidine-3,1'-isobenzofuran]-1-carboxylate Into a 100-mL round-bottom flask were placed methanol (10 mL), water (5 mL), tert-butyl 5'-formyl-3'H-spiro[azetidine-3,1'-isobenzofuran]-1-carboxylate (900 mg, 3.11 mmol, 1.00 equiv), NH₂OH.HCl (500 mg) and NaOAc (700 mg). The resulting solution was stirred overnight at room temperature. The resulting solution was diluted with 20 mL of H₂O then extracted with 3×20 mL of ethyl acetate. The organic layers were combined and dried over anhydrous sodium sulfate and concentrated under vacuum. This resulted in 0.9 g (95%) of tert-butyl (E)-5'-((hydroxyimino) methyl)-3'H-spiro[azetidine-3,1'-isobenzofuran]-1-carboxylate as a yellow solid.

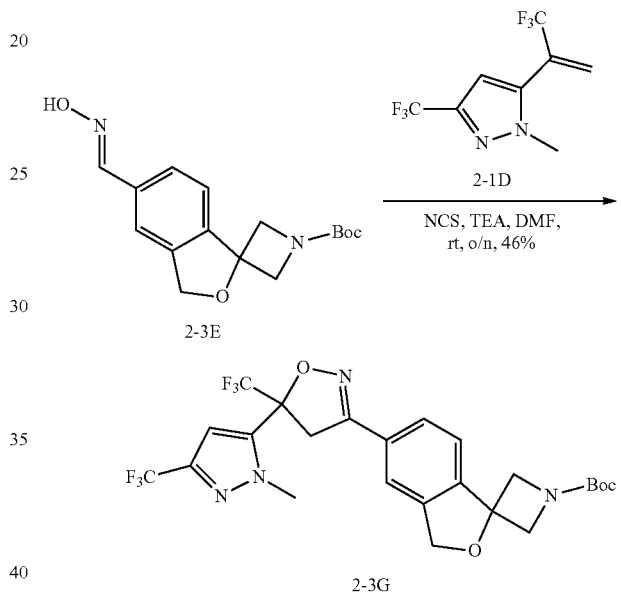

Tert-butyl 5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran]-1-carboxylate Into a 50-mL round-bottom flask were placed N,N-dimethylformamide (5 mL), tert-butyl (E)-5'-((hydroxyimino) methyl)-3'H-spiro[azetidine-3,1'-isobenzofuran]-1-carboxylate (300 mg, 0.99 mmol, 1.00 equiv) and NCS (220 mg, 1.65 mmol, 1.67 equiv). The reaction mixture was stirred for 30 min. then 1-methyl-3-(trifluoromethyl)-5-(3,3,3-trifluoroprop-1-en-2-yl)-1H-pyrazole (510 g, 2.09 mol, 2119.22 equiv) and TEA (300 mg, 2.96 mmol, 3.01 equiv) were added. The resulting solution was stirred overnight at room temperature. The crude product was purified by Flash-Prep-HPLC with the following conditions (IntelFlash-1): Column, C18 silica gel; mobile phase, H₂O: CH₃CN (20% CH₃CN increasing to 80% within 20 min); Detector, UV 254 nm. This resulted in 250 mg (46%) of tert-butyl 5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran]-1-carboxylate as a yellow solid.

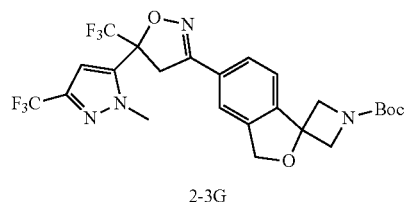

2-3G

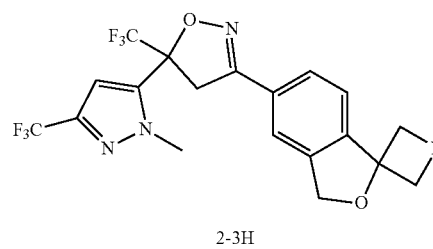

2-3H

5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran] hydrochloride Into a 50-mL round-bottom flask were placed dioxane/HCl (10 mL) and tert-butyl 5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran]-1-carboxylate (300 mg, 0.55 mmol, 1.00 equiv). The resulting solution was stirred for 2 h at 65° C. and then concentrated under vacuum. This resulted in 200 mg (75%) of 5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran] hydrochloride as yellow oil.

1-(5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran]-1-yl)-2-(methylsulfonyl)ethan-1-one Into a 50-mL round-bottom flask were placed N,N-dimethylformamide (4 mL), 5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran] hydrochloride (200 mg, 0.41 mmol, 1.00 equiv), 2-methanesulfonylacetic acid (56 mg, 0.41 mmol, 0.98 equiv), HATU (235 mg, 0.62 mmol, 1.49 equiv) and DIEA (160 mg, 1.24 mmol, 2.99 equiv). The resulting solution was stirred for 2 h at room temperature. The crude product (300 mg) was purified by Flash-Prep-HPLC with the following conditions (IntelFlash-1): Column, C18 silica gel; mobile phase, H$_2$O: CH$_3$CN (20% CH$_3$CN increasing to 80% within 20 min); Detector, UV 254 nm. This resulted in 35.6 mg (15%) of 1-(5'-(5-(1-methyl-3-(trifluoromethyl)-1H-pyrazol-5-yl)-5-(trifluoromethyl)-4,5-dihydroisoxazol-3-yl)-3'H-spiro[azetidine-3,1'-isobenzofuran]-1-yl)-2-(methylsulfonyl)ethan-1-one as a white solid; (ES, m/z): 567 [M+H]$^+$; $^1$H NMR (300 MHz, CD$_3$OD, ppm): δ 7.83-7.81 (m, 1H), 7.70-7.67 (m, 2H), 6.94 (s, 1H), 5.17 (s, 2H), 4.85 (s, 2H), 4.69 (s, 2H), 4.39-4.25 (m, 4H), 4.10 (s, 3H), 3.16 (s, 3H).

Preparation Example 28

Compounds 2-30 and 2-31 were prepared according to Scheme 16 below.

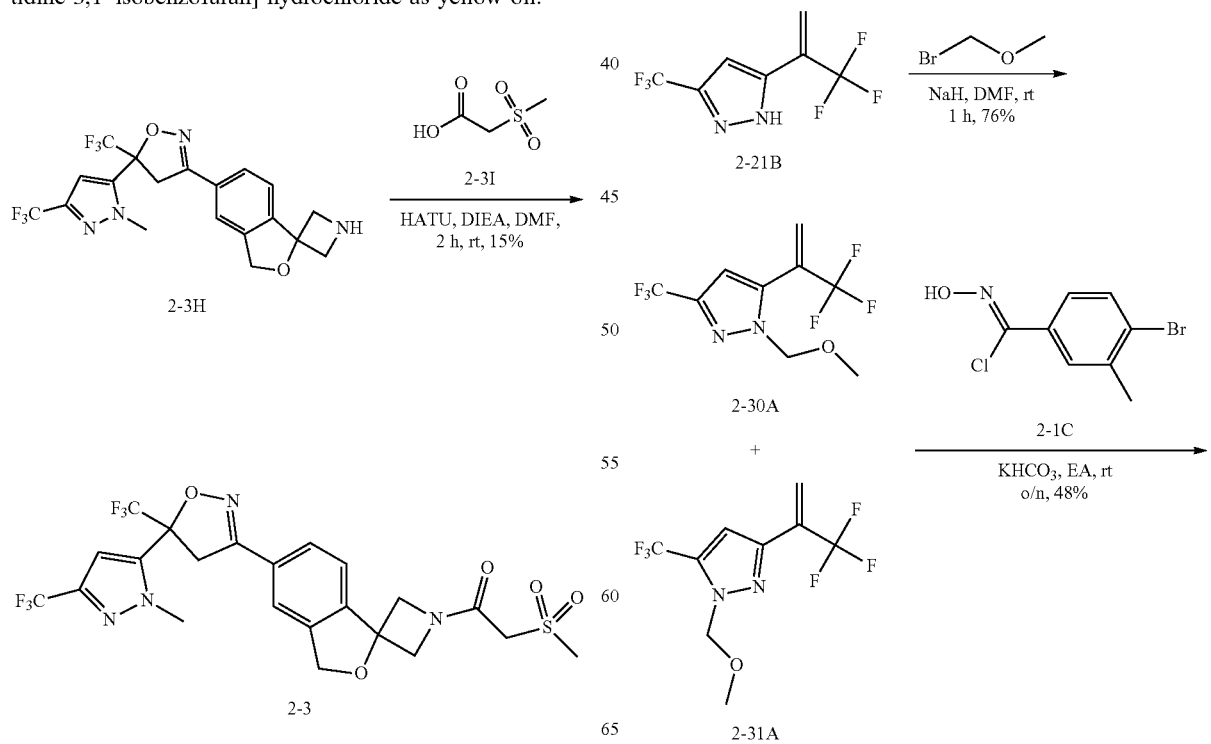

147
-continued

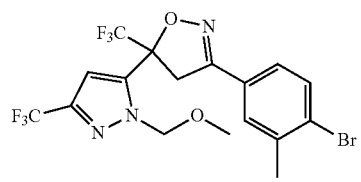
2-30B

+

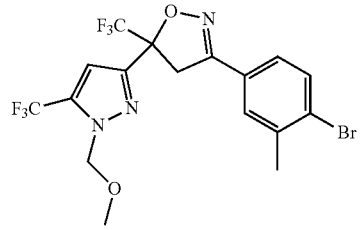
2-31B

Pd(dppf)Cl₂, AcONa
——————————————→
CO, dioxane, 100° C.
3 h, 77%

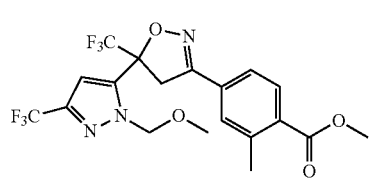
2-30C

+

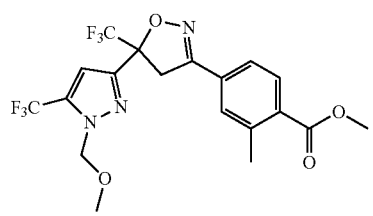
2-31C

LiOH, MeOH, H₂O
——————————————→
50° C., 1 h, 72%

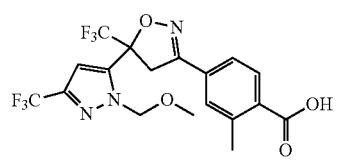
2-30D

+

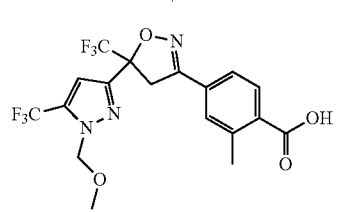
2-31D

148
-continued

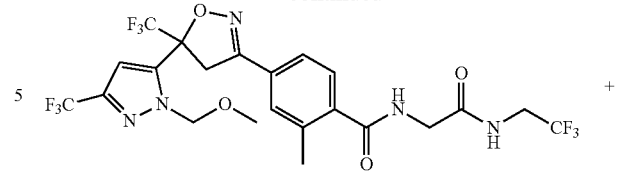
2-30

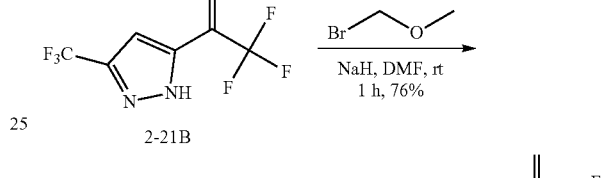
2-31

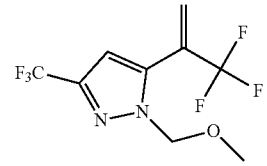
2-21B $\xrightarrow[\text{1 h, 76\%}]{\text{Br}\frown\text{O}\diagdown\text{, NaH, DMF, rt}}$

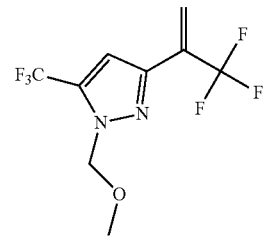
2-30A

+

2-31A

Mixture of 2-30A and 2-31A:

Into a 50-mL round-bottom flask were placed N,N-dimethylformamide (10 mL), 3-(trifluoromethyl)-5-(3,3,3-trifluoroprop-1-en-2-yl)-1H-pyrazole (1 g, 4.35 mmol, 1.00 equiv) and sodium hydride (300 mg, 12.50 mmol, 2.88 equiv). The reaction was stirred for 1 h. This was followed by the addition of bromo(methoxy)methane (900 mg, 7.20 mmol, 1.66 equiv). The resulting solution was stirred for 1 h at room temperature. The reaction was then quenched by the addition of NH₄Cl (aq.) and the resulting solution was extracted with 3×10 mL of ethyl acetate. The combined organic layers were dried over anhydrous sodium sulfate and concentrated under vacuum. The residue was applied onto a silica gel column with ethyl acetate/petroleum ether (1:5). This resulted in 0.9 g (76%) of 2-30A and 2-31A (Mixture) as yellow oil.

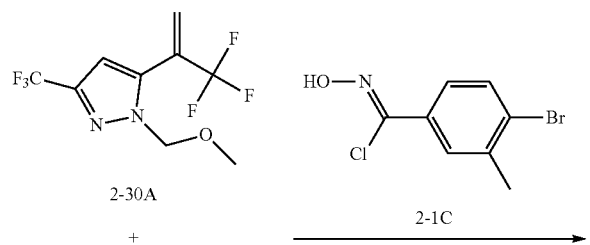
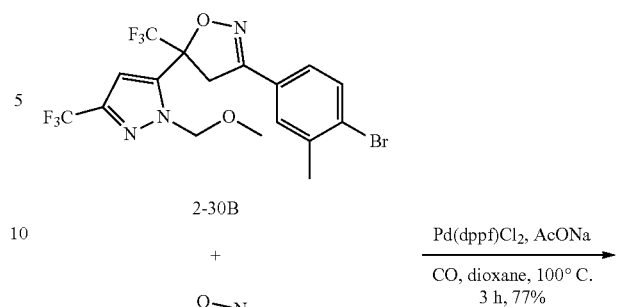
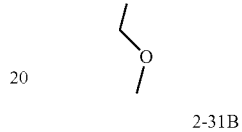
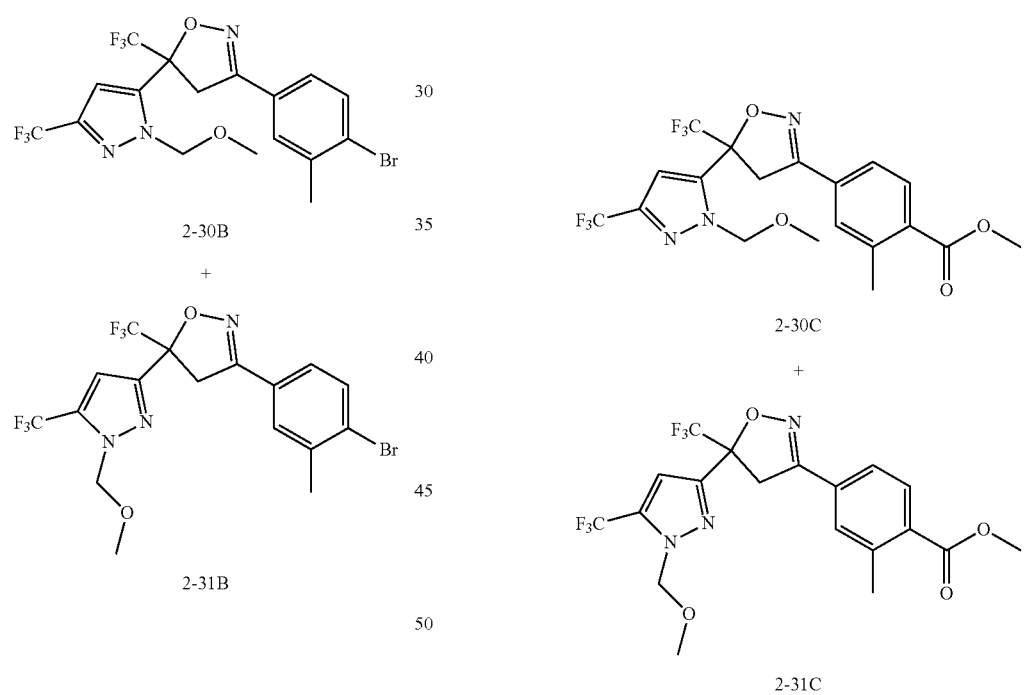

Mixture of 2-30B and 2-31B:

Into a 50-mL round-bottom flask were placed ethyl acetate (10 mL), 2-30A and 2-31A (Mixture) (700 mg, 2.55 mmol, 1.00 equiv), (Z)-4-bromo-N-hydroxy-3-methylbenzene-1-carbonimidoyl chloride (950 mg, 3.82 mmol, 1.50 equiv) and KHCO$_3$ (0.77 g). The resulting solution was stirred overnight at room temperature. The reaction mixture was concentrated under vacuum and the residue was applied onto a silica gel column with ethyl acetate/petroleum ether (1:3). This resulted in 0.6 g (48%) of 2-30B and 2-31B (Mixture) as a white solid.

Mixture of 2-30C and 2-31C:

Into a 50-mL pressure tank reactor were placed methanol (4 mL), dioxane (10 mL), 2-30B and 2-31B (Mixture) (500 mg, 1.03 mmol, 1.00 equiv), NaOAc (460 mg) and Pd(dppf)Cl$_2$ (180 mg, 0.25 mmol, 0.24 equiv). To this mixture was introduced CO (20 atm). The resulting solution was stirred for 3 h at 100° C. The reaction mixture was concentrated under vacuum and the residue was applied onto a silica gel column with ethyl acetate/petroleum ether (1:4). This resulted in 370 mg (77%) of 2-31C and 2-31C (Mixture) as a yellow solid.

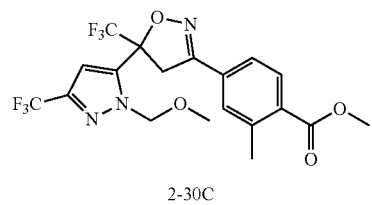

2-30C

+

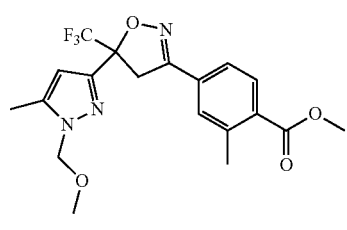

2-31C

LiOH, MeOH, H₂O
⟶
50° C., 1 h, 72%

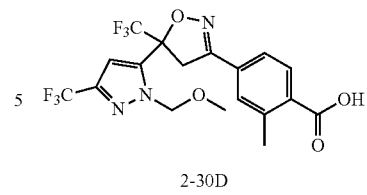

2-30D

+

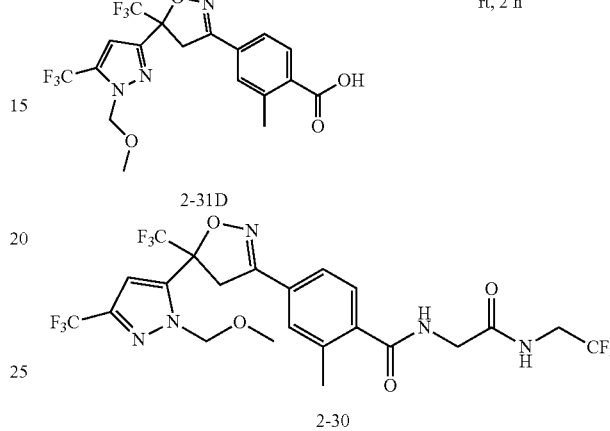

2-31D

2-[(4-[5-[1-(methoxymethyl)-3-(trifluoromethyl)-1H-pyrazol-5-yl]-5-(trifluoromethyl)-4,5-dihydro-1,2-oxazol-3-yl]-2-methylphenyl)formamido]-N-(2,2,2-trifluoroethyl)acetamide (Compound 2-30)

4-(5-(1-(methoxymethyl)-5-(trifluoromethyl)-1H-pyrazol-3-yl)-5-(trifluoromethyl)-4,5-dihydroisoxazol-3-yl)-2-methyl-N-(2-oxo-2-(2,2,2-trifluoroethylamino)ethyl)benzamide (Compound 2-31)

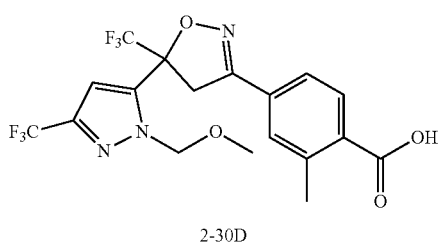

2-30D

+

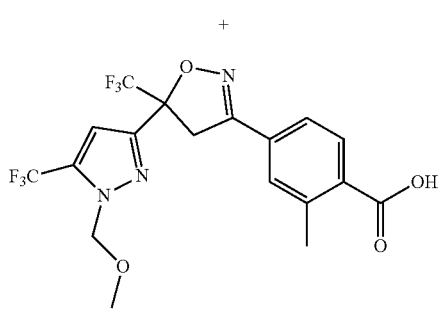

2-31D 2-30D and 2-31D (Mixture):

Into a 50-mL round-bottom flask were placed water (1 mL), methanol (5 mL), 2-30C and 2-31C (Mixture) (300 mg, 0.64 mmol, 1.00 equiv) and LiOH (100 mg, 4.18 mmol, 6.48 equiv). The resulting solution was stirred for 1 h at 50° C. and then cooled to room temperature. The pH value of the solution was adjusted to 4 with hydrogen chloride (2 mol/L). The resulting solution was extracted with 3×10 mL of ethyl acetate. The combined organic layers were dried over anhydrous sodium sulfate and concentrated under vacuum. This resulted in 0.21 g (72%) of 2-30D and 2-31D (Mixture) as a yellow oil.

Into a 50-mL round-bottom flask were placed N,N-dimethylformamide (5 mL), 2-30D and 2-31D (Mixture) (200 mg, 0.44 mmol, 1.00 equiv), 2-amino-N-(2,2,2-trifluoroethyl)acetamide (110 mg, 0.70 mmol, 1.59 equiv), HATU (410 mg, 1.08 mmol, 2.43 equiv) and DIEA (270 mg, 2.09 mmol, 4.71 equiv). The resulting solution was stirred for 2 h at room temperature. The crude solution was purified by Flash-Prep-HPLC with the following conditions (IntelFlash-1): Column, C18 silica gel; mobile phase, H₂O and CH₃CN (0% CH₃CN increasing to 80% within 25 min); Detector, UV 254 nm. This resulted in 125.5 mg of 2-[(4-[5-[1-(methoxymethyl)-3-(trifluoromethyl)-1H-pyrazol-5-yl]-5-(trifluoromethyl)-4,5-dihydro-1,2-oxazol-3-yl]-2-methylphenyl)formamido]-N-(2,2,2-trifluoroethyl)acetamide as a white solid;

and 76.1 mg of 4-(5-(1-(methoxymethyl)-5-(trifluoromethyl)-1H-pyrazol-3-yl)-5-(trifluoromethyl)-4,5-dihydroisoxazol-3-yl)-2-methyl-N-(2-oxo-2-(2,2,2-trifluoroethylamino)ethyl)benzamide (Compound 2-30) (ES, m/z): 590 [M+H]$^+$;

$^1$H NMR (Compound 2-30) (CDCl$_3$, 300 MHz, ppm) δ 7.59-7.56 (m, 2H), 7.51-7.48 (m, 1H), 7.28-7.22 (m, 1H), 7.04 (s, 1H), 6.88 (br, 1H), 5.58-5.49 (m, 2H), 4.43-4.38 (m, 1H), 4.26-4.24 (m, 2H), 4.01-3.93 (m, 3H), 3.37 (s, 3H), 2.49 (s, 3H).

Compound 2-31 (ES, m/z): 590 [M+H]$^+$;

$^1$H NMR-Compound 2-31 (300 MHz, CDCl$_3$, ppm): δ 7.58 (s, 1H), 7.55-7.49 (m, 2H), 7.04 (br, 1H), 6.82-6.80 (m, 2H), 5.77 (d, J=10.8 Hz, 1H), 5.49 (d, J=10.8 Hz, 1H), 4.26-4.24 (m, 2H), 4.24-3.92 (m, 4H), 3.37 (s, 1H), 2.50 (s, 3H).

Method A: Efficacy of Compounds Against *A. aegypti* Mosquitos

Compounds were formulated in 100% DMSO are added to microtiter plates containing 180 μl of diluted LB media (Luria-Bertani media is a combination of tryptone, salt and yeast extract). Ten *A. aegypti* L1 larvae are added and the plates are incubated at 25° C. for 48h. The efficacy of a compound is determined based on the motility of the larvae as compared to average motility of control wells containing DMSO only. A dose response assay was conducted to determine an EC$_{50}$ value. Compounds 2-8, 2-9, 2-10 and 2-11 were found to have EC$_5$s values of less than 20 μM and Compounds 2-1, 2-2, 2-3, 2-4, 2-5, 2-6, 2-7, 2-30 and 2-31 were found to have EC$_{50}$ values of less than 10 μM.

Method B: Efficacy of Compounds Against Fleas when Ingested

A cylindrical test container was filled with 10 adult *Ctenocephalides felis*. A cylindrical well was closed on one end with a self-sealing flexible film and placed on top of the test container in such a position that the fleas could pierce the film and feed on the contents of the cylinder. The test compound solution was then pipetted into bovine blood and added to the well. The container part with the *Ctenocephalides felis* was held at 20-22° C. and 40-60% relative humidity while the well part containing the treated blood was held at 37° C. and 40-60% relative humidity. Assessment was performed at 72 hours after application in comparison with untreated controls. Compounds numbers 2-6 and 2-7 were found to have LC$_{50}$ values below 50 μM at the 72 hour assessment. Compounds 2-1, 2-2, 2-3, 2-4 and 2-5 were found to have LC$_{50}$ values of less than 20 μM at the 72 hour assessment.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A pesticidal isoxazoline compound of formula (I):

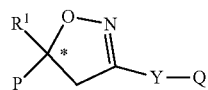

(I)

or a pharmaceutically or agriculturally acceptable salt thereof, wherein:

the asterisk (*) signifies a quaternary center;

P is an optionally substituted pyrazole ring;

$R^1$ is alkyl, haloalkyl, alkenyl, alkynyl, cycloalkyl, alkylcycloalkyl or cycloalkylalkyl, each optionally substituted with one or more substituents independently selected from $R^6$;

Y is an optionally substituted phenylene, naphthylene, indanylene, a 5- or 6-membered heteroarylene, an 8-12-membered heterobicyclylene or an 8-12-membered heterotricyclylene, each optionally independently substituted by one or more $R^7$;

Q is X—NR$^5$R$^6$, —NR$^5$R$^6$, X—R$^6$, OH, NH$_2$, alkoxy, haloalkoxy, alkylamino, haloalkylamino, dialkylamino, dihaloalkylamino, thiol, alkylthio, haloalkylthio, alkylsulfinyl, haloalkylsulfinyl, alkylsulfonyl, haloalkylsulfonyl, —SF$_5$, —C(=S)—NH$_2$, or an optionally substituted 5- or 6-membered carbocyclyl, heterocyclyl, heteroaryl ring or the groups T1 or T2:

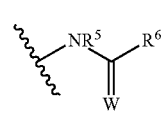

T1

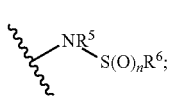

T2 wherein W is O or S;

X is (CH$_2$)n, CH(CH$_3$), CH(CN), C(=O) or C(=S);

$R^5$ is H, alkyl, alkenyl, alkynyl, cycloalkyl, alkylcycloalkyl, cycloalkylalkyl, alkylcarbonyl or alkoxycarbonyl;

$R^6$ is H, OR$^{10}$, NR$^{11}$, R$^{12}$ or Q$^1$; alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^7$; or $R^5$ and $R^6$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;

each $R^7$ is independently halogen; alkyl, cycloalkyl, alkoxy, alkylthio, haloalkylthio, alkylsulfinyl, haloalkylsulfinyl, alkyl sulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —SF$_5$, —C(=S)NH$_2$, —NH$_2$, —CN or —NO$_2$; or Q$^2$;

each $R^8$ is independently halogen, alkoxy, haloalkoxy, alkylthio, haloalkylthio, alkylsulfinyl, haloalkylsulfinyl, alkyl sulfonyl, haloalkylsulfonyl, alkylamino, dialkylamino, alkoxycarbonyl, —SF$_5$, —C(=S)NH$_2$, —CN or —NO$_2$;

each $R^9$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —SF$_5$, —C(=S)NH$_2$, —CN, —NO$_2$, phenyl or pyridinyl;

$R^{10}$ is H; or alkyl, alkenyl, alkynyl, cycloalkyl, alkylcycloalkyl or cycloalkylalkyl, each optionally substituted with one of more halogen;

$R^{11}$ is H, alkyl, alkenyl, alkynyl, cycloalkyl, alkylcycloalkyl, cycloalkylalkyl, alkylcarbonyl or alkoxycarbonyl;

$R^{12}$ is H; $Q^3$; or alkyl, alkenyl, alkynyl, cycloalkyl, alkylcycloalkyl or cycloalkylalkyl, each optionally substituted with one or more substituents independently selected from $R^7$; or $R^{11}$ and $R^{12}$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

$Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2.

2. The pesticidal isoxazoline compound of claim 1, wherein P is $P^1$, $P^2$, $P^3$ or $P^4$:

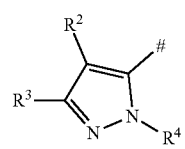

P$^1$

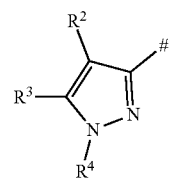

P$^2$

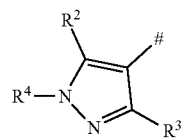

P$^3$

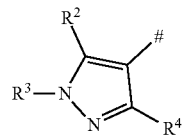

P$^4$ wherein, $R^2$ and $R^3$ are independently H, halogen, alkyl, haloalkyl, alkenyl, haloalkenyl, alkynyl, haloalkynyl, cycloalkyl, halocycloalkyl, alkoxy, haloalkoxy, alkoxyalkyl, alkoxyalkoxyalkyl, alkylthio, haloalkylthio, alkylsulfinyl, haloalkylsulfinyl, alkylsulfonyl, haloalkylsulfonyl, amino, alkylamino, dialkylamino, haloalkylamino, dihaloalkylamino, alkylcarbonyl, haloalkylcarbonyl, alkoxycarbonyl, aminocarbonyl, alkylaminocarbonyl, dialkylaminocarbonyl, aryl, heteroaryl, arylalkyl, heteroarylalkyl, SF$_5$, —CN, —NO$_2$ or —C(S)NH$_2$, wherein each alkyl, cycloalkyl, alkenyl, alkynyl, aryl or heteroaryl is optionally independently substituted by one or more $R^7$;

$R^4$ is H, alkyl, haloalkyl, alkenyl, haloalkenyl, alkynyl, haloalkynyl, arylalkyl, heteroarylalkyl, alkoxyalkyl, alkoxyalkoxyalkyl, alkylcarbonyl, haloalkylcarbonyl, alkoxycarbonyl, haloalkoxycarbonyl, alkylsulfinyl, haloalkylsulfinyl, alkyl sulfonyl, haloalkylsulfonyl, aryl, heteroaryl, arylalkyl or heteroarylalkyl, wherein each optionally substituted by one or more $R^7$.

3. The pesticidal isoxazoline compound of claim 1, wherein Y is Y-1, Y-2, Y-3, Y-4, Y-5 or Y-6:

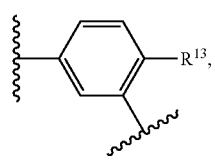

Y-1

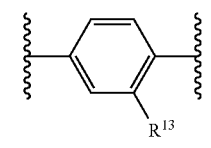

Y-2

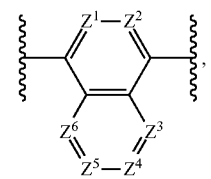

Y-3

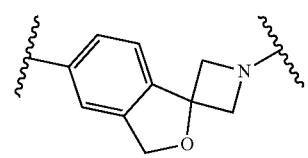

Y-4

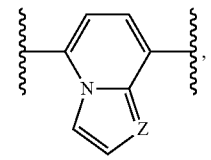

Y-5

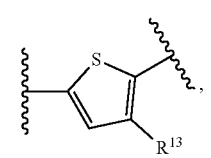

Y-6 wherein $Z^1$, $Z^2$, $Z^3$, $Z^4$, $Z^5$ and $Z^6$ are independently N or C—$R^{15}$ and wherein at most 3 Z groups are nitrogen;

Z is N or C-$R^{15}$; and $R^{13}$ and $R^{15}$ are independently H, halogen, $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$haloalkylsulfonyl, —CN, —$NO_2$ or —$SF_5$.

4. The pesticidal isoxazoline compound of claim 1, wherein $R^1$ is $CF_3$.

5. The pesticidal isoxazoline compound of claim 2, wherein $R^2$ and $R^3$ are independently hydrogen, methyl or $CF_3$; and $R^4$ is hydrogen or $C_1$-$C_3$-alkyl.

6. The pesticidal isoxazoline compound of claim 3 wherein:

Y is Y-2, Y-3, Y-5 or Y-6;

$Z^1$, $Z^2$, $Z^3$, $Z^4$, $Z^5$ or $Z^6$ are independently N or C—H;

Z is N or C—H; and each $R^{13}$ is H or $C^1$-$C^3$alkyl.

7. The pesticidal isoxazoline compound of claim 1, wherein Q is X—$NR^5R^6$.

8. The pesticidal isoxazoline compound of claim 7, wherein $R^5$ is H, $C_1$-$C_3$alkyl or $C_1$-$C_3$haloalkyl; and $R^6$ is $C_3$-$C_8$cycloalkyl, haloalkyl or alkyl optionally substituted by one or more $R^7$.

9. The pesticidal isoxazoline compound of claim 7, wherein Q is —C(O)NHCF$_3$, —C(O)NHCH$_2$CH$_2$CF$_3$, —C(O)NHCH$_2$CF$_3$, —C(O)NHCH$_2$C(O)NHCH$_2$CF$_3$, —C(O) NHCH$_2$CH$_2$S(O)$_n$CH$_3$ where n is 0, 1 or 2 or —C(O)CH$_2$S(O)$_n$CH$_3$ where n is 0, 1 or 2.

10. The pesticidal isoxazoline compound of claim 7, wherein $R^5$ is H or $C_1$-$C_3$alkyl; and $R^6$ is cyclopropyl, cyclobutyl, cyclopentyl or cyclohexyl.

11. The pesticidal isoxazoline compound of claim 1, wherein Q is T1 or T2.

12. The pesticidal isoxazoline compound of claim 1, wherein the compound is selected from the group consisting of:

| Compound # | Structure |
|---|---|
| 2-1 | 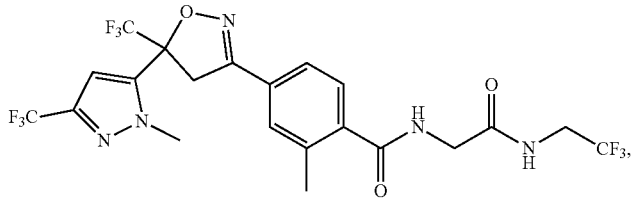 |
| 2-2 | 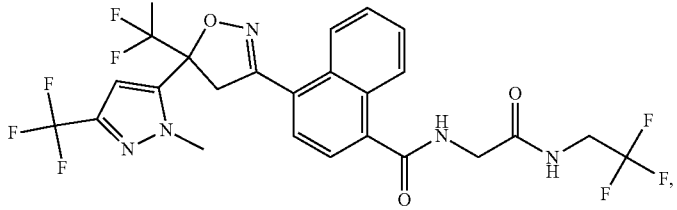 |
| 2-3 | 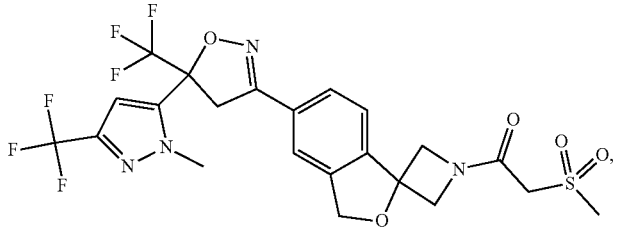 [SMILES: Cn1nc(C(F)(F)F)cc1C1(C(F)(F)F)CC(c2ccc3c(c2)COC32CN(C(=O)CS(C)(=O)=O)C2)=NO1] |
| 2-4 | 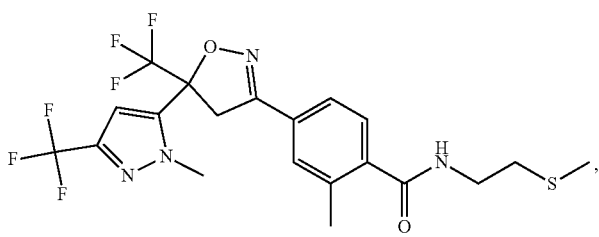 [SMILES: CSCCNC(=O)c1ccc(C2=NOC(c3cc(C(F)(F)F)nn3C)(C(F)(F)F)C2)cc1C] |

-continued
| Compound # | Structure |
|---|---|
| 2-5 | 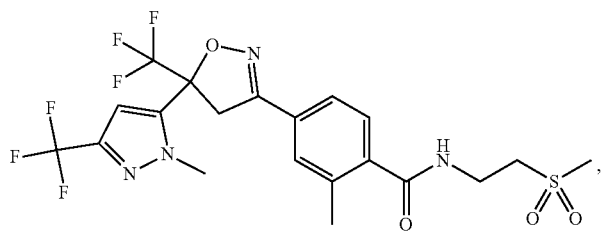 [SMILES: Cc1cc(C2=NOC(c3cc(C(F)(F)F)nn3C)(C(F)(F)F)C2)ccc1C(=O)NCCS(C)(=O)=O] |
| 2-6 | 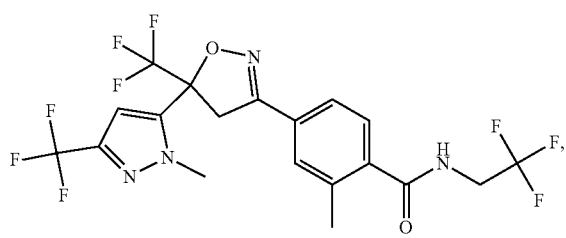 [SMILES: Cc1cc(C2=NOC(c3cc(C(F)(F)F)nn3C)(C(F)(F)F)C2)ccc1C(=O)NCC(F)(F)F] |
| 2-7 | 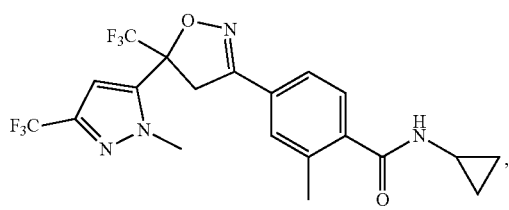 [SMILES: Cc1cc(C2=NOC(c3cc(C(F)(F)F)nn3C)(C(F)(F)F)C2)ccc1C(=O)NC1CC1] |
| 2-8 | 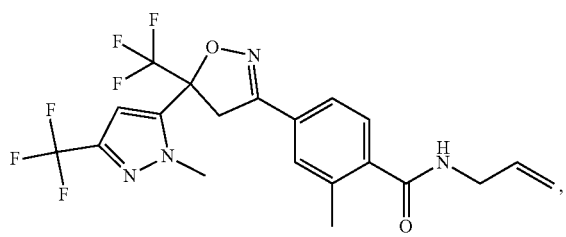 [SMILES: C=CCNC(=O)c1ccc(C2=NOC(c3cc(C(F)(F)F)nn3C)(C(F)(F)F)C2)cc1C] |
| 2-9 | 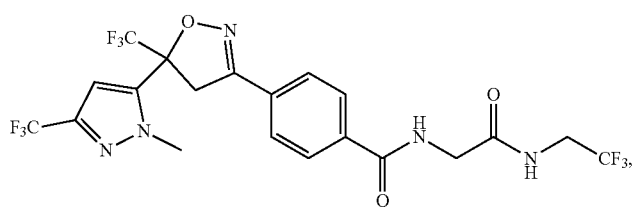 [SMILES: Cn1nc(C(F)(F)F)cc1C1(C(F)(F)F)CC(c2ccc(C(=O)NCC(=O)NCC(F)(F)F)cc2)=NO1] |
| 2-10 | 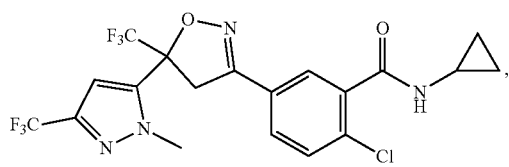 [SMILES: Cn1nc(C(F)(F)F)cc1C1(C(F)(F)F)CC(c2ccc(Cl)c(C(=O)NC3CC3)c2)=NO1] |
| 2-11 | 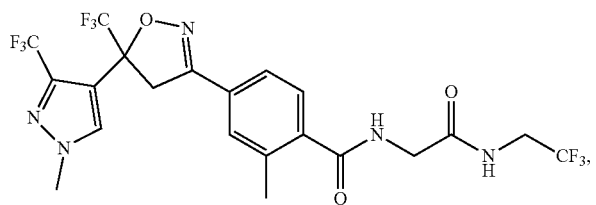 [SMILES: Cc1cc(C2=NOC(c3cn(C)nc3C(F)(F)F)(C(F)(F)F)C2)ccc1C(=O)NCC(=O)NCC(F)(F)F] |

| Compound # | Structure |
|---|---|
| 2-12 | 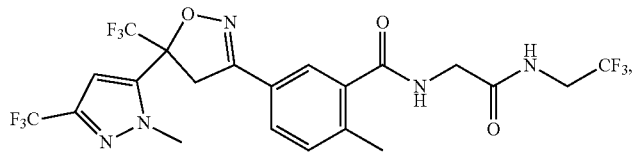 [SMILES: Cc1ccc(C2=NOC(c3cc(C(F)(F)F)nn3C)(C(F)(F)F)C2)cc1C(=O)NCC(=O)NCC(F)(F)F] |
| 2-13 | 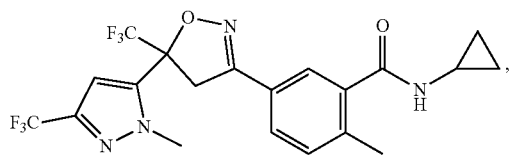 [SMILES: Cc1ccc(C2=NOC(c3cc(C(F)(F)F)nn3C)(C(F)(F)F)C2)cc1C(=O)NC1CC1] |
| 2-14 | 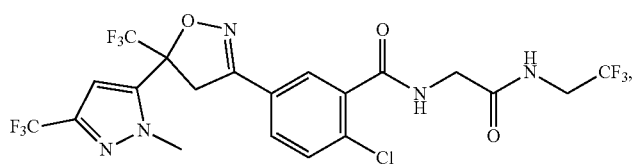 [SMILES: Cn1nc(C(F)(F)F)cc1C1(C(F)(F)F)CC(c2ccc(Cl)c(C(=O)NCC(=O)NCC(F)(F)F)c2)=NO1] |
| 2-15 | 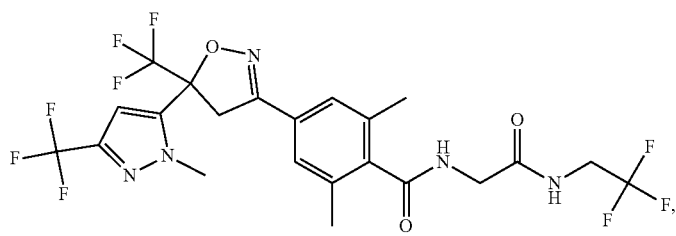 [SMILES: Cc1cc(C2=NOC(c3cc(C(F)(F)F)nn3C)(C(F)(F)F)C2)cc(C)c1C(=O)NCC(=O)NCC(F)(F)F] |
| 2-16 | 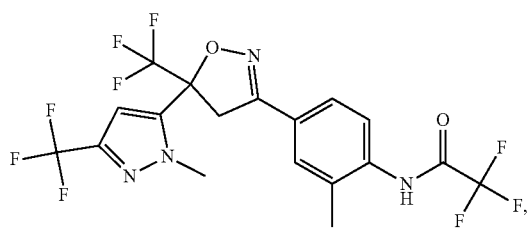 [SMILES: Cc1cc(C2=NOC(c3cc(C(F)(F)F)nn3C)(C(F)(F)F)C2)ccc1NC(=O)C(F)(F)F] |
| 2-17 | 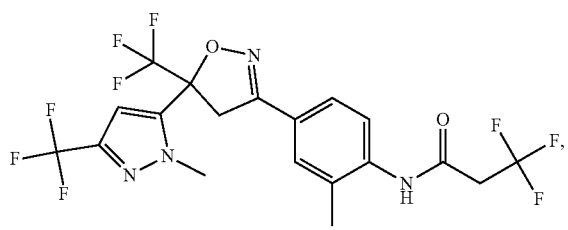 [SMILES: Cc1cc(C2=NOC(c3cc(C(F)(F)F)nn3C)(C(F)(F)F)C2)ccc1NC(=O)CC(F)(F)F] |
| 2-18 | 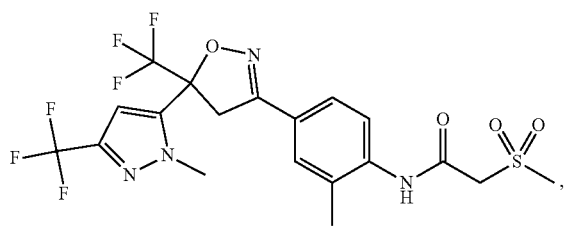 [SMILES: Cc1cc(C2=NOC(c3cc(C(F)(F)F)nn3C)(C(F)(F)F)C2)ccc1NC(=O)CS(C)(=O)=O] |

163 -continued 164
| Compound # | Structure |
|---|---|
| 2-19 | 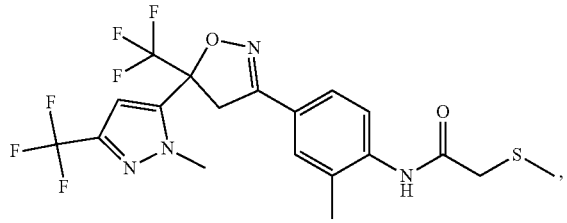 [SMILES: CSCC(=O)Nc1ccc(C2=NOC(c3cc(C(F)(F)F)nn3C)(C(F)(F)F)C2)cc1C] |
| 2-20 | 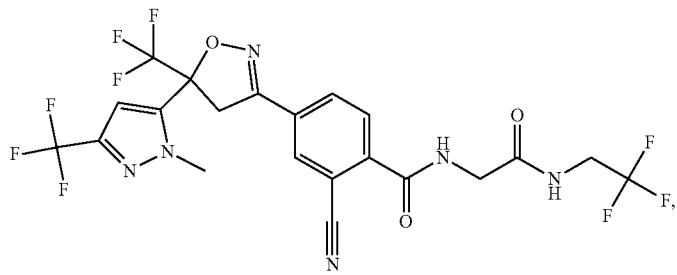 [SMILES: Cn1nc(C(F)(F)F)cc1C1(C(F)(F)F)CC(c2ccc(C(=O)NCC(=O)NCC(F)(F)F)c(C#N)c2)=NO1] |
| 2-21 | 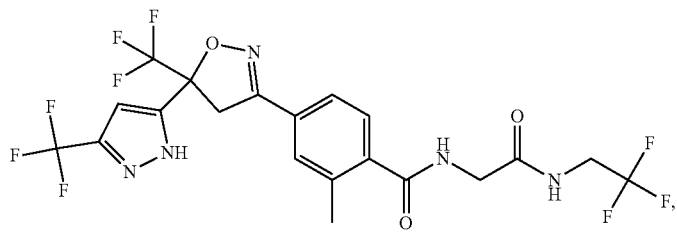 [SMILES: Cc1cc(C2=NOC(c3cc(C(F)(F)F)n[nH]3)(C(F)(F)F)C2)ccc1C(=O)NCC(=O)NCC(F)(F)F] |
| 2-22 | 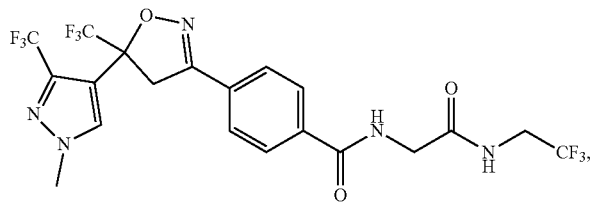 [SMILES: Cn1cc(C2(C(F)(F)F)CC(c3ccc(C(=O)NCC(=O)NCC(F)(F)F)cc3)=NO2)c(C(F)(F)F)n1] |
| 2-23 | 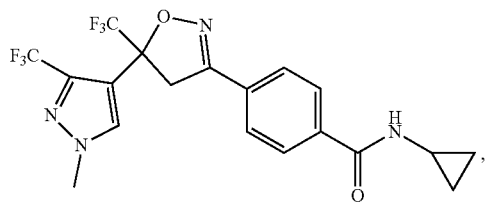 [SMILES: Cn1cc(C2(C(F)(F)F)CC(c3ccc(C(=O)NC4CC4)cc3)=NO2)c(C(F)(F)F)n1] |
| 2-24 | 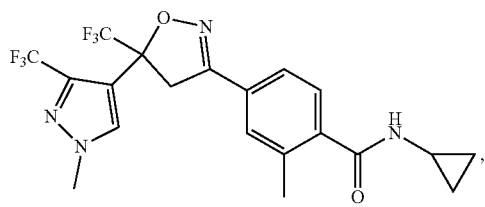 [SMILES: Cc1cc(C2=NOC(c3cn(C)nc3C(F)(F)F)(C(F)(F)F)C2)ccc1C(=O)NC1CC1] |
| 2-25 | 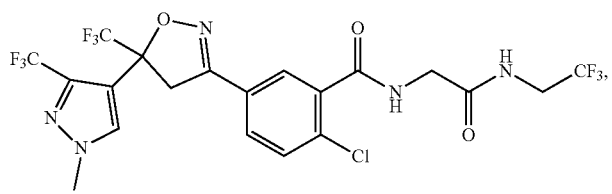 [SMILES: Cn1cc(C2(C(F)(F)F)CC(c3ccc(Cl)c(C(=O)NCC(=O)NCC(F)(F)F)c3)=NO2)c(C(F)(F)F)n1] |

-continued

| Compound # | Structure |
|---|---|
| 2-26 | 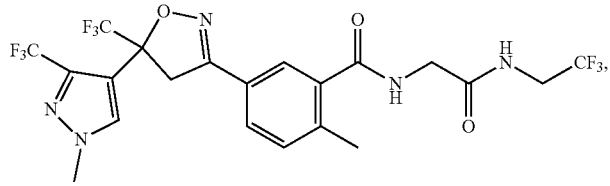 [SMILES: Cc1ccc(C2=NOC(c3cn(C)nc3C(F)(F)F)(C(F)(F)F)C2)cc1C(=O)NCC(=O)NCC(F)(F)F] |
| 2-27 | 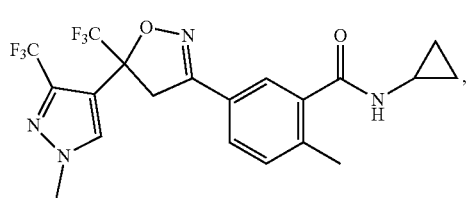 [SMILES: Cc1ccc(C2=NOC(c3cn(C)nc3C(F)(F)F)(C(F)(F)F)C2)cc1C(=O)NC1CC1] |
| 2-28 | 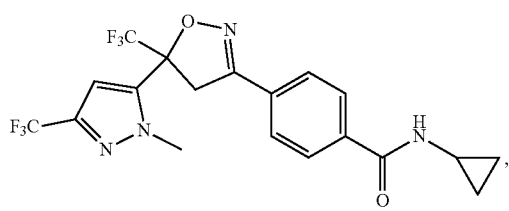 |
| 2-29 | 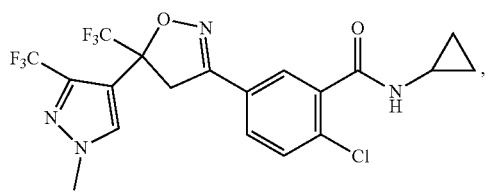 [SMILES: Cn1cc(C2(C(F)(F)F)CC(c3ccc(Cl)c(C(=O)NC4CC4)c3)=NO2)c(C(F)(F)F)n1] |
| 2-30 | 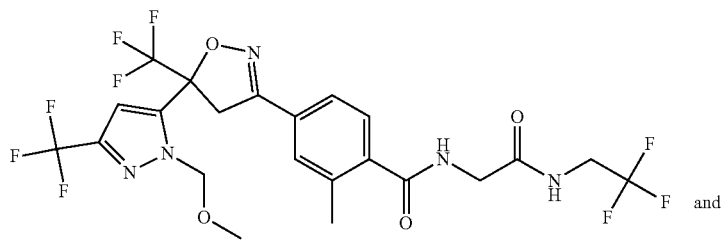 [SMILES: COCn1nc(C(F)(F)F)cc1C1(C(F)(F)F)CC(c2ccc(C(=O)NCC(=O)NCC(F)(F)F)c(C)c2)=NO1 ; "and"] and |
| 2-31 | 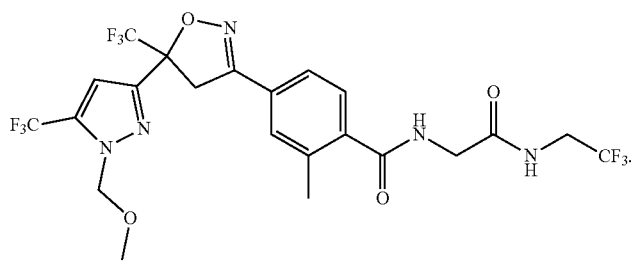 [SMILES: COCn1nc(C2(C(F)(F)F)CC(c3ccc(C(=O)NCC(=O)NCC(F)(F)F)c(C)c3)=NO2)cc1C(F)(F)F] |

13. The pesticidal isoxazoline compound of claim 1 wherein the isoxazoline compound is substantially enriched in the (S)-enantiomer.

14. A pesticidal composition comprising the isoxazoline compound of formula (I) of claim 1, or an agriculturally acceptable salt thereof, in combination with a agriculturally acceptable carrier.

15. A parasiticidal composition comprisingan isoxazoline compound of formula (I) of claim 1, or a pharmaceutically acceptable salt thereof, in combination with a pharmaceutically acceptable carrier.

* * * * *